(12) United States Patent
Engelen et al.

(10) Patent No.: US 10,767,190 B2
(45) Date of Patent: Sep. 8, 2020

(54) BRASSICACEAE PLANTS RESISTANT TO PLASMODIOPHORA BRASSICAE (CLUBROOT)

(71) Applicant: BASF AGRICULTURAL SOLUTIONS SEED, US LLC, Research Triangle Park, NC (US)

(72) Inventors: Steven Engelen, Zeveneken-Lochristi (BE); Michel Van Thournout, Sint Michiels (BE); Stephen Rae, De Pinte (BE); Kim Crommar, Drongen (BE); Vanessa Hostyn, Mariakerke (BE); Godfrey Chongo, Saskatoon (CA)

(73) Assignee: BASF AGRICULTURAL SOLUTIONS SEED, US LLC, Research Triangle Park, NC (US)

( * ) Notice: Subject to any disclaimer, the term of this patent is extended or adjusted under 35 U.S.C. 154(b) by 0 days.

(21) Appl. No.: 15/775,580

(22) PCT Filed: Dec. 15, 2016

(86) PCT No.: PCT/EP2016/081146
§ 371 (c)(1),
(2) Date: May 11, 2018

(87) PCT Pub. No.: WO2017/102923
PCT Pub. Date: Jun. 22, 2017

(65) Prior Publication Data
US 2019/0241904 A1    Aug. 8, 2019

Related U.S. Application Data

(60) Provisional application No. 62/267,460, filed on Dec. 15, 2015.

(51) Int. Cl.
| | | |
|---|---|---|
| *C12N 15/82* | (2006.01) | |
| *C07K 14/415* | (2006.01) | |
| *C12Q 1/6895* | (2018.01) | |
| *A01H 5/10* | (2018.01) | |
| *A01H 1/04* | (2006.01) | |

(52) U.S. Cl.
CPC .......... *C12N 15/8282* (2013.01); *A01H 1/04* (2013.01); *A01H 5/10* (2013.01); *C07K 14/415* (2013.01); *C12Q 1/6895* (2013.01); *C12Q 2600/13* (2013.01); *C12Q 2600/158* (2013.01)

(58) Field of Classification Search
None
See application file for complete search history.

(56) References Cited

U.S. PATENT DOCUMENTS

| | | |
|---|---|---|
| 5,491,288 A | 2/1996 | Chaubet et al. |
| 5,510,471 A | 4/1996 | Lebrun et al. |
| 5,633,448 A | 5/1997 | Lebrun et al. |
| 5,644,066 A | 7/1997 | Sakai et al. |
| 5,689,041 A | 11/1997 | Mariani et al. |
| 5,789,566 A | 8/1998 | Bonhomme et al. |
| 5,792,929 A | 8/1998 | Mariani et al. |
| 5,792,930 A | 8/1998 | Chaubet et al. |
| 5,866,782 A | 2/1999 | Iwabuchi et al. |
| 6,229,072 B1 | 5/2001 | Burns et al. |
| 6,365,798 B1 | 4/2002 | Brown |
| 6,509,516 B1 | 1/2003 | Weston et al. |
| 8,153,865 B2 * | 4/2012 | Wu .......................... A23L 25/30 800/306 |
| 2002/0032916 A1 | 3/2002 | Charne et al. |
| 2005/0142122 A1 | 6/2005 | Diederichsen et al. |
| 2013/0254929 A1 | 9/2013 | Matsumoto et al. |

FOREIGN PATENT DOCUMENTS

| | | |
|---|---|---|
| EP | 0242236 A1 | 10/1987 |
| EP | 0242246 A1 | 10/1987 |
| EP | 0344029 A1 | 11/1989 |
| EP | 0507698 A1 | 10/1992 |
| EP | 0508909 A1 | 10/1992 |
| EP | 1547462 A1 | 6/2005 |
| EP | 2745679 A1 | 6/2014 |
| WO | WO 89/10396 A1 | 11/1989 |
| WO | WO 92/13956 A1 | 8/1992 |
| WO | WO 95/09910 A1 | 4/1995 |
| WO | WO 96/06932 A1 | 3/1996 |
| WO | WO 96/26283 A1 | 8/1996 |
| WO | WO 97/02737 A1 | 1/1997 |
| WO | WO 97/13865 A1 | 4/1997 |
| WO | WO 98/10081 A2 | 3/1998 |
| WO | WO 98/54340 A1 | 12/1998 |
| WO | WO 2005/049842 A2 | 6/2005 |
| WO | WO 2005/083096 A1 | 9/2005 |
| WO | WO 2005/090578 A1 | 9/2005 |
| WO | WO 2007/030510 A2 | 3/2007 |
| WO | WO 2008/101343 A1 | 8/2008 |
| WO | WO 2008/148559 A1 | 12/2008 |
| WO | WO 2011/044694 A1 | 4/2011 |
| WO | WO 2011/154158 A1 | 12/2011 |
| WO | WO 2011/154159 A1 | 12/2011 |
| WO | WO 2012/039445 A1 | 3/2012 |

OTHER PUBLICATIONS

Rahman et al. Can. J. Plant. Sci. (2011) 91:447-458.*

(Continued)

*Primary Examiner* — Medina A Ibrahim
(74) *Attorney, Agent, or Firm* — Arent Fox LLP

(57) ABSTRACT

The present invention relates to the identification of clubroot resistance genes from *Brassica*. Clubroot resistant Brassicaceae plants are provided, as well as clubroot resistance genes and methods and means to increase clubroot resistance in Brassicaceae.

18 Claims, 7 Drawing Sheets
Specification includes a Sequence Listing.

(56) References Cited

OTHER PUBLICATIONS

Cho et al. The Plant Journal (2010), vol. 61, pp. 591-599.*
UniProt Accession No. A0A078GQZ4, retrieved from http://www.uniprot.org/uniprot/A0A078GQZ4.fasta on Jun. 5, 2018 (1 page).
UniProt Accession No. UPI0004EE8C51, retrieved from http://www.uniprot.org/uniparc/UPI0004EE8C51.fasta on Jun. 5, 2018 (1 page).
Allen et al., Transcript-specific, single-nucleotide polymorphism discovery and linkage analysis in hexaploid bread wheal (*Triticum aestivum* L.), Plant Biotechnology Journal, 2011, vol. 9, pp. 1086-1099.
An el al., "Conserved Expression of the *Arabidopsis* ACT1 and ACT3 Actin Subclass in Organ Primordia and Mature Pollen," Plant Cell, Jan. 1996, vol. 8(1), pp. 15-30.
Barret et al., "Development of a SCAR (sequence characterised amplified region) marker for molecular tagging of the dwarf BREIZH (Bzh) gene in *Brassica napus* L.," 1998, Theor. Appl. Genet, vol. 97, pp. 828-833.
Botstein et al., "Construction of a Genetic Linkage Map in Man Using Restriction Fragment Length Polymorphisms," Am. J. Hum. Genet, 1980, vol. 32, pp. 314-331.
Bouktila et al., "Large-scale analysis of NBS domain-encoding resistance gene analogs in Triticeae," Genetics and Molecular Biology, 2014, vol. 37, pp. 598-610.
Chaubet et al., "Nucleotide sequences of two corn histone H3 genes. Genomic organization of the corn histone H3 and H4 genes," Plant Molecular Biology, 1986, vol. 6, pp. 253-263.
Christensen et al., "Maize polyubiquitin genes: structure: thermal perturbation of expression and transcript splicing, and promoter activity following transfer to protoplasts by electroporation," Plant Molecular Biology, 1992, vol. 18, pp. 675-689.
De Block et al., "Engineered fertility control in transgenic *Brassica napus* L.: Histochemical analysis of another development," Planta, 1993, vol. 189, pp. 218-225.
De Block et al., "Transformation of *Brassica napus* and *Brassica oleracea* Using Agrobacterium tumefaciens and the Expression of the bar neo Genes in the Transgenic Plants," Plant Physiol., 1989, vol. 91, pp. 694-701.
De Pater et al., "The promoter of the rice gene GOS2 is active in various different monocot tissues and binds rice nuclear factor ASF-1," The Plant Journal, 1992, vol. 2(6), pp. 837-844.
Depicker et al., "Nopaline Synthase: Transcript Mapping and DNA Sequence," Journal of Molecular and Applied Genetics, 1982, pp. 561-573.
Diederichsen et al., "Status and Perspectives of Clubroot Resistance Breeding in Crucifer Crops," J. Plant Growth Regul, 2009, vol. 28, pp. 265-281.
Dieffenbach and Dveksler, PCR Primer: A Laboratory Manual, Cold Spring Harbor Laboratory Press, 1995, 2 pages.
Dixon, "Plasmodiophora brassicae in its Environment," J. Plant Growth Regul, 2009, vol. 28, pp. 212-228.
Dussle et al., "Conversion of AFLP fragments tightly linked to SCMV resistance genes Scmv1 and Scmv2 into simple PCR-based markers," Theor. Appl. Genet, 2002, vol. 105, pp. 1190-1195.
GenBank Accession No. XP_013696562.1, "uncharacterized protein LOC106400730 isoform X3 [*Brassica napus*]," https://www.ncbi.nlm.nih.gov/protein/XP_013696562, last updated date Oct. 4, 2017 (2 pages).
GenBank Accession No. XP_013696569.1, "PREDICTED: uncharacterized protein LOC106400730 isoform X2 [*Brassica napus*]," https://www.ncbi.nlm.nih.gov/protein/XP_013696569.1?report=genpept, last updated date Aug. 31, 2015 (2 pages).
GenBank Accession No. XP_013696576.1, "PREDICTED: uncharacterized protein LOC 106400730 isoform X3 [*Brassica napus*]," https://www.ncbi.nih.gov/protein/XP_013696576.1?report=genpept, last updated date Aug. 31, 2015 (2 pages).
GenBank Accession No. XP_013696585.1, "PREDICTED: probable disease resistance protein At1g58390 isoform X4 [*Brassica napus*]," last updated date Aug. 31, 2015 (2 page).
Guo et al., "AFLP and STS tagging of a major QTL for Fusarium head blight resistance in wheat," Theor. Appl. Genet, 2003, vol. 106, pp. 1011-1017.
Harpster et al., "Relative strengths of the 35S cauliflower mosaic virus. 1', 2', and nopaline synthase promoters in transformed tobacco sugarbeet and oilseed rape callus tissue," Mol. Gen Genet, 1988, vol. 212, pp. 182-190.
Hatakeyama et al., "Identification and Characterization of Crr1a, a Gene for Resistance to Clubroot Disease (Plasmodiophora brassicae Woronin) in *Brassica rapa* L," PLOS ONE, Jan. 2013, vol. 8(1), pp. 1-10.
Hirani et al., "Understanding the Genetics of Clubroot Resistance for Effectively Controlling this Disease in *Brassica* Species," Plants for the Future, 2015, pp. 1-22.
Hu et al., "Genetic diversity of 38 spinach (*Spinacia oleracea* L.) germplasm accessions and 10 commercial hybrids assessed by TRAP markers," Genet Resour Crop Evol., 2007, vol. 54, pp. 1667-1674.
Hudspeth et al., "Structure and expression of the maize gene encoding the phosphoenolpyruvate carboxylase isozyme involved in C4 photosynthesis," Plant Molecular Biology, vol. 12, 1989, pp. 579-589.
Humpherson-Jones, "Effect of surfactants and fungicides on clubroot (Plasmodiophora brassicae) of *Brassicas*," Ann. Appl. Biol., 1993, vol. 122, pp. 457-465.
Hwang et al., "Plasmodiophora brassicae: a review of an emerging pathogen of the Canadian canola (*Brassica napus*) crop," Molecular Plant Pathology, 2012; vol. 13(2), pp. 105-113.
Hyten et al., "High-throughput genotyping with the Golden Gate assay in the complex genome of soybean," Theor. Appl. Genet, 2008, vol. 116, pp. 945-952.
Kato et al., "Fine mapping of the clubroot resistance gene CRb and development of a useful selectable marker in *Brassica rapa*," Breeding Science, 2013, vol. 63, pp. 116-124.
Keil et al., "Both wound-inducible and tuber-specific expression of mediated by the promoter of a single member of the potato proteinase inhibitor II gene family," the EMBO Journal, vol. 8(5), 1989, pp. 1323-1330.
Keller et al., "Glycine-rich cell wall proteins in bean: gene structure and association of the protein with the vascular system," the EMBO Journal, 1988, vol. 7(12), pp. 3625-3633.
Keller et al., "Specific expression of a novel cell wall hydroxyproline-rich glycoprotein gene in lateral root initiation," Genes & Development, vol. 3, 1989, pp. 1639-1646.
Mariani et al., "Induction of male sterility in plants by a chimaeric ribonuclease gene," Nature, vol. 347, Oct. 1990, pp. 737-741.
McElroy et al., "Isolation of an Efficient Actin Promoter for Use in Rice Transformation," The Plant Cell, vol. 2, Feb. 1990, pp. 163-171.
McHale et al., "Plant NBS-LRR proteins: adaptable guards," Genome Biology, 2006, vol. 7(4), Article 212, pp. 1-11.
McPherson et al., PCR—Basics: From Background to Bench, First Edition, Springer Verlag, Germany, 2000 (6 pages total).
Meksem et al., "Conversion of AFLP bands into high-throughput DNA markers," Mol. Genet Genomics, 2011, vol. 265, pp. 207-214.
Meyers et al., "Genome-Wide Analysis of NBS-LRR-Encoding Genes in *Arabidopsis*," The Plant Cell, vol. 15, Apr. 2003, pp. 809-834.
Needleman et al., "A General Method Applicable to the Search for Similarities in the Amino Acid Sequence of Two Proteins," J. Mol. Biol., 1970, vol. 48, pp. 443-453.
Negi et al., "Identification of AFLP fragments linked to seed coat colour in *Brassica juncea* and conversion to the SCAR marker for rapid selection," Theor. Appl. Genet, 2000, vol. 101, pp. 146-152.
Peleman et al., "Structure and expression analyses of the S-adenosylmethionine synthetase gene family in *Arabidopsis thaliana*," Gene, vol. 84, 1989, pp. 359-369.
Piao et al., "Genetics of Clubroot Resistance in *Brassica* Species," J. Plant Growth Regul, 2009, vol. 28, pp. 252-264.
Rice et al., "EMBOSS: The European Molecular Biology Open Software Suite," Trends in Genetics, 2000, vol. 16(6), pp. 276-277.

(56) References Cited

OTHER PUBLICATIONS

Sakamoto et al., "Mapping of isolate-specific QTLs for clubroot resistance in Chinese cabbage (*Brassica rapa* L. ssp. *pekinensis*)," Theor Appl Genet, 2008, vol. 117, pp. 759-767.
Sambrook et al., Molecular Cloning, a Laboratory Manual, vol. 1, Third Edition, 2001, 9 pages total.
Sambrook, Molecular Cloning, a Laboratory Manual, Second Edition, 1989, 31 pages total.
Strelkov et al., "Characterization of Plasmodiophora brassicae populations from Alberta, Canada," J. Plant Pathol., 2006, vol. 28, pp. 467-474.
Tanksley et al., "RFLP Mapping in Plant Breeding: New Tools for an Old Science," Bio/Technology, Mar. 1989, vol. 7, pp. 257-263.
Tautz, "Hypervariability of simple sequences as a general source of polymorphic DNA markers," NucleicAcid Research, 1989, vol. 17(6), pp. 6463-6471.
Ueno et al., "Molecular characterization of the CRa gene conferring clubroot resistance in *Brassica rapa*," Plant Mol Biol, 2012, vol. 80, pp. 621-629.
UniProt Accession No. UPI0006AA7366, retrieved from http://www.uniprot.org/uniparc/UPI0006AA7366.fasta on Jun. 5, 2018 (1 page).
UniProt Accession No. UPI0006AA8AFA, retrieved from http://www.uniprot.org/uniparc/UPI0006AA8AFA.fasta on Jun. 5, 2018 (1 page).
UniProt Accession No. UPI0006AB5B72, retrieved from http://www.uniprot.org/uniparc/UPI0006AB5B72.fasta on Jun. 5, 2018 (1 page).
UniProt Accession No. UPI0006AB5F4F, retrieved from http://www.uniprot.org/uniparc/UPI0006AB5F4F.fasta on Jun. 5, 2018 (1 page).
Van Ooijen et al., "Structure-function analysis of the NB-ARC domain of plant disease resistance proteins," Journal of Experimental Botany, 2008, vol. 59(6), pp. 1383-1397.
Verdaguer et al., "Isolation and expression in transgenic tobacco and rice plants, of the cassava vein mosaic virus (CVMV) promoter," Plant Molecular Biology, 1996, vol. 31, pp. 1129-1139.
Vos et al., "AFLP: a new technique for DNA fingerprinting," Nucleic Acids Research, 1995, vol. 23(21), pp. 4407-4414.
Werner et al., "Genetic mapping of clubroot resistance genes in oilseed rape," Theor Appl Genet, 2008, vol. 116, pp. 363-372.
Williams et al., "DNA polymorphisms amplified by arbitrary primers are useful as genetic markers," Nucleic Acids Research, 1990, Nucleic Acids Research, vol. 18(22), pp. 6531-6535.
Xu et al., "Development of sequence-characterized amplified regions (SCARs) from amplified fragment length polymorphism (AFLP) markers tightly linked to the Vf gene in apple," Genome, 2001, vol. 44, pp. 63-70.
Xue et al., "Isolation and Variation in Virulence of Single-Spore Isolates of Plasmodiophora brassicae from Canada," Plant Disease, 2008, vol. 92(3), pp. 456-462.

* cited by examiner

```
SEQ ID NO: 3     1  MGTLNAMIYE LLKRVSKEKD RGIETLAEVE EWISMAEETE SKASSLLDES
SEQ ID NO: 5     1  MGTLNAMIYE LLKRVSKEKD RGIETLAEVE EWISMAEETE SKASSLLDES
SEQ ID NO: 7     1  MGTLNAMIYE LLKRVSKEKD RGIETLAEVE EWISMAEETE SKASSLLDES
SEQ ID NO: 11    1  .......... .......... .......... ....MAEETE SKASSLLDES
                                                                   EDVID
                 >>..............CC-domain1...............>>

SEQ ID NO: 3    51  ISGCHDLSMY DDISKISQST LHYSETVCTT LKEVKALRSK GVFKVIVERA
SEQ ID NO: 5    51  ISGCHDLSMY DDISKISQST LHYSETVCTT LKEVKALRSK GVFKVIVERA
SEQ ID NO: 7    51  ISGCHDLSMY DDISKISQST LHYSETVCTT LKEVKALRSK GVFKVIVERA
SEQ ID NO: 11   17  ISGCHDLSMY DDISKISQST LHYSETVCTT LKEVKALRSK GVFKVIVERA

SEQ ID NO: 3   101  PLSYVKKMLP LHPIDSGEML AEEAWDFFQE IIGETTLKSH PDIPQLARIV
SEQ ID NO: 5   101  PLSYVKKMLP LHPIDSGEML AEEAWDFFQE IIGETTLKSH PDIPQLARIV
SEQ ID NO: 7   101  PLSYVKKMLP LHPIDSGEML AEEAWDFFQE IIGETTLKSH PDIPQLARIV
SEQ ID NO: 11   67  PLSYVKKMLP LHPIDSGEML AEEAWDFFQE IIGETTLKSH PDIPQLARIV
                                RNBS-C_NBS
                              >>...........NBS-truncated.............>
                              >>..............ARC1...............>

SEQ ID NO: 3   151  CRKCRGLPIA LSLIGETMSR KRTVQEWHQA ISVLVSSTPE VSGTEDELLY
SEQ ID NO: 5   151  CRKCRGLPIA LSLIGETMSR KRTVQEWHQA ISVLVSSTPE VSGTEDELLY
SEQ ID NO: 7   151  CRKCRGLPIA LSLIGETMSR KRTVQEWHQA ISVLVSSTPE VSGTEDELLY
SEQ ID NO: 11  117  CRKCRGLPIA LSLIGETMSR KRTVQEWHQA ISVLVSSTPE VSGTEDELLY
                       GLPLA_NBS
                    >............>> NBS-truncated
                    >......................ARC1.....................>>
                                                                ARC2 >>

SEQ ID NO: 3   201  ILKFAYDNLP GENIKSCFLY CALFPKSCDI NKQDLVDCWI AEGVIEDEDR
SEQ ID NO: 5   201  ILKFAYDNLP GENIKSCFLY CALFPKSCDI NKQDLVDCWI AEGVIEDEDR
SEQ ID NO: 7   201  ILKFAYDNLP GENIKSCFLY CALFPKSCDI NKQDLVDCWI AEGVIEDEDR
SEQ ID NO: 11  167  ILKFAYDNLP GENIKSCFLY CALFPKSCDI NKQDLVDCWI AEGVIEDEDR
                    >......................ARC2.......................>

SEQ ID NO: 3   251  EIAEIQGYEM MADLVMMRLL IDDESEHEVK MHDMVRGMAL WIATDCGRQK
SEQ ID NO: 5   251  EIAEIQGYEM MADLVMMRLL IDDESEHEVK MHDMVRGMAL WIATDCGRQK
SEQ ID NO: 7   251  EIAEIQGYEM MADLVMMRLL IDDESEHEVK MHDMVRGMAL WIATDCGRQK
SEQ ID NO: 11  217  EIAEIQGYEM MADLVMMRLL IDDESEHEVK MHDMVRGMAL WIATDCGRQK
                    >....................ARC2.....................>>

SEQ ID NO: 3   301  ENFVVVSGED RHQMPEVNDW SNVRRMSVTS TQVDKISDSH DCPKLTTLFL
SEQ ID NO: 5   301  ENFVVVSGED RHQMPEVNDW SNVRRMSVTS TQVDKISDSH DCPKLTTLFL
SEQ ID NO: 7   301  ENFVVVSGED RHQMPEVNDW SNVRRMSVTS TQVDKISDSH DCPKLTTLFL
SEQ ID NO: 11  267  ENFVVVSGED RHQMPEVNDW SNVRRMSVTS TQVDKISDSH DCPKLTTLFL
                                                                 LRR-motif
                                                        LRR-domain1 >>..>

Figure 1
```

```
SEQ ID NO: 3    351  QENNLKWVSG DFFRWMTSLV VLNLSRNLEL SELPEEVSSL VSLRLLNLSW
SEQ ID NO: 5    351  QENNLKWVSG DFFRWMTSLV VLNLSRNLEL SELPEEVSSL VSLRLLNLSW
SEQ ID NO: 7    351  QENNLKWVSG DFFRWMTSLV VLNLSRNLEL SELPEEVSSL VSLRLLNLSW
SEQ ID NO: 11   317  QENNLKWVSG DFFRWMTSLV VLNLSRNLEL SELPEEVSSL VSLRLLNLSW
                                     LRR-motif             LRR-motifLRR-motif
                     >...................LRR-domain1.....................>

SEQ ID NO: 3    401  TWIKRLPLGL TELKRLMHLD LDDTPRLLEV DVIGYLLNLQ VLRLFRSVPM
SEQ ID NO: 5    401  TWIKRLPLGL TELKRLMHLD LDDTPRLLEV DVIGYLLNLQ VLRLFRSVPM
SEQ ID NO: 7    401  TWIKRLPLGL TELKRLMHLD LDDTPRLLEV DVIGYLLNLQ VLRLFRSVPM
SEQ ID NO: 11   367  TWIKRLPLGL TELKRLMHLD LDDTPRLLEV DVIGYLLNLQ VLRLFRSVPM
                       LRR-motif      LRR-motif           LRR-motifLRR-motif
                     >...................LRR-domain1.....................>

SEQ ID NO: 3    451  DRSLLENIQL LENLKELNLT VREVDVLERL QSIHKLASCI RHLHLKGITI
SEQ ID NO: 5    451  DRSLLENIQL LENLKELNLT VREVDVLERL QSIHKLASCI RHLHLKGITI
SEQ ID NO: 7    451  DRSLLENIQL LENLKELNLT VREVDVLERL QSIHKLASCI RHLHLKGITI
SEQ ID NO: 11   417  DRSLLENIQL LENLKELNLT VREVDVLERL QSIHKLASCI RHLHLKGITI
                                  LRR-motif                          LRR-motif
                     >...................LRR-domain1.....................>

SEQ ID NO: 3    501  KDGGTLLLNS MLSLRELNIG MCDIPEITVD WRSTIQRETI HFGNIQKIPY
SEQ ID NO: 5    501  KDGGTLLLNS MLSLRELNIG MCDIPEITVD WRSTIQRETI HFGNIQKIPY
SEQ ID NO: 7    501  KDGGTLLLNS MLSLRELNIG MCDIPEITVD WRSTIQRETI HFGNIQKIPY
SEQ ID NO: 11   467  KDGGTLLLNS MLSLRELNIG MCDIPEITVD WRSTIQRETI HFGNIQKIPY
                     LRR-motif  LRR-motif
                     >...................LRR-domain1.....................>

SEQ ID NO: 3    551  LQNIRTVALS WCKGLKDLTW LLLAPNLGDL RLLECQQIEH IINKEKPTGD
SEQ ID NO: 5    551  LQNIRTVALS WCKGLKDLTW LLLAPNLGDL RLLECQQIEH IINKEKPTGD
SEQ ID NO: 7    551  LQNIRTVALS WCKGLKDLTW LLLAPNLGDL RLLECQQIEH IINKEKPTGD
SEQ ID NO: 11   517  LQNIRTVALS WCKGLKDLTW LLLAPNLGDL RLLECQQIEH IINKEKPTGD
                                        LRR-motif  LRR-motif
                     >...................LRR-domain1.....................>

SEQ ID NO: 3    601  MSEEPFQNLT RLSLESLPQL ESIYWTPLPF PVLKDLCIRG CPKLRRRPFS
SEQ ID NO: 5    601  MSEEPFQNLT RLSLESLPQL ESIYWTPLPF PVLKDLCIRG CPKLRRRPFS
SEQ ID NO: 7    601  MSEEPFQNLT RLSLESLPQL ESIYWTPLPF PVLKDLCIRG CPKLRRRPFS
SEQ ID NO: 11   567  MSEEPFQNLT RLSLESLPQL ESIYWTPLPF PVLKDLCIRG CPKLRRRPFS
                             LRR-motif
                     >..LRR-domain1.>>

SEQ ID NO: 3    651  NKGNQVRSDV GQKGVEREDE AMKQHLSNFD DRDFLKMDED QNMEGLASES
SEQ ID NO: 5    651  NKGNQVRSDV GQKGVEREDE AMKQHLSNFD DRDFLKMDED QNMEGLASES
SEQ ID NO: 7    651  NKGNQVRSDV GQKGVEREDE AMKQHLSNFD DRDFLKMDED QNMEGLASES
SEQ ID NO: 11   617  NKGNQVRSDV GQKGVEREDE AMKQHLSNFD DRDFLKMDED QNMEGLASES

SEQ ID NO: 3    701  HPNKNIALVD TSERGKFSTN ANSMTDFDD. ......RSGY VEAETYASAE
SEQ ID NO: 5    701  HPNKNIALVD TSERGKFSTN ANSMTDFDD. ......RSGY VEAETYASAE
SEQ ID NO: 7    701  HPNKNIALVD TSERGKFSTN ANSMTDFDDS PMLHGNRSGY VEAETYASAE
SEQ ID NO: 11   667  HPNKNIALVD TSERGKFSTN ANSMTDFDD. ......RSGY VEAETYASAE

Figure 1, continued
```

```
SEQ ID NO: 3    744   ARLLRKLGSG DIPTVAEDQK MGGLVSELHP NENVALVETS ERGKSTIANS
SEQ ID NO: 5    744   ARLLRKLGSG DIPTVAEDQK MGGLVSELHP NENVALVETS ERGKSTIANS
SEQ ID NO: 7    751   ARLLRKLGSG DIPTVAEDQK MGGLVSELHP NENVALVETS ERGKSTIANS
SEQ ID NO: 11   710   ARLLRKLGSG DIPTVAEDQK MGGLVSELHP NENVALVETS ERGKSTIANS

SEQ ID NO: 3    794   ITNFDDRDFP TLAEDQKMDG LASESHPVED IVLVETLESE KGTIPNSITE
SEQ ID NO: 5    794   ITNFDDRDFP TLAEDQKMDG LASESHPVED IVLVETLESE KGTIPNSITE
SEQ ID NO: 7    801   ITNFDDRDFP TLAEDQKMDG LASESHPVED IVLVETLESE KGTIPNSITE
SEQ ID NO: 11   760   ITNFDDRDFP TLAEDQKMDG LASESHPVED IVLVETLESE KGTIPNSITE

SEQ ID NO: 3    844   ENVFQSGKHA TLEHTQSYPV LAPDGMIHNM TDTPAGGTIM AGELVSFGIQ
SEQ ID NO: 5    844   ENVFQSGKHA TLEHTQSYPV LAPDGMIHNM TDTP.GGTIM AGELVSFGIQ
SEQ ID NO: 7    851   ENVFQSGKHA TLEHTQSYPV LAPDGMIHNM TDTP.GGTIM AGELVSFGIQ
SEQ ID NO: 11   810   ENVFQSGKHA TLEHTQSYPV LAPDGMIHNM TDTP.GGTIM AGELVSFGIQ

SEQ ID NO: 3    894   KLWELLRQES ERFQGASDEI DMVKSDLLYL RGFLADANAK KHTREVKSCI
SEQ ID NO: 5    893   KLWELLRQES ERFQGASDEI DMVKSDLLYL RGFLADANAK KHTREVKSCI
SEQ ID NO: 7    900   KLWELLRQES ERFQGASDEI DMVKSDLLYL RGFLADANAK KHTREVKSCI
SEQ ID NO: 11   859   KLWELLRQES ERFQGASDEI DMVK...... .....NANAK KHTREVKSCI
                      >>.................CC-domain2..................>

SEQ ID NO: 3    944   EEIKEIFFDA EDIIETYLLE ENPPKTGVFK RLFRGRAGRK FALDMNSLSK
SEQ ID NO: 5    943   EEIKEIFFDA EDIIETYLLE ENPPKTGVFK RLFRGRAGRK FALDMNSLSK
SEQ ID NO: 7    950   EEIKEIFFDA EDIIETYLLE ENPPKTGVFK RLFRGRAGRK FALDMNSLSK
SEQ ID NO: 11   898   EEIKEIFFDA EDIIETYLLE ENPPKTGVFK RLFRGRAGRK FALDMNSLSK
                                 EDVID-motif
                      >...>> CC-domain2

SEQ ID NO: 3    994   RISKIISVMQ AFGVHQVITE GKDSQPLLQR QKRMRQKFAG EYKPNFVGLE
SEQ ID NO: 5    993   RISKIISVMQ AFGVHQVITE GKDSQPLLQR QKRMRQKFAG EYKPNFVGLE
SEQ ID NO: 7    1000  RISKIISVMQ AFGVHQVITE GKDSQPLLQR QKRMRQKFAG EYKPNFVGLE
SEQ ID NO: 11   948   RISKIISVMQ AFGVHQVITE GKDSQPLLQR QKRMRQKFAG EYKPNFVGLE

SEQ ID NO: 3    1044  ENVEKLVSLL VEEDNIQVVS ITGMGGLGKT TLARQTFNHD MVKHKFDRFA
SEQ ID NO: 5    1043  ENVEKLVSLL VEEDNIQVVS ITGMGGLGKT TLARQTFNHD MVKHKFDRFA
SEQ ID NO: 7    1050  ENVEKLVSLL VEEDNIQVVS ITGMGGLGKT TLARQTFNHD MVKHKFDRFA
SEQ ID NO: 11   998   ENVEKLVSLL VEEDNIQVVS ITGMGGLGKT TLARQTFNHD MVKHKFDRFA
                                        P-loop kinase1 NBS2
                                        >>..........NBS-domain2............>

SEQ ID NO: 3    1094  WVGISQACNR KIVWQMILRS LLAKKDEDSI LHMTESELQE QIFLLLEASK
SEQ ID NO: 5    1093  WVGISQACNR KIVWQMILRS LLAKKDEDSI LHMTESELQE QIFLLLEASK
SEQ ID NO: 7    1100  WVGISQACNR KIVWQMILRS LLAKKDEDSI LHMTESELQE QIFLLLEASK
SEQ ID NO: 11   1048  WVGISQACNR KIVWQMILRS LLAKKDEDSI LHMTESELQE QIFLLLEASK
                          RNBS-A NBS2
                      >....................NBS-domain2.....................>

SEQ ID NO: 3    1144  SLIVIDDIWK EEDWKRISQI LPNTKGWKVL LTSRNENVAG DTRHINFNLE
SEQ ID NO: 5    1143  SLIVIDDIWK EEDWKRISQI LPNTKGWKVL LTSRNENVAG DTRHINFNLE
SEQ ID NO: 7    1150  SLIVIDDIWK EEDWKRISQI LPNTKGWKVL LTSRNENVAG DTRHINFNLE
SEQ ID NO: 11   1098  SLIVIDDIWK EEDWKRISQI LPNTKGWKVL LTSRNENVAG DTRHINFNLE
                      Kinase-2 NBS2                  RNBS-B NBS2
                      >....................NBS-domain2.....................>
```

Figure 1, continued

```
SEQ ID NO: 3   1194   LLTTDDSWTL LQTIAFPRKD AFGEAYEEME KMGKHMIKYC GGLPLAVRIL
SEQ ID NO: 5   1193   LLTTDDSWTL LQTIAFPRKD AFGEAYEEME KMGKHMIKYC GGLPLAVRIL
SEQ ID NO: 7   1200   LLTTDDSWTL LQTIAFPRKD AFGEAYEEME KMGKHMIKYC GGLPLAVRIL
SEQ ID NO: 11  1148   LLTTDDSWTL LQTIAFPRKD AFGEAYEEME KMGKHMIKYC GGLPLAVRIL
                        RNBS-C_NBS2                                 GLPLA_NBS2
                      >....................NBS-domain2....................>>
                         >>...................ARC1-domain.....................>

SEQ ID NO: 3   1244   GGLLAKKYKL HEWEMICENV ERHLMGRTDF NDDNNILRFH VMSLSFEELS
SEQ ID NO: 5   1243   GGLLAKKYKL HEWEMICENV ERHLMGRTDF NDDNNILRFH VMSLSFEELS
SEQ ID NO: 7   1250   GGLLAKKYKL HEWEMICENV ERHLMGRTDF NDDNNILRFH VMSLSFEELS
SEQ ID NO: 11  1198   GGLLAKKYKL HEWEMICENV ERHLMGRTDF NDDNNILRFH VMSLSFEELS
                      >............ARC1-domain...........>>
                                                 >>...ARC2-domain...>

SEQ ID NO: 3   1294   SYLKQCFLYL AIFPEDHRIS VGKLSYYWAA EGFTGTYYDE ETIRDVGDSY
SEQ ID NO: 5   1293   SYLKQCFLYL AIFPEDHRIS VGKLSYYWAA EGFTGTYYDE ETIRDVGDSY
SEQ ID NO: 7   1300   SYLKQCFLYL AIFPEDHRIS VGKLSYYWAA EGFTGTYYDE ETIRDVGDSY
SEQ ID NO: 11  1248   SYLKQCFLYL AIFPEDHRIS VGKLSYYWAA EGFTGTYYDE ETIRDVGDSY
                              RNBS-D
                      >....................ARC2-domain.....................>

SEQ ID NO: 3   1344   IEELARRNMV TFERDSTGLR FETCSMHDIM REMCLTKAKE ENFLQTDVTR
SEQ ID NO: 5   1343   IEELARRNMV TFERDSTGLR FETCSMHDIM REMCLTKAKE ENFLQTDVTR
SEQ ID NO: 7   1350   IEELARRNMV TFERDSTGLR FETCSMHDIM REMCLTKAKE ENFLQTDVTR
SEQ ID NO: 11  1298   IEELARRNMV TFERDSTGLR FETCSMHDIM REMCLTKAKE ENFLQTDVTR
                                                                     LRRNT
                      >...............ARC2-domain...............>>

SEQ ID NO: 3   1394   RFVCQNTTTL DVERDINNPK LRSLLVILNS EGDFCRLSGL RFTRLQLLRV
SEQ ID NO: 5   1393   RFVCQNTTTL DVERDINNPK LRSLLVILNS EGDFCRLSGL RFTRLQLLRV
SEQ ID NO: 7   1400   RFVCQNTTTL DVERDINNPK LRSLLVILNS EGDFCRLSGL RFTRLQLLRV
SEQ ID NO: 11  1348   RFVCQNTTTL DVERDINNPK LRSLLVILNS EGDFCRLSGL RFTRLQLLRV
                          LRR-motif           LRR-motif           LRR-motif
                          >>................LRR-domain2...................>

SEQ ID NO: 3   1444   LDLDKAKFEG GKLPSDIGKL IHLRYLSLES AEVSHLPSSL RNLMLLIYLN
SEQ ID NO: 5   1443   LDLDKAKFEG GKLPSDIGKL IHLRYLSLES AEVSHLPSSL RNLMLLIYLN
SEQ ID NO: 7   1450   LDLDKAKFEG GKLPSDIGKL IHLRYLSLES AEVSHLPSSL RNLMLLIYLN
SEQ ID NO: 11  1398   LDLDKAKFEG GKLPSDIGKL IHLRYLSLES AEVSHLPSSL RNLMLLIYLN
                      LRR-motif              LRR-motif            LRR-motif
                      >....................LRR-domain2.....................>

SEQ ID NO: 3   1494   IDVADIDIHV PNVLMEMREL RYLALPKFMH EKTKLELGNL VNLETLENFS
SEQ ID NO: 5   1493   IDVADIDIHV PNVLMEMREL RYLALPKFMH EKTKLELGNL VNLETLENFS
SEQ ID NO: 7   1500   IDVADIDIHV PNVLMEMREL RYLALPKFMH EKTKLELGNL VNLETLENFS
SEQ ID NO: 11  1448   IDVADIDIHV PNVLMEMREL RYLALPKFMH EKTKLELGNL VNLETLENFS
                                             LRR-motif   LRR-motif
                      >....................LRR-domain2.....................>
```

Figure 1, continued

```
SEQ ID NO: 3     1544  TKNSRLEDLR CMIRLRTLSI KVTGETSSET LSLSISGLRH LENLVIHDRL
SEQ ID NO: 5     1543  TKNSRLEDLR CMIRLRTLSI KVTGETSSET LSLSISGLRH LENLVIHDRL
SEQ ID NO: 7     1550  TKNSRLEDLR CMIRLRTLSI KVTGETSSET LSLSISGLRH LENLVIHDRL
SEQ ID NO: 11    1498  TKNSRLEDLR CMIRLRTLSI KVTGETSSET LSLSISGLRH LENLVIHDRL
                                   LRR-motif      LRR-motif      LRR-motif
                       >....................LRR-domain2.....................>

SEQ ID NO: 3     1594  SWIKEGIVLH CDDLIKLELF MYRPVRLEKQ RFPSHITYIS LTECRFEHDP
SEQ ID NO: 5     1593  SWIKEGIVLH CDDLIKLELF MYRPVRLEKQ RFPSHITYIS LTECRFEHDP
SEQ ID NO: 7     1600  SWIKEGIVLH CDDLIKLELF MYRPVRLEKQ RFPSHITYIS LTECRFEHDP
SEQ ID NO: 11    1548  SWIKEGIVLH CDDLIKLELF MYRPVRLEKQ RFPSHITYIS LTECRFEHDP
                                   LRR-motif
                       >....................LRR-domain2.....................>

SEQ ID NO: 3     1644  MPLLETLQHL RKVKLLDRSH CARRMVCSGS GFPQLRELEL VLLEQLEEWI
SEQ ID NO: 5     1643  MPLLETLQHL RKVKLLDRSH CARRMVCSGS GFPQLRELEL VLLEQLEEWI
SEQ ID NO: 7     1650  MPLLETLQHL RKVKLLDRSH CARRMVCSGS GFPQLRELEL VLLEQLEEWI
SEQ ID NO: 11    1598  MPLLETLQHL RKVKLLDRSH CARRMVCSGS GFPQLRELEL VLLEQLEEWI
                                                LRRCT          LRR-motif
                       >....................LRR-domain2.....................>

SEQ ID NO: 3     1694  IEEGSMPLLH SLDITDCNKL KEIPEGLRII PSLKNLTCYS MGKEWEGRLS
SEQ ID NO: 5     1693  IEEGSMPLLH SLDITDCNKL KEIPEGLRII PSLKNLTCYS MGKEWEGRLS
SEQ ID NO: 7     1700  IEEGSMPLLH SLDITDCNKL KEIPEGLRII PSLKNLTCYS MGKEWEGRLS
SEQ ID NO: 11    1648  IEEGSMPLLH SLDITDCNKL KEIPEGLRII PSLKNLTCYS MGKEWEGRLS
                                                LRR-motif
                       >..........LRR-domain2...........>>

SEQ ID NO: 3     1744  EGGEEYYKVQ HIPSVKFYGA .......... .......... ..........
SEQ ID NO: 5     1743  EGGEEYYKVQ HIPSVKFYGA .......... .......... ..........
SEQ ID NO: 7     1750  EGGEEYYKVQ HIPSVKFYGA .......... .......... ..........
SEQ ID NO: 11    1698  EGGEEYYKVQ HIPSVKFYDE SDLKLAVFCW SIMKKNKNFF VVGIKVDFIY

SEQ ID NO: 3           .......... .......... .......... .......... ..........
SEQ ID NO: 5           .......... .......... .......... .......... ..........
SEQ ID NO: 7           .......... .......... .......... .......... ..........
SEQ ID NO: 11    1698  EGGEEYYKVQ HIPSVKFYDE SDLKLAVFCW SIMKKNKNFF VVGIKVDFIY

SEQ ID NO: 3           .....
SEQ ID NO: 5           .....
SEQ ID NO: 7           .....
SEQ ID NO: 11    1748  FCLFD

Figure 1, continued
```

```
SEQ ID NO: 9      1  MAEFVSAICS VVQCLTPCFN SWAAHARYVS KFDGYLNELR NALRDLEAKR
                                                        >>...CC-domain....>

SEQ ID NO: 9     51  NDVKHKVDDE ELTGKVPLDE VKRWLSKFNT IKTETDRLVA DASAEQQRRT
                                                           EDVID-motif
                     >.........CC-domain........>>

SEQ ID NO: 9    101  TSGCCCNNIT STYRCGKKLS KMLREVQQLY SEQFSQGLTR RGTIPVVVEE

SEQ ID NO: 9    151  PVRQTVGLDT KLASTWSLLM DEGTRMLGLY GFGGVGKTTL LTLISNKFVE
                                                       P-loop_kinase-1
                                                        >>......NBS-domain........>

SEQ ID NO: 9    201  VEDKFDVVIW VDVSKDVDIL KIQDDIGKRL GLDDEKWCKE TQRGKSLNIR
                                RNBS-A_NBS
                     >...................NBS-domain...................>

SEQ ID NO: 9    251  RVLKEKKPRF VLLFDGLWKG VSLSAIGIPL RGKEYKIVFT TRQKDVCQKM
                       Kinase-2_NBS_WalkerB                RNBS-B_NBS
                     >...................NBS-domain...................>

SEQ ID NO: 9    301  GGIYRKVECL AEKDALDLLT QISGRDSLTS EMLSLAEKIA KKCYGLPLAL
                          RNBS-C_NBS                              GLAPLA_NBS
                     >...................NBS-domain...................>
                         >>..............ARC1......................>

SEQ ID NO: 9    351  QVIGKCLSSK TTEDEWRGVH EYLVRFPDQL EGMVDMFGVL KLSYDNLEEG
                     >>> NBS-domain
                     >............ARC1..................>>
                                                          >>ARC2........>

SEQ ID NO: 9    401  DAQSCFLYCA LFPMAYSIHQ DELVEYWIGE GIIEVGRRRD RAKNRGAQII
                             RNBS-D
                     >...............ARC2...........................>

SEQ ID NO: 9    451  DTLVRAGLLL KDDESNPKVY MHNIIREMAL WIVSEIKGGQ MYLVETDAGL
                                           LRRNT
                     >..............ARC2..................>>

SEQ ID NO: 9    501  RTLPPNTDWT IVSRMSLMNN DIQDIPDDPE FPDQALLMTL FLQNNKLVEI
                                                                  LRR-motif
                                                                  >>LRR-domain.>

SEQ ID NO: 9    551  GCRFFVVMSA LVVLDLSLNP DITKLPDQIS ELVSLRYLKL FGTRIKFLPE
                                 LRR-motif                         LRR-motif
                     >...................LRR-domain...................>

SEQ ID NO: 9    601  GFSKLLKLIH LDLELTSNLR SIRQISGLLK LQVLRFYGSA AALDGSLLKN
                     LRR-motifLRR-morif             LRR-morif
                     >...................LRR-domain...................>
```

Figure 2

```
SEQ ID NO: 9    651   LERLKSLQFL TITVREVDVL NAFLGSKELP RCTQGLDLGG LEISGVSGKS
                                                          LRR-motif
                      >.....................LRR-domain.....................>

SEQ ID NO: 9    701   FAATFGELVT LSKLRMTDCD IKESDIEWEE NIKVQCSSPV PSNQIIPRTI
                      >.....................LRR-domain.....................>

SEQ ID NO: 9    751   WFKNLSAVVL HSCLGLKDLT WLMYAANLES LEVKTSPKMK EVISQQKAGD
                                 LRR-motif
                      >.....................LRR-domain.....................>

SEQ ID NO: 9    801   LGVEPFQNLQ VLELGFLNEL ESIYWTSLLF PRLQNVTITE CPKLRKLPLN
                                 LRR-motif                              LRR-motif
                      >.....................LRR-domain.....................>

SEQ ID NO: 9    851   STSVERVDAL RIEVDDGWLV GVEWENGAEE RFRLAIHTAS IS
                      > LRR-domain Figure 2, continued
```

BRASSICACEAE PLANTS RESISTANT TO *PLASMODIOPHORA BRASSICAE* (CLUBROOT)

CROSS REFERENCE TO RELATED APPLICATIONS

This application is a 35 U.S.C. 371 National Phase of PCT Application No. PCT/EP2016/081146 filed Dec. 15, 2016, which claims benefit to U.S. Provisional Application No. 62/267,460 filed, Dec. 15, 2015, the disclosure of which is hereby incorporated by reference in its entirety.

FIELD OF THE INVENTION

The invention relates to the field of disease control in Brassicaceae. Provided are methods for the production of clubroot resistant plants through introduction of a clubroot resistance locus in their genome. Also provided are Brassicaceae plants and seeds comprising one or more clubroot resistance loci in their genome. Further provided are detection tools for detecting the presence of one or more resistance alleles in Brassicaceae plants, tissue or seeds, as well as methods for transferring one or more resistance loci to other Brassicaceae plants and methods for combining different resistance loci in hybrid seeds and plants. Methods for enhancing durability of resistance to *Plasmodiophora brassicae* are also provided, as well as uses of the plants and seeds and the processes or kits of the invention.

BACKGROUND OF THE INVENTION

Clubroot is a disease caused by *Plasmodiophora brassicae* which affects the Brassicaceae family of plants, including many important vegetable and broad acre crops. All members of the family Brassicaceae are thought to be potential hosts for *Plasmodiophora brassicae* (Dixon, 2009, J Plant Growth Regul 28: 194). Susceptible cultivated crops include all varieties of *B. oleracea*, the Occidental Cole vegetables (Brussels sprout, cabbages, calabrese/green broccoli, cauliflower, culinary and fodder kale, kohlrabi); *B. rapa* (syn. *B. campestris*) including turnip, turnip rape, sarson, and the enormous range of Oriental variants which provide leaf and root vegetables such as *Brassica rapa* var. *pekinensis* and *B. rapa* var. *chinensis* (Chinese cabbages); *B. napus* including swede (rutabaga), oil seed rape, and fodder rape; and seed, condiment (mustard), and vegetable crops derived from *B. carinata*, *B. nigra*, and *B. juncea*. Related genera such as radish (*Raphanus*), cruciferous weeds, for example, *Sinapis*, and decorative ornamentals including stocks (*Matthiola* spp) and wallflower (*Cheiranthus cheiri*) can be infected. The scientific model plant *Arabidopsis* is also susceptible (Dixon, 2009, supra).

Clubroot disease symptom development is characterized by the formation of club-shaped galls on the roots of affected plants. As a result, the nutrient and water uptake by infected roots is inhibited. Above-ground symptoms include wilting, stunting, yellowing and premature senescence (Hwang et al, 2012, Mol Plant Pathol 13: 105).

Clubroot disease is estimated to be present in approximately 10% of all areas where host plants are cultivated (Diederichsen et al, 2009, J Plant Growth Regul 28: 265). Clubroot has been largely a disease of vegetable crops in the last century. However, in 2003, 12 clubroot-infested commercial fields were found in the central part of the province of Alberta. Thereafter, the number of fields with confirmed clubroot infestations has increased steadily, and, by 2010, more than 560 fields (over 35 000 ha) in Alberta had been identified as being infested with *P. brassicae* (Hwang et al., 2012, supra). Yield losses of 80%-91% were reported in studies with canola grown on clubroot-infested fields in Quebec. Seed quality was also reduced significantly, with declines of 4.7%-6.1% in oil content and 13%-26% in 1000-seed weights (Hwang et al., 2012, supra).

Plant resistance is a powerful tool to combat clubroot disease. Breeding for clubroot resistance focuses today on Chinese cabbage (*B. rapa* spp. *Pekinensis*) in Japan and Korea, oilseed rape in Germany and Sweden, and several *B. oleracea* vegetables. Recently released resistant cultivars belong to three *Brassica* species: *B. napus*, *B. oleracea*, and *B. rapa* (Diederichsen et al., 2009, supra).

Resistant sources of the European fodder turnips (*B. rapa* ssp, *rapifera*) have been identified, which have been used to transfer the clubroot resistance genes to Chinese cabbage. At least three independent dominant genes, which confer differential (race-specific or vertical) resistance to particular pathotypes of *P. brassicae*, appear to be present in turnip genotypes (Piao et al., 2009, J Plant Growth Regul 28: 252). Eight possible clubroot resistance genes present in *B. rapa* have been identified through QTL mapping: CRa from resistant source ECD02, CRb from Gelria R, Crr1, Crr2 and Crr4 from Siloga, Crr3 from Milan White, and CRk and CRc from Debra. Crr1, Crr2, Crr3, Crr4 and CRc are mapped to chromosomes R8, R1, R3, R6 and R2, respectively. CRa, CRb and CRk with Crr3 are mapped on the same linkage group of R3, but they are not located in the same chromosome region, except for CRk and Crr3 (Piao et al., 2009, supra; Sakamoto et al., 2008, Theor Appl Genet 117:759).

In *B. oleracea*, completely resistant accessions have been rarely identified. The inheritance of the clubroot resistance in *B. oleracea* appears polygenic and controlled by many dominant alleles with predominance of additive effects of with incomplete dominance. It has also been suggested that one of the resistances studied is controlled by two complementary genes (Piao et al., 2009, supra). At least 22 QTLs have been found in *B. oleracea*, indicating a complex genetic basis of clubroot resistance in *B. oleracea*. As the different mapping studies used different clubroot resistance sources and different *P. brassicae* isolates, a comparison of these QTLs is not possible (Piao et al., 2009, supra).

Clubroot resistance has also been observed in several *B. napus* cultivars. At least 22 QTLs for clubroot resistance have been identified in *B. napus*. A major gene, Pb-Bn1, has been mapped onto linkage group DY4, and at least two additive QTLs have been identified on chromosomes DY4 and DY15, respectively. In addition, epistatic interactions between nine regions with or without additive effects have been located. A major gene and two recessive genes derived from ECD04 have been identified in double-haploid populations. In resynthesized *B. napus* developed by crossing cv. Böhmerwaldkohl (*B. oleracea*) and ECD-04 (*B. rapa*), nineteen QTLs expressing resistance to seven isolated were detected on eight chromosomes, four of which were closely linked to each other on chromosome N03, and three were linked on chromosome N08. Genes CRk and Crr3 are located in the similar region of PbBn-k-2, PbBn-1-1, and PbBn-01:60-1 on NO3. CRa and CRb are independent from them. PbBn-01.07-2, PbBn-1-2, and PbBn-a-1 are linked to BRMS088 on chromosome N08 in *B. napus*, which is also linked with Crr1 on R8 in *B. rapa*. PbBn-k-1 is located on chromosome N02. The QTLs located on N03 and N19 contribute strong effects and confer broad-spectrum resistance (Piao et al., 2009, supra; and Werner et al., 2008, Theor Appl Genet 116:363).

The CRa gene of *Brassica rapa* has been fine-mapped and a TIR-NBS-LRR gene has been identified as the CRa gene (Ueno et al., 2012, Plant Mol Biol 80: 621). The Crr1 gene has been mapped and isolated from the *B. rapa* European fodder turnip "Siloga". Crr1a also encodes a TIR-NB-LRR disease resistance protein (Hatakeyama et al., 2013, PLOS one 8: e54745 and WO2012/039445).

The CRb gene from *B. rapa* has been fine-mapped to a 140 kb genomic region. In this region, in which fourteen functional proteins were predicted, amongst which a Rho family proteins and two TIR-NBS-LRR proteins, which could be candidate genes for CRb (Kato et al., 2013, Breeding Science 63: 116).

To increase the durability of clubroot-resistant cultivars, the combination of the different clubroot resistance genes into a single line will be an important means for breeding cultivars with resistance to a broader spectrum of physiological races. Therefore, in order to stack genes without linkage drag using marker-assisted selection and transgenic approaches, there remains a need to develop molecular markers linked to the clubroot resistance genes. This invention provides the sequence of a clubroot resistance locus from a resistant *Brassica napus* line, as herein after described in the different embodiments, examples and claims.

SUMMARY OF THE INVENTION

It is one embodiment of the invention to provide a Brassicaceae plant or plant cell comprising a CRL1 and a CRL2 clubroot resistance gene as transgene, wherein said CRL1 clubroot resistance gene comprises a coding sequence having at least 90% sequence identity to nt 52-5343 of SEQ ID NO: 2, nt 52-5340 of SEQ ID NO: 4, nt 52-5361 of SEQ ID NO: 6, or to SEQ ID NO: 10; or encodes a protein having an amino acid sequence having at least 90% sequence identity to SEQ ID NO: 3, SEQ ID NO: 5, SEQ ID NO: 7, or SEQ ID NO: 11; and said CRL2 clubroot resistance gene comprises a coding sequence having at least 90% sequence identity to nt 220-2898 of SEQ ID NO: 8; or encodes a protein having an amino acid sequence having at least 90% sequence identity to SEQ ID NO: 9. In a further embodiment, said CRL1 clubroot resistance gene comprises a sequence having at least 90% sequence identity to nt 32750-51049 of SEQ ID NO: 1. In another embodiment, said Brassicaceae plant or plant cell comprises a transgene comprising a sequence having at least 90% sequence identity to SEQ ID NO: 1.

It is another object of the invention to provide a method for increasing clubroot resistance in a Brassicaceae plant, said method comprising introducing or providing a CRL1 and a CRL2 clubroot resistance gene according to the invention as a transgene, to a Brassicaceae plant cell, to create transgenic cells; and regenerating transgenic plants from said transgenic cells.

In yet another embodiment, a method is provided for increasing clubroot resistance in a Brassicaceae plant, comprising the step of introducing a CRL clubroot resistance locus in said Brassicaceae plant, and selecting said clubroot resistant Brassicaceae plant for the presence of the CRL clubroot resistance locus by analyzing genomic DNA from said plant for the presence of at least one molecular marker, wherein said at least one molecular marker is linked to the CRL clubroot resistance locus, wherein said CRL clubroot resistance locus comprises the CRL1 and CRL2 clubroot resistance genes, wherein said CRL1 clubroot resistance gene comprises a nucleotide sequence having at least 90% sequence identity to nt 32750 to 51049 of SEQ ID NO: 1; having a coding sequence having at least 90% sequence identity to nt 52-5343 of SEQ ID NO: 2, nt 52-5340 of SEQ ID NO: 4, nt 52-5361 of SEQ ID NO: 6, or to SEQ ID NO: 10; or encoding a protein having at least 90% sequence identity to SEQ ID NO: 3, SEQ ID NO: 5, SEQ ID NO: 7, or SEQ ID NO: 11; and wherein said CRL2 clubroot resistance gene comprises a nucleotide sequence having a coding sequence having at least 90% sequence identity to nt 220-2898 of SEQ ID NO: 8; or encoding a protein having at least 90% sequence identity to SEQ ID NO: 9, such as a clubroot resistance locus comprising a sequence having at least 90% sequence identity to SEQ ID NO: 1.

Yet another embodiment provides a method for producing a clubroot resistant Brassicaceae plant comprising the steps of identifying a clubroot resistant Brassicaceae plant comprising a CRL clubroot resistance locus according to the invention by analyzing genomic DNA from said plant for the presence of at least one molecular marker, wherein said at least one molecular marker is linked to said CRL clubroot resistance locus, and generating progeny from said clubroot resistant Brassicaceae plant, wherein said progeny is clubroot resistant and comprises said CRL clubroot resistance locus. In a further embodiment, said CRL clubroot resistance locus comprises a sequence having at least 90% sequence identity to SEQ ID NO: 1.

A further embodiment provides Brassicaceae plants or plant cells obtainable by the methods according to the invention.

In a further embodiment, a clubroot resistant Brassicaceae plant or plant cell according to the invention is provided, comprising the CRL1 and CRL2 clubroot resistance genes according to the invention, and at least one other disease resistance gene, said other disease resistance gene selected from the group consisting of a clubroot resistance gene, a blackleg resistance gene, a Sclerotinia resistance gene, a Verticillium resistance gene, a *Fusarium* resistance gene, an Aster Yellows resistance gene, an Alternaria resistance gene, and a Grey Stem resistance gene. In a further embodiment, said other disease resistance gene is a transgene which is genetically linked with said CRL clubroot resistance genes or said CRL clubroot resistance locus.

In yet another embodiment, the plant according to the invention is selected from the group consisting of *Brassica napus, Brassica juncea, Brassica oleracea, Brassica rapa, Brassica nigra* and *Brassica carinata*. In yet another embodiment, seeds of the plants according to the invention are provided comprising the CRL1 and CRL2 clubroot resistance genes according to the invention.

A further embodiment provides methods to determine the presence or absence of a CRL clubroot resistance locus in a biological sample, comprising providing genomic DNA from said biological sample, and analyzing said DNA for the presence of at least one molecular marker, wherein the at least one molecular marker is linked to said CRL clubroot resistance locus, wherein said CRL clubroot resistance locus comprises the CRL1 and CRL2 clubroot resistance genes, wherein said CRL1 clubroot resistance gene comprises a nucleotide sequence having at least 90% sequence identity to nt 32750-51049 of SEQ ID NO: 1; having a coding sequence having at least 90% sequence identity to nt 52-5343 of SEQ ID NO: 2, nt 52-5340 of SEQ ID NO: 4, nt 52-5361 of SEQ ID NO: 6, or to SEQ ID NO: 10; or encoding a protein having at least 90% sequence identity to SEQ ID NO: 3, SEQ ID NO: 5, SEQ ID NO: 7, or SEQ ID NO: 11; and wherein said CRL2 clubroot resistance gene comprises a nucleotide sequence having a coding sequence having at least 90% sequence identity to nt 220-2898 of SEQ ID NO: 8; or encoding a protein having at least 90% sequence identity to SEQ ID NO: 9. In yet a further embodiment, a kit is provided for the detection of the CRL clubroot resistance locus according to the invention in Brassicaceae DNA samples, wherein said kit comprises at least one primer or probe which specifically recognizes a molecular marker linked to said CRL clubroot resistance locus. Yet another embodiment provides the use of a molecular marker linked to the CRL clubroot resistance locus according to the invention for determining the presence or absence of said CRL clubroot resistance locus in Brassicaceae plants, or the use of the sequence of any one of SEQ ID NOs: 1, 2, 4, 6 and 8 for determining the presence or absence of the CRL clubroot resistance locus according to the invention in Brassicaceae plants.

It is another object of the invention to provide a chimeric gene comprising the following genetic elements: a plant-expressible promoter, a DNA sequence coding for a CRL1 or for a CRL2 protein, and optionally, a transcription termination and polyadenylation region functional in plant cells, wherein said DNA sequence coding for a CRL1 protein comprises a nucleotide sequence having at least 90% sequence identity to nt 52-5343 of SEQ ID NO: 2, nt 52-5340 of SEQ ID NO: 4, nt 52-5361 of SEQ ID NO: 6, or to SEQ ID NO: 10; or encoding a protein having an amino acid sequence having at least 90% sequence identity to ID NO: 3, SEQ ID NO: 5, SEQ ID NO: 7, or SEQ ID NO: 11; and wherein said DNA sequence coding for a of CRL2 protein comprises a nucleotide sequence having at least 90% sequence identity to 220-2898 of SEQ ID NO: 8; or encoding a protein having an amino acid sequence having at least 90% sequence identity to SEQ ID NO: 9.

In another embodiment of the invention, the marker linked to the CRL clubroot resistance locus is located in a marker interval between and including markers mBRS00013411 and mBRS00013511, such as a marker selected from the markers of Table 2.

A further object provides the use of the chimeric gene according to the invention to increase clubroot resistance in Brassicaceae, and the use of the plants or plant cells according to the invention to produce oilseed rape oil or an oilseed rape seed cake, or a seed, or a crop of oilseed rape.

Also provided is a method of producing food, feed, or an industrial product, comprising obtaining the plant according to the invention or a part thereof; and preparing the food, feed or industrial product from the plant or part thereof. In a further object, said food or feed is oil, meal, grain, starch, flour or protein; or said industrial product is biofuel, fiber, industrial chemicals, a pharmaceutical or a nutraceutical.

BRIEF DESCRIPTION OF THE DRAWINGS

FIG. 1: Alignment of proteins encoded by the three different splice variants of CRL1: SEQ ID NO: 3 encoded by the CRL1a splice variant; SEQ ID NO: 5 encoded by the CRL1b splice variant, SEQ ID NO: 7 encoded by the CRL1c splice variant, and SEQ ID NO: 11 encoded by the CRL1d splice variant. The conserved domains are indicated. CC-domain1=first coil-coil domain; EDVID: EDVID motif; NBS-truncated: truncated NBS domain with missing N-terminal part; RNBS-C NBS: RNBS-C region from the NBS domain; ARC1: ARC1 domain; GLPLA NBS: GLPLA or hydrophobic region of the NBS domain; ARC2: ARC2 domain; LRR-domain1: first Leucine Rich Region; LRR motif: Leucine rich repeat motif (xxLxLxx), CC-domain2: Second coil-coil domain; NBS-domain2: second NBS domain; P-loop kinase1 NBS2: P-loop/kinase 1 from the second NBS domain; RNBS-A_NBS2: RNBS-A region from the second NBS domain; Kinase-2_NBS2: Kinase 2 region of the second NBS domain; RNBS-B_NBS2: RNBS-B region from the second NBS domain. Also called Kinase3a or Sensor I; RNBS-C_NBS2: RNBS-C region from the second NBS domain: GLPLA_NBS2: GLPLA or hydrophobic region of the second NBS domain; RNBS-D: RNBS-D region; LRRNT: N-terminal cap—also known as MHD-region; LRR-domain2: second Leucine Rich Region; LRRCT: C-terminal cap.

FIG. 2: CRL2 protein (SEQ ID NO: 9) and conserved domains. CC-domain: Coil-coil domain; P-loop_kinase-1: P-loop/kinase 1 from the NBS domain, also known as Walker A; RNBS-A_NBS: RNBS-A region from the NBS domain; Kinase-2_NBS: Kinase 2 region of the NBS domain; WalkerB: Walker B region; RNBS-B_NBS: RNBS-B region from the NBS domain. Also called Kinase 3a or Sensor I; RNBS-C_NBS: RNBS-C region from the NBS domain; GLAPLA_NBS: GLPLA or hydrophobic region of the NBS domain; RNBS-D: RNBS-D region; LRRNT: N-terminal cap—also known as MHD-region; LRR-domain: Leucine Rich Region; LRR-motif: Leucine rich repeat motif (xxLxLxx).

DETAILED DESCRIPTION

The current invention is based on the identification of a CRL clubroot resistance locus in *Brassica*. Surprisingly, it was found that the CRL clubroot resistance locus as identified contains two CRL clubroot resistance genes.

The invention relates to sequences of the CRL clubroot resistance locus, and sequences encoding a protein conferring resistance to clubroot resistance in Brassicaceae. The protein may comprise the amino acid sequence having at least 80% sequence identity to SEQ ID NO: 3, to SEQ ID NO: 5, to SEQ ID NO: 7, or to SEQ ID NO: 9, or a functional fragment of these amino acid sequences.

It is a first embodiment of the invention to provide a Brassicaceae plant or plant cell comprising a CRL1 and a CRL2 clubroot resistance gene as transgene, wherein said CRL1 clubroot resistance gene comprises a coding sequence having at least 90% sequence identity to nt 52-5343 of SEQ ID NO: 2, nt 52-5340 of SEQ ID NO: 4, nt 52-5361 of SEQ ID NO: 6 or to SEQ ID NO: 10; or encodes a protein having an amino acid sequence having at least 90% sequence identity to SEQ ID NO: 3, SEQ ID NO: 5, SEQ ID NO: 7, ro SEQ ID NO: 11; and said CRL2 clubroot resistance gene comprises a coding sequence having at least 90% sequence identity to nt 220-2898 of SEQ ID NO: 8; or encodes a protein having an amino acid sequence having at least 90% sequence identity to SEQ ID NO: 9. In a further embodiment, said CRL1 clubroot resistance gene comprises a sequence having at least 90% sequence identity to nt 32750-51049 of SEQ ID NO: 1. In another embodiment, said Brassicaceae plant or plant cell comprises a transgene comprising a sequence having at least 90% sequence identity to SEQ ID NO: 1. Said transgene may also comprise a sequence having least 80%, or at least 85%, or at least 90%, or at least 92%, or at least 95%, or at least 98%, or at least 99%, or 100% sequence identity to nt 3145-51049 of SEQ ID NO: 1, or to the sequence of SEQ ID NO: 1 without transposon regions, i.e. to the contiguous sequence of nt 3145-8010, 22965-30182, 30297-32257, 32645-45078 and 47953-51049 of SEQ ID NO: 1.

A "CRL protein", as used herein, is a protein encoded by a CRL clubroot resistance gene. A CRL protein can have an amino acid sequence having at least 80%, or at least 85%, or at least 90%, or at least 92%, or at least 95%, or at least 98%, or at least 99%, or 100% sequence identity to SEQ ID NO: 3, to SEQ ID NO: 5, to SEQ ID NO: 7, or to SEQ ID NO: 9.

A "functional fragment" of the amino acid sequence having at least 80% sequence identity to SEQ ID NO: 3, denotes a protein or peptide comprising a stretch of the amino acid sequences as depicted above which still exerts the desired function, i.e. which increases clubroot resistance when present in a Brassicaceae plant. An assay for determining of whether a functional fragment increases clubroot resistance is provided herein.

A "CLR clubroot resistance gene", or "CRL resistance gene", or "CRL gene", as used herein, is a gene that confers resistance to *Plasmodiophora brassicae* strain Leduc-ss2 corresponding to pathotype 6 as described by Xue et al., 2008, Plant Disease 92:456 (herein incorporated by reference). A CRL resistance gene is present, for example, in *Brassica napus* cvs. Laurentian, Nevin and Wilhelmsburger or, for example, in *Brassica oleracea* cv. Badger Shipper (see Xue et al, 2008, supra). A "CRL clubroot resistance gene", "CRL resistance gene" or "CRL gene" can be sufficient for resistance to *Plasmodiophora brassicae* strain Leduc-ss2 corresponding to pathotype 6. A "CRL clubroot resistance gene" or "CRL gene" can also be required together with another CRL clubroot resistance gene for resistance to *Plasmodiophora brassicae* strain Leduc-ss2 corresponding to pathotype 6.

A CRL clubroot resistance gene, or CRL gene can encode a CRL amino acid sequence having at least 80%, or at least 85%, or at least 90%, or at least 92%, or at least 95%, or at least 98%, or at least 99%, or 100% sequence identity to SEQ ID NO: 3, or to SEQ ID NO: 5, or to SEQ ID NO: 7, or to SEQ ID NO: 9. A CRL clubroot resistance gene, or CRL gene, can comprise a nucleotide sequence having at least 80%, or at least 85%, or at least 90%, or at least 92%, or at least 95%, or at least 98%, or at least 99%, or 100% sequence identity to SEQ ID NO: 2, or to SEQ ID NO: 4, or to SEQ ID NO: 6, to SEQ ID NO: 8, to SEQ ID NO: 10, to nt 52-5343 of SEQ ID NO: 2, to nt 52-5340 of SEQ ID NO: 4, to nt 52-5361 of SEQ ID NO: 6, or to nt 220-2898 of SEQ ID NO: 8. Said CRL clubroot resistance gene, or CRL gene may further comprise an intron, and can comprise a nucleotide sequence having at least 80%, or at least 85%, or at least 90%, or at least 92%, or at least 95%, or at least 98%, or at least 99%, or 100% sequence identity to nt 32750 to 51049 of SEQ ID NO: 1, or can comprise a nucleotide sequence having at least 80%, or at least 85%, or at least 90%, or at least 92%, or at least 95%, or at least 98%, or at least 99%, or 100% sequence identity to nt 32750 to 51049 without transposon region, i.e. to the contiguous sequence of nt 32750-45078 and nt 47953-51049 of SEQ ID NO: 1.

A CRL1 clubroot resistance gene, as used herein, is a CRL clubroot resistance gene encoding the CRL1 protein having an amino acid sequence having at least 80%, or at least 85%, or at least 90%, or at least 92%, or at least 95%, or at least 98%, or at least 99%, or 100% sequence identity to SEQ ID NO: 3 (CRL1a protein), or to SEQ ID NO: 5 (CRL1b protein), to SEQ ID NO: 7 (CRL1c protein), or to SEQ ID NO: 11 (CRL1d protein). The CRL1 clubroot resistance gene may comprise a coding sequence having at least 80%, or at least 85%, or at least 90%, or at least 92%, or at least 95%, or at least 98%, or at least 99%, or 100% sequence identity to nt 52-5343 of SEQ ID NO: 2 (CRL1a coding sequence), to nt 52-5340 of SEQ ID NO: 4 (CRL1b coding sequence), to nt 52-5361 of SEQ ID NO: 6 (CRL1c coding sequence) or to SEQ ID NO: 10 (CRL1d coding sequence). The CRL1 clubroot resistance gene may contain an intron, and can comprise a nucleotide sequence having at least 80%, or at least 85%, or at least 90%, or at least 92%, or at least 95%, or at least 98%, or at least 99%, or 100% sequence identity to nt 32750 to 51049 of SEQ ID NO: 1, or to nt 32750 to 50758 of SEQ ID NO: 1, or to nt 32903 to 51049 of SEQ ID NO: 1.

A CRL2 clubroot resistance gene, as used herein, is a CRL clubroot resistance gene encoding the CRL2 protein having an amino acid sequence having at least 80%, or at least 85%, or at least 90%, or at least 92%, or at least 95%, or at least 98%, or at least 99%, or 100% sequence identity to SEQ ID NO: 9. The CRL2 clubroot resistance gene may comprise a coding sequence having at least 80%, or at least 85%, or at least 90%, or at least 92%, or at least 95%, or at least 98%, or at least 99%, or 100% sequence identity to nt 220-2898 of SEQ ID NO: 8. The CRL1 clubroot resistance gene may comprise a nucleotide sequence having at least 80%, or at least 85%, or at least 90%, or at least 92%, or at least 95%, or at least 98%, or at least 99%, or 100% sequence identity to SEQ ID NO: 8.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other, is regarded as a position with non-identical residues. The "optimal alignment" of two sequences is found by aligning the two sequences over the entire length according to the Needleman and Wunsch global alignment algorithm (Needleman and Wunsch, 1970, J Mol Biol 48(3):443-53) in The European Molecular Biology Open Software Suite (EMBOSS, Rice et al., 2000, Trends in Genetics 16(6): 276-277; see e.g. http://www.ebi.ac.uk/emboss/align/index.html) using default settings (gap opening penalty=10 (for nucleotides)/10 (for proteins) and gap extension penalty=0.5 (for nucleotides)/0.5 (for proteins)). For nucleotides the default scoring matrix used is EDNAFULL and for proteins the default scoring matrix is EBLOSUM62. It will be clear that whenever nucleotide sequences of RNA molecules are defined by reference to nucleotide sequence of corresponding DNA molecules, the thymine (T) in the nucleotide sequence should be replaced by uracil (U). Whether reference is made to RNA or DNA molecules will be clear from the context of the application.

"Stringent hybridization conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point ($T_m$) for the specific sequences at a defined ionic strength and pH. The $T_m$ is the temperature (under defined ionic strength and pH) at which 50% of the target sequence hybridizes to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridizations (Northern blots using a probe of e.g. 100 nt) are for example those which include at least one wash in 0.2×SSC at 63° C. for 20 min, or equivalent conditions.

"High stringency conditions" can be provided, for example, by hybridization at 65° C. in an aqueous solution containing 6×SSC (20×SSC contains 3.0 M NaCl, 0.3 M Na-citrate, pH 7.0), 5×Denhardt's (100×Denhardt's contains 2% Ficoll, 2% Polyvinyl pyrollidone, 2% Bovine Serum Albumin), 0.5% sodium dodecyl sulphate (SDS), and 20 µg/ml denaturated carrier DNA (single-stranded fish sperm DNA, with an average length of 120-3000 nucleotides) as non-specific competitor. Following hybridization, high stringency washing may be done in several steps, with a final wash (about 30 min) at the hybridization temperature in 0.2-0.1×SSC, 0.1% SDS.

"Moderate stringency conditions" refers to conditions equivalent to hybridization in the above described solution but at about 60-62° C. Moderate stringency washing may be done at the hybridization temperature in 1×SSC, 0.1% SDS.

"Low stringency" refers to conditions equivalent to hybridization in the above described solution at about 50-52° C. Low stringency washing may be done at the hybridization temperature in 2×SSC, 0.1% SDS. See also Sambrook et al. (1989) and Sambrook and Russell (2001).

A "CRL clubroot resistance locus" as used herein refers to the genetic locus that comprises a CRL clubroot resistance gene. A "CRL clubroot resistance locus" refers to the position on the chromosome where a "CRL clubroot resistance gene" is located. This position can be identified by the location on the genetic map of a chromosome. Included in this definition is the fragment (or segment) of genomic DNA of the chromosome on which the CRL clubroot resistance locus is located. Said CRL clubroot resistance gene can be a native CRL clubroot resistance gene in its native chromosomal position, or can be a transgene on a chromosomal position on which it does not occur naturally. Brassica seeds comprising the CRL clubroot resistance locus have been deposited at the NCIMB (NCIMB Ltd, Ferguson Building, Craibstone Estate, Bucksburn, Aberdeen AB21 9YA, Scotland, UK) on 7 December 2015, under accession number NCIMB 42499 and on 22 Jul. 2016, under accession number NCIMB 42610.

The CRL clubroot resistance locus can comprise the CRL1 and CRL2 clubroot resistance genes according to the invention. The CRL clubroot resistance locus can comprise a sequence having at least 80%, or at least 85%, or at least 90%, or at least 92%, or at least 95%, or at least 98%, or at least 99%, or 100% sequence identity to SEQ ID NO: 1.

A "locus" as used herein is the position that a gene occupies on a chromosome. A "clubroot resistance locus" refers to the position on the chromosome where a "clubroot resistance gene" is located. This position can be identified by the location on the genetic map of a chromosome. Included in this definition is the fragment (or segment) of genomic DNA of the chromosome on which the clubroot resistance locus is located. Said clubroot resistance gene can be a native clubroot resistance gene in its native chromosomal position, or can be a transgene on a chromosomal position on which it does not occur naturally. Said clubroot resistance gene can be the CRL clubroot resistance gene or another clubroot resistance gene. A locus which does not comprise the CRL clubroot resistance gene according to the invention, which is at the position on the chromosome corresponding to the position where the CRL clubroot resistance gene is located in a resistant line, can be referred to as "CRL clubroot susceptibility locus".

As used herein, the term "plant-expressible promoter" means a DNA sequence that is capable of controlling (initiating) transcription in a plant cell. This includes any promoter of plant origin, but also any promoter of non-plant origin which is capable of directing transcription in a plant cell, i.e., certain promoters of viral or bacterial origin such as the CaMV35S (Harpster et al. (1988) Mol Gen Genet. 212(1):182-90, the subterranean clover virus promoter No 4 or No 7 (WO9606932), or T-DNA gene promoters but also tissue-specific or organ-specific promoters including but not limited to seed-specific promoters (e.g., WO89/03887), organ-primordia specific promoters (An et al. (1996) Plant Cell 8(1):15-30), stem-specific promoters (Keller et al., (1988) EMBO J. 7(12): 3625-3633), leaf specific promoters (Hudspeth et al. (1989) Plant Mol Biol. 12: 579-589), mesophyl-specific promoters (such as the light-inducible Rubisco promoters), root-specific promoters (Keller et al. (1989) Genes Dev. 3: 1639-1646), tuber-specific promoters (Keil et al. (1989) EMBO J. 8(5): 1323-1330), vascular tissue specific promoters (Peleman et al. (1989) Gene 84: 359-369), stamen-selective promoters (WO 89/10396, WO 92/13956), dehiscence zone specific promoters (WO 97/13865) and the like.

Suitable promoters for the invention are constitutive plant-expressible promoters. Constitutive plant-expressible promoters are well known in the art, and include the CaMV35S promoter (Harpster et al. (1988) Mol Gen Genet. 212(1):182-90), Actin promoters, such as, for example, the promoter from the Rice Actin gene (McElroy et al., 1990, Plant Cell 2:163), the promoter of the Cassava Vein Mosaic Virus (Verdaguer et al., 1996 Plant Mol. Biol. 31: 1129), the GOS promoter (de Pater et al., 1992, Plant J. 2:837), the Histone H3 promoter (Chaubet et al., 1986, Plant Mol Biol 6:253), the *Agrobacterium tumefaciens* Nopaline Synthase (Nos) promoter (Depicker et al., 1982, J. Mol. Appl. Genet. 1: 561), or Ubiquitin promoters, such as, for example, the promoter of the maize Ubiquitin-1 gene (Christensen et al., 1992, Plant. Mol. Biol. 18:675).

A further promoter suitable for the invention is the endogenous promoter driving expression of the gene encoding an CRL protein.

A "transcription termination and polyadenylation region" as used herein is a sequence that drives the cleavage of the nascent RNA, whereafter a poly(A) tail is added at the resulting RNA 3' end, functional in plant cells. Transcription termination and polyadenylation signals functional in plant cells include, but are not limited to, 3'nos, 3'35S, 3' his and 3' g7.

"Brassicaceae" or "Brassicaceae plant" as used herein refers to plants belonging to the family of Brassicaceae plants, also called Cruciferae or mustard family. Examples of Brassicaceae are, but are not limited to, Brassica species, such as *Brassica napus, Brassica oleracea, Brassica rapa, Brassica carinata, Brassica nigra*, and *Brassica juncea*; Raphanus species, such as *Raphanus caudatus, Raphanus raphanistrum*, and *Raphanus sativus*; Matthiola species; Cheiranthus species; Camelina species, such as *Camelina sativa*; Crambe species, such as *Crambe abyssinica* and *Crambe hispanica*; Eruca species, such as *Eruca vesicaria*; Sinapis species such as *Sinapis alba*; Diplotaxis species; Lepidium species; Nasturtium species; Orychophragmus species; Armoracia species, Eutrema species; Lepidium species; and Arabidopsis species.

A "*Brassica* plant" refers to allotetraploid or amphidiploid Brassica napus (AACC, 2n=38), Brassica juncea (AABB, 2n=36), Brassica carinata (BBCC, 2n=34), or to diploid Brassica rapa (syn. B. campestris) (AA, 2n=20), Brassica oleracea (CC, 2n=18) or Brassica nigra (BB, 2n=16).

The CRL protein according to the invention may comprise a conserved Coil-Coil domain (CC-domain), EDVID motif, NBS domain, RNBS-A region, RNBS-B region, RNBS-C region, RNBS-D region, a GLPLA (or hydrophobic) region, ARC1 domain, ARC2 domain, LRR domain (leucine rich region) with one or more LRR motifs (xxLxLxx), P-loop kinase1 region (also known as Walker A), Kinase-2 region (with Walker B region), LRRNT region (N-terminal cap, also known as MHD-region) LRRCT region (C-terminal cap) (see, Meyers et al (2003), Plant Cell 15:809; van Ooijen et al (2008) J Exp Bot 59:1383; McHale et al (2006), Genome Biol 7: 212; Bouktila et al (2014) Genet Mol Biol 37: 598 (all documents herein incorporated by reference).

The positions of the conserved domains in the CRL proteins according to the invention in shown in Table 1 and in FIG. 1.

TABLE 1a

Positions of conserved domains in the CRL1 proteins

| | SEQ ID NO: 3 | | SEQ ID NO: 5 | | SEQ ID NO: 7 | |
|---|---|---|---|---|---|---|
| | start | end | start | end | start | end |
| CC-domain1 | 1 | 39 | 1 | 39 | 1 | 39 |
| EDVID | 44 | 47 | 44 | 47 | 44 | 47 |
| NBS-truncated | 115 | 164 | 115 | 164 | 115 | 164 |
| RNBS-C_NBS | 115 | 132 | 115 | 132 | 115 | 132 |
| ARC1 | 120 | 198 | 120 | 198 | 120 | 198 |
| GLPLA_NBS | 151 | 164 | 151 | 164 | 151 | 164 |
| ARC2 | 199 | 294 | 199 | 294 | 199 | 294 |
| LRR-domain1 | 346 | 616 | 346 | 616 | 346 | 616 |
| LRR-motif | 346 | 352 | 346 | 352 | 346 | 352 |
| LRR-motif | 370 | 376 | 370 | 376 | 370 | 376 |
| LRR-motif | 391 | 397 | 391 | 397 | 391 | 397 |
| LRR-motif | 394 | 400 | 394 | 400 | 394 | 400 |
| LRR-motif | 404 | 410 | 404 | 410 | 404 | 410 |
| LRR-motif | 417 | 423 | 417 | 423 | 417 | 423 |
| LRR-motif | 435 | 441 | 435 | 441 | 435 | 441 |
| LRR-motif | 440 | 446 | 440 | 446 | 440 | 446 |
| LRR-motif | 465 | 471 | 465 | 471 | 465 | 471 |
| LRR-motif | 491 | 497 | 491 | 497 | 491 | 497 |
| LRR-motif | 504 | 510 | 504 | 510 | 504 | 510 |
| LRR-motif | 510 | 516 | 510 | 516 | 510 | 516 |
| LRR-motif | 569 | 575 | 569 | 575 | 569 | 575 |
| LRR-motif | 578 | 584 | 578 | 584 | 578 | 584 |
| LRR-motif | 610 | 616 | 610 | 616 | 610 | 616 |
| CC-domain2 | 900 | 949 | 899 | 948 | 906 | 955 |
| EDVID-motif | 954 | 957 | 953 | 956 | 960 | 963 |
| NBS-domain2 | 1062 | 1243 | 1061 | 1242 | 1068 | 1249 |
| P-loop_kinase1 | 1062 | 1080 | 1061 | 1079 | 1068 | 1086 |
| RNBS-A_NBS2 | 1085 | 1113 | 1084 | 1112 | 1091 | 1119 |
| Kinase-2_NBS2 | 1142 | 1152 | 1141 | 1151 | 1148 | 1158 |
| RNBS-B_NBS2 | 1168 | 1182 | 1167 | 1181 | 1174 | 1188 |
| RNBS-C_NBS2 | 1190 | 1209 | 1189 | 1208 | 1196 | 1215 |
| ARC1-domain | 1195 | 1275 | 1194 | 1274 | 1201 | 1281 |
| GLPLA_NBS2 | 1230 | 1243 | 1229 | 1242 | 1236 | 1249 |
| ARC2-domain | 1276 | 1382 | 1275 | 1381 | 1282 | 1388 |
| RNBS-D | 1300 | 1307 | 1299 | 1306 | 1306 | 1313 |
| LRRNT | 1367 | 1377 | 1366 | 1376 | 1373 | 1383 |
| LRR-domain2 | 1401 | 1724 | 1400 | 1723 | 1407 | 1730 |
| LRR-motif | 1401 | 1407 | 1400 | 1406 | 1407 | 1413 |
| LRR-motif | 1415 | 1421 | 1414 | 1420 | 1421 | 1427 |
| LRR-motif | 1436 | 1442 | 1435 | 1441 | 1442 | 1448 |
| LRR-motif | 1442 | 1448 | 1441 | 1447 | 1448 | 1454 |
| LRR-motif | 1467 | 1473 | 1466 | 1472 | 1473 | 1479 |
| LRR-motif | 1484 | 1490 | 1483 | 1489 | 1490 | 1496 |
| LRR-motif | 1514 | 1520 | 1513 | 1519 | 1520 | 1526 |
| LRR-motif | 1526 | 1532 | 1525 | 1531 | 1532 | 1538 |
| LRR-motif | 1559 | 1565 | 1558 | 1564 | 1565 | 1571 |
| LRR-motif | 1572 | 1578 | 1571 | 1577 | 1578 | 1584 |
| LRR-motif | 1585 | 1591 | 1584 | 1590 | 1591 | 1597 |
| LRR-motif | 1608 | 1614 | 1607 | 1613 | 1614 | 1620 |
| LRRCT | 1664 | 1670 | 1663 | 1669 | 1670 | 1676 |
| LRR-motif | 1679 | 1685 | 1678 | 1684 | 1685 | 1691 |
| LRR-motif | 1718 | 1724 | 1717 | 1723 | 1724 | 1730 |

TABLE 1b

Positions of conserved domains in the CRL2 protein

| | SEQ ID NO: 9 | |
|---|---|---|
| | start | end |
| CC-domain | 33 | 77 |
| EDVID-motif | 86 | 89 |
| NBS-domain | 177 | 353 |
| P-loop_kinase-1 | 177 | 196 |
| RNBS-A_NBS | 201 | 224 |
| Kinase-2_NBS | 256 | 267 |
| WalkerB | 259 | 268 |
| RNBS-B_NBS | 283 | 297 |
| RNBS-C_NBS | 305 | 323 |
| ARC1-domain | 310 | 386 |
| GLAPLA_NBS | 340 | 353 |
| ARC2-domain | 387 | 489 |
| RNBS-D | 406 | 413 |
| LRRNT | 469 | 480 |
| LRR-domain | 538 | 851 |
| LRR-motif | 538 | 544 |
| LRR-motif | 562 | 568 |
| LRR-motif | 586 | 592 |
| LRR-motif | 604 | 610 |
| LRR-motif | 609 | 615 |
| LRR-motif | 627 | 633 |
| LRR-motif | 684 | 690 |
| LRR-motif | 762 | 768 |
| LRR-motif | 810 | 816 |
| LRR-motif | 845 | 851 |

It is another object of the invention to provide a method for increasing clubroot resistance in a Brassicaceae plant, said method comprising introducing or providing a CRL1 and a CRL2 clubroot resistance gene according to the invention as a transgene, to a Brassicaceae plant cell, to create transgenic cells; and regenerating transgenic plants from said transgenic cells.

A transgene can be provided to a plant or plant cell using methods well-known in the art. Methods for introduction of genes into plant cells to create transgenic plants are not deemed critical for the current invention and any method to provide plant cells with a transgene suitable for a particular plant species can be used. Such methods are well known in the art and include *Agrobacterium*-mediated transformation, particle gun delivery, microinjection, electroporation of intact cells, polyethyleneglycol-mediated protoplast transformation, electroporation of protoplasts, liposome-mediated transformation, silicon-whiskers mediated transformation etc. Said transgene may be stably integrated into the genome of said plant cell, resulting in a transformed plant cell. The transformed plant cells obtained in this way may then be regenerated into mature fertile transformed plants.

In yet another embodiment, a method is provided for increasing clubroot resistance in a Brassicaceae plant, comprising the step of introducing a CRL clubroot resistance locus in said Brassicaceae plant, and selecting said clubroot resistant Brassicaceae plant for the presence of the CRL clubroot resistance locus by analyzing genomic DNA from said plant for the presence of at least one molecular marker, wherein said at least one molecular marker is linked to the CRL clubroot resistance locus, wherein said CRL clubroot resistance locus comprises the CRL1 and CRL2 clubroot resistance genes, wherein said CRL1 clubroot resistance gene comprises a nucleotide sequence having at least 90% sequence identity to nt 32750 to 51049 of SEQ ID NO: 1 or to nt 32750 to 50758 of SEQ ID NO: 1, or to nt 32903 to 51049 of SEQ ID NO: 1; having a coding sequence having at least 90% sequence identity to nt 52-5343 of SEQ ID NO:

2, nt 52-5340 of SEQ ID NO: 4, nt 52-5361 of SEQ ID NO: 6, or to SEQ ID NO: 10; or encoding a protein having at least 90% sequence identity to SEQ ID NO: 3, SEQ ID NO: 5, SEQ ID NO: 7, or SEQ ID NO: 11; and wherein said CRL2 clubroot resistance gene comprises a nucleotide sequence having a coding sequence having at least 90% sequence identity to nt 220-2898 of SEQ ID NO: 8; or encoding a protein having at least 90% sequence identity to SEQ ID NO: 9, such as a CRL clubroot resistance locus comprising a sequence having at least 90% sequence identity to SEQ ID NO: 1. Said method can comprise the provision of a first Brassicaceae plant comprising a CRL clubroot resistance locus, providing a second Brassicaceae plant lacking a CRL clubroot resistance locus, crossing the first Brassicaceae plant with the second Brassicaceae plant to provide progeny Brassicaceae plant; analyzing said progeny Brassicaceae plant to determine the presence of a CRL clubroot resistance locus by analyzing genomic DNA from the plant for the presence of at least one molecular marker, wherein said at least one molecular marker is linked to the CRL clubroot resistance locus; and selecting Brassicaceae progeny that tests positive for the presence of the CRL clubroot resistance locus as being Brassicaceae plant into which the CRL clubroot resistance locus has been introgressed. Said first Brassicaceae plant may be obtained by screening a population of Brassicaceae plants for the presence of a CRL clubroot resistance locus by analyzing genomic DNA from the plant for at least one molecular marker, wherein said at least one molecular marker is linked to the CRL clubroot resistance locus. Said first Brassicaceae plant and said progeny Brassicaceae plant may be *Brassica rapa*; and first Brassicaceae plant and said progeny Brassicaceae plant may be *Brassica napus*, or said first Brassicaceae plant may be *Brassica rapa*, said second Brassicaceae plant may be *Brassica oleracea*, and said progeny Brassicaceae plant may be *Brassica napus* obtained through an interspecific cross between said first and said second Brassicaceae plant.

Yet another embodiment provides a method for producing a clubroot resistant Brassicaceae plant comprising the steps of identifying a clubroot resistant Brassicaceae plant comprising a CRL clubroot resistance locus according to the invention by analyzing genomic DNA from said plant for the presence of at least one molecular marker, wherein said at least one molecular marker is linked to said CRL clubroot resistance locus, and generating progeny from said clubroot resistant Brassicaceae plant, wherein said progeny is clubroot resistant and comprises said CRL clubroot resistance locus. In a further embodiment, said CRL clubroot resistance locus comprises a sequence having at least 90% sequence identity to SEQ ID NO: 1.

A Brassicaceae plant comprising said CRL clubroot resistance locus can be a Brassicaceae plant obtainable from the seed deposited at the NCIMB (NCIMB Ltd, Ferguson Building, Craibstone Estate, Bucksburn, Aberdeen AB21 9YA, Scotland, UK) on 7 Dec. 2015, under accession number NCIMB 42499 or from the seed deposited at the NCIMB (NCIMB Ltd, Ferguson Building, Craibstone Estate, Bucksburn, Aberdeen AB21 9YA, Scotland, UK) on 22 Jul. 2016, under accession number NCIMB 42610.

A "molecular marker", or a "marker", as used herein, refers to a polymorphic locus, i.e. a polymorphic nucleotide (a so-called single nucleotide polymorphism or SNP) or a polymorphic DNA sequence (which can be insertion of deletion of a specific DNA sequence at a specific locus, or polymorphic DNA sequences). A marker refers to a measurable, genetic characteristic with a fixed position in the genome, which is normally inherited in a Mendelian fashion, and which can be used for mapping of a trait of interest. Thus, a molecular marker may be a short DNA sequence, such as a sequence surrounding a single base-pair change, i.e. a single nucleotide polymorphism or SNP, or a long DNA sequence, such as microsatellites or Simple Sequence Repeats (SSRs). The nature of the marker is dependent on the molecular analysis used and can be detected at the DNA, RNA or protein level. Genetic mapping can be performed using molecular markers such as, but not limited to, RFLP (restriction fragment length polymorphisms; Botstein et al. (1980), Am J Hum Genet 32:314-331; Tanksley et al. (1989), Bio/Technology 7:257-263), RAPD [random amplified polymorphic DNA; Williams et al. (1990), NAR 18:6531-6535], AFLP [Amplified Fragment Length Polymorphism; Vos et al. (1995) NAR 23:4407-4414], SSRs or microsatellites [Tautz et al. (1989), NAR 17:6463-6471]. Appropriate primers or probes are dictated by the mapping method used.

The term "marker allele" refers to the version of the marker that is present in a particular plant at one of the chromosomes. Typically, a marker can exist as or can be said to have or to comprise two marker alleles. The term "haplotype", as used herein, refers to a specific combination of marker alleles as present within a certain plant or group of (related) plants. As described herein, a marker allele can be the version of the marker that is present in the resistant line (CRL clubroot resistance marker allele). The version of the same marker that is present in the susceptible line can be referred to as CRL clubroot susceptibility marker allele.

The term "AFLP®" (AFLP® is a registered trademark of KeyGene N.V., Wageningen, The Netherlands), "AFLP analysis" and "AFLP marker" is used according to standard terminology [Vos et al. (1995), NAR 23:4407-4414; EP0534858; http://www.key gene.com/key gene/techs-apps/]. Briefly, AFLP analysis is a DNA fingerprinting technique which detects multiple DNA restriction fragments by means of PCR amplification. The AFLP technology usually comprises the following steps: (i) the restriction of the DNA with two restriction enzymes, preferably a hexacutter and a tetra-cutter, such as EcoRI, PstI and MseI; (ii) the ligation of double-stranded adapters to the ends of the restriction fragments, such as EcoRI, PstI and MseI adaptors; (iii) the amplification of a subset of the restriction fragments using two primers complementary to the adapter and restriction site sequences, and extended at their 3' ends by one to three "selective" nucleotides, i.e., the selective amplification is achieved by the use of primers that extend into the restriction fragments, amplifying only those fragments in which the primer extensions match the nucleotides flanking the restriction sites. AFLP primers thus have a specific sequence and each AFLP primer has a specific code (the primer codes and their sequences can be found at the Keygene website: http://www.keygene.com/keygene/pdf/PRIMERCO.pdf; herein incorporated by reference); (iv) gel electrophoresis of the amplified restriction fragments on denaturing slab gels or cappilaries; (v) the visualization of the DNA fingerprints by means of autoradiography, phosphor-imaging, or other methods. Using this method, sets of restriction fragments may be visualized by PCR without knowledge of nucleotide sequence. An AFLP marker, as used herein, is a DNA fragment of a specific size, which is generated and visualized as a band on a gel by carrying out an AFLP analysis. Each AFLP marker is designated by the primer combination used to amplify it, followed by the approximate size (in base pairs) of the amplified DNA fragment. It is understood that the size of these fragments may vary slightly depending on laboratory conditions and equipment used. Every time reference is made herein to an AFLP marker by referring to a primer combination and the specific size of a fragment, it is to be understood that such size is approximate, and comprises or is intended to include the slight variations observed in different labs. Each AFLP marker represents a certain locus in the genome.

The term "SSR" refers to Simple Sequence Repeats or microsatellite [Tautz et al. (1989), NAR 17:6463-6471]. Short Simple Sequence stretches occur as highly repetitive elements in all eukaryotic genomes. Simple sequence loci usually show extensive length polymorphisms. These simple sequence length polymorphisms (SSLP) can be detected by polymerase chain reaction (PCR) analysis and be used for identity testing, population studies, linkage analysis and genome mapping.

It is understood that molecular markers can be converted into other types of molecular markers. When referring to a specific molecular marker in the present invention, it is understood that the definition encompasses other types of molecular markers used to detect the genetic variation originally identified by the specific molecular markers. For example, if an AFLP marker is converted into another molecular marker using known methods, this other marker is included in the definition. For example, AFLP markers can be converted into sequence-specific markers such as, but not limited to STS (sequenced-tagged-site) or SCAR (sequence-characterized-amplified-region) markers using standard technology as described in Meksem et al. [(2001), *Mol Gen Genomics* 265(2):207-214], Negi et al. [(2000), *TAG* 101: 146-152], Barret et al. (1989), *TAG* 97:828-833], Xu et al. [(2001), *Genome* 44(0:63-70], Dussel et al. [(2002), *TAG* 105:1190-1195] or Guo et al. [(2003), *TAG* 103:1011-1017]. For example, Dussel et al. [(2002), *TAG* 105:1190-1195] converted AFLP markers linked to resistance into PCR-based sequence tagged site markers such as indel (insertion/deletion) markers and CAPS (cleaved amplified polymorphic sequence) markers.

Suitable molecular markers are, for example SNP markers (Single Nucleotide Polymorphisms), AFLP markers, microsatellites, minisatellites, Random Amplified Polymorphic DNA's (RAPD) markers, RFLP markers, Sequence Characterized Amplified Regions (SCAR) markers, and others, such as TRAP markers described by Hu et al. 2007, Genet Resour Crop Evol 54: 1667-1674).

Methods and assays for marker detection, or for analyzing the genomic DNA for the presence of a marker, are widely known in the art. The presence of a marker can, for example be detected in hybridization-based methods (e.g. allele-specific hybridization), using Taqman, Invader, PCR-based methods, oligonucleotide ligation based methods, or sequencing-based methods.

A useful assay for detection of SNP markers is for example KBioscience Competitive Allele—Specific PCR. For developing the KASP-assay 70 base pairs upstream and 70 basepairs downstream of the SNP are selected and two allele-specific forward primers and one allele specific reverse primer is designed. See e.g. Allen et al. 2011, Plant Biotechnology J. 9, 1086-1099, especially p 1097-1098 for KASP assay method (incorporated herein by reference).

Suitable for analyzing the genomic DNA for the presence of a marker are the primers as specified in Table 2. The primers indicated as Primer 1 can be used together with the common primer to detect the marker allele specific for the CRL clubroot resistance locus (CRL clubroot resistance marker allele). The primers indicated as Primer 2 can be used together with the common primer to detect the marker allele specific for the CRL clubroot susceptibility locus (CRL clubroot resistance susceptibility allele). The three primers for each marker as specified in Table 2 can be used together in a KASP assay to detect the presence of the CRL clubroot resistance locus and of the CRL clubroot susceptibility locus.

A "molecular marker linked to the CRL clubroot resistance locus", or a "molecular marker linked to the presence of the CRL clubroot resistance locus" as used herein refers to a molecular marker in a region in the genome that inherits with the CRL clubroot resistance locus as a single genetic unit in at least 50% of the cases. Thus, in this respect, the term linked can be a separation of about 50 cM, or less such as about 40 cM, about 30 cM, about 20 cM, about 10 cM, about 7.5 cM, about 6 cM, about 5 cM, about 4 cM, about 3 cM, about 2.5 cM, about 2 cM, or even less. Particular examples of markers linked to the CRL clubroot resistance locus are specified in Table 2. Said "molecular marker linked to the CRL clubroot resistance locus" is thus a marker which is linked to the CRL clubroot resistance gene. Said marker can be based on the CRL clubroot resistance gene itself, such as presence or absence of the CRL clubroot resistance gene.

A "molecular marker linked to the CRL clubroot resistance locus", or a "molecular marker linked to the presence of the CRL clubroot resistance locus" can also be a marker located in a marker interval between and including markers mBRS00013411 and mBRS00013511. Such a marker can thus be any marker at a position on a chromosome between markers mBRS00013411 and mBRS00013511, including markers mBRS00013411 and mBRS00013511. Examples of markers located in a marker interval between and including markers mBRS00013411 and mBRS00013511 are the markers as specified in Table 2.

Suitable are markers that are linked to the CRL clubroot resistance locus can be developed using methods known in the art. New markers suitable for the invention can be developed based on the CRL sequence. It is understood that such markers can be developed by comparing the sequence of the CRL clubroot resistance locus from the resistant Brassicaceae line with the sequence of the same locus in a susceptible Brassicaceae line; identifying a specific sequence region in the CRL clubroot resistance locus which does not occur in the corresponding locus of the susceptible Brassicaceae line. A molecular marker linked to the CRL clubroot resistance locus can thus be a marker detecting the presence of the CRL clubroot resistance locus, or can be a marker directly detecting the presence of the sequence of SEQ ID NO: 1. A molecular marker linked to the CRL clubroot resistance locus can also be a marker in the sequences flanking the CRL clubroot resistance locus, which is polymorphic between lines comprising the CRL clubroot resistance locus and lines lacking, but which inherits with the CRL clubroot resistance locus as a single genetic unit in at least 50% of the cases. Suitable primers to detect the presence of the CRL clubroot resistance locus are Primer 1 and the common primer of any one of the markers mBRS00013440, mBRS00154152, mBRS00013441, and mBRS00161831.

Markers suitable to determine the presence of the CRL clubroot resistance locus can be the markers that are linked to CRL clubroot resistance locus, such as the markers the of Table 2, in particular the CRL clubroot resistance marker alleles with the polymorphic base detected by Primer 1 and indicated with R.

The absence of the CRL clubroot resistance locus can be determined by the absence of marker alleles that are linked to the presence of the CRL clubroot resistance locus (CRL clubroot resistance marker alleles), such as by the absence of the CRL clubroot resistance marker alleles of Table 2 with the polymorphic base detected by Primer 1 and indicated with R. Furthermore, markers suitable to determine the absence of the CRL clubroot resistance locus can be marker alleles which are linked to the CRL clubroot susceptibility locus (CRL clubroot susceptibility marker alleles). Examples of CRL clubroot susceptibility marker alleles that are linked to the CRL clubroot susceptibility locus are the marker alleles of Table 2 with the polymorphic base detected by Primer 2 and indicated with S.

Analysis for the presence of markers according to the invention can be performed with a first primer and a second primer, and, optionally, a probe, selected from the group consisting of a first primer consisting of a sequence of 15 to 30 nucleotides, or 15 to 25 nucleotides, or 18 to 22 nucleotides of the CRL clubroot resistance genes according to the invention, a second primer being complementary to a sequence of 15 to 30 nucleotides, or 15 to 25 nucleotides, or 18 to 22 nucleotides of the CRL clubroot resistance genes according to the invention, and wherein the distance between said first and said second primer on the CRL clubroot resistance gene is between 1 and 400 bases, or between 1 and 150 bases, and wherein the first primer is located, with respect to the CRL coding sequence, upstream of said second primer, and a probe which is identical to at least 15 nucleotides, or at least 18 nucleotides, but not more than 25 nucleotides, or not more than 22 nucleotides of the sequence of the CRL clubroot resistance gene between said first and said second primer, provided that either the sequence of the first primer, or the sequence of the second primer, or the sequence of said probe is not present in the corresponding locus in a susceptible Brassicaceae plant. Said probe may be labelled, such as, for example, described in U.S. Pat. No. 5,538,848.

Analysis for the presence of markers according to the invention can be performed with a first and second primer as described above recognizing both the CRL sequence and the corresponding locus in the susceptible Brassicaceae line, a first probe recognizing a sequence of the CRL clubroot resistance gene as described above, but not recognizing a sequence between said first and said second primer in the susceptible Brassicaceaea line, and a second probe recognizing a sequence between said first and said second primer in the susceptible Brassicaceaea line, but not of the CRL clubroot resistance gene, and wherein said the label of the first probe is different from that of the second probe.

Further suitable primers for analysis of the presence of markers according to the invention are markers a first primer as described above recognizing both the CRL sequence and the corresponding locus in the susceptible Brassicaceae line, a second primer recognizing the CRL sequence but not the corresponding locus in the susceptible Brassicaceae line, and a third primer recognizing the corresponding locus in the susceptible Brassicaceae line but not the CRL sequence. Said second and third primer may be labelled as indicated above, and said second primer may contain a label which is different from said third primer.

Identification of PCR products specific for the CRL clubroot resistance genes and for the corresponding locus in the susceptible Brassicaceae line can occur e.g. by size estimation after gel or capillary electrophoresis (e.g. for the CRL clubroot resistance locus and for the corresponding locus in the susceptible Brassicaceae line comprising a number of inserted or deleted nucleotides which results in a size difference between the fragments amplified from the CRL clubroot resistance locus and for the corresponding locus in the susceptible Brassicaceae, such that said fragments can be visibly separated on a gel); by evaluating the presence or absence of the two different fragments after gel or capillary electrophoresis, whereby the diagnostic PCR amplification of the CRL clubroot resistance locus can, optionally, be performed separately from the diagnostic PCR amplification of the corresponding locus in the susceptible line; by direct sequencing of the amplified fragments; or by fluorescence-based detection methods.

A further embodiment provides Brassicaceae plants or plant cells obtainable by the methods according to the invention, such as *Brassica napus, Brassica juncea, Brassica oleracea, Brassica rapa, Brassica nigra* or *Brassica carinata* plants.

In a further embodiment, a clubroot resistant Brassicaceae plant or plant cell according to the invention is provided, comprising the CRL1 and CRL2 clubroot resistance genes according to the invention, and at least one other disease resistance gene, said other disease resistance gene selected from the group consisting of a clubroot resistance gene, a blackleg resistance gene, a Sclerotinia resistance gene, a Verticillium resistance gene, a *Fusarium* resistance gene, an Aster Yellows resistance gene, an Alternaria resistance gene, and a Grey Stem resistance gene. In a further embodiment, said other disease resistance gene is a transgene which is genetically linked with said CRL clubroot resistance genes.

Said clubroot resistance gene may be a Crr2, Crr4, Crr3, CRk, CRc, CR2a, CR2b, pb-3, pb-4, Pb-Bo1, Pb-Bo2, Pb-Bo3, Pb-Bo4, Pb-Bo5a, Pb-Bo5b, Pb-Bo8, Pb-Bo9a, Pb-Bo9b, Pb-Bn1, PbBn-01:60-1, PbBn-01:60-2, PbBn-01:60-3, PbBn-01:60-4, PbBn-01:07-1, PbBn-01:07-2, PbBn-01:07-3, PbBn-e4x04-1, PbBn-a-1, PbBn-1-1, PbBn-1-2, PbBn-k-1, PbBn-k-2. PbBn-k-3, PbBn-Korp-1, PbBn-Korp-2, PbBn-Korp-3, PbBn-Korp-4, PbBn-Korp-5 as described by Piao et al., 2009, supra, or may be a CRa gene as described by Ueno et al., 2012, supra, a Crr1 gene as described by Hatakeyama et al., 2013, supra and in WO2012/039445, or a CRb gene as described by Kato et al., 2013, supra (herein incorporated by reference).

Said Blackleg resistance gene may, for example, be BLMR1 and BLMR2 (WO 2011/044694), LepR3 (Larkan et al., 2013, New Phytol 197:595 and WO 2008/101343), or Lem-08-syl (EP 1547462 and US 2005/0142122). Said Sclerotinia resistance gene may be a sclerotinia resistance gene as described in WO 2005/090578.

Said other disease resistance gene may be present in their native chromosomal position. For example, said other disease resistance genes can be introduced by introgression in the plant according to the invention from the cultivar or -species from which they are derived.

A "clubroot resistance gene" as used herein refers to a DNA sequence which confers, or is associated with, enhanced resistance of a plant, such as a Brassicaceae plant, such as a *Brassica* plant, to *Plasmodiophora brassicae*, compared to a plant lacking the resistance gene(s) or having a non-functional (or inactivated) form of the gene(s).

"Clubroot" as used herein refers to the disease caused by the pathogen *Plasmodiophora brassicae*.

"Clubroot resistance" as used herein refers to resistance to one or more *Plasmodiophora brassicae* isolates, such as, but not limited to, resistance to the *Plasmodiophora brassicae* strain Leduc-ss2 corresponding to pathotype 6 (Xue et al., 2008, Plant Disease 92:456). Said resistance refers to a reduction in damage caused by clubroot infection compared to damage caused on control plants. Damage can be assessed as, for example, formation of club-shaped galls on the roots, occurrence of wilting, stunting, yellowing, premature senescence etc. In particular, a reduction in damage is manifested in a reduced yield loss when plants are grown under disease pressure in the field, compared to control plants. Such reduction in yield loss can, for example, be due to the fact that the infection, reproduction, spread or survival of the pathogen is reduced or prevented in plants with enhanced resistance. Said resistance may also refer to plants that are completely resistant, i.e., plants on which no disease symptoms are found.

Clubroot resistance can be assessed using a scale from zero to three: zero: no clubbing, one: <25% of root system clubbed; two: 25 to 50% of root system clubbed; three: >50% of root system clubbed (Humpherson-Jones, 1989, Tests Agro Cult 10:36). The Disease Index (ID) can be calculated using the following equation:

[(# plants in class 0*0)+([(# plants in class 1*1)+(# plants in class 2*2)+(# plants in class 3*3)]/ total number of plants*3

(Strelkov et al., 2006, Can J Plant Pathol 28:467).

It is understood that environmental conditions, such as location, weather conditions and disease pressure, as well as individual perception of the person assessing disease symptoms, can have an effect on the scoring of clubroot resistance. Hence, variation in these factors in comparative tests should be minimized. Any other resistance ratings known in the art can be applied in accordance with this invention to compare the plants of the invention with control plants.

A plant which is clubroot resistant refers to a plant assessed at scale zero or one upon natural infection with the clubroot pathogen, or to a plant assessed at scale zero, one or two upon natural infection with the clubroot pathogen. A clubroot resistant population is a population with a disease index (ID) of less than 30%. A plant with increased clubroot resistance is a plant in which the percentage of the root system which is clubbed is decreased with at least 5%, or at least 10%, or at least 15%, or at least 20%, or at least 30%, or at least 40%, or at least 50%, or at least 70%, or at least 95%, or with 100%, i.e. no clubbing, or refers to a population of plants in which the disease index is reduced with at least 3%, or at least 5%, or at least 8%, or at least 10%, or at least 15%, or at least 20%, or at least 30%, or at least 40%, or at least 50%, or at least 70%, or at least 95%, or with 100%, i.e. all plants of the population are classified in class 0 (no clubbing).

In a further embodiment, said other disease resistance gene is a transgene which is genetically linked with the clubroot resistance gene. A transgene, as used herein, refers to a gene which is stably integrated in the plant cell at another position than where it occurs naturally. A transgene can, for example, be integrated into the genome of a plant cell, or it can be present on an artificial chromosome. A transgene can, for example, be a gene introduced into a plant species or cultivar in which it does not occur naturally, or it can be a gene introduced in a plant species or cultivar in which it does occur naturally, but at another chromosomal position. A transgene may, but does not need to be a chimeric gene. A transgene may, for example, comprise an expression cassette comprising a coding sequence linked to its endogenous promoter. A transgene may also, for example, comprise a coding sequence linked to a heterologous promoter.

The terms "genetically linked", "linked", "linked to" or "linkage", as used herein, refers to a measurable probability that genes or markers located on a given chromosome are being passed on together to individuals in the next generation. Thus, the term "linked" may refer to one or more genes or markers that are passed together with a gene with a probability greater than 0.5 (which is expected from independent assortment where markers/genes are located on different chromosomes). Because the proximity of two genes or markers on a chromosome is directly related to the probability that the genes or markers will be passed together to individuals in the next generation, the term genetically linked may also refer herein to one or more genes or markers that are located within about 50 centimorgan (cM) or less of one another on the same chromosome. Genetic linkage is usually expressed in terms of cM. Centimorgan is a unit of recombinant frequency for measuring genetic linkage, defined as that distance between genes or markers for which one product of meiosis in 100 is recombinant, or in other words, the centimorgan is equal to a 1% chance that a marker at one genetic locus on a chromosome will be separated from a marker at a second locus due to crossing over in a single generation. It is often used to infer distance along a chromosome. The number of base-pairs to which cM correspond varies widely across the genome (different regions of a chromosome have different propensities towards crossover) and the species (i.e. the total size of the genome). Thus, in this respect, the term linked can be a separation of about 50 cM, or less such as about 40 cM, about 30 cM, about 20 cM, about 10 cM, about 7.5 cM, about 6 cM, about 5 cM, about 4 cM, about 3 cM, about 2.5 cM, about 2 cM, or even less. Particular examples of markers linked to the CRL clubroot resistance locus are specified in Table 2.

The CRL clubroot resistance gene and the other disease resistance gene can be genetically linked when they are stacked as transgenes. For example, CRL clubroot resistance gene and the other disease resistance gene can be present on one construct that is used for transformation. Alternatively, the CRL clubroot resistance gene can be transformed in a *Brassica* species comprising the other disease resistance gene, provided that it is integrated in the close proximity of the other disease resistance gene, using directed genome engineering techniques. In the latter case, the other disease resistance gene can be present either in its native chromosomal context or as a transgene. Directed genome engineering techniques are, for example, based on homologous recombination, or double-strand break induced targeted integration, or site-specific recombination, such as described in, for example, WO2005/049842, WO2008/148559, WO2011/154158 or WO2011/154159. Alternatively, the other disease resistance gene can be transformed in a *Brassica* species comprising the CRL clubroot resistance gene, provided that it is integrated in the close proximity of the CRL clubroot resistance gene, using directed genome engineering techniques. In the latter case, the other CRL clubroot resistance gene can be present either in its native chromosomal context or as a transgene. The CRL clubroot resistance gene and the other disease resistance gene may also be present on an artificial chromosome. "Artificial chromosomes", as used herein are constructs that contain DNA sequences and that perform the critical functions of natural chromosomes that allow them to exist independent (autonomously) from native chromosomes. Autonomy during cell division (mitosis) and gamete formation (meiosis) follows from own functional origins of replication and own functional centromere. Artificial chromosomes are described, for example, in WO 2005/083096 and WO 2007/030510.

In yet another embodiment, the plant according to the invention is selected from the group consisting of *Brassica napus, Brassica juncea, Brassica oleracea, Brassica rapa, Brassica nigra* and *Brassica carinata*. In yet another embodiment, seeds, such as hybrid seeds of the plants according to the invention comprising the CRL1 and CRL2 clubroot resistance genes are provided.

Hybrid seeds of the plants according to the invention may be generated by crossing two inbred parental lines, wherein one of the inbred parental lines comprises the CRL clubroot resistance genes according to the invention. In order to produce pure hybrid seeds one of the parental lines is male sterile and is pollinated with pollen of the other line. By growing parental lines in rows and only harvesting the F1 seed of the male sterile parent, pure hybrid seeds are produced. To generate male sterile parental lines, the system as described in EP 0,344,029 or U.S. Pat. No. 6,509,516 may be used, wherein a gene encoding a phytotoxic protein (barnase) is expressed under the control of a tapetum specific promoter, such as TA29, ensuring selective destruction of tapetum cells. Transformation of plants with the chimeric gene pTA29:barnase results in plants in which pollen formation is completely prevented [Mariani et al. (1990), Nature 347: 737-741]. Cytochemical and histochemical analysis of anther development of Brassica napus plants comprising the chimeric pTA29-barnase gene is described by De Block and De Brouwer [(1993), Planta 189:218-225]. To restore fertility in the progeny of a male-sterile plant the male-sterile plant (MS parent) is crossed with a transgenic plant (RF parent) carrying a fertility-restorer gene, which when expressed is capable of inhibiting or preventing the activity of the male-sterility gene [U.S. Pat. Nos. 5,689,041; 5,792,929; De Block and De Brouwer, supra]. The use of co-regulating genes in the production of male-sterile plants to increase the frequency of transformants having good agronomical performance is described in WO96/26283. Typically, when the sterility DNA encodes a barnase, the co-regulating DNA will encode a barstar, preferably an optimized barstar gene is used as described in published PCT patent application WO 98/10081. It is understood that different promoters may be used to drive barnase expression in order to render the plant male sterile. Likewise, barstar may be operably linked to different promoters, such as 35S from Cauliflower mosaic virus.

Male sterile plants can also be generated using other techniques, such as cytoplasmic male sterility/restorer systems [e.g. the Ogura system, published US patent application 20020032916, U.S. Pat. No. 6,229,072, WO97/02737, U.S. Pat. No. 5,789,566 or the Polima system of U.S. Pat. No. 6,365,798, WO98/54340 or the Kosena system of WO95/09910, U.S. Pat. No. 5,644,066].

Either the MS parent or the RF parent, or both, may comprise the CRL clubroot resistance genes according to the invention. This can be accomplished by either introducing the CRL clubroot resistance genes into an elite B. napus line and then transforming this line with pTA29-barnase or with pNOS-barstar using known methods. Alternatively the CRL clubroot resistance genes can be introduced directly into a transgenic MS or RF parent line, by crossing a plant comprising the CRL clubroot resistance genes with the MS parent or RF-parent, or by transformation of the MS parent or the RF parent. The F1 hybrid seeds generated from the cross between the MS and RF parent will then contain the CRL clubroot resistance genes.

A further embodiment provides methods to determine the presence or absence of a CRL clubroot resistance locus in a biological sample, comprising providing genomic DNA from said biological sample, and analyzing said DNA for the presence of at least one molecular marker, wherein the at least one molecular marker is linked to the presence or absence of the CRL clubroot resistance locus, wherein said CRL clubroot resistance locus comprises the CRL1 and CRL2 clubroot resistance genes, wherein said CRL1 clubroot resistance gene comprises a nucleotide sequence having at least 90% sequence identity to nt 32750-51049 of SEQ ID NO: 1 or to nt 32750 to 50758 of SEQ ID NO: 1, or to nt 32903 to 51049 of SEQ ID NO: 1; having a coding sequence having at least 90% sequence identity to nt 52-5343 of SEQ ID NO: 2, nt 52-5340 of SEQ ID NO: 4, nt 52-5361 of SEQ ID NO: 6, or to SEQ ID NO: 10; or encoding a protein having at least 90% sequence identity to SEQ ID NO: 3, SEQ ID NO: 5, SEQ ID NO: 7, or SEQ ID NO: 9; and wherein said CRL2 clubroot resistance gene comprises a nucleotide sequence having a coding sequence having at least 90% sequence identity to nt 220-2898 of SEQ ID NO: 8; or encoding a protein having at least 90% sequence identity to SEQ ID NO: 9. In yet a further embodiment, a kit is provided for the detection of the CRL clubroot resistance locus according to the invention in Brassicaceae DNA samples, wherein said kit comprises at least one primer or probe which specifically recognizes a molecular marker linked to said CRL clubroot resistance locus. Yet another embodiment provides the use of a molecular marker linked to the CRL clubroot resistance locus according to the invention for determining the presence or absence of said CRL clubroot resistance locus in Brassicaceae plants, or the use of the sequence of any one of SEQ ID NOs: 1, 2, 4, 6 and 8 for determining the presence or absence of the CRL clubroot resistance locus according to the invention in Brassicaceae plants.

In particular, the methods and kits according to the invention are suitable to determine the presence of the CRL clubroot resistance locus. The presence of the CRL clubroot resistance locus can be determined using at least one molecular marker, wherein said one molecular marker is linked to the presence of the CRL clubroot resistance locus as defined herein.

A "biological sample" can be a plant or part of a plant such as a plant tissue or a plant cell.

"Providing genomic DNA" as used herein refers to providing a sample comprising genomic DNA from the plant. The sample can refer to a tissue sample which has been obtained from said plant, such as, for example, a leaf sample, comprising genomic DNA from said plant. The sample can further refer to genomic DNA which is obtained from a tissue sample, such as genomic DNA which has been obtained from a tissue, such as a leaf sample. Providing genomic DNA can include, but does not need to include, purification of genomic DNA from the tissue sample. Providing genomic DNA thus also includes obtaining tissue material from a plant or larger piece of tissue and preparing a crude extract or lysate therefrom.

A "kit", as used herein, refers to a set of reagents for the purpose of performing the method of the invention, more particularly, the identification of the CRL clubroot resistance genes in biological samples or the determination of the zygosity status of plant material comprising the CRL clubroot resistance genes. More particularly, a preferred embodiment of the kit of the invention comprises at least two specific primers for identification of the CRL clubroot resistance genes, or at least two or three specific primers for the determination of the zygosity status. Optionally, the kit can further comprise any other reagent. Alternatively, according to another embodiment of this invention, the kit can comprise at least one specific probe, which specifically hybridizes with nucleic acid of biological samples to identify the presence of the CRL clubroot resistance genes therein, or at least two or three specific probes for the determination of the zygosity status. Optionally, the kit can further comprise any other reagent (such as but not limited to hybridizing buffer, label) for identification of the CRL clubroot resistance genes in biological samples, using the specific probe.

The kit of the invention can be used, and its components can be specifically adjusted, for purposes of quality control (e.g., purity of seed lots), detection of the presence or absence of the CRL clubroot resistance genes in plant material or material comprising or derived from plant material, such as but not limited to food or feed products. The zygosity status of the CRL clubroot resistance genes can be determined by using alternative sets of primers and/or probes that specifically the CRL locus and the corresponding locus in a susceptible Brassicaceae line.

The term "primer" as used herein encompasses any nucleic acid that is capable of priming the synthesis of a nascent nucleic acid in a template-dependent process, such as PCR. Typically, primers are oligonucleotides from 10 to 30 nucleotides, but longer sequences can be employed. Primers may be provided in double-stranded form, though the single-stranded form is preferred. Probes can be used as primers, but are designed to bind to the target DNA or RNA and need not be used in an amplification process.

The term "recognizing" as used herein when referring to specific primers, refers to the fact that the specific primers specifically hybridize to a specific nucleic acid sequence under the conditions set forth in the method (such as the conditions of the PCR identification protocol), whereby the specificity is determined by the presence of positive and negative controls.

It is another object of the invention to provide a chimeric gene comprising the following genetic elements: a plant-expressible promoter, a DNA sequence coding for a CRL1 or for a CRL2 protein, and optionally, a transcription termination and polyadenylation region functional in plant cells, wherein said DNA sequence coding for a CRL1 protein comprises a nucleotide sequence having at least 90% sequence identity to nt 52-5343 of SEQ ID NO: 2, nt 52-5340 of SEQ ID NO: 4, nt 52-5361 of SEQ ID NO: 6, or to SEQ ID NO: 10; or encoding a protein having an amino acid sequence having at least 90% sequence identity to ID NO: 3, SEQ ID NO: 5, SEQ ID NO: 7, or SEQ ID NO: 11; and wherein said DNA sequence coding for a of CRL2 protein comprises a nucleotide sequence having at least 90% sequence identity to 220-2898 of SEQ ID NO: 8; or encoding a protein having an amino acid sequence having at least 90% sequence identity to SEQ ID NO: 9.

The chimeric gene comprising the sequence coding for a CRL1 protein can be on the same vector as the chimeric gene comprising the sequence coding for a CRL2 protein which can be used for plant transformation. Alternatively, the chimeric gene comprising the sequence coding for a CRL1 protein and the chimeric gene comprising the sequence coding for a CRL2 protein can be on different vectors which can together be used for plant transformation. Plants can either be transformed with the two vectors simultaneously. Alternatively, plants can first be transformed with one of the vectors to create transgenic plants, and said transgenic plants can subsequently be transformed with the other vector.

As used herein a "chimeric gene" refers to a nucleic acid construct which is not normally found in a plant species. A chimeric nucleic acid construct can be DNA or RNA. "Chimeric DNA construct" and "chimeric gene" are used interchangeably to denote a gene in which the promoter or one or more other regulatory regions of the gene are not associated in nature with part or all of the transcribed DNA region, or a gene which is present in a locus in the plant genome in which it does not occur naturally.

"Isolated DNA" as used herein refers to DNA not occurring in its natural genomic context, irrespective of its length and sequence. Isolated DNA can, for example, refer to DNA which is physically separated from the genomic context, such as a fragment of genomic DNA. Isolated DNA can also be an artificially produced DNA, such as a chemically synthesized DNA, or such as DNA produced via amplification reactions, such as polymerase chain reaction (PCR) well-known in the art. Isolated DNA can further refer to DNA present in a context of DNA in which it does not occur naturally. For example, isolated DNA can refer to a piece of DNA present in a plasmid. Further, the isolated DNA can refer to a piece of DNA present in another chromosomal context than the context in which it occurs naturally, such as for example at another position in the genome than the natural position, in the genome of another species than the species in which it occurs naturally, or in an artificial chromosome.

Further, expression of the CRL clubroot resistance gene can be modulated, such as increased by, for example, T-DNA activation tagging, or by targeted genome engineering technologies in which, for example, the endogenous promoter is modified such that it drives higher levels of expression, or in which the endogenous promoter is replaced with a stronger promoter.

Suitable to the invention is a method to produce clubroot free Brassicaceae plants, comprising the steps of sowing seeds from the Brassicaceae plants according to the invention comprising a CRL clubroot resistance gene, growing the plants in the field, optionally spraying the plants with fungicides, and harvesting.

A further object provides the use of the chimeric gene according to the invention to increase clubroot resistance in Brassicaceae, and the use of the plants according to the invention to produce oilseed rape oil or an oilseed rape seed cake, or a seed, or a crop of oilseed rape.

The sequence of the CRL clubroot resistance locus can further be used to develop molecular markers linked to the CRL clubroot resistance locus.

The isolated DNA according to the invention can be used to develop molecular markers for the CRL clubroot resistance locus by developing primers specifically recognizing the CRL clubroot resistance gene. Further, the isolated DNA can be used to identify the genomic sequence flanking the CRL clubroot resistance gene, and develop primers and probes based on the genomic sequences flanking the CRL clubroot resistance gene.

Also provided is a method of producing food, feed, or an industrial product, comprising obtaining the plant according to the invention or a part thereof; and preparing the food, feed or industrial product from the plant or part thereof. In a further object, said food or feed is oil, meal, grain, starch, flour or protein; or said industrial product is biofuel, fiber, industrial chemicals, a pharmaceutical or a nutraceutical.

Further provided is the use of the nucleotide sequence of SEQ ID NO: 1, SEQ ID NO: 2, SEQ ID NO: 4, SEQ ID NO: 6, SEQ ID NO: 8, or SEQ ID NO: 10 or of the amino acid sequence of SEQ ID NO: 3, or SEQ ID NO: 5, or SEQ ID NO: 7, SEQ ID NO: 9, or SEQ ID NO: 11 to identify homologous clubroot resistance genes.

Homologous clubroot resistance genes can be identified using methods known in the art. Homologous nucleotide sequence may be identified and isolated by hybridization under stringent conditions using as probes a nucleic acid comprising the nucleotide sequence of SEQ ID NO: 1, SEQ ID NO: 2, SEQ ID NO: 4, SEQ ID NO: 6, SEQ ID NO: 8, or SEQ ID NO: 10 or part thereof. Other sequences encoding CRL may also be obtained by DNA amplification using oligonucleotides specific for genes encoding CRL as primers, such as but not limited to oligonucleotides comprising or consisting of about 20 to about 50 consecutive nucleotides from SEQ SEQ ID NO: 1, SEQ ID NO: 2, SEQ ID NO: 4, SEQ ID NO: 6, SEQ ID NO: 8, or SEQ ID NO: 10 or its complement. Homologous clubroot resistance genes can be identified in silico using Basic Local Alignment Search Tool (BLAST) homology search with other nucleotide or amino acid sequences. Functionality of the identified homologous clubroot resistance genes can be validated using the methods described herein, such as transforming a the clubroot resistance gene under control of a plant-expressible promoter in a plant not being clubroot resistant.

Also provided is a method of producing food, feed, or an industrial product, comprising obtaining the plant according to the invention or a part thereof; and preparing the food, feed or industrial product from the plant or part thereof. In a further object, said food or feed is oil, meal, grain, starch, flour or protein; or said industrial product is biofuel, fiber, industrial chemicals, a pharmaceutical or a nutraceutical.

"Crop of oilseed rape" as used herein refers to oilseed rape cultivated as a crop, such as *Brassica napus, Brassica juncea, Brassica carinata, Brassica rapa* (syn. *B. campestris*), *Brassica oleracea* or *Brassica nigra*.

The plants according to the invention may additionally contain an endogenous or a transgene, which confers herbicide resistance, such as the bar or pat gene, which confer resistance to glufosinate ammonium (Liberty®, Basta® or Ignite®) [EP 0 242 236 and EP 0 242 246 incorporated by reference]; or any modified EPSPS gene, such as the 2mEPSPS gene from maize [EPO 508 909 and EP 0 507 698 incorporated by reference], or glyphosate acetyltransferase, or glyphosate oxidoreductase, which confer resistance to glyphosate (RoundupReady®), or bromoxynitril nitrilase to confer bromoxynitril tolerance, or any modified AHAS gene, which confers tolerance to sulfonylureas, imidazolinones, sulfonylaminocarbonyltriazolinones, triazolopyrimidines or pyrimidyl(oxy/thio)benzoates, such as oilseed rape imidazolinone-tolerant mutants PM1 and PM2, currently marketed as Clearfield® canola. Further, the plants according to the invention may additionally contain an endogenous or a transgene which confers increased oil content or improved oil composition, such as a 12:0 ACP thioesteraseincrease to obtain high laureate, which confers pollination control, such as such as barnase under control of an anther-specific promoter to obtain male sterility, or barstar under control of an anther-specific promoter to confer restoration of male sterility, or such as the Ogura cytoplasmic male sterility and nuclear restorer of fertility.

The plants and seeds according to the invention may be further treated with a chemical compound, such as a chemical compound selected from the following lists: Herbicides: Clethodim, Clopyralid, Diclofop, Ethametsulfuron, Fluazifop, Glufosinate, Glyphosate, Metazachlor, Quinmerac, Quizalofop, Tepraloxydim, Trifluralin. Fungicides/PGRs: Azoxystrobin, N-[9-(dichloromethylene)-1,2,3,4-tetrahydro-1,4-methanonaphthalen-5-yl]-3-(difluoromethyl)-1-methyl-1H-pyrazole-4-carboxamide (Benzovindiflupyr, Benzodiflupyr), Bixafen, Boscalid, Carbendazim, Carboxin, Chlormequat-chloride, Coniothryrium minitans, Cyproconazole, Cyprodinil, Difenoconazole, Dimethomorph, Dimoxystrobin, Epoxiconazole, Famoxadone, Fluazinam, Fludioxonil, Fluopicolide, Fluopyram, Fluoxastrobin, Fluquinconazole, Flusilazole, Fluthianil, Flutriafol, Fluxapyroxad, Iprodione, Isopyrazam, Mefenoxam, Mepiquatchloride, Metalaxyl, Metconazole, Metominostrobin, Paclobutrazole, Penflufen, Penthiopyrad, Picoxystrobin, Prochloraz, Prothioconazole, Pyraclostrobin, Sedaxane, Tebuconazole, Tetraconazole, Thiophanate-methyl, Thiram, Triadimenol, Trifloxystrobin, *Bacillus firmus, Bacillus firmus* strain I-1582, *Bacillus subtilis, Bacillus subtilis* strain GB03, *Bacillus subtilis* strain QST 713, *Bacillus pumulis, Bacillus. pumulis* strain GB34.

Insecticides: Acetamiprid, Aldicarb, Azadirachtin, Carbofuran, Chlorantraniliprole (Rynaxypyr), Clothianidin, Cyantraniliprole (Cyazypyr), (beta-)Cyfluthrin, gamma-Cyhalothrin, lambda-Cyhalothrin, Cypermethrin, Deltamethrin, Dimethoate, Dinetofuran, Ethiprole, Flonicamid, Flubendiamide, Fluensulfone, Fluopyram, Flupyradifurone, tau-Fluvalinate, Imicyafos, Imidacloprid, Metaflumizone, Methiocarb, Pymetrozine, Pyrifluquinazon, Spinetoram, Spinosad, Spirotetramate, Sulfoxaflor, Thiacloprid, Thiamethoxam, 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide, 1-(3-chloropyridin-2-yl)-N-[4-cyano-2-methyl-6-(methylcarbamoyl) phenyl]-3-{[5-(trifluoromethyl)-1H-tetrazol-1-yl]methyl}-1H-pyrazole-5-carboxamide, 1-{2-fluoro-4-methyl-5-[(2,2,2-trifluorethyl)sulfinyl]phenyl}-3-(trifluoromethyl)-1H-1,2,4-triazol-5-amine, (1E)-N-[(6-chloropyridin-3-yl)methyl]-N'-cyano-N-(2,2-difluoroethyl)ethanimidamide, *Bacillus firmus, Bacillus firmus* strain I-1582, *Bacillus subtilis, Bacillus subtilis* strain GB03, *Bacillus subtilis* strain QST 713, Metarhizium anisopliae F52.

Whenever reference to a "plant" or "plants" according to the invention is made, it is understood that also plant parts (cells, tissues or organs, seed pods, seeds, severed parts such as roots, leaves, flowers, pollen, etc.), progeny of the plants which retain the distinguishing characteristics of the parents (especially the fruit dehiscence properties), such as seed obtained by selfing or crossing, e.g. hybrid seed (obtained by crossing two inbred parental lines), hybrid plants and plant parts derived there from are encompassed herein, unless otherwise indicated.

In some embodiments, the plant cells of the invention, i.e. a plant cell comprising a CRL clubroot resistance gene as well as plant cells generated according to the methods of the invention, may be non-propagating cells.

The obtained plants according to the invention can be used in a conventional breeding scheme to produce more plants with the same characteristics or to introduce the characteristic of the presence of the CRL gene according to the invention in other varieties of the same or related plant species, or in hybrid plants. The obtained plants can further be used for creating propagating material. Plants according to the invention can further be used to produce gametes, seeds (including crushed seeds and seed cakes), seed oil, embryos, either zygotic or somatic, progeny or hybrids of plants obtained by methods of the invention. Seeds obtained from the plants according to the invention are also encompassed by the invention.

"Creating propagating material", as used herein, relates to any means know in the art to produce further plants, plant parts or seeds and includes inter alia vegetative reproduction methods (e.g. air or ground layering, division, (bud) grafting, micropropagation, stolons or runners, storage organs such as bulbs, corms, tubers and rhizomes, striking or cutting, twin-scaling), sexual reproduction (crossing with another plant) and asexual reproduction (e.g. apomixis, somatic hybridization).

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a nucleic acid which is functionally or structurally defined, may comprise additional DNA regions etc.

All patents, patent applications, and publications or public disclosures (including publications on internet) referred to or cited herein are incorporated by reference in their entirety.

The sequence listing contained in the file named "BCS15-2016_ST25.txt", which is 289 kilobytes (size as measured in Microsoft Windows®), contains 176 sequences SEQ ID NO: 1 through SEQ ID NO: 176 is filed herewith by electronic submission and is incorporated by reference herein.

In the description and examples, reference is made to the following sequences:

SEQUENCES

SEQ ID NO: 1: CRL genome sequence
SEQ ID NO: 2: CRL1a coding sequence
SEQ ID NO: 3: CRL1a protein sequence
SEQ ID NO: 4: CRL1b coding sequence
SEQ ID NO: 5: CRL1b protein sequence
SEQ ID NO: 6: CRL1c coding sequence
SEQ ID NO: 7: CRL1c protein sequence
SEQ ID NO: 8: CRL2 coding sequence
SEQ ID NO: 9: CRL2 protein sequence
SEQ ID NO: 10: CRL1d coding sequence
SEQ ID NO: 11: CRL1d protein sequence
SEQ ID NO: 12: Primer 12
SEQ ID NO: 13: Primer 13
SEQ ID NO: 14: Primer 14
SEQ ID NO: 15: Primer 15
SEQ ID NO: 16: Primer 16
SEQ ID NO: 17: Primer 17
SEQ ID NO: 18: Primer 18
SEQ ID NO: 19: Primer 19
SEQ ID NO: 20: Primer 20
SEQ ID NO: 21: Primer 21
SEQ ID NO: 22: Primer 22
SEQ ID NO: 23: Primer 23
SEQ ID NO: 24: Primer 24
SEQ ID NO: 25: Primer 25
SEQ ID NO: 26: Primer 26
SEQ ID NO: 27: Primer 27
SEQ ID NO: 28: Primer 28
SEQ ID NO: 29: Primer 29
SEQ ID NO: 30: Primer 30
SEQ ID NO: 31: Primer 31
SEQ ID NO: 32: Primer 32
SEQ ID NO: 33: Primer 33
SEQ ID NO: 34: Primer 34
SEQ ID NO: 35: Primer 35
SEQ ID NO: 36: Primer 36
SEQ ID NO: 37: Primer 37
SEQ ID NO: 38: Primer 38
SEQ ID NO: 39: Primer 39
SEQ ID NO: 40: Primer 40
SEQ ID NO: 41: Primer 41
SEQ ID NO: 42: Primer 42
SEQ ID NO: 43: Primer 43
SEQ ID NO: 44: Primer 44
SEQ ID NO: 45: Primer 45
SEQ ID NO: 46: Primer 46
SEQ ID NO: 47: Primer 47
SEQ ID NO: 48: Primer 48
SEQ ID NO: 49: Primer 49
SEQ ID NO: 50: Primer 50
SEQ ID NO: 51: Primer 51
SEQ ID NO: 52: Primer 52
SEQ ID NO: 53: Primer 53
SEQ ID NO: 54: Primer 54
SEQ ID NO: 55: Primer 55
SEQ ID NO: 56: Primer 56
SEQ ID NO: 57: Primer 57
SEQ ID NO: 58: Primer 58
SEQ ID NO: 59: Primer 59
SEQ ID NO: 60: Primer 60
SEQ ID NO: 61: Primer 61
SEQ ID NO: 62: Primer 62
SEQ ID NO: 63: Primer 63
SEQ ID NO: 64: Primer 64
SEQ ID NO: 65: Primer 65
SEQ ID NO: 66: Primer 66
SEQ ID NO: 67: Primer 67
SEQ ID NO: 68: Primer 68
SEQ ID NO: 69: Primer 69
SEQ ID NO: 70: Primer 70
SEQ ID NO: 71: Primer 71
SEQ ID NO: 72: Primer 72
SEQ ID NO: 73: Primer 73
SEQ ID NO: 74: Primer 74
SEQ ID NO: 75: Primer 75
SEQ ID NO: 76: Primer 76
SEQ ID NO: 77: Primer 77
SEQ ID NO: 78: Primer 78
SEQ ID NO: 79: Primer 79
SEQ ID NO: 80: Primer 80
SEQ ID NO: 81: Primer 81
SEQ ID NO: 82: Primer 82
SEQ ID NO: 83: Primer 83
SEQ ID NO: 85: Primer 85
SEQ ID NO: 86: Primer 86
SEQ ID NO: 87: Primer 87
SEQ ID NO: 88: Primer 88
SEQ ID NO: 89: Primer 89
SEQ ID NO: 90: Primer 90
SEQ ID NO: 91: Primer 91
SEQ ID NO: 92: Primer 92
SEQ ID NO: 93: Primer 93
SEQ ID NO: 94: Primer 94
SEQ ID NO: 95: Primer 95
SEQ ID NO: 96: Primer 96
SEQ ID NO: 97: Primer 97
SEQ ID NO: 98: Primer 98
SEQ ID NO: 99: Primer 99
SEQ ID NO: 100: Primer 100
SEQ ID NO: 101: Primer 101
SEQ ID NO: 102: Primer 102
SEQ ID NO: 103: Primer 103
SEQ ID NO: 104: Primer 104
SEQ ID NO: 105: Primer 105
SEQ ID NO: 106: Primer 106
SEQ ID NO: 107: Primer 107
SEQ ID NO: 108: Primer 108
SEQ ID NO: 109: Primer 109
SEQ ID NO: 110: Primer 110

SEQ ID NO: 111: Primer 111
SEQ ID NO: 112: Primer 112
SEQ ID NO: 113: Primer 113
SEQ ID NO: 114: Primer 114
SEQ ID NO: 115: Primer 115
SEQ ID NO: 116: Primer 116
SEQ ID NO: 117: Primer 117
SEQ ID NO: 118: Primer 118
SEQ ID NO: 119: Primer 119
SEQ ID NO: 120: Primer 120
SEQ ID NO: 121: Primer 121
SEQ ID NO: 122: Primer 122
SEQ ID NO: 123: Primer 123
SEQ ID NO: 124: Primer 124
SEQ ID NO: 125: Primer 125
SEQ ID NO: 126: Primer 126
SEQ ID NO: 127: Primer 127
SEQ ID NO: 128: Primer 128
SEQ ID NO: 129: Primer 129
SEQ ID NO: 130: Primer 130
SEQ ID NO: 131: Primer 131
SEQ ID NO: 132: Primer 132
SEQ ID NO: 133: Primer 133
SEQ ID NO: 134: Primer 134
SEQ ID NO: 135: Primer 135
SEQ ID NO: 136: Primer 136
SEQ ID NO: 137: Primer 137
SEQ ID NO: 138: Primer 138
SEQ ID NO: 139: Primer 139
SEQ ID NO: 140: Primer 140
SEQ ID NO: 141: Primer 141
SEQ ID NO: 142: Primer 142
SEQ ID NO: 143: Primer 143
SEQ ID NO: 144: Primer 144
SEQ ID NO: 145: Primer 145
SEQ ID NO: 146: Primer 146
SEQ ID NO: 147: Primer 147
SEQ ID NO: 148: Primer 148
SEQ ID NO: 149: Primer 149
SEQ ID NO: 150: Primer 150
SEQ ID NO: 151: Primer 151
SEQ ID NO: 152: Primer 152
SEQ ID NO: 153: Primer 153
SEQ ID NO: 154: Primer 154
SEQ ID NO: 155: Primer 155
SEQ ID NO: 156: Primer 156
SEQ ID NO: 157: Primer 157
SEQ ID NO: 158: Primer 158
SEQ ID NO: 159: Primer 159
SEQ ID NO: 160: Primer 160
SEQ ID NO: 161: Primer 161
SEQ ID NO: 162: Primer 162
SEQ ID NO: 163: Primer 163
SEQ ID NO: 164: Primer 164
SEQ ID NO: 165: Primer 165
SEQ ID NO: 166: Primer 166
SEQ ID NO: 167: Primer 167
SEQ ID NO: 168: Primer 168
SEQ ID NO: 169: Primer 169
SEQ ID NO: 170: Primer 170
SEQ ID NO: 171: Primer 171
SEQ ID NO: 172: Primer 172
SEQ ID NO: 173: Primer 173
SEQ ID NO: 174: Primer 174
SEQ ID NO: 175: Primer 175
SEQ ID NO: 176: Primer 176

EXAMPLES

Unless stated otherwise in the Examples, all recombinant DNA techniques are carried out according to standard protocols as described in Sambrook and Russell (2001) Molecular Cloning: A Laboratory Manual, Third Edition, Cold Spring Harbor Laboratory Press, NY, in Volumes 1 and 2 of Ausubel et al. (1994) Current Protocols in Molecular Biology, Current Protocols, USA and in Volumes I and II of Brown (1998) Molecular Biology LabFax, Second Edition, Academic Press (UK). Standard materials and methods for plant molecular work are described in Plant Molecular Biology Labfax (1993) by R. D. D. Croy, jointly published by BIOS Scientific Publications Ltd (UK) and Blackwell Scientific Publications, UK. Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Example 1—Rough Mapping of Clubroot Resistance by GGGT Analysis

Generation of Mapping Population

A DH population was made by microspore regeneration from the F1 cross between a resistant female parent and a susceptible male parent. The population consisted of 106 DH individuals.

Golden Gate Genotyping (iSCAN 1536-GGGT) Analysis

DNA Extraction.

DNA was extracted from 106 DH plants and the 2 corresponding parents (resistant female parent and susceptible male parent) using the automated KingFisher DNA extraction method (Thermo Scientific) using the manufacturer's purification kits and protocol.

GGGT Analysis.

A custom Illumina GoldenGate BeadArray was designed by evaluating individual loci with the Illumina Assay Design Tool (ADT) and selecting most successful custom genotyping assays (score>0.6 (Hyten et al., 2008, Theor Appl Genet 116:945)). A custom 1536 single nucleotide polymorphism (SNP) Oligonucleotide Pool Assay was selected.

Assays were performed as described by the manufacturer's protocol and as described in Fan et al., 2003, Cold Spring Harb Symp Quant Biol 68:69. A total of 250 ng (50 ng/µl) of genomic DNA was used to make single-use DNA. The single-use DNA underwent an allele specific oligonucleotide hybridization, which involves three oligos at each of the 1536 different SNP loci. At each SNP locus, two of the oligos are allele-specific oligos that are complementary to the genomic sequence directly adjacent to the SNP being assayed except they differ at the 3' base in order to be complementary with one of the two SNP alleles and each oligo has a universal primer site attached at the 5' end with one allele for each SNP having universal primer site. Amplification over the oligo region involves three primers, the two allele specific primers having either a Cy3- or Cy5-label allowing allele specific detection after excitation by lasers emitting at 532 nm and 635 nm. A genotype that is homozygous for one SNP allele will display a signal in either the Cy3 or the Cy5 channel, whereas a genotype that is heterozygous will display a signal in both channels. The Locus Specific oligo is labelled with biotin and contains the "IllumniCode" sequence which is unique to each SNP locus.

It is the IllumniCode that binds to its complementary sequence attached to a bead on the sentrix array matrix (SAM).

The hybridised SAM was analysed on the Illumina iSCAN system (array reader) using the iScan Control Software (ICS). After images are scanned, they are registered according to the corresponding bead map (*.dmap) file and two-colour signal intensity values are extracted for every bead on the image (*.idat). By default, the ICS AutoConvert was enabled, normalising the intensity data and generating genotype calls.

Analysis of BeadArray idat files was performed using GenomeStudio™ Data Analysis Software (GenomeStudio Software V2011.1 (Illumina)). Primary data analyses, such as raw data normalization, clustering, and genotype calling are performed using integrated algorithms (GenTrain & GenCall) in the GenoTyping (GT) Module. Genotype calls are made from BeadChip marker two-colour signal intensities by comparison to canonical genotype clusters. Cluster position identification is performed by the GenTrain algorithm. With one sample precluded due to failed DNA extraction no further poorly performing samples were identified so further sample removal and reclustering of all SNPs was not required. Never-the-less the position of SNP clusters required editing by visualising the Cy3 and Cy5 fluorescence intensity clustering in 2D Cartesian plots and re-centring the clusters. The refined genotype calls were scrutinised further before exporting genotype calls knowing that the parents and the lines of this population were doubled haploids and so any SNPs that failed to show only two-group clustering were not credible: SNPs with more than two call clustered were set to 'no-call'.

Phenotyping of DH Plants
a) Choice of the Isolates

The isolate used was obtained from the University of Alberta, AB, Canada. The University collected it from Leduc, Alberta Canada. It was single spored and named Leduc ss2 which was characterized as Pathotype 6 by Xue et. Al. (Xue et al. 2008. Isolation and variation of single spore isolates of *Plasmodiophora brassicae* from Canada, Plant Dis. 92:456-462, Strelkov et. el. 2006. Characterization of *Plasmodiophora brassicae* populations from Alberta, Canada. Can. J. Plant Pathol. 28:467-474).

b) Phenotyping of the DH Population

106 DH lines with a sufficient amount of seeds have been phenotyped for Clubroot disease resistance by inoculation with isolate Leduc ss2 and disease ratings on a 1-3 scale.

Genetic Map and QTL Analysis

A total of 363 polymorphic SNP marker instances were observed over the individuals of the DH mapping population (1022 markers were monomorphic and 151 markers produced no calls). Additionally, in this DH1 (a doubled haploid population produced from the gametes of the F1 of a cross between two homozygous diploid parents) population, the Clubroot Resistance phenotype was scored as with the sensitive parent allele 'A' and the resistant parent allele 'B', allowing this score to be treated as though it was a marker. Genetic linkage mapping was performed using JoinMap® 3.0 software (Van Ooijen, J. W. and R. E. Voorrips, 2001, JoinMap® 3.0 software for the calculation of genetic linkage maps. Plant Research International, Wageningen, Netherlands).

Linked marker genotype groupings were identified by examining the Lod-grouping tree results that ranged from Lod3.0 to Lod10. With groups of linked markers identified, ordering of the markers was performed using the default calculation options, with the 3rd round option and using the Kosambi mapping function.

Additional Markers Added to Rough Mapping 96 additional KASP markers were genotyped on the rough mapping population. No recombination point was observed based on these additional markers. Based on the marker sequences the genomic region comprising the CRL clubroot resistance gene was identified.

Example 2—Fine Mapping of Clubroot Resistance Using SNP Marker Analysis

An F2 population of 1000 individuals originating from the F1 cross between the resistant female parent and the susceptible male parent was obtained. 1000 F2 plants were genotyped together with the parents using 96 KASP markers located at the bottom of NO2 using the Fluidigm platform. 74 markers were mapped. Two markers defining the border were identified (markers mBRS00013411 and mBRS00013511; see Table 2). 6 markers between the border gave no call in the susceptible parent, whereas they gave a call in the resistant parent (markers mBRS00013440, mBRS00154152, mBRS00013441, mBRS00013442, mBRS00161831, and mBRS00174679; see Table 2), indicating the absence of a region between the flanking markers in the susceptible parent. After finemapping the plotted region of interest (present in the resistant parent but absent in the susceptible parent) comprising the CRL gene has been defined as a 563 kb region.

TABLE 2

Markers linked to CRL clubroot resistance and susceptibility and primer combinations for detecting of these markers. R = Resistant line; S = Susceptible line. The polymorphic base detected by Primer 1 and indicated with R is the marker allele present in the resistant line (CRL clubroot resistance marker allele); the polymorphic base detected by Primer 2 and indicated with S is the marker allele present in the susceptible line (CRL clubroot susceptibility marker allele). None: the polymorphic base is not present in the resistant line and is not present in the susceptible line.

| Marker | Primers | Polymorphic base | Allele in R/S | SEQ ID NO: |
|---|---|---|---|---|
| mBRS00013411 | Primer 1 | C | R | 12 |
|  | Primer 2 | T | S | 13 |
|  | common primer | — | Common | 14 |
| mBRS00013412 | Primer 1 | C | R | 15 |
|  | Primer 2 | T | S | 16 |
|  | common primer | — | Common | 17 |
| mBRS00013414 | Primer 1 | C | R | 18 |
|  | Primer 2 | G | S | 19 |
|  | common primer | — | Common | 20 |
| mBRS00013415 | Primer 1 | T | R | 21 |
|  | Primer 2 | G | S | 22 |
|  | common primer | — | Common | 23 |
| mBRS00003251 | Primer 1 | T | R | 24 |
|  | Primer 2 | C | S | 25 |
|  | common primer | — | Common | 26 |
| mBRS00013416 | Primer 1 | A | R | 27 |
|  | Primer 2 | G | S | 28 |
|  | common primer | — | Common | 29 |
| mBRS00013417 | Primer 1 | A | R | 30 |
|  | Primer 2 | T | S | 31 |
|  | common primer | — | Common | 32 |
| mBRS00143666 | Primer 1 | G | R | 33 |
|  | Primer 2 | A | S | 34 |
|  | common primer | — | Common | 35 |
| mBRS00013418 | Primer 1 | T | R | 36 |
|  | Primer 2 | C | S | 37 |
|  | common primer | — | Common | 38 |

TABLE 2-continued

Markers linked to CRL clubroot resistance and susceptibility and primer combinations for detecting of these markers. R = Resistant line; S = Susceptible line. The polymorphic base detected by Primer 1 and indicated with R is the marker allele present in the resistant line (CRL clubroot resistance marker allele); the polymorphic base detected by Primer 2 and indicated with S is the marker allele present in the susceptible line (CRL clubroot susceptibility marker allele). None: the polymorphic base is not present in the resistant line and is not present in the susceptible line.

| Marker | Primers | Polymorphic base | Allele in R/S | SEQ ID NO: |
|---|---|---|---|---|
| mBRS00013421 | Primer 1 | T | R | 39 |
| | Primer 2 | A | S | 40 |
| | common primer | — | Common | 41 |
| mBRS00006010 | Primer 1 | T | R | 42 |
| | Primer 2 | G | S | 43 |
| | common primer | — | Common | 44 |
| mBRS00139820 | Primer 1 | A | R | 45 |
| | Primer 2 | C | S | 46 |
| | common primer | — | Common | 47 |
| mBRS00013422 | Primer 1 | A | R | 48 |
| | Primer 2 | G | S | 49 |
| | common primer | — | Common | 50 |
| mBRS00152839 | Primer 1 | A | R | 51 |
| | Primer 2 | T | S | 52 |
| | common primer | — | Common | 53 |
| mBRS00007859 | Primer 1 | G | R | 54 |
| | Primer 2 | A | S | 55 |
| | common primer | — | Common | 56 |
| mBRS00013424 | Primer 1 | A | R | 57 |
| | Primer 2 | G | S | 58 |
| | common primer | — | Common | 59 |
| mBRS00007860 | Primer 1 | T | R | 60 |
| | Primer 2 | C | S | 61 |
| | common primer | — | Common | 62 |
| mBRS00013426 | Primer 1 | C | R | 63 |
| | Primer 2 | T | S | 64 |
| | common primer | — | Common | 65 |
| mBRS00013427 | Primer 1 | G | R | 66 |
| | Primer 2 | A | S | 67 |
| | common primer | — | Common | 68 |
| mBRS00013428 | Primer 1 | A | R | 69 |
| | Primer 2 | T | S | 70 |
| | common primer | — | Common | 71 |
| mBRS00159860 | Primer 1 | A | R | 72 |
| | Primer 2 | G | S | 73 |
| | common primer | — | Common | 74 |
| mBRS00013429 | Primer 1 | T | R | 75 |
| | Primer 2 | C | S | 76 |
| | common primer | — | Common | 77 |
| mBRS00013431 | Primer 1 | T | R | 78 |
| | Primer 2 | C | S | 79 |
| | common primer | — | Common | 80 |
| mBRS00013432 | Primer 1 | A | R | 81 |
| | Primer 2 | C | S | 82 |
| | common primer | — | Common | 83 |
| mBRS00013433 | Primer 1 | T | R | 84 |
| | Primer 2 | C | S | 85 |
| | common primer | — | Common | 86 |
| mBRS01078993 | Primer 1 | A | R | 87 |
| | Primer 2 | G | S | 88 |
| | common primer | — | Common | 89 |
| mBRS00144440 | Primer 1 | T | R | 90 |
| | Primer 2 | A | S | 91 |
| | common primer | — | Common | 92 |
| mBRS00013434 | Primer 1 | G | R | 93 |
| | Primer 2 | C | S | 94 |
| | common primer | — | Common | 95 |
| mBRS00013435 | Primer 1 | T | R | 96 |
| | Primer 2 | A | None | 97 |
| | common primer | — | Common | 98 |
| mBRS00013436 | Primer 1 | T | R | 99 |
| | Primer 2 | A | S | 100 |
| | common primer | — | Common | 101 |
| mBRS00013437 | Primer 1 | T | R | 102 |
| | Primer 2 | A | S | 103 |
| | common primer | — | Common | 104 |
| mBRS00013438 | Primer 1 | T | R | 105 |
| | Primer 2 | G | S | 106 |
| | common primer | — | Common | 107 |
| mBRS00147882 | Primer 1 | T | R | 108 |
| | Primer 2 | C | S | 109 |
| | common primer | — | Common | 110 |
| mBRS00158190 | Primer 1 | T | R | 111 |
| | Primer 2 | A | S | 112 |
| | common primer | — | Common | 113 |
| mBRS00175448 | Primer 1 | T | R | 114 |
| | Primer 2 | A | S | 115 |
| | common primer | — | Common | 116 |
| mBRS00013440 | Primer 1 | A | R | 117 |
| | Primer 2 | C | None | 118 |
| | common primer | — | Common | 119 |
| mBRS00154152 | Primer 1 | C | R | 120 |
| | Primer 2 | G | None | 121 |
| | common primer | — | Common | 122 |
| mBRS00013441 | Primer 1 | T | R | 123 |
| | Primer 2 | C | None | 124 |
| | common primer | — | Common | 125 |
| mBRS00013442 | Primer 1 | T | R | 126 |
| | Primer 2 | A | None | 127 |
| | common primer | — | Common | 128 |
| mBRS00161831 | Primer 1 | C | R | 129 |
| | Primer 2 | T | None | 130 |
| | common primer | — | Common | 131 |
| mBRS00013444 | Primer 1 | A | R | 132 |
| | Primer 2 | C | S | 133 |
| | common primer | — | Common | 134 |
| mBRS00174679 | Primer 1 | C | R | 135 |
| | Primer 2 | T | None | 136 |
| | common primer | — | Common | 137 |
| mBRS00013446 | Primer 1 | C | R | 138 |
| | Primer 2 | T | S | 139 |
| | common primer | — | Common | 140 |
| mBRS00013450 | Primer 1 | C | R | 141 |
| | Primer 2 | A | S | 142 |
| | common primer | — | Common | 143 |
| mBRS00013451 | Primer 1 | G | R | 144 |
| | Primer 2 | A | S | 145 |
| | common primer | — | Common | 146 |
| mBRS00159719 | Primer 1 | T | R | 147 |
| | Primer 2 | C | S | 148 |
| | common primer | — | Common | 149 |
| mBRS00011851 | Primer 1 | C | R | 150 |
| | Primer 2 | A | S | 151 |
| | common primer | — | Common | 152 |
| mBRS00013453 | Primer 1 | G | R | 153 |
| | Primer 2 | C | S | 154 |
| | common primer | — | Common | 155 |
| mBRS00013456 | Primer 1 | C | R | 156 |
| | Primer 2 | G | S | 157 |
| | common primer | — | Common | 158 |
| mBRS01079015 | Primer 1 | T | R | 159 |
| | Primer 2 | G | S | 160 |
| | common primer | — | Common | 161 |
| mBRS00013459 | Primer 1 | G | R | 162 |
| | Primer 2 | C | S | 163 |
| | common primer | — | Common | 164 |
| mBRS00153607 | Primer 1 | G | R | 165 |
| | Primer 2 | A | S | 166 |
| | common primer | — | Common | 167 |
| mBRS00013497 | Primer 1 | C | R | 168 |
| | Primer 2 | A | None | 169 |
| | common primer | — | Common | 170 |

TABLE 2-continued

Markers linked to CRL clubroot resistance and susceptibility and primer combinations for detecting of these markers. R = Resistant line; S = Susceptible line. The polymorphic base detected by Primer 1 and indicated with R is the marker allele present in the resistant line (CRL clubroot resistance marker allele); the polymorphic base detected by Primer 2 and indicated with S is the marker allele present in the susceptible line (CRL clubroot susceptibility marker allele). None: the polymorphic base is not present in the resistant line and is not present in the susceptible line.

| Marker | Primers | Polymorphic base | Allele in R/S | SEQ ID NO: |
|---|---|---|---|---|
| mBRS00013499 | Primer 1 | A | R | 171 |
|  | Primer 2 | C | S | 172 |
|  | common primer | — | Common | 173 |
| mBRS00013511 | Primer 1 | C | R | 174 |
|  | Primer 2 | T | S | 175 |
|  | common primer | — | Common | 176 |

Example 3—Identification of Clubroot Resistance Genes

Identification of Syntenic Region in *B. napus*

The DNA sequence of the part of the pseudochromosome between the closest flanking markers of a *B. rapa* line, was blasted against the genome sequence scaffolds of the resistant female parent. The genome sequence between the flanking markers of the resistant female parent is shown in SEQ ID NO: 1. SEQ ID NO: 1 contains two putative genes with a CC-NBS-LRR domain or disease resistance classification (CRL1 and CRL2, respectively), wherein four different splice variants exist for CRL1 (CRL1a, CRL1b, CRL1c, and CRL1d respectively). The cDNA sequences of the CRL1a, CRL1b, CRL1c, CRL1d, and CRL2 genes are shown in SEQ ID NO: 2, SEQ ID NO: 4, SEQ ID NO: 6, SEQ ID NO: 10, and SEQ ID NO: 8, respectively. The coding sequences of CRL1a, CRL1b, CRL1c, CRL1d, and CRL2 are at nt 52-5343 of SEQ ID NO: 2, nt 52-5340 of SEQ ID NO: 4, nt 52-5361 of SEQ ID NO: 6, nt 1-5259 of SEQ ID NO: 10, and nt 220-2898 of SEQ ID NO: 8, respectively. The encoded CRL1a, CRL1b, CRL1c, CRL1d, and CRL2 proteins are shown in SEQ ID NO: 3, SEQ ID NO: 5, SEQ ID NO: 7, SEQ ID NO: 11, and SEQ ID NO: 9, respectively. The CRL1b splicing variant was most abundant, followed by the CRL1a splicing variant. The CRL1c and CRL1d splicing variants were the least abundant.

Seeds of *B. napus* comprising the CRL clubroot resistance locus have been deposited at the NCIMB (NCIMB Ltd, Ferguson Building, Craibstone Estate, Bucksburn, Aberdeen AB21 9YA, Scotland, UK) on 7 Dec. 2015, under accession number NCIMB 42499 and on 22 Jul. 2016, under accession number NCIMB 42610.

Validation of Clubroot R Genes

Mutations in the CRL1 and CRL2 genes of *Brassica napus* identified in Example 3 were generated and identified as follows:

30,000 seeds from an elite spring oilseed rape breeding line (M0 seeds) were pre-imbibed for 2 h on wet filter paper in deionized or distilled water. Half of the seeds were exposed to 0.8% EMS and half to 1% EMS (Sigma: M0880) and incubated for 4 h.

The mutagenized seeds (M1 seeds) were rinsed three times and dried in a fume hood overnight. 30,000 M1 plants were grown in soil and selfed to generate M2 seeds. M2 seeds were harvested for each individual M1 plant.

Two times 4800 M2 plants, derived from different M1 plants, were grown and DNA samples were prepared from leaf samples of each individual M2 plant according to the CTAB method (Doyle and Doyle, 1987, Phytochemistry Bulletin 19:11-15).

The DNA samples were screened for the presence of point mutations in the CRL1 and CRL2 genes that cause the introduction of STOP codons and another amino acid in the protein-encoding regions of the CRL1 and CRL2 genes, by direct sequencing by standard sequencing techniques (LGC) and analyzing the sequences for the presence of the point mutations using the NovoSNP software (VIB Antwerp).

The mutant CRL1 and CRL2 alleles as depicted in Table 3 were thus identified.

Table 3: STOP codon mutations in CRL1 and CRL2

TABLE 3a

| | | mutations in CRL1 | | | |
|---|---|---|---|---|---|
| Plant name | Nt pos in SEQ ID NO: 1 | Nt pos cDNA (SEQ ID NO) | AA pos. (SEQ ID NO) | WT → mut codon | WT → mut AA |
| CLUB301 | 33323 | 574 (2) | 175 (3) | C<u>A</u>A→<u>T</u>AA | Q→STOP |
|  |  | 574 (4) | 175 (4) |  |  |
|  |  | 574 (6) | 175 (5) |  |  |
| CLUB202 | 44587 | 3371 (2) | 1107 (3) | TG<u>G</u>→T<u>A</u>G | W→STOP |
|  |  | 3368 (4) | 1106 (5) |  |  |
|  |  | 3389 (6) | 1113 (7) |  |  |
| CLUB101 | 49414 | 4060 (2) | 1337 | C<u>G</u>A→T<u>G</u>A | R→STOP |
|  |  | 4057 (4) | 1336 |  |  |
|  |  | 4078 (6) | 1343 |  |  |

TABLE 3b

| | | mutations in CRL2 | | | |
|---|---|---|---|---|---|
| Plant name | Nt pos in SEQ ID NO: 1 | Nt pos cDNA SEQ ID NO: 6 | AA pos. SEQ ID NO: 7 | WT → mut codon | WT → mut AA |
| CLUB401 | 3992 | 848 | 210 | TG<u>G</u>→T<u>A</u>G | W→STOP |

Plants comprising the CLUB301, CLUB202, CLUB101 or CLUB401 mutation were analyzed for loss of resistance to *Plasmodiophora brassicae* pathotype 6.

Briefly, between 15 and 30 plants were grown for each homozygous mutant and corresponding wild type segregant. Plants were inoculated with Pathotype6 and disease symptoms on roots were rated 32 days post inoculation using a 0-3 rating scale. A Disease Index (DI) was calculated:
0=no galling
1=a few small galls on ⅓ of the roots
2=moderate galling on ⅓ to ⅔ of the roots
3=severe galling on more than ⅔ of the roots $$DI(\%) = \frac{\sum(n \times 0 + n \times 1 + n \times 2 + n \times 3)}{N \times 3} \times 100\%$$

Where Σ is the sum total; n is the number of plants in a class; N is the total number fo plants; and 0, 1, 2, and 3 are the symptom severity classes.

Each one of the four mutations lead to loss of resistance to *Plasmodiophora brassicae* pathotype 6. These results show that both the CRL1 and the CRL2 genes are required for clubroot resistance.

The CRL1a, CRL1, CRL1c, CRL1d, and CRL2 coding sequences are cloned under control of a constitutive 35S promoter, and under control of their native promoters in a T-DNA expression vector. The genomic region comprising the CRL1a, CRL1b, CRL1c, and CRL1d cDNAs, i.e. nt 32750 to 51049 of SEQ ID NO: 1, is also cloned under control of a constitutive 35S promoter and under control of its native promoter in a T-DNA expression vector. The genomic region comprising the CRL1 and CRL2 coding sequences of SEQ ID NO: 1 is cloned under the control of a in a T-DNA expression vector. All T-DNA expression vectors comprise a selectable marker. The resulting vectors are transformed in *Brassica napus* cv. Westar, which is susceptible to clubroot, using the hypocotyl transformation protocol essentially as described by De Block et al. (1989), Plant Physiol. 91: 694. The copy number of the transgene in the transgenic plant is determined by real time PCR on the bar gene. The transformed plants with comprising the CRL1 and CRL2 genes, or the CRL1a, CRL1b, CRL1c, or CRL1d, and CRL2 coding sequences as transgene show increased clubroot resistance as compared to *Brassica napus* cv. Westar plants not comprising the CRL1 and CRL2 gene as transgene.

Example 4—Transfer of CRL1 and CRL2 into Other Brassicaceae Lines

The CRL1 and CRL2 genes are transferred into Brassicaceae breeding lines by the following method: A plant containing the CRL1 and CRL2 genes (donor plant), is crossed with a Brassicaceae line (elite parent/recurrent parent) or variety lacking the CRL1 and CRL2 genes. The following introgression scheme is used, wherein the presence of the CRL1 and CRL2 genes is indicated with CRL, and the absence of the CRL gene is indicated with:

Initial cross: CRL/CRL (donor plant) X−/− (elite parent)
F1 plant: CRL/−
BC1 cross: CRL/−X−/− (recurrent parent)
BC1 plants: 50% CRL/− and 50%−/−
The 50% CRL/− are selected using molecular markers (e.g. AFLP, PCR, Invader™, KASP, such as the markers of Table 2, and the like) for the presence of the CRL gene.
Further backcrosses can be performed. Upon one or more steps of backcrossing (BCx), backcrossed plants heterozygous for CRL are selfed:
BCx 51 cross: CRL/− X CRL/−
BCx 51 plants: 25% CRL/CRL and 50% CRL/− and 25%−/−
Plants containing CRL are selected using molecular markers, such as the markers of Table 2, for the linked with the CRL gene. Individual BCx 51 plants that are homozygous for CRL (CRL/CRL) are selected using molecular markers linked with CRL, such as the markers of Table 2. These plants can then be used for seed production.

The invention claimed is:

1. A method for increasing clubroot resistance in a *Brassica* plant comprising: introducing a CRL clubroot resistance locus in said *Brassica* plant, and selecting said CRL clubroot resistant *Brassica* plant for the presence of the CRL clubroot resistance locus by analyzing genomic DNA from said plant for the presence of at least one molecular marker, wherein said at least one molecular marker is linked to the CRL clubroot resistance locus, wherein said CRL clubroot resistance locus comprises the CRL1 and CRL2 clubroot resistance genes, wherein
   a) said CRL1 clubroot resistance gene comprises a nucleotide sequence
      i) having at least 95% sequence identity to the sequence of nucleotide positions 32750 to 51049 of SEQ ID NO: 1;
      ii) having a coding sequence having at least 95% sequence identity to the sequence of nucleotide positions 52 to 5343 of SEQ ID NO: 2, nucleotide positions 52 to 5340 of SEQ ID NO: 4, nucleotide positions 52 to 5361 of SEQ ID NO: 6, or to SEQ ID NO: 10; or
      ii) encoding a protein having at least 95% sequence identity to SEQ ID NO: 3, SEQ ID NO: 5, SEQ ID NO: 7, or SEQ ID NO: 11; and
   b) said CRL2 clubroot resistance gene comprises a nucleotide sequence having at least 95% sequence identity to the sequence of nucleotide positions 220 to 2898 of SEQ ID NO: 8, or encoding a protein having at least 95% sequence identity to SEQ ID NO: 9.

2. A method for producing a clubroot resistant *Brassica* plant comprising:
   introducing a CRL clubroot resistance locus in said *Brassica* plant, and selecting said CRL clubroot resistant *Brassica* plant for the presence of the CRL clubroot resistance locus by analyzing genomic DNA from said plant for the presence of at least one molecular marker, wherein said at least one molecular marker is linked to the CRL clubroot resistance locus, wherein said CRL clubroot resistance locus comprises the CRL1 and CRL2 clubroot resistance genes, wherein
   a) said CRL1 clubroot resistance gene comprises a nucleotide sequence
      i) having at least 95% sequence identity to the sequence of nucleotide positions 32750 to 51049 of SEQ ID NO: 1;
      ii) having a coding sequence having at least 95% sequence identity to the sequence of nucleotide positions 52 to 5343 of SEQ ID NO: 2, nucleotide positions 52 to 5340 of SEQ ID NO: 4, nucleotide positions 52 to 5361 of SEQ ID NO: 6, or to SEQ ID NO: 10; or
      iii) encoding a protein having at least 95% sequence identity to SEQ ID NO: 3, SEQ ID NO: 5, SEQ ID NO: 7, or SEQ ID NO: 11; and
   b) said CRL2 clubroot resistance gene comprises a nucleotide sequence having at least 95% sequence identity to the sequence of nucleotide positions 220 to 2898 of SEQ ID NO: 8; or encoding a protein having at least 95% sequence identity to SEQ ID NO: 9; and
   generating progeny from the clubroot resistant *Brassica* plant comprising the CRL clubroot resistance locus, wherein said progeny is clubroot resistant and comprises said CRL clubroot resistance locus.

3. The method according to claim 2, wherein said CRL clubroot resistance locus comprises a sequence having at least 95% sequence identity to SEQ ID NO: 1.

4. A *Brassica* plant or plant cell comprising a CRL1 and a CRL2 clubroot resistance gene as transgene, wherein
   a) said CRL1 clubroot resistance gene
      (i) comprises a coding sequence having at least 95% sequence identity to the sequence of nucleotide positions 52 to 5343 of SEQ ID NO: 2, nucleotide positions 52 to 5340 of SEQ ID NO: 4, nucleotide positions 52 to 5361 of SEQ ID NO: 6, or to SEQ ID NO: 10; or (ii) encodes a protein having an amino acid sequence having at least 95% sequence identity to SEQ ID NO: 3, SEQ ID NO: 5, SEQ ID NO: 7, or SEQ ID NO: 11; and
   b) said CRL2 clubroot resistance gene comprises a coding sequence having at least 95% sequence identity to the sequence of nucleotide positions 220 to 2898 of SEQ ID NO: 8, or encodes a protein having an amino acid sequence having at least 95% sequence identity to SEQ ID NO: 9.

5. The *Brassica* plant or plant cell of claim 4, wherein said CRL1 clubroot resistance gene comprises a sequence having at least 95% sequence identity to the sequence of nucleotide positions 32750 to 51049 of SEQ ID NO: 1.

6. The *Brassica* plant or plant cell of claim 4, comprising a transgene comprising a sequence having at least 95% sequence identity to SEQ ID NO: 1.

7. A method for increasing clubroot resistance in a *Brassica* plant, comprising:
   a) providing a CRL1 and a CRL2 clubroot resistance gene as transgene, b) introducing the CRL1 and CLR2 gene into a *Brassica* plant cell, to create transgenic cells; and
   c) regenerating transgenic plants from said transgenic cells; wherein
   said CRL1 clubroot resistance gene i) comprises a coding sequence having at least 95% sequence identity to the sequence of nucleotide positions 52 to 5343 of SEQ ID NO: 2, nucleotide positions 52 to 5340 of SEQ ID NO: 4, nucleotide positions 52 to 5361 of SEQ ID NO: 6, or to SEQ ID NO: 10; or ii) encodes a protein having an amino acid sequence having at least 95% sequence identity to SEQ ID NO: 3, SEQ ID NO: 5, SEQ ID NO: 7, or SEQ ID NO: 11; and wherein
   said CRL2 clubroot resistance gene comprises a nucleotide sequence having a coding sequence having at least 95% sequence identity to the sequence of nucleotide positions 220 to 2898 of SEQ ID NO: 8, or encodes a protein having at least 95% sequence identity to SEQ ID NO: 9.

8. A clubroot resistant *Brassica* plant or plant cell obtainable by the method according to claim 2, said plant or plant cell further comprising at least one other disease resistance gene, said other disease resistance gene is a clubroot resistance gene, a blackleg resistance gene, a *Sclerotinia* resistance gene, a *Verticillium* resistance gene, a *Fusarium* resistance gene, an Aster Yellows resistance gene, an Altemaria resistance gene, or a Grey Stem resistance gene; wherein said other disease resistance gene is a transgene which is genetically linked with said CRL clubroot resistance gene or said clubroot resistance locus.

9. A chimeric gene comprising the following operably linked elements:
   a) a heterologous plant-expressible promoter;
   b) a DNA sequence coding for a CRL1 or for a CRL2 protein; and c) optionally, a transcription termination and polyadenylation region functional in plant cells, wherein
a) said DNA sequence coding for a CRL1 protein comprises a nucleotide sequence i) having at least 95% sequence identity to the sequence of nucleotide positions 52 to 5343 of SEQ ID NO: 2, nucleotide positions of 52 to 5340 of SEQ ID NO: 4, nucleotide positions of 52 to 5361 of SEQ ID NO: 6, or to SEQ ID NO: 10; or ii) encoding a protein having an amino acid sequence having at least 95% sequence identity to SEQ ID NO: 3, SEQ ID NO: 5, SEQ ID NO: 7, or SEQ ID NO: 11; and
b) said DNA sequence coding for a CRL2 protein comprises a nucleotide sequence having at least 95% sequence identity to the sequence of nucleotide positions 220 to 2898 of SEQ ID NO: 8; or encoding a protein having an amino acid sequence having at least 95% sequence identity to SEQ ID NO: 9.

10. A method to produce clubroot free *Brassica* plants, comprising sowing seeds from the plants of claim 4, and growing plants from said seeds.

11. A method of producing food, feed, or an industrial product comprising providing the *Brassica* plant or plant cell of claim 4, and preparing food, feed or industrial product from the plant or plant cell.

12. The method of claim 11 wherein
a) the food or feed is oil, meal, grain, starch, flour or protein; or
b) the industrial product is biofuel, fiber, industrial chemicals, a pharmaceutical or a nutraceutical.

13. The method according to claim 1, wherein said CRL1 clubroot resistance gene comprises a nucleotide sequence
said CRL1 clubroot resistance gene comprises a nucleotide sequence
i) having at least 98% sequence identity to the sequence of nucleotide positions 32750 to 51049 of SEQ ID NO: 1;
ii) having a coding sequence having at least 98% sequence identity to the sequence of nucleotide positions 52 to 5343 of SEQ ID NO: 2, nucleotide positions 52 to 5340 of SEQ ID NO: 4, nucleotide positions 52 to 5361 of SEQ ID NO: 6, or to SEQ ID NO: 10; and
iii) encoding a protein having at least 98% sequence identity to SEQ ID NO: 3, SEQ ID NO: 5, SEQ ID NO: 7, or SEQ ID NO: 11; and
b) said CRL2 clubroot resistance gene comprises a nucleotide sequence
having a coding sequence having at least 98% sequence identity to the sequence of nucleotide positions 220 to 2898 of SEQ ID NO: 8, or encoding a protein having an amino acid sequence having at least 98% sequence identity to SEQ ID NO: 9.

14. The method according to claim 2, wherein said CRL clubroot resistance locus comprises a sequence having at least 98% sequence identity to SEQ ID NO: 1.

15. The *Brassica* plant or plant cell of claim 4, wherein said CRL1 clubroot resistance gene
i) comprises a coding sequence having at least 98% sequence identity to the sequence of nucleotide positions 52 to 5343 of SEQ ID NO: 2, nucleotide positions 52 to 5340 of SEQ ID NO: 4, nucleotide positions 52 to 5361 of SEQ ID NO: 6, or to SEQ ID NO: 10; or
(ii) encodes a protein having an amino acid sequence having at least 98% sequence identity to SEQ ID NO: 3, SEQ ID NO: 5, SEQ ID NO: 7, or SEQ ID NO: 9; and
said CRL.2 clubroot resistance gene
comprises a coding sequence having at least 98% sequence identity to the sequence of nucleotide positions 220 to 2898 of SEQ ID NO: 8;
or encodes a protein having an amino acid sequence having at least 98% sequence identity to SEQ ID NO: 9.

16. The *Brassica* plant or plant cell of claim 4, wherein said CRL1 clubroot resistance gene comprises a sequence having at least 98% sequence identity to the sequence of nucleotide positions 32750 to 51049 of SEQ ID NO: 1.

17. The *Brassica* plant or plant cell of claim 4, comprising a transgene comprising a sequence having at least 98% sequence identity to SEQ ID NO: 1.

18. The chimeric gene of claim 9, wherein
said DNA sequence coding for a CRL1 protein comprises a nucleotide sequence
i) having a coding sequence having at least 98% sequence identity to the sequence of nucleotide positions 52 to 5343 of SEQ ID NO: 2, nucleotide positions 52 to 5340 of SEQ ID NO: 4, nucleotide positions 52 to 5361 of SEQ ID NO: 6, or to SEQ ID NO: 10; or
iii) encoding a protein having at least 98% sequence identity to SEQ ID NO: 3, SEQ ID NO: 5, SEQ ID NO: 7, or SEQ ID NO: 11; and
b) said DNA sequence coding for CRL2 protein comprises a nucleotide sequence having at least 98% sequence identity to the sequence of nucleotide positions 220 to 2898 of SEQ ID NO: 8, or encoding a protein having at least 98% sequence identity to SEQ ID NO: 9.

* * * * *

SEQUENCE LISTING

```
<160> NUMBER OF SEQ ID NOS: 176

<210> SEQ ID NO 1
<211> LENGTH: 56333
<212> TYPE: DNA
<213> ORGANISM: Brassica napus
<220> FEATURE:
<221> NAME/KEY: 5'UTR
<222> LOCATION: (3145)..(3363)
<220> FEATURE:
<221> NAME/KEY: misc_feature
<222> LOCATION: (3364)..(6042)
<223> OTHER INFORMATION: open reading frame of CRL2 gene
<220> FEATURE:
<221> NAME/KEY: 3'UTR
<222> LOCATION: (6043)..(6412)
<223> OTHER INFORMATION: 3' UTR of CRL2 gene
<220> FEATURE:
<221> NAME/KEY: misc_feature
<222> LOCATION: (8011)..(22964)
<223> OTHER INFORMATION: transposon region
<220> FEATURE:
<221> NAME/KEY: misc_feature
<222> LOCATION: (30183)..(30296)
<223> OTHER INFORMATION: transposon region
<220> FEATURE:
<221> NAME/KEY: misc_feature
```

```
<222> LOCATION: (32258)..(32644)
<223> OTHER INFORMATION: transposon region
<220> FEATURE:
<221> NAME/KEY: 5'UTR
<222> LOCATION: (32750)..(32800)
<223> OTHER INFORMATION: 5' UTR of CRL1 gene splicing variants a, b and
      c
<220> FEATURE:
<221> NAME/KEY: misc_feature
<222> LOCATION: (32801)..(34845)
<223> OTHER INFORMATION: Exon 1 of CRL1 gene splicing variants a, b and
      c
<220> FEATURE:
<221> NAME/KEY: misc_feature
<222> LOCATION: (32903)..(34845)
<223> OTHER INFORMATION: Exon 1 of CRL1 gene splicing variant d
<220> FEATURE:
<221> NAME/KEY: misc_feature
<222> LOCATION: (34981)..(35124)
<223> OTHER INFORMATION: Exon 2 of CRL1 gene
<220> FEATURE:
<221> NAME/KEY: misc_feature
<222> LOCATION: (35191)..(35280)
<223> OTHER INFORMATION: Exon 3 of CRL1 gene splicing variant c
<220> FEATURE:
<221> NAME/KEY: misc_feature
<222> LOCATION: (35212)..(35280)
<223> OTHER INFORMATION: Exon 3 of CRL1 gene splicing variants a, b and
      d
<220> FEATURE:
<221> NAME/KEY: misc_feature
<222> LOCATION: (36334)..(36496)
<223> OTHER INFORMATION: n is a, c, g, or t
<220> FEATURE:
<221> NAME/KEY: misc_feature
<222> LOCATION: (41342)..(41482)
<223> OTHER INFORMATION: Exon 4 of CRL1 gene
<220> FEATURE:
<221> NAME/KEY: misc_feature
<222> LOCATION: (41697)..(41929)
<223> OTHER INFORMATION: Exon 5 of CRL1 gene
<220> FEATURE:
<221> NAME/KEY: misc_feature
<222> LOCATION: (43900)..(44772)
<223> OTHER INFORMATION: Exon 6 of CRL1 gene splicing variant a
<220> FEATURE:
<221> NAME/KEY: misc_feature
<222> LOCATION: (43903)..(44772)
<223> OTHER INFORMATION: Exon 6 of CRL1 gene splicing variants b and c
<220> FEATURE:
<221> NAME/KEY: misc_feature
<222> LOCATION: (43903)..(44019)
<223> OTHER INFORMATION: Exon 6 of CRL1 gene splicing variant d
<220> FEATURE:
<221> NAME/KEY: misc_feature
<222> LOCATION: (44053)..(44772)
<223> OTHER INFORMATION: Exon 6a of CRL1 gene splicing variant d
<220> FEATURE:
<221> NAME/KEY: misc_feature
<222> LOCATION: (45079)..(47952)
<223> OTHER INFORMATION: transposon region
<220> FEATURE:
<221> NAME/KEY: misc_feature
<222> LOCATION: (48811)..(48957)
<223> OTHER INFORMATION: Exon 7 of CRL1 gene
<220> FEATURE:
<221> NAME/KEY: misc_feature
<222> LOCATION: (49058)..(50697)
<223> OTHER INFORMATION: Exon 8 of CRL1 gene splicing variants a, b and
      c
<220> FEATURE:
<221> NAME/KEY: misc_feature
<222> LOCATION: (49058)..(50689)
<223> OTHER INFORMATION: Exon 8 of CRL1 gene splicing variant d
<220> FEATURE:
<221> NAME/KEY: 3'UTR
<222> LOCATION: (50698)..(50758)
<223> OTHER INFORMATION: 3'UTR of CRL1 gene splicing variants a, b and c
<220> FEATURE:
```

<220> FEATURE:
<221> NAME/KEY: misc_feature
<222> LOCATION: (50833)..(50848)
<223> OTHER INFORMATION: Exon 9 of CRL1 gene splicing variant d
<220> FEATURE:
<221> NAME/KEY: misc_feature
<222> LOCATION: (50953)..(51049)
<223> OTHER INFORMATION: Exon 10 of CRL1 gene splicing variant d
<220> FEATURE:
<221> NAME/KEY: misc_feature
<222> LOCATION: (54662)..(54662)
<223> OTHER INFORMATION: n is a, c, g, or t

<400> SEQUENCE: 1

```
tattcttcta acaaaagggg tctcacggtt tttaatctta tttttctctc tctttattga      60
caacaaaact taagaaaga tacaaaaaca atggttttac agataaaaga tgaagaagtt     120
gagggtgaaa aagttttgtt gcattttctt tttatttaat tcatgatctt ctttggcaat    180
aaagtgtgac gacaacaaaa tctattgttg tcttcgaacc tgtccgtcca ccgtctacgt    240
cttttcact acccgctaaa ttagggtcag atctgtactg caagcaccaa acggccacac     300
cctctgttat tgctcgagct atcatgtgtg aagcgactgt aaatcaaaaa cgaccacatc    360
ctctgttatt gctcgagtaa cggcgagctc ctacggagaa tcatcactcc actgcctcat    420
ttagtcatcg aagaatcacc tccgccgcgc tctttaactc atctcccttg tgtttttaa     480
ctcatctccc ttgaccaaaa attcactatt tttaaaatct gaatttaaaa acatttat      540
aaatgataaa actaagatca tgaaatataa cctataatta aaacttaaaa gaatgaaaga    600
ttatgtgaaa gaaccaatg gcggccgtaa ttgttttgca gaaaacccta aaattttggg     660
gaagatgaag acatatttac taaaatgcca ctgattaaaa aattgaaatt aaacaaaata    720
tatacacatt catggatcgt acacatggat aataatatgt atgtacacta ttatactaat    780
tatttgtaaa cacatctaaa ggtgtttgcg tgtttaacat atacttataa aagaaattta    840
caactatgta tactatttta tcagatattg cattcagctg tgtttttata ttggtaagtt    900
tggacatggc caaatagtgt acatatgcac aaagcgaaac ctttgtacat gtgtacataa    960
ttatctctgt acatgtgtac atagtttgga catggccaaa tacttgtaaa tatgtacaag   1020
tcgagaaagc ttacatatgg acaaggtgaa accattgtac atgagacata tgtttaaatt   1080
gcagatgttt catgttttta atgtggacac ggtgatgtgg ccacggtata caatgtaaac   1140
tgtgatgtga acatagtata ttgataaaaa gagtccatgt ggagatgtta ataccaatg    1200
tacacgttgc gatatcttaa aagattaaaa gatgtaatga atattgattg aaattcacct   1260
ttgttgtagt agtagtaaca atttacatga tcaggtagtg tccatatgga caagttggaa   1320
actctgtgta gatgttgcta tacgtttaga tgttttgtaa tgcttgtaaa tttgtacatg   1380
tccagaaaac gtagatatgg aacatagtg ttgcagatgt ttttaacgtg catatggtgg    1440
ctgaatccaa gcaaagcatc aatgctcaca aatccatcta caaggaagt accattgtgt    1500
cctagattac ttggttttgtc gtttagggtc aaactcagat acatcatttg agcatttccc  1560
ccttgacttc ttgatttgtt tttttcatta tctttgtaaa tagtgagata agaattgtgt   1620
aagtattcta cgagacaact gaaaaatcac attggatcaa gatatcttag agaccataaa   1680
tagaggttat attgtaactt aacaatactc acaactaaac atgtaattgg atcaatatgg   1740
gagcaaaaca tttagcaccg caaaaaatca tcaacgtgta cgcatatatt cactgtccac    1800
atgtacaatg tattttaaaa aaaatcagat gtacactgat tcttttgtac actgcacaag   1860
ttatgatata tgatgattct aatggttttg agtatcttat tattgttgct catcgcgctt   1920
ttgcaaaaaa ggaggcgaga tgaaggagat gaaaggggcg agacagaggc aacaacgaga   1980
```

```
aggaggcgac gaaggcaaca acgagaaatg aatctgatgt acatgtgtat tgttgtacat    2040
gtggatggta aaaaaattat gtacctagtt tattgttgta catgcgtact gtagtacaat    2100
atgatacttc atatttgttt gtgttcattt aagtcattta ggtgtgtctt tagctatttt    2160
attgtatttt catagatgta ttcctactac aaggggttaa aatcttgttt ctgaagttta    2220
gaaggaaatt aatgaccaaa tttaacattt aaaaagtatt gggttacaaa ataaataaca    2280
aataagttta gggaccaaat ctgcaaaaat gctcaaatta gccattgttg ctctcaagct    2340
tatcgtgcca gtttcagagc gcgtcagaga ggcatgaagg tcacagcaat gatgaatcac    2400
gacgaggaaa gatgagttga gacacaacat ggtatagcga gctcgaacca ccactgtttc    2460
gccttgcggt gaaggagaag atatgacgtt tcgacggcgg cgagagcgta ggtcacggcg    2520
acgatagaga cgagttgcaa aacacatacc gaaggtgaga cgaaataatt gtggcggaga    2580
agaaagagtt gtggcggaaa aaaagagat gcggcggaga aggagaaaag tgcgacgatg     2640
tgaagaaaag aaaagaagtt ttgataattt ctgattttttt taatatgttt ttaggtttca   2700
aacgtgtggt cccaaggaaa agaagaaaag ttactaattc ctaaaaattg tgggaccatt    2760
ttagttacac caatgatttt agataacaaa aactacctca gtagtcataa ctgttttata    2820
ttgttattaa aaacttaaaa ctgccttaca gtgtaatatt ttcttgtttt tttcttttttc   2880 ttgtaaggtt tcgaatggta accaactgtc tcgtacgtac cgccgtcaac agtaataaaa    2940
atctttacat atacttatat atctatacat ttttgttact atttgaacag caccgcactt    3000
atccctctat tgtcccgacg ttaccattcg gagcctaaat catattgctt cgaaattta    3060 tggtaggcca gggtagccac tcgcttcttt cttttaaatc atattgcttt ttgaaatttc    3120
aacgacaaac taaattcata ttacaaggac accatttatt ttagatactg ctccaatctt    3180
tttttttaaa aaaagcttct cttttggaaa tgattgccaa gctctacctt attccaaagt    3240
ctcaacacaa aatgattatg cagaatggtc tgcttccctc tggctgctcc ctagtcctta    3300
cgtactttta gtctttcttt tcaaataatc tgcacttccc attttcttg aatcctaagc     3360 acaatggctg aatttgtgtc ggctatttgt tcagtggttc aatgtttaac accatgtttt    3420
aattcctggg ctgcacatgc aaggtacgtt tctaagtttg atggttatct taacgagttg    3480
aggaatgctt taagggatct tgaagcaaaa agaaatgatg tgaaacacaa ggttgatgat    3540
gaagaactca ctggtaaggt tccgctagac gaagtgaaaa ggtggctttc aaaattcaac    3600
accattaaaa cagaaaccga taggctggtt gctgatgctt ccgctgagca acaaaggcgg    3660
acaacatctg ggtgttgttg caacaacatc acttcaacct accgttgtgg caaaaagtta    3720
tccaagatgt tgagggaagt tcagcaactc tattctgaac aattttcgca agggttaact    3780
aggcgaggga cgattcctgt ggtagtagaa gaacctgtcc ggcaaactgt tggtcttgac    3840
acaaaacttg ctagcacatg gagccttctt atggacgaag gtaccagaat gttgggtcta    3900
tacggttttg ggggagtagg taaaactacc ctccctcactc ttatatctaa caagttcgtt    3960
gaagtcgagg ataagtttga tgttgtcatt tgggttgacg tgtctaaaga tgtagatatc    4020
ttgaagattc aagatgatat cggcaaaagg ttaggcctcg atgatgagaa atggtgcaag    4080
gaaacgcaaa gggggaaaag ccttaatata agaagggttc taaaagaaaa gaaacccga    4140 tttgtgctgt tatttgatgg cttgtggaag ggagtgagtt tatcagccat tggaattcca    4200 ttgagggggga aagaatacaa aatcgttttt acgactcgtc agaaggatgt atgccaaaag    4260 atgggggggaa tttacagaaa agttgaatgt ttggcggaga aggacgcatt ggatttgtta    4320
```

```
acacaaatat caggaagaga ctccttaact agcgagatgc ttagtctcgc agaaaagatt    4380 gcaaaaagt gttatggctt accccttgca cttcaagtca ttggaaagtg tctgtcatct     4440
aaaacgactg aagatgaatg gcgtggtgta cacgagtatt tggttcgttt tccagatcaa    4500
ttggaaggta tggtggatat gtttggtgtt ttaaaactaa gctatgataa tttagaagag    4560
ggggatgcac agtcgtgttt cctgtactgt gctttatttc ccatggcata cagtatccac    4620
caagatgagc tggtcgagta ctggataggt gagggtatca tagaggtagg acgcagaaga    4680
gacagagcaa agaatcgagg tgctcagata atcgatacac ttgttagggc aggtttgctg    4740
ttgaaggatg acgagtctaa tccgaaagtg tatatgcaca atataatccg agagatggcg    4800
ttgtggatag tatctgaaat taaggatgga caaatgtatc ttgttgaaac agatgctggg    4860
ttaaggacac tgccacctaa cacgactgg  acaatcgtgt cgaggatgtc tctgatgaac    4920
aatgatattc aggacatacc agatgatcct gaatttcctg accaagctct tcttatgact    4980
ctgttccttc aaaacaacaa gctggtcgag attggttgca gattcttttgt ggtcatgtcg    5040 gctctggtcg ttttggattt atctttgaac cccgatatca ccaagttgcc ggatcagatt    5100
tcagaattgg tttctttgcg gtatctcaaa ttattcggga cgaggataaa gttttttaccg    5160 gagggtttca gcaaattgct caaactgatc cacttggatt tggagcttac atccaatctt    5220
cgtagtatca gacagatttc aggactacta aagttgcagg ttttaagatt ttatggttcc    5280
gctgctgcat tagatggctc cctactgaag aacttggagc gtttgaagtc tttacaattt    5340
ttgaccatta ctgtgagaga agttgatgtt ttgaatgctt tcctaggaag caagaattg     5400 ccaaggtgta cacaaggtct tgatcttggg ggtcttgaaa tatcaggagt atcaggaaaa    5460
tcatttgcag ccacctttgg tgagttggtt actctttcta aacttcgaat gacagattgc    5520
gatatcaaag agtcagatat agaatgggaa gaaaacataa aggtccaatg ttcatctcca    5580
gttccatcca atcaaatcat tccaaggact atatggttca agaacctctc agctgtggta    5640
ctacactcat gcttaggtct aaaggatttg acatggctga tgtatgctgc aaatctcgag    5700
tctctagagg tcaaaacttc acctaagatg aaagaagtaa taagccaaca gaaagctggg    5760
gatctcgggg ttgagccttt tcaaaaccta caagttcttg agttgggttt tttgaacgaa    5820
ctggagagca tctattggac ctcactcctt tttccaagac tgcagaatgt cactataaca    5880
gagtgcccga agctgcgtaa gcttccatta aattccacga gtgtagagag agttgatgct    5940
cttcgcatag aagtggatga cggatggtta gtcggagttg aatgggagaa tggagctgaa    6000
gagcggtttc gtcttgccat ccacacagct tctatttctt aacttcatcc ggtactatat    6060
atgtatttca tatgttccat tatagaatct ctggttttac catattttat attatatctt    6120
cacttcgttt acttttttttt cttcctatca tcttttttagg tgcacgagac atgcaagcct    6180
gcacaaaaga ccttgtgtga caagcagaca tcaatgcatg caattcaatg tcctctcttt    6240
gttttgttct tttacggtaa aacctgactc gaagtcattt gttcattatc aatgggtgtg    6300
tcaagaaacg tttgtgtata atggtttctc ttatctcatt catactagca taaaacctgc    6360
accttgtgca agataaattt gtatgaaaat tatttaaaaa atatcatacg gaaaaaaat    6420 tatattattg atcgaattaa tatatttgga ccttaaacaa tttcttaaaa acttttttg     6480 ttaattatat aatttgttta ctaatgaact gatctcattt ttaaaaatat tttaggttaa    6540
aaaattattt atcacataaa aacctaacgt tcaggccgaa gaatctcatg cctactattt    6600
ggttacaatg aaactatgtc agttcgattt tatatcatgg tttagcaatt taaaagttaa    6660
ttatggttat gagaagtcta cgttctcgtg tcaatcctat ttatctttga tattttctca    6720
```

```
cttttttgtgt catttttggtt attgctcgat ataaatattg atttttgagt ttttttctca   6780
tttctttctt ttatttttggc ctcagattta gaaaatgttc aagattcaaa tttattaaag   6840
agatacatac ttaggttaag atttgtacct tgtgcagaat aaatacttat tttatatttt   6900
tctgcatatt atgaaataat aaaataataa ttatatatta ataactaag aaatcagtta    6960 ctattatgta ataaattggc ttgcacatat aaatcaaatg accggtctgg tttattcgca   7020
attattatag aataaataaa tcaaaacaat caatcttgtc tatcgtatat gatatataat   7080
taaatttaaa caatatgaag tatatatata tatattaaca taaacaccta ttaaaataaa   7140
attatttatt tatatatatg attttattat cattgtatct tattatagaa aaaaattttaa  7200 acattgatca caaagtttta tgtgagactt ttaacagttt tattaattta aactcgtttt   7260
gaaaaattca aaatacaaaa tttaaaaaaa tctaaatttt taatatatga ttaatgtaat   7320
tgtgtaattt atttttaatag taaaaaatta aacaaaaatg atagaaaaca tacatattat  7380
tagtaaaaat cttcattact taaaatcatt aattactata tatatcataa tcacattagg   7440
taattccgta ggtttttattt aaggaagtaa tatataataa gtagacacct tgctttagtt  7500
aatatcatat ggtatcatat agttggtatt aaatgtctat agtgagatat aaaaatcgaa   7560
ttggaccaac atatttttca atttcaatgt gaggcttaca cttaagatta attaactaca   7620
taattgattg acacataagc aagaattttt tttaattatt accaaattga ggttacatt    7680 ttttcaaatg ttcctcaatt aatatatagg ggatgtgccg ccaccacctt ctatacaata   7740
cgatctccta aagacgttta acctaatgtc aaagtaaaag actaaaatgg acaaatacac   7800
ttaaggaaag tttcatatac ataatctcca aatacccctc ctcaagttgg agaatgtaga   7860
tcacacacac ccaacttgcc aataaactta tcgaactcct tctttcctag tgctttggta   7920
aaaatgtcag ccagttgttc ccgcatagaa acatgctttg ccatgatagt acctcgaagt   7980
agctcatctc gtataaagtg acaatccttc tcgatgtgtt tcgtcttttc atgaaatacc   8040
gggttcgcag caatgtgcaa agccgcttta ctgtcacaaa ataatgtcac cggaggcttg   8100
tgtatcactc ccatgtccaa taacaatgcc ttaacccaca taatctcctt cactacaaga   8160
gtcatggctc tatattctgc atccgccgaa gacagagaca caacctttg cttcttcgtt    8220 ttcgaagaaa taggtgaatc acctatctga acaaaccatc cactagtcga ccgccgtgtt   8280
aaaggacatc ctgcccaatc cgagtcacac caagccacca acgagagctc tacattcgca   8340
ttcagaagaa taccttggcc gggatttcct ttcaagtacc tcactacccg caatgctgct   8400
tcccagtgtg cttgctttgg tttcttcata aactgtgata acacgtacag aatatgaaaa   8460
atcaggtcta gtaacagcca gataaatcaa cattcctaca agccaacgat agccagcaac   8520
attctccaag tcagcccat catctaacac cagcttttga ttctgttcca acggaaagac    8580
cagtgtccat tagaatatcg atcacatata cttcctctgg cacatataaa ttcctctcag   8640
actcctagcc acttcaatac ccaaaaaata tttcagcaat cccaaatctt tcattcggaa   8700
acatttactc aagtagtcct tgaaggtagt aatgatcgcc aaagaagaac ccgaaataat   8760
caaatcatct acgtacacca aaacatgaag acgctcacca ttgttctcca gtccaaagaa   8820
ggaataatca gagactgact tagtaaatcc atagtaacgt agagcagtac tcagcttcgc   8880
aaaccaacag cgcggtgact gtttaagacc atatattgat ttgcgtaacc gacatacctt   8940
agtagcgtct caacctcgaa agcctggtgg taatcgaata tacacctcct cgtgtaaatc   9000
accatgtagg aatgcattat gtaccttcat ctgatgaact ttccagttcc gagccgccga   9060
```

```
aacttcaaga aaagagtgaa ccgttgtcat tttagctact ggagaaaacg tctcatcata   9120
atcactgcct tccacctgcc tattgccaca cgcaacaaga cgagctttat aacgttccag   9180
agttccatca gctcgaagct tcaccgtaaa tgcccatttg caagctatct ctcgtttacc   9240
ttttggtagt gtctccgccg tccaagtttc attttcttcc agtgcatcaa tctcaaaccg   9300
cacagcatca cgccaaactt ctaacatgac agcctcagca taattcttag gaatcgtata   9360
tgacgtcaac ggatcatgct aagctttatg tgaatcagaa aaccgttcaa agtccaccgt   9420
aaatgacaac gaatgtggag ctgctgagac ctcttgcgtt ggagtaatgg tatgaagaac   9480
ataatcttgg agctttgtgg gaagtctcct ctcacgttta cctctaccca gcgtaatcac   9540
atctgtattc accatatctg gtgagaccag agcttctcac tgtagagaag taggaattgg   9600
tactgacgaa ggcattgacc ctgaagcaac aagtgtaggg tcaggatctg aacacaaga    9660
tagaatggta ggtaaatctg atccagccat gcgagtctcc atctcctctt gaaatacagg   9720
ggcgtcatcc tcgtctgcct cagtcaagtc gtcctctgta tcaggcgcgg acatgagtat   9780
atttggtgat gcaaggtctg gcaatggctc accagactcc tcagaaacga ctccatgact   9840
ttccatatgc agcagccgat tatcatcaac ttcatgcact gtaggttcca tctcagatgg   9900
aagctgttgt gaactaagat ccgtaccagt cgatataatg agcaaaagga aattccgcct   9960
cagcaaaaac aacatctgtg aagagaata tctttccagt gtcagggttg tatatacacc   10020
aacctttctt tccagatgga tacccaataa acacaccttt cacacttcga gatacaaact   10080
tatcacccgt atgttttga ctgtgagaat agcataaaca accaaagcct cgtaactgtg    10140
agagaagtgg tggtctatta tataattttt cgaatggtgt cttcccatta agtataggtg    10200
tcagcgtctt attaataata tatgatgccg tcaaaacacg ttctccccaa aactccattg   10260
gaagagaagc ttcaaaacgc aaagcacggg ccacattaag tatgtgtcta tgcttacgct   10320
caacatgaca gttctgttgt ggtgtcccca cacacgatgt ctcatctatg atccccttc    10380
ctcgaaaatt tgaagtcata cacatgaact ctgtaccatt aacacttctg atgcccttca   10440
gcaatgtact atactgcttt tcaacataag aaatgaagtc ttttagtgga gcagagacac   10500
cttgcttagt cggaaacaaa tacaaccagt cactccgaga aaagtcatcg ataagagtaa   10560
gaaaataact ggctccacaa tgagcctttg ttctgtaaag accccataga tcacaatgca   10620
ccatctcaaa taaggtagtt gttttattag aacttgtagg aaaaacactt cttgcttgtt   10680
ttgattttac acaaatctca caaactttat tctgaaaact cttatcacga gacaaatttg   10740
aaatagataa acgacctaaa actccatgag agggatgtcc aagatgccga tgccacactt   10800
ctacagacgc cttatttgtt cgagtcatcc ctccagcgaa ttccatccct cgcagaaaat   10860
acagtctaga caactgttca gccactccaa tcagcatctt ggtaatgcgg tcctgtatca   10920
agcacaaccg ataagtagtc tgcataatac atctcttctc cttagttaat ttggaaacag   10980
aaatcaaatg gcattgcaat ctgttcacaa acagaacaat ctgaatcata agcaacatgc   11040
tcaaaacaac agttccttgc tgtgtagcaa gtgtaactct cccatcagga acttaacttg   11100
caacggaatc acttctcgaa tatcagagat aaaaccaaga gtgccggtca tgtgattttt   11160
tgcgcctgaa tctataatcc aagaagataa gaaagacata ccagttagct tctgagcatg   11220
ttgtttgcat tcattccgaa gagtcactaa agatttccac ttctcgtctg ttaacccggt   11280
gaggccagct cgatcactcg ctgtaactgc atgagccgat atctcctgat gtaccaaacc   11340
tccaatagac acagcattag ctcgcgcaga agatcgctcc ttctgcgagc cactacctct   11400
tccaggctgt ggtccggatg attgcttacc acgttgaagc tctccccacc actcaggata   11460
```

```
gcccaatgtg tgaaaacagt tggaggccag atgtccatta cgtccaccac ttgagcagtg   11520
ttgtttcatt ctttcttcct tattaaggta cggctgttga gaagaacctg atcctgcaga   11580
gtgatcagaa ttcccttaac cagttgaata ttgtccagtt tgaacagcat gtgcagagtt   11640
ctcgtatttc tcatcttgaa gtaagacatt gtatgcttca tcaattgatg gaagcgggtc   11700
tcgagagagc aggtttgact tcactgctcc atgtatcgcc tcatcaatct cagtcaagaa   11760
ctcatgcaac ttatcttctt gacgttcacg ttccatcacg atcccaatag agcaaccgcc   11820
gctcttggac tgcctgaact cggcaagaga cgtccacagc tgcatcattc tgtccctgtt   11880
atctgcaggt tgcaatttca gttttgattc tctgaactct ctgtccattc ttcacggagt   11940
accggcatgt atatgatccc aatactcact tgccacatcg aaattagaga gtgttgattg   12000
aatacttctg aaatcgtgag ccttatccaa gacataacta acgcattgtt agtccaccaa   12060
tcctccaaat ctcccgaatc cttgcttggt tttggaatcg tgccatgcac gaaaccaaac   12120
ttctttcgag ccctaagagc catcttcaag tttccagacc actcactgta gttggatcct   12180
ttcaacagta gttgagagat caatgatccc ggattatcac tagaggatag atcatatggt   12240
gatatggtcc atcgtcgaat ctcaacccgt gtattcatct ctgacatcgt ctccttagcc   12300
ttcaaagtca cagctgattc gacacctttα tctccatcct tctccatcgt gtatcaagaa   12360
agaaaatgaa taagtataag tttgagaaca cgatcaaagt ataggatcag tgctctgata   12420
ccatgtcaag aaatgtttgt gtataatggt ttctcttatc tcattcatat gtgccaccac   12480
caccttatat acaatacgat ctcctaagaa cgtttaacca acgtcaaag taaaagacta   12540 atatggacaa atagacttaa ggaaagtttc atatacataa tgtcccaata gggtgttttg   12600
taaaacttaa ttgtgctttt gcaattatat gtgtgtgatt aaaacattat attgctaaga   12660
tgtatatgtg ttgttgtgac tgccaccttg accttcgtca accataaaat tcatcgctga   12720
agttttcttt cttgtcaagt acagtgagtg attgaatcta catctgatta tgtcttctag   12780
tcactttgat tactgtgttt gtcatttctg cataggattg gaaaaatgtc gatttgtatc   12840
tgaagtcgca tcgtttagtt atataattaa aatacaaagc atatagtatt gacaaaatta   12900
agatttaaat atggtcagat ctttttttaa tatgtataca attttggatt atttatataa   12960
gcatctatac gttgagccga aaacagctat aattggaata gtagatcaaa acttagaatt   13020
tatgatcgat taaatacatt tagatatttt ttactaactt atagatgaat aaaatttata   13080
tacgatgaaa tttaggttaa cgtaatatat atagcattaa cttgtacgaa aggccattat   13140
taccgttttc ctaaactatg aaaaacaatt aagaaattca ttccttggtg ccaaagtttt   13200
tctttatcgt caatataaat ttcctaattt aatttctaaa gaacagtaca tcaaggaaaa   13260
tatttgatat ataagtttgt ttggtaataa agttttctgt atttattttt ttatttatt   13320 aacaaaacaa cttaattatt ttgacctaaa tttccattaa gctatatatg tgtttcatga   13380
cgttaaattt tcttccattc taaccataaa agactgaatg tatatgattg attttggttc   13440
ggttcggttc aactgaaatt tcattgttag ttaactaaca tcaataatag acaaaccata   13500
tattatacat gtcttctgtt gacatggttt cttatatttt tctttacatt ataaaacaat   13560
tttgtaattg tttatcacat aagttccaag catactgttg tctacaacac agaataacaa   13620
aaacaaaact aatatagaaa tcccgattac ttagcttatg cgttgaacaa aataacaaag   13680
aagaatatgc tttactttct tttgttttac tgcatgtttt ctgaatgaat ttagacaaat   13740
tgtgcacaaa ctattattat aatccacaaa taatcacaat cgccacactc ttcttccaac   13800
```

```
cttggtcaca gtacaattgg ataactggca atttataatg ctgaagaatc ttatacatta    13860
ttaatcgata gggccaatac cttttttcagt tttttaaatg tatgtgttgt ttaatcaaaa    13920
tgttgccttc agaaatctac attgacatct atatctatat tttctatatt acatatgaaa    13980
cgttaatata attacattgg gccatactca tattgtactc gtttgggggtt tgctaaagag    14040 ccaatatata cgtttcctag atgtttcttt agccaatagg ttcatttgct aatattaaat    14100
cgatagggcc aataggttcg agttaattat tgctaaagaa ctagtcagtg ttttttaaaac    14160 tagaccggaa actgaactgg aaaatagttt caatatggtt tgacctgttt aaactggttc    14220
aataatttga ttcaatttat ttcagtacta tataaatttt aaagtaatgt tagtaaatat    14280
tatacataaa taaaatgaga aaatcataga aaaaatcgtg aaagtgtcac ttagtaacat    14340
attgaacttg aagtttttttt tactaacact tttaactttc aaaatgatat ttttatcata    14400
aaaattttca aattaaaaag ttggcttgtt aaacaggtaa aaaaataagg tatcagtttt    14460
ttttaaaaat tatttaattg ataaaataaa taaaatttca gaaaatttaa taaaatttca    14520
gaaaaaccaa aaaaaaaatc aaaaaatgaa atgagaattc agaaaattaa ataaataaac    14580
aaaattgcta aaaagtctat agtaaataag attaaataca gaaactaaat aaaattcata    14640
aatttcaaaa aaattagaaa attgatcgca aatctattgt tgaatgttgc ttttatcttt    14700
gtaatcggct aaggttcatg aatgaaatat gttgtgttaa aaaaattaaa aaaatatatt    14760
gttatttact aatgctcacc atttgaaaca atatggttat tagaagattt ttaaatatat    14820
gtatatatat atatatattt atattatcgt tttatatagt tagtttatca tatcatgtca    14880
tcgtttatat taaaaaatat atatcatatc atcttttttt tagttcatgg atgtggagcc    14940
acatgtttgg tttccagagt caatatgagt ctgtttagtt gatgacaaaa aaaatatata    15000
gctataacta tataaaatat tataaatagt taaaaaaaat atagttagtt tatgaattta    15060 tgattttttgt ttatatagtt agtttcttaa ttttttgatgc ttttaatagc ttgtattgag    15120
taaatagctt tgagaccccca tatggctatg tgaccggtcc atggttgaat catttattag    15180
atccaactca gctaaatgcc cggttcatgg tcgaatctgg tccaaccatt gggtcggtcc    15240
ggtttaaaaa ctctggaacc agtgttatat tcggtcgtaa ttgtagtcgt ccatgtattt    15300
aactctataa aaaaaaatat tgtactgtgg tttgcctaaa ctcattgtaa tgatgtcaca    15360
tcagcaattt aaaaatgtaa ggtattgaca cataagcaag atcactttgt aattactaca    15420
aaactaaagt tataaatttt caaagaccaa taaggaccgg gccaggcata gcgggtttgg    15480
gccggaccgg gccggcccga aatgacaacc ccaattaata tatataaggg atacctaatg    15540
aacagtatgt ggattcaact tcttttttgg tcaaagttgg gattaacctt ataaccattc    15600
aaaatgccat ataagattaa ttaaaaaatg tgttaaaact taagaaaaac aaagacgttg    15660
actctaacga taacaccgtc agaaagaccc taaattctaa actctacctc caatgatgct    15720
cccatcatgt tcttctttga atctcgctcg aaatgtcttt tgtttgttgc aattgaagtt    15780
tctgcttaaa ttttacgaag aaaacaaaca agactttgtt tcctcaaaaa agttaaagtc    15840
aaacatttag tcgagaatgg ttaacttaac acctttgtat ctttgactaa atgaattaag    15900
ttttatcatt tcgttagacc aacaacataa aaacgtacat cgtacaaatc aacgatttct    15960
ccgagaaaaa acgtaaaaat gcgtaagtcg taaaatggtc tgaaatgatc taaaacacaa    16020
tgaaagccca cttatgactt ggatcaataa ccagcccaga tcgcaatgac agttttcttg    16080
gcttggagaa gaataaagaa aaataggata aatggaagat ttctgaggat aaaatcaaat    16140
ctcgagcaga taaggaaaaa tcttcgaaac ggatatacac aaataacgat ggataaggaa    16200
```

```
agatggccga ctttggaggc atatataaga aaaatcgggg cagagatgaa aaaaaaaaag    16260
aaaattttag gcacttagaa accttaagca ttattcttga catacttaat tttctttggc    16320
ttgcactcaa ttactagacg aacgtcgcga aaacagtttc atctcttgtt caactctttg    16380
taaattaaat tacattcggc ttgatcctcg aaaggtatac ttaggcagcc ttttataaag    16440
ccatgtctga aatttataaa ctcttttcgc atcttttca gcttttgata acaagcttc    16500 gactcagata tgtcttctcg acttaggtgg ttattctagt gaacttagtt aggttttact    16560
gcctatgtta tttgatttcc attgtaatat tgcttccaaa caaacttaat gtacattttt    16620
gtctctggaa cgttcatacg caagttcgaa ataaagattt acttttttct aaattcgttt    16680
tgttgtcttt ctgtattttt cgcatttatt tgatcagttg tcgttggccc tcgcagagaa    16740
tccggacgtc aaggaatgtt atgctttctt cctctaataa atttgactgt ttgaatttcg    16800
attcccacag tttggcgcta gaaagagggg gagggatact cttactcatg gccgcaaaac    16860
gcttgatcga aagatgtct ggaagtgcag aagacaaact taaagctcgt gttgacacta    16920
gcaacaacgg caacaatgct ggtagcaaaa ctccatcagt gactgctcct atggccaacg    16980
ctagcaaatc ccgcagcgct cgacaaaata caaaaccttg tcacaactct tctccacaag    17040
aaaaccgacc aaaaaagctt gtgatttctc tgtcttaata gaaattgggc aacgactgga    17100
tctatctaac ccacaaaaat cttcttgtta ccaggctaga gaaatctcaa cttgaatatg    17160
aactcaatca aatttttttt gcttaaaact ctttgtaaaa ataagatatc atcttcttga    17220
gattttatta ctcacggaaa aggaagcaca acaaatcggg tatatatact tcactgcagt    17280
aattcttcca aaaacaatc ggaaaacata gttgatttct ccagaattcc tcaaaactca    17340
aatccattga caagaactaa agaaaacaaa actggagatc gtatcccaca ctgctaaaac    17400
gtctcctcga acataagatc acagaaaaat tcaagcatcg cttctgtaca aacatattct    17460 atgattttc gatatttgtc tactaagctt acttcagaaa actactcaga actccctcgg    17520
gtcagtccta cggaaatgag aaaattatct attaagtttg atagctatct taaagctagg    17580
ggtgtcaatt agggccaatt cccgcagccc ggccagccct aaattttact aattttgttt    17640
ttttacaata ggtttttaag tatttaaaaa gtaaaaaaaa atctgataga gaagaaaagt    17700
ttaaactctt atatttttt aaaaaaaaat tgaaaccaat ttttttttat aaaaatttgc    17760
atgtattaaa atgatagaat tgacaatgaa aaattatttt tagataattc caaaaagctc    17820
gaaaagccct aaagccctat aaaggcctta tgggcttgaa ttatagtccc aaaatatttt    17880
tcggtctggc aaacatattt actgttttag ctggctttga ccgggtcgag ccagcccgaa    17940
tttacacacc taaataaagc ccatttcaac atgaatttcc aatataaaat tgagaaatta    18000
agttgcagaa cagccgcaaa acgtcagttt ttcgaaatat ctctcataaa gcagaactta    18060
aaaatatttt tacggagtaa ctttcgtaaa tttaagcttg ataacatttt gaaaaaccac    18120
ttttgttaaa tcaaactcaa caaaattcta cgagatagct ttcgtaaaat taaactcgac    18180
aatgtttgat gaaaatattt cgcaaaatta atctggaca acattttacg aaataacttt    18240
cttaaaatta aactcgaaaa cattttttcaa aatgattttg taaattatac atgtcaagat    18300
tttacgaaat aactttcatg ctattgtctc ttgcttttgt gaacaccaag taataggaca    18360
cttctcaagg taaaaaatat gaccatttgt acttctccca tcgtctgcat ctccattatg    18420
actgatgtca ctataaccga tcaaattcat gccactcact cgctcgtctg ataaaccata    18480
cgacaaagtt ccacacaaat accgctagaa gtgtccttt gttatccaat ttttttggt    18540
```

```
gcatgcaacc caccatgacc tgagtttctt tagctctgtt cccagctcat ccaagagaaa    18600
tttcactaac ttagatccag cgaacaacaa cccttccgct tcaccgcaaa gatcttacca    18660
gtattttctt ctcgacgccg aatcaacctt tgtccctaaa aaacctgaag atctttacag    18720
agaagatatt tttcaactaa tctcaccatt tcaagtctcc gatggtaacc cgctgatcca    18780
ccagcactga tcctcggtga tcttcctttc ctggtaatct gttaacctt ttagtttcct    18840 tttctggatt tcataacttt cctaattctt attgttttct tctcctctgc acactataag    18900
aaaacttgtt tatagccacg agtcagccac aaatattttg cggccagaga aatatagcca    18960
caaaatacct ataaaatagc tacaacaaat tttgtagctt tttgtcgcta tgtacctaca    19020
aaatatgatt tgtggctatt ataagaccca aaacacaatt agctacaata taaattgtgg    19080
aagtagatat ccaaaatttt ccatggtata attcgtaact aatatagccg caactatgac    19140
catagctcga cccggagaaa taaaattata aaatatttaa actaactaca aacttaaaaa    19200
aattccagtt acgaacttag ttatgatttt tggccacttg aaaacatcgc tgcaaaattt    19260
tttgtggcta cccgtaacaa agagtgtaac atgtagatgc acgtatcatt cctaaaacaa    19320
aaaataataa tatacatata tatatatata tgtgatgcca aatttttat aacatttaca    19380 atgttatatg gaatgtcaag atcatttttt caaatctata ttattgaaac agaaacattg    19440
tgttggacct aacatttatt ttataagttt ttaaattaaa tacatcttcc tactttatag    19500
ttaaacctac attaaatcac taatattctt ttccttatac tactatcaat gtttccaaac    19560
aatatagtca tttttttata ctactatcca ttttttcaaa caacactata attaatctta    19620
tatccaaaca atataaaata ttggaactta tcttttaat aaccaaatat ttaaataat    19680 taaataatta aaaaaatatt caaaaacttt ataaaaacg aaaataaata aaacttactt    19740
ttacaggttt aaatactaca aaaacatttc aatcaatgat aaatcaatta aattaacata    19800
ttattttatt tatatttact acataatggt tctatcattt atttaagtaa gataacaatt    19860
caataatagc cattacataa aaataaatat ataaacatta tacagtgtac aataactata    19920
ataacaaaaa taattatgaa aaattgttca aaatatatgt tatctaaaga aaaatgctta    19980
atactaattg ttaacaaaaa atttaaagcg attataatat aaatgattaa caagaaaaat    20040
tacacaaaac aattataata aaattaatta agttatataa aatggagtaa tatgatcaag    20100
acatttatag ttcttaatta tatctattat tttctctatc aaaattttat aaaaaaaatc    20160
ataatttaat aaagttgtaa aacaataaac tttaaaattt ggattaaaag gtgacaaatt    20220
atgaaactat agcactttaa atcaaattgg atatgttaac atatcagaca tccatcggtt    20280
caattggtta gtctcagata tagtgatttt tataaatatg gatatttta aaacttaaat    20340 tgaattatcg aatcaccgga ttaaccgatt tgaccgtgga ttcaggtcaa atttaaaagc    20400
attgatttaa aagcaaagaa aattaaaata aacaaaattc ttacaaatta acaaaatatt    20460
tattaattat tagtaaaaaa attcatcata aaaaatctg cgcttgcaaa gcgcgggtca    20520
tgatctagta taacattaaa atcgaatcaa gtttcataat atcgagacac tacatatgca    20580
ttgcattaat atgttatttg gtttcattaa ctatctacga ttttgtttgg ttacattata    20640
tattcattat gttatttagt tttagataaa ctatttggtc tccttttttt tttagcttct    20700
aggcgatcga atttgaatt cacgtattta gatctgattt ttttataaaa aaaataggaa    20760
aacaagaggc atgaaaaaca atttatagat tggcaacttt ataactattg taatatatat    20820
tcttaattaa aaaagtagaa agttcaaata ataactttat gacacagtgt ataggtttga    20880
cactatagag tagtagtcac aaaacagtca ctaattaacg actattttct gattatatgt    20940
```

```
gcaaatcaca ttaaatagtt gcaaattagc ctccagaact caaattccaa aactcaaaat   21000
ataaaaatct aatattttaa aaattaaatt ccaaaaatta aaatataaaa ttttattacc   21060
aaatcttaaa tttaacctca aatcataaat ttaaacttaa acattaatca tttttaataa   21120
ttaatctcaa atgttaaatc taactcaaat accatacagc aaaccctaca tatattccaa   21180
ctcacaaaaa aattcaaatt aaattcaaat ccaatttctt ataactatta tcacttaacc   21240
ttaatcatat ctttcttctc taacattgat tccatatttc ttcaatttct tatcataaac   21300
tataaattca acatttaaaa caatctgata aaactaatta taaaccaaat ttgttaaaat   21360
aatctaataa ataaaacatt agaacaactt tgatgttttg cctttaccgt tggatctcac   21420
tttccagtga ctagagtttt agactcatac cttcctctgc aaccaccaa tccttatgca    21480 tttgaccttg cctttacaat gagtctagtc ttttaactca acttccttgt tgtatgcaga   21540
aatagttacc tcctttaagg ttaaagtttc attgccagtc ccatacttga gattacgcac   21600
tagtgaattg aattgtttag gcacgcttga cagaatctgt atagcttgat tttcataact   21660
aactgtgagg tttaagcttt ccaaatcatc tacgggtctc aagaatacat cagggttttc   21720
ttctatactt caatgtgtag gtattcatac cggtttataa cgatttataa atctacttct   21780
gaattcagtt tgcctagatc tcatgtaaat actaaaataa acttaagatc gtagggtttc   21840
gaatatacct gattattttg tagcggaaaa ataaacaaac caagtcgaga tttcaatcgc   21900
tccaaatgtt gtgcctctac gggtatccac aaacacacaa actggatcag atcgggatgc   21960
tagtgccgtt gagatcgtat ctcaaaattc cacgaacact ttcgtctcta ttggattttt   22020
caattgcttg ttttaagaaa aaaacctctt tttttctttt tgattatgag aacacgtttt   22080
cttagggtat gaatggtgac cagagaatgg cgaggaataa tacattccct aacgtttcta   22140
caaaaaatca ccattcacaa ggaataataa ttccctctta ttccctttca ttcttttttt   22200
tgtagagaac taaagaacaa aattattcct ccttaaattt gataaagaac aaccattctt   22260
tttcattcct gctatttat ttccgtacat tttttttttt attcgttcct cttgtttccc    22320
gaatggtcac cagtcagacc cttagtctat tcggagacgt aatgcagcaa gcaattgtgt   22380 gttttagaa ggaagacttt aggtttatat atatatatat tacgtgacct aatctcatta    22440
aacaagtcca ttatgttaat tgatcttaat catattaaga caattcagtg attcacatcc   22500
aacaatatac tattattata tatatatcaa atatatataa tatctaaaca tgaaattcca   22560
atttatttat tatccaattt gattaggtgt gtgatcctat agtatcatat aatattagta   22620
acgaattcac aattcataga ttataagcag tttctagcaa aacattataa ccacctgata   22680
ttatacgatt gtcgaacctc cacgttacga ctttagcaag agtaagtaca aattatttta   22740
gaacattccc aacacaatgt tcttccattc tgaaactaga aaaatcttta tttcaagtag   22800
attatgtttg gtagggtctt agtttgatag tccttctcga gtgccttcca aactccctcg   22860
agtgccttcc aaactcctaa ggcattaatc tgctttatca ctttcgtaga aactagatta   22920
ctcagacttg cacatatcat attcttggcc cttttgtgtt tctccttcct taataatacc   22980
cttgaagtcg taccaggttt gatatctgtt acaacatcct tttccttttt ggatgaggag   23040
attatatcgt ccttattaag cacactgtcc aaaccagaat tctcaagttg cataaggatc   23100
ttgaatttcc acatgccaaa atctctcttc cgattacact tctccacctc aatctttact   23160
tgagtagtct gcatgattct caactcaacc gagagaatga caataacttg agaatgtttt   23220
ctttaacacc aattagtaga taagaaactg aaaccattcc tttagcttaa caacatgctc   23280
```

```
tgataccaca tgtaaggttt atggcacaat ttgttttagt taaaccttat gtagctaagt   23340
ttgtttagct aacagttgat cagttaacct tggcacgttt gttatggttt gcggcacaat   23400
atttggttat ccagttccct tgcggtacgt ctggaagaac actgcttcca agtttcactg   23460
tataaagtac aaggatgcaa taaaagagat ataagctgta ggtgcttctc agggccgtca   23520
ctgtataaag tacaagaatt tttatttata cttttttattt ataactaaac tactatatca   23580
tatattttaa aaaaataaat atatgttacc acataaattt gctttagacc atgaaatcta   23640
ctgggatggc actggtgctt ctagactgaa gcgtaaagca agaactacaa cctagttctt   23700
gttcacctac tctcaacact tcaggtaagc tcagataatc tcttaaccct gacaacctgc   23760 tagataccctg atcaccgcaa tctgtctttc gttttccccg tgagttacaa gacacctgaa   23820
catctccatt tatacttagg tcaaaactaa aaccttagta cacttgggct tcagcatgct   23880
tggtgacacc taaggcccat tacgccttta tgcctgcttg tggacttcag actcgaactt   23940
gtcccaatgc ggagttgaga caacatctct acaaaatatt tttcatttta aatatttcca   24000
ttttatgaat tatttcttga attaaatttt agttttttat ttttcaattt tttcttgaaa   24060
tttaaaattt ttaatttttt tcctgatttt tttcctggtt tttacctcta attttttgtct   24120 tttttatcaa tttttataat ttattttgaa ttttatctac tttttatttg ttatttaatt   24180
tctattagtc ataataatta aaaatgttta aaaaacccctt gctatgttac cttttttttat   24240 ccgctaatga ataatatttg tcataacttt gatgtggcaa ataagtaaat taattttatt   24300
attcaatata ttaaaattat ttttattttt taaaatctttt gaagttgagt ttgaaagttt   24360
aaaatacaaa gttttgctaa tttgttaatt ttaaatgaga tattcacatt tattttttacc   24420 ctctgggatt gtttgatatt caatgcacaa aagagacgt ttggtcttat ttaattgatt   24480
agtacactcc aataatgtct catcatttct ttcttttgtg tggacccaaa aaaggaggca   24540
ttattgcagt aggagccaat taagaaagag aaaatcagat caagcgttgt tgatctgcgg   24600
actgagtgaa atatgagcgg atcaagcgga tttagtggtt caagagtaga tcaaacaaat   24660
ttagcggtgc aaaacatatg tttgaatggt gaaaatagat aaaaaaagt ggtctaaagt   24720 attatacaag tttaaattaa tctatataga aatttataac actatttatg tcatgattga   24780
aaagagttat tttcaaaaat actttataaa tgaagaatat aaaagtttat tcaaaagaaa   24840
atagaaaatt aatttgaaca tacagattat tattttgaat tttaaaattt aatatgtatc   24900
tgattttgga tgatcttaaa aaacagtgta tattaattta aaattattc aaagaattaa   24960 attgttattt acttttataa ataaatttaa ttattttaaa atagttattt tgaattcatt   25020
aaatatcata aataattaaa taaatatact gtcatatctc tttcaaaata atatattgtt   25080
atagctaggt aaagatcaat tggaacataa atagtataat gtattaacaa ttttttaact   25140
tattacaaat gtgaagtaaa aatcataaat attatttag ctgagaaaat aatttataaa   25200
tacattacat taaatactag gtttgttgta tataacatat gcaaattcaa aatttatagta   25260 tttagagcaa attatcaaga aaatagaatt gtgacatcaa ctgcccatta tagtcttcat   25320 atttatttt gttatttaat tagttatatt atcatcattt aaaaaaaaaa aaaaggttta   25380
tgttgaccaa aaaaagtgta tagtattcat aaggcggagg aacctctcca tatacgagat   25440
aaaaaaccgt tcttttcttt tgagaatcac ttttctaatc cacctgtgta tcatccgtca   25500
ttttttgtat aattgcagag atccgggacc tctgggaaat tatatacaaa taaagacaaa   25560
acgcggacag cccactatct ctgtatggtc caccattttt tccacctccc actcacaacc   25620
taaatcagtc taagcgtctc aagatctgct tctctttcaa accttgagca ccatgagcaa   25680
```

```
caaacccttg tggcgaaatt gttttcaaga tgttgagtga agctaaaaat ctcccccctt   25740
acttgagatt tgcaatttgt tgctgatcta ccgtagtagc tttattctct tgctcccaag   25800
caaagatggg taatattctc ttcgtttcta gtttgtctca cctcttgcaa tttattgttt   25860
gattagttta tttggaataa tcggtgaaag agatagcttg atttttttccc ttcgtcgttc   25920 tgattcatat caatttctga actccttcaa aaacaaagaa gagagattgg tttgtgatga   25980
ttctgaaaca tttgttggca ctgaacgtac ataataatt ataataaaaa actcacgtaa    26040
gcatatcaaa ccaatttccc atatggagga aactttaggt ttaccactac cataaacctc   26100
acatctcaac tctaaacccct aaatcttaga ttagtcagct ttaggggtat aatggttttt   26160
tacatttcat taaaaattag gataaaaatg attattgtaa acatgaaaag tgatactata   26220
aatgtaatat ttgtggtaat ttactggtga tttgcttgtg ctttaaccct ccttattata   26280
aactatttgg gctattgtca gcaatttgtt ttgtatgact gaaatatgtt attagaatat   26340
tatgtgtttg cgtcaaacta aaatgagtc acaaatattc aaaaaaccca ataagacgtg    26400
atataggacc cgtcagtttt aacaaaaatc atacaaataa agttaatatt atatgcaaaa   26460
tatgaagctg atatttgctg gaatattgtt ataagaaact cacgtaagca tatcaaacca   26520
atttcccata tggaggaaac tttatgttta ccactaccat aaacctcacc tctcaactct   26580
aaaccctaaa tcttagatta gtcagttcta ggggtataag ggtttttttac atttcattaa   26640 aaattaggat aaaaacgatt attgtaaaca tgaaaagtga tactataaat gtaatatttg   26700
tggtaattta ctggtgattc gcttgtgctt taaccctcct tgttataaac tatttgggct   26760
attgtcatca atttgtttta taaaaaaaca atattccagc aaatatcagc ttcatatttt   26820
gcatataata ttaactttat ttgtatgatt tttgttaaaa ttgacgggtc ctatatcacg   26880
tcttattggg ttttttgaat atttgtgact cattttagt ttgacgcaaa cacataatat    26940
tctaataaca catttcaatc atacaattaa ataagaaaga aatgtcaata taaatttgat   27000
ccaacatagt atattaatat gtacatccaa tatttttttt tatagttaca taactgctct   27060
aacacacact tataaaaaaaa aaatataaca tgatacagta acaaaatata ttatatgatt   27120
aataaattaa aatcaccaag aaaaaccatt aatggtaacg tgcgggataa gtgcactgtg   27180
gttgtaatag taatacaaac atatagagat ataggtgtac gcctttgttc ggaaactcgc   27240
taggcgctat gtgtgcggca cactcggacc tagtgattta ttgaaaaatc agaaaaaaaa   27300
tcgggaagta cgcggagaag aattattttg tatttttgta tgtataatac tctatttata   27360
catataatac atgtttatgc atcatatatc actcaatatt taggtataat tttcatgcgg   27420
ccttactctt aaaaacaatc aattcggatt tcaatcttgt gaggacaatg aaactatcaa   27480
tcttaaagat atttaatcaa tcagtcaatt tctagcatgt ctcagcaata ctatttctat   27540
gtgctcataa tattatggtt tatcaagact agcaaaaacg gattcaatta atcatgcaat   27600
tagggtttaa caatcaatgg attttagcaa gactagtaaa aagatttatt aatcacaaaa   27660
tcagtttcaa ggctgatttt agtaatacaa gaatatagat ttcaagcatg aatttcaatg   27720
aatcaatttc aaggctgatt ggtatttagc ataaaccgtg tgtaaataat ctatctagta   27780 tccgaatttta ttaaaccctca aaaacatata atcagatcaa tcaattaat agaactcata   27840 agcataatga atttagggtt tcaagtttca gatatgcgga ttaaggttag gactagaatt   27900
agggtttcgt gatttctaat cagatcaatc aataaaaaat caaacctagc atacaatctt   27960
aaacctcaag acattagatt ttatcataaa tctatcgacc tagcatacgg attctctatt   28020
```

```
ctcaaagaca tccaaatcag atcaatataa cctatcatac ggattattta gggtttctat   28080
ttaaaacaga tcagattaca aaactatcaa tcctagcaga tgatattaaa cctcaagaat   28140
catgcaatca tatcattcgg atttaaacaa gtaaacctct atcaatctgt caacctatcg   28200
gattatatat aagcaaagca agctagcaac ctatcgtatt caatcaatgt tttaacaggc   28260
tggtcggttt aaacaatttt aaatcagatg aacaattaac caaggaggat gagaaaataa   28320
atctatcaat ttaacagtca aacaattcta gcaacatagt atcagattca atcagattta   28380
aaacctcaat gatcaaaacc gaaaacattt ttgatttcaa atattcgat tagggtttta   28440 atatgtgatt tgataattat agtataatta attatgatac ttatattatt tagggtttat   28500
agatatagag ttagggttta tcggatttta acttgtaaaa ttcgatttgg agttttaatc   28560
atgttggaac atgatttagg gtttgggggt atcgaacttt ttagagcttc gatttactca   28620
attaggattt ttgatctatt accctatggt tttgattcat aaagattagg gttttagggt   28680
ttcattcttt atcaatcaat tcatgttcga ttatgggttc ttaggttatg aattaccttt   28740
taaccttaga tgattgttga atcggactac cgaaggagtt gagccgcgag ctggacacga   28800
acgggacgcg agctggaatg gatcgagtcg cttctatcgg gtcacagacg tcctttgttg   28860
ctgatcggga acgccttgat tgtcggacgc gagctgtctg gtgctgtcgt gaacgaggaa   28920
gaggtcgcgt gctggagctg ctctcgggtc gcgaacgtct gagctaggat caggaatgcc   28980
ttgggctgaa gctgattggg aacgcgagct ggaacagatg cggaacaag agacgcgatt    29040 ggggtttagg gttcttcgga tctccggcta gggttagggt tttagggttt tcgatttgg    29100 gtattagttt agggatttag agcatcgtgc tgataacgtg ttgtgaaagt aatggaaaag   29160
tctatcttta ttcataacat agaggttcct tatataggag attacaccgt catagataaa   29220
tagaaagatt ataaatcata atttcttggt tatgagccat ccacaatctg gttcataacc   29280
aacccttaat ttttcttaat atttatcatt ttatgtcatc taatctatta aaacaaaagt   29340
acaaatgata cttaatcctt aatttttcgtt aatatttacc attctagcca ttgggcataa   29400
aacaatgttt tgtgaattag caaattctgc ctaataattt tacgtgtaca aaaccaacac   29460
ctaaaatcac gtgaatacac gaagtcatat gttgttgtag accaaattaa gcactcttaa   29520
ttcttcgtta agtaaatgta tttaccataa aattctatta gaccagccca tggatttgtt   29580
ttattgtttt ttcaaacttt ttagatagac ccaataattt acttaaaata tatattacca   29640
attgaatctc aaagttatgt taataggctt aacatattag atacaggccc attttagatg   29700
tagcttcagt tttttttctt tttcttttag taaagatgta gcttcagttc attatacatt   29760
aatatatata ccaaaatgga ttcatgttag ttaaaccata tgaagcataa aattatagtt   29820
tcaccatcat aataattaat ataataaaa ttctatatat atgttcttat atattatttt   29880
aatagattag attacaaatt tttgaaaagt acatatacat acatgtaaat aaacaactaa   29940
agaactgaat attttaaaca ataaattaca aacctataaa caaacagcta tagcaaatgc   30000
gcatttgctt ctcttacgaa aggctgattc tttcttatca attcaaacac ttctcggaaa   30060
atgatttaag tgagcttcca ttgtatggct gtaaatcaag atatcatcga ttatatacat   30120
tagtcagaac atacaatttc agtagtatgg taataggccc aagttatac aagtttagtt    30180 gatgtgattt gcttccacca aaataccttt ggtaagccag agtcactcaa catagttctt   30240 acttttcca tgatagtgta aattgtccaa cttgcaactc tattttgctg cgatgttaga    30300
gtaagcttca cgtgctgata acttccttct ctttacatga atcactgaac ctaatctatg   30360
attgaaaatc taaagtccat tgtttataag atctttttct tcctctcagc tccatcatta   30420
```

```
tcctctaaca cctcttatgt tccatcaatg tattatttat tattgtggtc ttcgtactcc   30480
tcacactcca tcaaaagcgg ttgagttttc ttattttcca agaaatgctt tcacacatac   30540
tactcatcgt agtaatggca caattcttct actttgcatt aactcatctt catttgacaa   30600
gaacttcctc aaaggtggac cttgatctct aggtttcacc acttctctat ggtggtatt   30660 catcatcttt tttatttcta acacatcttt cctccattga agtattttc tgattcttag    30720 taatcggcca actagactga aaaagtttta cgacgatgtg ctttctcata aaattttccc   30780
caaaaccaag cattgtattg ttgattctat actcacatat ctttatgtat ctttcaactc   30840
tttctattcg acaatcggat catgaagaat ttcatcatat ctttctctga tcaacaactt   30900
atatgttctc caactatgct taatctcttg ttgttcatca tcttgaataa ttggctcatg   30960
gcaagttaag gaagtggttc ctacgtttga atattccaaa gtgttatcga tcacgaaaaa   31020
ctgtcctgct ttgcttaccc attccttgat cttttcacca tcaaatcgca gaaagtcaag   31080
ttttgctaat ctcatacccc cgtgtaatgt ttaggcgtcc ttggatggtg ctgatgatga   31140
tgttcacttg aatattttgc ctcacagata cagttagaga gtttatctga ggattttgat   31200
tgttacttag agtttattgt gcaactccca tctttgcact aagaatccta tttttttta    31260 ttcacaagca cattcatcct ccattgttcc caaagaaagc aagttatgat tcatcctgga   31320
atataaatta cttaacattg gtaagaagta ggctaggcaa ataaactgaa cctgatccga   31380
taaaaatgaa tctgaaccga tctcaaccga tataaatgcc gaatgaatct tgtttacaga   31440
ttttatccaa accgaactca aacctaaatg gatatccaat aaacccaaaa tattcaaaac   31500
tcccaaaaga gaaacttgta ccaaacatga tatcaattcc taatatataa ccaaaataca   31560
ctaagatatt attgaacatc taaataatt atctattaca tgaataattg actcaaaatac   31620 ttagtttaat atatattttt ggtgtttggt taatattaat gttttatat tttgataatg    31680 gcatttgaaa ttaaattatt aataattttg cttctcaagt ttaaacattg cttttaaaat   31740
aaaatttaat agtgttttt gttaattttt aatatgttac atttcattat gtatgatttt    31800
tttgtcgtac aagattttgg tttgtcatgc catatctgat gttgttatgt attgttcaaa   31860
gaggagtctt gtatggttga tagacgagtc tcccaaaatt attttgaagg aaaacaatat   31920
ggtttgaggg agtcacgtaa aacaattat tgaaattatt gaatatatat tgaatttaat    31980
ccagtacaaa tcaatatttt tggaacatat gacctgatta atatccaaaa tcgaaactat   32040
ttcaggttca atcgaatctt ggacatgtaa ttaaaccaaa ccgaacccga ctaaacccaa   32100
aaacctgact aaatccaaac cgaacccagc taaatccaaa ccgaatatga cccaaaattt   32160
tataatatcc agatggagct gaaattcatg aactcggaaa ctcgaaattc gaatgaatct   32220
aaaccgaatc ctgattgaga tcccgattgc ccaatcctag taagaaggtt gtcacatcct   32280
catttctgat aatgccattc ccagctccct taacctttga tgttgtttta tttcccatac   32340
aaacagatca tccaacgcct tctgtcgtat tctcaaatca ctctctgttg tgtatcatac   32400
atatgaccgt tgcagcttgt gtccatcatc cattcatatt acatacacta tatctgtcaa   32460
atgtagagcc tttgagacat ataaccatgc agcatcacgc ttggtttctt ttaccataac   32520
agattctcct caactactac tccttggtac ttggatttag tctgaaactt gtttctactt   32580
ggacaagaac tcttgaaatg tctttcttct ctgaaaatct gacaccottt cttgttttta   32640 gactgcgacc aagggtttga ctgttttaat gattttgtct ctatattcta ccttcctctt   32700
taaaatgggt gcaaatatct tattagttt tttttttgttt tttgaaaag aggagtactc    32760
```

```
acacaaccta gagaaaaatc tggaggattt ggaggtggaa atgggaaccc tcaatgcaat   32820
gatatatgag ttgttaaaaa gggtgtcgaa agagaaggac agaggtatag aaacgctagc   32880
tgaagtggag gaatggattt caatggcaga agaaactgaa tcgaaggcga gtagtctcct   32940
tgatgaaagt atttcaggat gtcacgattt atcaatgtat gatgatattt ccaagatatc   33000
tcaatcgacc cttcattata gcgagacggt gtgtacgacg ttgaaagaag ttaaagcact   33060
gagatctaag ggagttttta aagtaatagt tgagagagct cccttgtctt acgtcaaaaa   33120
gatgctccca cttcacccaa ttgattctgg agaaatgttg gcagaagaag catgggattt   33180
ttttcaagag attattggag aaacaacgtt aaaaagtcat ccagacatac cccagctggc   33240
aagaatagtt tgtagaaaat gtcgtggttt gcccattgct ctcagtctca tcggcgagac   33300
catgtcacgc aaaaggactg tacaagaatg catcaagca attagtgttt tggtttcgtc    33360
taccccagaa gtttcaggca ctgaagatga gcttctttac attttgaagt ttgcgtacga   33420
taatctgcct ggtgagaata tcaagtcgtg cttcttgtat tgtgctctgt ttccgaaaag   33480
ttgtgatata aataaacaag atctggtaga ctgttggata gccgaaggag taattgaaga   33540
tgaagacaga gagatagctg agatacaggg atatgaaatg atggctgatt tggttatgat   33600
gagattgttg attgatgatg aatctgaaca tgaggtaaag atgcatgaca tggttcgtgg   33660
aatggccttg tggatagcca ctgactgcgg gaggcagaaa gaaaactttg tcgtggtaag   33720
cggtgaggat agacatcaga tgccagaggt gaatgattgg agtaacgtta aaggatgtc    33780
agtaacatct actcaggttg acaagatatc cgactctcat gattgtccca agcttacgac   33840
tctatttctc caagaaaaca acttaaaatg ggtctcgggt gatttctttc ggtggatgac   33900
cagtcttgtg gtcttgaatc tatcgcgtaa cttagaactt tctgagttgc cggaagaagt   33960
ttcaagcctg gtgtccctgc ggcttctcaa cttatcatgg acgtggataa aacgtttgcc   34020
gcttggtctg acagagctga aaaggttgat gcacttggat ttggatgaca ccctcgtct    34080
tctagaagtt gacgtgatag gttatttact gaatttgcaa gtgctgagat tattccggtc   34140
agttccgatg gatcgcagct tattggagaa tatacaactt ttggaaaatc tgaaagagct   34200
gaatctaacc gtgagagaag ttgatgtttt ggagcggcta caaagtatcc acaagttggc   34260
aagttgtatc cgacatttac atctcaaagg gattacaata aaagatggag gaacactact   34320
gctgaactct atgttgagtc ttcgcgaact taatattggg atgtgtgata tcccggagat   34380
aaccgttgat tggagaagca ccatccaaag agagacgata cattttggta acattcagaa   34440
aattccgtat ttacagaaca tacgcacagt ggctcttttct tggtgcaaag gtctcaagga   34500
cttgacatgg ttgctattag ccccgaatct cggcgatcta aggttacttg aatgtcagca   34560
aatagaacat ataataaaca aagagaaacc cacaggtgat atgagtgagg agccttttca   34620
aaatctaact aggctcagcc tagaaagttt gcctcaacta gagagcatct actggactcc   34680
tctaccttt ccagttctga agatctttg cataagaggt tgtccaaagc tgaagaacg     34740
tccgtttagc aataaaggaa atcaagtgcg atcagatgtt ggccaaaaag gagttgaaag   34800
ggaggatgaa gctatgaagc aacatctctc caattttgat gacaggtctc ttctttccta   34860
aatcttattt catcctgttc ttcagttgac agaaactgag aagctattgt gataaatttc   34920
aatggtgata ttccgttata attgtttata ctagttatgt aacaaattga acgggtgcag   34980
ggattttctg aagatggatg aagaccagaa catggagggt ttggcatctg agtcgcatcc   35040
caataagaac atagccctgg tcgacacttc agagagagga aaatttagta ccaatgcaaa   35100
cagcatgacc gattttgatg acaggtctct tattccttac tcttctaaac tttgtccttc   35160
```

```
atgttttctg atttaaataa acctctccag tcctatgtta catggaaaca ggagcggata    35220
cgtggaagcg gaaacgtatg caagcgcaga agcgagatta ttaagaaaat taggaagcgg    35280
gtacgtattg gaagcgtatg tatatatata tatatacatt ataagaattt tttaaaaaaa    35340
tctagaacta aaaattatat gatttaaatt taaaataaat catttatatt tataataatt    35400
atatgatttc gtattaaaac tgtgaaatac acataaatta aattattata ttaattattt    35460
ttattacttt atagttaatt gacataatat atttgaatat atgatttatc tttaataaat    35520
acctcaatgc ataaagataa tttatagtat taatttttaat tgttttatat ttctattcaa    35580
tatattcaat actattaaat tttggattt atataaatta aaattaaaat tttatatttt    35640
tattgatata agacattgtg tttaaaaaaa aatggaagcg tgattccaaa acggaatcgt    35700
aagcttccaa cgtgttttta aagataatat tttagaagcg ttttggaagc gagattccgt    35760
aagcttccac aaggtttcaa ttctgattcc agttccgaaa cgggaagcgg acgtctgatg    35820
aagcttccgt gcaacgtagc tccagtcaac aactcgaatt tcatcacctt ccatctttcg    35880
tgtcatcccc gctcttattt taccgaaaat ggaaagctat tgtgatacgt tttgcaatgg    35940
ttttattttt ttatattgat cactcgagtt tcaaaattat tttttataat tttaatctta    36000
atctgaattt agtgtgtata tatatatatt aaatctaatt tattaattta gaattttact    36060
ttttgtctac tgataaaaag ttgttcatct tatatattaa aagagaagtc atgacttctc    36120
attcatgtat gattttaac taaatggact cttactagaa attataactt taaatacagt    36180
atgtgcaata tttattcaac tatacattat attttaagct aacaataaaa aacataacta    36240
attaaaatca gtttcttccc attattttag ggatttcata aataggagta acaatatatt    36300
agatatttga actattttaa ttatatttaa tatnnnnnnn nnnnnnnnn nnnnnnnnn     36360 nnnnnnnnn nnnnnnnnn nnnnnnnnn nnnnnnnnn nnnnnnnnn nnnnnnnnn          36420 nnnnnnnnn nnnnnnnnn nnnnnnnnn nnnnnnnnn nnnnnnnnn nnnnnnnnn          36480 nnnnnnnnn nnnnnatta tgcattaata tatgtagaga gttattattt atataattta    36540
aaataaaaat tctagcatac ttttatctat tttatattcg taatcaatca tgttaaaata    36600
aaattgttat attaaactac atatgataaa attatattaa attgatagct aataaatttt    36660
attttcatat ataataatt tatgttaaaa taatatctga tgttagacta caatacattt    36720
ataaaaatta acatatctta gattttgta tatacaataa tatattatgt aaaataaata    36780
aacataaaaa tattacaaaa atgaaatcca gttttgaaag ggcaggtaaa aattcaatat    36840
aaattaaata caaataatt attaaaatta tgttttatg cacattaatt tatttaataa    36900
ttaaatataa atatataata agaagagaaa acatgtaact ataaattatt atatttgaaa    36960
tataaacatt taaatagtga ttaacattaa ataataatct aaaacaaaaa atatatgtat    37020
ataattgaaa ataacacccg cgcggttgcg cgggtcgaaa tctagtgtaa gttatttaa    37080 tggtcctact aaaattgacc tatcttatat attaatcata aaaataataa taataacaat    37140
aatgtcgagc acacataatc tatctattac accattttat taaaaataac ataacctatga    37200 ttatgggtaa ataaaactgt caaaatagtt taacccactc aatattttt cattggtttt    37260 atatactaaa gatttagttt tttttttttt tttaacgtc aaaaggctat tctattacac    37320
aaacttgagg tggtctgggt aaccaaaccg gaatagaaca accaacaaag tgtaactcct    37380 tatgaaaga tctagtagtc ttagctaaga aatcatcagt ctgattgtgc gcccgtggaa    37440
cgtaagtgat attgaaatcc gggaagcata tctgtagtgt ctctattctc tccaattccg    37500
```

```
tcgcaaagct tggccatgca tgaggatcct ttaccattgc aatcagttcc ttacagtctg    37560
tcccaaagtt ctggcaggtc gaatgctgca gcatattttc catcgcccac cgcagtgctt    37620
ctacctccga atgcaaggat ggttcacgtt gaggaaattt ttttgtcccc ataagttgag    37680
tgttcccaga actatccatc catgtccatc cacatccact aaagttagca gaaggtgtcc    37740
aagatccatc taataagcaa atattttcca agcttacggc ttggggttcc tcatttatag    37800
tgtcttgtgt cactgcttgt accacttcat tagcctcaaa ccaggcctgg cattcactct    37860
caacatctct aactagttcc aaaggatctc tatctattct cctgaagaat tttttattcc    37920
taaccttcca aatgaaccat attatccagg gataaagatt tagttgagtc atgtacctgg    37980
tcttattgta tatcatatta acccctgttc taaaacgcgg cgccgagggc cgcgtaatcg    38040
ccggaaagtc gcggtgcggg ccggagccgt cgggagtaga ctgtaatcgg ccaaaaaatc    38100
gggtgtttat gaaaaacttc gttttcttc atttaaactc tacaaatcga ataatatttc    38160
atagattcat caataattag tacagatcta gcaaaagaat taagaaatca ctgtaaaaac    38220
gataaaaaag tagccgccat gtttaggttt aaggtcgtgc acaagaaaga aagaagatga    38280
aaggaaaata tccttttac ccttcattaa acctggattt aaaaaaatga ccaaaattag    38340
gcaagagaga ttcgaacccg gccctactgc gggcattaat acaacgatgg ccagtggacc    38400
actttagatt ctttgtaatt ctatcaagtt atctagtata tatatcgata aattaaataa    38460
aactttaaaa attccgcccc cataatttct gattaatctc cgattttctt gttaggcgct    38520
aggcccaacc cgaccgcccg actagcgcct aacgaattct cgaacatgga tattaaccaa    38580
tactaactta catgttatag atcagtttgt caaccaaata ataactca tctacaaaag    38640 ttttattata caaactgtta tacaatttag atgactaaga aaagtaaaat aatttatata    38700
caataacaaa aaaaaccatt ttgcataaca taaatcaatc tttatgtata cattacagtt    38760
atgcataatt tcatcatata ttactatgca taaccgtcaa gccatttat atttattta    38820 tttgaagatg aaagcaacta attataaaat atcacatata ttaggtttca cataatcaaa    38880
taaaatacat aattaatatt atgtgtgaga tgtaatagac tcataacaca atagtctaat    38940
tgtttgttta aacggatctc aacaataat aaatacaaaa ctatcattta catctaatct    39000
attaaaaata aagtcctact ttttatctac ttaaaatagg ttgtcattga aatttagact    39060
tattcactta tcattaaaaa taatatagc attcattatt attagattaa cattacataa    39120
taactttccc ctctaattaa aaaatttgtc gactacccat aatacactaa cgtagttata    39180
tttgaaccta caccttcata agttcatcaa gcatgaataa attatgaggt tgattgtttg    39240
caaattctag attagatttt ggttttgtt tctgtagaat ctactttttt cccaatcaag    39300 attttggta aaatagattt tctatttttt agggaaccca gattttaact ttttgccat    39360 tttactcata aaaatcaaaa tccagatttt atgggtttct aatgcatcat cccacgacta    39420 atttttttt cttttctt taactagttt ttttgtaact atcttttaac tagctattaa    39480
ttatattaat atataaacc acatcaacat tttataaaac aaacacaaac tcacgaaaat    39540
aatattttcc acatatcaaa ctattagagg ttttttattt aaatgaattc tataataatt    39600
taaacatatt ctaagaacta atattacagg aaaaaaaac aaagaaatta gattaaatat    39660
cttaataaat ttaaaaacaa aaatcaaaat ctcattcttg tttcagaaaa ctaattatct    39720
actgcaaaat ccaaaattaa aaataaaact aaaaattaaa aatcgaaatc ttagcctaac    39780
aaacaatcat gaccatagaa tcaacaaaat aattttattga tcattaaatt tttaatttct    39840
aaaactatga attgaaatta ttaagaatca acaaaataat ttatttattt ttaaaataag    39900
```

```
ttcatatgtg ctttgataat attattttct atattttca taaaaatgtt tttactatta    39960
atcatatttt tcattttctt aatttttaaa aacaaaaacc aaaatctaaa aaccaaaaat    40020
taaaaaccaa aaactaaaaa ccaaaatcta aaacaaccat tcatgctttt caaaaatcta    40080
gaatctaatg caaaatcaaa aactaaaatt taaaatctaa aatctaaaaa ccaaaaacca    40140
aaatctaaaa actagcaaaa caatcatcac ctatatttga atctttcaca gttcattaat    40200
acaactgtgt ctaatcccct acagcataac tataattgag acaaacatat acacaatata    40260
tatacacaca tttcatttgt tttttcctct cctcattgtc tacatgtttg aatctatgga    40320
agttgggtag gtcctcatta gcaataatct gatctataga catttgcttc ttcttctcca    40380
tgacttctct tggtcatgaa tgaaagaaaa tattttggtc cctgcaaaga gaaatgaaaa    40440
cagattcata acatttatca ttcatgcata ttagaaaaac tcaaaaacct gaatcattac    40500
ttacctcata gaaaatatca taatctattc tatagagtag atgtataaaa tggaattata    40560
aacatttcca tatgaaatga cgaatcattt tttaaaaaat tatattctaa caatcgtaac    40620
tagaacaaac attaaatttt ctaacattac gctaacaaat ttttttttaa atgatttta    40680 tttcatcttt ctatctaaac tattaaaatt aaagtacaaa tttgacctaa cctctaattc    40740
aactttataa ttagaactct atgcctctgc tttttaatag cgcgaattta caaaataact    40800
aaaccagcaa aattatattc acatcgcaaa ccaactttgc cgtgagattc acatcgcaaa    40860
ccaactttgc cgtgagtcat agccaattaa ttatcggttt aatattgtct acacaataaa    40920
atcatatcta ttcaaaattc cattctatac ttttatattc taaagttta tataccaatt    40980 atttatgtgt ttggcatacc catttatttc tcgatttagt attgtcaaca gaatcaaatc    41040
caaccaaatg aaaattcaat agactacttc tttataccaa ttgtttaaaa cctaccacac    41100
acaagaaaaa aaaaagatta ttcaaccagg tctaagtcgg ttacatgttt tggtcgatta    41160
caaagaaaat tagttagata attttaaaag atattttgg tccaccaaat ctaaactaat    41220
aattttacgc aaccttgtta tattattaaa tgcactatca tacaaatatt agtttcatag    41280
tgattctaat ttaatagaat agagtttgtt cgaactagtt aaaacattga aaggggtgca    41340
gggatatccc aacagtggct gaagaccaga agatgggtgg tttggtatct gagttacacc    41400
ccaatgaaaa cgtagccctg gtcgagactt cagagagagg aaaaagtacc atcgcaaaca    41460
gcatcaccaa ttttgatgac aggtctactc ttccttatta agcattatgt tctctaaact    41520
ttttcgatcc tgttttctta tttaaataaa ccttgctgtc aacaactcaa tctccccacc    41580
gaaatttcct caccttccat cttgcgtgtc atatgcgttc ttgttttaac cgaaactgaa    41640
aagctatcgt gttagcttcc atgaactagt tatgtaataa attatagggc ttgcagggat    41700
tttccgacat tggctgaaga ccagaagatg gatggtttgg catctgagtc acacccagtc    41760
gaagacatag tcctggtaga gactttagaa agtgaaaaag gtaccatccc aaacagcatc    41820
accgaagaga atgtgtttca atcgggaaaa cacgcaactc tggaacacac acaatcatac    41880
ccagttttgg cgccagatgg catgatccac aatatgactg acactcctgg tatttctttt    41940
tacaaagaat ttaattgaca aattttagga cataaatatt aaaatacct aaaatatcgc    42000 aactattaag agtcaaatat ctagtgtata acatttttct tcttcaagag gttttggaaa    42060
gaatcataag caaaaatata taaaattaat taattaatac tgtataatgg attaaataat    42120
atacaatttc gaattgttga acaaacacat aaaatatttt tatatcattg ctatatagat    42180
atataaataa tattttaaat aaaaaaaaaa tttatagttt ttgaattata cctttttcaaa   42240
```

```
ttcaaaattt ttattaaaaa aaatttgaac ttttttttgaa attcgaatat tcttttttgaa    42300 tctattttta taaaacaaaa tcctaaactc acattccaaa atttcaccat tcaactctaa    42360
acctaagtct agattatttg accctaagat tataagtgta tatcttatat attaaaagag    42420
aagtcacaac tttgactcat gtgtgatttt tttaaaaaat ggacttaatg gacatatttc    42480
taaaatgtca tataacattt aatctctaac taattattct taccaatatg gctaactaat    42540
ccacgcaata ctaaaatcgt acccttttaa ttacggttta cataaccacc ataatttatc    42600
tttgaattaa attatctttt atattttggt taagcacgtg atgtttgcaa tatggtttga    42660
ttataattat tttcatattt tggttttggt gtgtctgtac tgccggttaa ccagttatac    42720
caacattaaa catatcttaa tccttaccca ttctaatttt caaaccactt acaagttgtg    42780
tgatctaatt caaaattgat attttattca ttataaatcc atatcaatcg taagtttgat    42840
tcaatttttt ttttttggtt ttgatgtgac tagactgccg gttaaccagt tataccaaca    42900
ttaaacatat cttaatcctt acccatacta gatttaaaac catctataag ttttgtgata    42960
aaattcattt ttttcttcta aataaaccta taccaatcag tagttttgaa acagctacaa    43020
aatttgtgat caaagtcaaa atatatttt tctcgaaaag caagtataat cataaaatca    43080
aattagttgt aatatctttt aacttgaaaa gcaagtatat aggagcaaaa tatctcaata    43140
gatacgattt ttccagattt cttgcttgag acttgcaaaa tattctaacg atatatatca    43200
aacatatgta ttagatttca ctaattgttg ttgccgttaa ctactcaaca aatctactat    43260
attttccata acaactaata cataatatcg tactatttaa tgtctattaa tcatagatt    43320 caaagaatat actctctaca ataccctaac tatttaacca tctataaata acgacgctaa    43380
gaatcataca tcgaaatatt acaatatttt caaggtaaca ataaaaaaat atttaccaat    43440
ctttatatat aattacgagt taaataatga ataacaatc caaaaaacat aataaaaaaa    43500
tctgacgtat gtgatagttt gaaacaattt attcaataaa aaacatatat ggtaaaatta    43560
ttatgtttta aaaagtgata aacacatttt atatatatat tataatatat tctaatttag    43620
gattgtaaac aaaatgttta tataaaaaaa atggaaacaa acacctgcgc ggttgcgcgg    43680
gtcgagatct agtttatctc tttaaaaata gagtaaatgt ggttaaagta agtggtatta    43740
cgtggtaatt ttgacaattt ctcatttttt catttatcta agcgggcaat ataaactttc    43800
tatcaactta aagatttaat caacatatga atgtttgcgt tttaggaact tgtaatattt    43860
aactccttac gtagcttgct tcttttcata ctgcttaagc aggaggaacc attatggctg    43920
gggaacttgt gtcttttgga atacaaaagc tttgggagtt gcttcgccaa gaaagcgagc    43980
gttttcaggg agcttcggat gaaatagata tggtaaaaag tgatttactc tatttaaggg    44040
gatttttagc agatgcaaat gccaaaaaac atacaaggga ggtgaaaagt tgtattgaag    44100
agatcaaaga aattttttt gacgcggaag atattattga gacatatctt cttgaagaaa    44160
accccccaaa aactggtgtc ttcaagaggc tttcagagg gcgtgctggc aggaaatttg    44220
ctttggatat gaatagctta agcaagagga tttctaagat aatcagcgtt atgcaagctt    44280
ttggagtaca ccaggttatt actgaaggca aggattcaca acctcttcta caaagacaaa    44340
aaaggatgcg acaaaaattt gctggagagt acaaacccaa ttttgtgggg ctggaagaaa    44400
atgttgagaa attggttagt cttttggtcg aggaagacaa tattcaagtg gtttccataa    44460
ccgggatggg tggtcttggt aaaactaccc tcgctagaca aactttaat cacgatatgg    44520 taaaacacaa gtttgatagg ttcgcatggg tgggtatttc acaagcttgt aaccgaaaga    44580
ttgtgtggca aatgatcttg cggagtctct tggccaaaaa agatgaagat agtattttgc    44640
```

```
atatgactga atctgaactc caagagcaaa tctttctatt gctggaagca tccaaatcat   44700
tgattgtcat agatgacata tggaaagaag aagactggaa gcgaatcagt caaatacttc   44760
caaacacaaa aggtgacctt atattatagt acatatatta aacacttctt tttatcgaac   44820
caacttaaag ttgcacaaac acaaagatta taagatctag cacttcttat tagatttaga   44880
aactctctca aaactaaacc tttcaatgtg tttctcttga tggaacatct ctccatgaga   44940
actctttata taggaagaag ctacatcttt tcctaaggac aaagctacat cttttcctaa   45000
taataatatg gaaacattcc taagctcgat atgttttcct ttttccttaa cccatcaaac   45060
ttcactttaa tgagttaact tgctcctcaa gttaattgga attatccaac attctccccc   45120
ttaattccaa ctcgaatctc gggtatgttg atcttctgaa ctccgatgaa cttccataga   45180
ccgttaatag gtgcatcgca tttcttcgat acgatgttgc atcagaacgt gagtatagat   45240
gcttcactgc ttctccatga ctctctctta agcatcctat gatgctttga tacgatgttg   45300
catcaatctc aggctcttcc tctgcctttg atactttcaa actcgtgtgc atcggaacat   45360
gagaatagtt acatgactcc atcttcgtct tgacaagtat accttgcgcg tatccttctt   45420
gtttgatgtg aatgccatca gctccttgcg ttacttctat accaagatag tatgtaagct   45480
tcccgaggtc tgacatctca aatcttcttg acatatcatc tttgaattgc ttgataactt   45540
tgagtgaaga ccctgttaca aacaaatcat caacgtatat agctatgatc agaagctccc   45600
ccttctcttt cttttgatat accgcaggtt ccttggtgca cttcgtgaac tccatctcct   45660
tgagaacacg gtcgagtttg atgttccaag ctctcggagc ttgacgcaaa ccgtatagtg   45720
ctttgctaag tttgtacaca tgatcctcct ttcctttctc cacaaagcct tctggttgag   45780
tcacgtatac atcctcattt aagtctccat tcaggaacac agttttcaca tctaagtgat   45840
ggatctccca tccattagtt gctgctaacg ccaagagtag tcgtatggtt tctatccgag   45900
caactggtgc aaatgcttcg tcgaagtcta tgccttgttg ttgcacgtag ccttttgcaa   45960
ctaaccttgc tttgtatttg atcacggttc catctgcatt catcttgatc ttatagatcc   46020
acttcaaacc tatcggattc acacctaccg gcttcttgac gagcttccag gtcttgtttt   46080
tgatgataga ttcgatctct gccttcgttg catcgatcca agcttgtatc actgcagctt   46140
cgatgtaact ttctggttca ccatcgatgg tgagcaagag tctgccacct tcaacttcag   46200
cgagtaggat gtaatcatcg aaccgctttg gttttctgat gttacgacca tatcttgatg   46260
ttacatgcgc atcgttgttc tctgctactt gctcttgttc acctgcgtct acagcttctt   46320
cttcttcatt atcgtttttgc tcttcgtgat gttggtgatc ttgatgctca tcaccatctc   46380
cttcttctgt aacatcgata tgaggaagct tgaataatca tggttcttca tccacatttt   46440
gttgcggtgt atatgatgcg gtgagatgtc tagttacacc gttttcttca taaaaacgaa   46500
tgaactcaga agatgtgaac tctcctcctc tatcggtgcg aaaagtcttg agttgtagct   46560
tcgtttgatt ctccacatac tccttgaact ttttgaaccg atcgaacgct tcactcttct   46620
ctcttagcag catcgtccac atatatcttg agtatcatca attaaagaca aatacatatc   46680
cattgtttgc tggtgttgat ggtgatatcg gaccgcacaa gtcaccatgt accaactcca   46740
atgcgtgtga tgctcgatac tttgcttag gcaggaaaga cttccgagtt tgcttcccaa   46800
ctaagcaggc gnnnnnnnnn nnnnnnnnnn nnnnnnnnnn nnnnnnnnnn nnnnnnnnnn   46860
nnnnnnnnnn nnnnnnnnnn nnnnnnnnnn nnnnnnnnnn nnnnnnnnnn nnnnnnnnnn   46920
nnnnnnnnnn nnnnnnnnnn nnnnnnnnnn nnnnnnnnnn nnnnnnnnnn nnnnnnnnnn   46980
```

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 47040 |
| nnnnnnnnnn | nnnnnnnnnn | nnnnnnnnnn | nnnnnnnnnn | nnnnnnnnnn | nnnnnnnnnn | 47100 |
| nnnnnnnnnn | nnnnnnnnnn | nnnnnnnnnn | nnnnnnnnnn | nnnnnnnnnn | nnnnnnnnnn | 47160 |
| nnnnnnnnnn | nnnnnnnnnn | nnnnnnnnnn | nnnnnnnnnn | nnnnnnnnnn | nnnnnnnnnn | 47220 |
| nnnnnnnnnn | nnnnnnnnnn | nnnnnnnnnn | nnnnnnnnnn | nnnnnnnnnn | nnnnnnnnnn | 47280 |
| nnnnnnnnnn | nnnnnnnnnn | nnnnnnnnnn | nnnnnnnnnn | nnnnnnnnnn | nnnnnnnnnn | 47340 |
| nnnnnnnnnn | nnnnnnnnnn | nnnnnnnnnn | nnnnnnnnnn | nnnnnnnnnn | nnnnnnnnnn | 47400 |
| nnnnnnnnnn | nnnnnnnnnn | nnnnnnnnnn | nnnnnnnnnn | nnnnnnnnnn | nnnnnnnnnn | 47460 |
| nnnnnnnnnn | nnnnnnnnnn | nnnnnnnnnn | nnnnnnnnnn | nnnnnnnnnn | nnnnnnnnnn | 47520 |
| nnnnnnnnnn | nnnnnnnnnn | nnnnnnnnnn | nnnnnnnnnn | nnnnnnnnnn | nnnnnnnnnn | 47580 |
| nnnnnnnnnn | nnnnnnnnnn | nnnnnnnnnn | nnnnnnnnnn | nnnnnnnnnn | nnnnnnnnnn | 47640 |
| nnnnnnnnnn | nnnnnnnnnn | nnnnnnnnnn | nnnnnnnnnn | nnnnnnnnnn | nnnnnnnnnn | 47700 |
| nnctacgatg | tgaatgaact | tcgttcttgg | aagtcccttc | agaaacttct | ttatcagctt | 47760 |
| tgatgcttcc | attatctctc | ctaacgcggc | tgctctcgat | gctaagcctg | aaagttttcc | 47820 |
| tgcgtagtca | tccaccgtgt | ctgtgtctgt | catcttcagt | tgtcgaact | cagacatcaa | 47880 |
| agtctgtaac | cttgcttctc | tcacgcgatc | agcacctagg | ttacgagatt | tgatagtttc | 47940 |
| ccaaatcttc | ttcgatgtat | catgttctcc | tatctgaagt | attagcactt | ccgggactga | 48000 |
| ttgaaagatc | agagcaatcg | ccatattgtt | cttctttgca | tcatcactcc | ctggatcaat | 48060 |
| tgtatcccaa | acttcgtata | aacgaagcat | cactttcatt | cgcatcgacc | atacggtgta | 48120 |
| gttggtcgat | gttaacatcg | gacatcgtat | gtccttcttc | atctcaagac | ctttatcacg | 48180 |
| tccttgagaa | tcgtctccca | tgttttgatc | gaagttacaa | ctcctcttgt | aaacgacctt | 48240 |
| cgaaacccgg | agctctgata | ccaatttaaa | gttgcacaaa | cacaaagatt | ataagaacta | 48300 |
| gcacttctta | ttagatttag | aaactctctc | aaaactaaac | cttttcaatgt | gtttctcttg | 48360 |
| atggaacatc | tctccatgaa | aactctttat | ataggaagaa | gatacatctt | ttcctaagga | 48420 |
| caaagctaca | tcttttctta | ataataatat | ggaaacattc | ctaagctcga | tatgttttcc | 48480 |
| ttttttcctta | acccatcaaa | cttcacttta | atgagttaac | ttgcttctca | aggtaattgg | 48540 |
| aattatccaa | caccaacatt | gcattagtta | aagatgtttt | ctctgattat | tacgcttaaa | 48600 |
| atatcttgaa | ggatcttgtt | tctatataat | tgtgactagc | cattttatttt | acttttaagt | 48660 |
| tctatttatt | tttcaacttt | cgtatcgcta | ccaactgttt | tccgtgtatt | aataaataaa | 48720 |
| aagtagataa | taattataac | taaaaaatgt | taaaagtgat | atttgctatt | ttgtgtttgg | 48780 |
| gtattattaa | aagagtaaat | atcttttttag | gttggaaggt | gctacttact | tctcgaaatg | 48840 |
| agaatgtcgc | tggagacaca | agacacatca | acttcaatct | agaattatta | acaactgatg | 48900 |
| acagttggac | actttttgcaa | acgatagcat | ttcctagaaa | ggatgcattc | ggggaaggta | 48960 |
| cttcttataa | ttttatgaga | ttttatcctt | taggtatact | gtaatttggt | tttgtaatct | 49020 |
| acctgcacaa | taatttagta | ttgatgatgt | tgtgcagcat | atgaggaaat | ggaaaagatg | 49080 |
| ggtaagcata | tgatcaaata | ttgtgggggga | ctgccattgg | ctgtgagaat | attaggaggt | 49140 |
| ttattagcga | agaaatacaa | actgcatgag | tgggaaatga | tatgtgagaa | tgttgaacgc | 49200 |
| catctcatgg | gaagaactga | tttcaatgat | gacaacaata | ttttgcgctt | ccatgtaatg | 49260 |
| tctctgagct | ttgaagagtt | gtctagttat | ttgaagcaat | gcttcccttta | tttggcaatt | 49320 |
| tttccagaag | atcatcgaat | aagtgtgggg | aaactgtctt | attactgggc | agcagaagga | 49380 |

```
ttcaccggta cgtattacga tgaagagacc attcgagatg ttggagatag ctatatagag    49440
gagctcgcga ggagaaatat ggttactttc gaaagagaca gcacgggctt gaggtttgaa    49500
acctgtagta tgcatgacat tatgagggaa atgtgtttga ctaaagcaaa agaagagaac    49560
ttcctacaaa ctgatgttac tcgcagattt gtctgccaaa atactaccac attagatgtt    49620
gagagagata taaataatcc aaaacttcgg tctctcttag ttatccttaa ttcggagggg    49680 gattttttgta ggctatctgg tttaaggttc acaaggctac aacttctgag ggtgttagat    49740
ctcgataaag ccaagtttga aggagggaag ttaccttctg acataggaaa gctcatccac    49800
ttaagatact tgagcttaga atctgctgag gtatctcatc taccttcttc cctacgaaac    49860
ctgatgttgc tgatctattt gaacatagat gtagctgata ttgatataca tgtgcccaac    49920
gttctgatgg agatgcgaga attgagatac cttgcattac caaagtttat gcatgagaag    49980
accaagttgg aattgggtaa tctagtaaac ttggagacct tggagaattt ctcaacaaag    50040
aatagcagat tagaggatct ccgttgtatg atcagattga ggactctttc aatcaaagta    50100
actggtgaga cctcttcaga aactctctct ttatcaataa gtggcctgag acacctggaa    50160
aatctcgtca tacatgatcg cctgagctgg atcaaagagg gaattgtttt acattgcgat    50220
gatctcataa agctggagct gtttatgtat aggccagtga ggctagaaaa acaacgcttc    50280
ccttctcaca ttacatacat atctctaact gagtgtcgtt tcgagcatga tccgatgcca    50340
ctattagaga cgttgcagca cttgagaaag gttaagttat tggatcggtc tcattgtgcg    50400
agaagaatgg tttgctcggg tagtgggttt ccgcagttgc gtgagcttga gttagtctta    50460
ctagagcagt tggaagagtg gataatagag gaaggctcca tgcctcttct tcatagtttg    50520
gacattactg actgtaacaa gttaaaggaa attccagagg ggctgcgaat tatcccttcc    50580
ttaaagaatc tgacttgtta tagtatgggt aaggaatggg agggaagatt gtcggaagga    50640
ggagaagaat attacaaagt ccagcacatt ccctctgtta agttctatgg tgcatgaggt    50700
cctcagcaat tacaggtaaa atgttttctt ccctaattaa aataacatcc ataagaaaaa    50760
taaataattt ctgtttgttt tcaaatgggt aaaaggtttt tgtgacctt tttggttctt    50820 atgttttttgt agacgaatct gatctgaagt gaatctctta tcgagttggg aatcagctta    50880
tcgaagataa caagcaagaa cagtaataat aataaactct ctgcattttt cttatgctct    50940
ataatttatc agacttgccg ttttctgttg gagtatcatg aagaagaaca aaaatttctt    51000
tgttgttgga atcaaagttg attttatata ttttttgcttg tttgactgat gatactcacc    51060
ttgttcaatc attgatattg tattagagcg gaagatagac tcattggttt gtttctttt    51120 ctatctgttg tgagcatata tgtttctctt tctggaaact ttatatttgt tttgcccatc    51180
tcatattttg gcgagcacag atacttgatt aattgcttcc atgcccccat ttccactcgt    51240
ttatttgaat ccagttttga ttcagtttaa ttttttggatt ttacttccac ttaagctaca    51300
attttatcat ccatgggcaa gcaaaagtgc agactgactc agtttgagaa tcatctacag    51360
tacagagaaa ggatttagat ttatagaaag aatacaattg cagaatgaac atatatgaac    51420
agatgatgtg tcttctagcc taatgtcttt tcctgtagct aaattagtca aagggtagcc    51480
tactagtctt ggaagttgga agacaagtaa tctaacatag ccacgagtag tactagtatg    51540
ggcaaatttt ccacattgta ggtctagggg ctcaaaatta cttgtaaata taggagttag    51600
aaaatttaca tttaagtaa cttaggattc taataaaatat ataaataaat acttaaaata    51660
aaaaaatagt ttcaaacata atttctgatt ttcaaaataa aattttgaaa aataatcga    51720
```

```
aaaaaattca aaaaaaatta taaaaaattt tgaatttgaa aaagtaaaat tcaaaagcaa    51780
aaaaaaatat atatttttt atttatttaa attctgattt attatatata tagaaaacaa    51840
aggtataaga gttttttgc cacttaatga agaagatatt tttgaaaata tcatttaat    51900 agtggtaaag atgaaaaatg gtaccatgaa agtggtaaac atgaaatttt cccaaaaaaa    51960
ttcaacaaaa tagaagaatt ttctgcattt caatgtaatg gctaatttc ttaggaaaac    52020 aattttagaa atagtacaga atctatttta tattaaaata aaaacattaa aatatttgag    52080
tgttgcaatg tgtcatcact agaatgactt tcaaaatgga gaaatcttat gtttaccatt    52140
ttcaagctac cacttttcat ctttaccatc actaaataga cattttcaaa agtaccttct    52200
ttattaagtg gcaaaagact ctaatatcct tgttataaac ttttttcaag ctaccacttt    52260
tcgaattata atttttcaaa atcaaacttt ttataaactt ttttttgaa ttttttttca    52320 aattctttt gtaaataaa aaaatatt tggaaactat ttttagtaaa ttttttata    52380 ttttaatatt tttaagtatt tatttatata tttattagaa tcctaaattt cgcattccaa    52440
aaaccctacc ccaccccctca actctaaact ttaagtctag attagttaac cctaagggta    52500
taagtgtctt ttacccttca ttaaaagtaa gggtaaaagt gattagtgta aacatgaaaa    52560
gtagtactat gaatgtgcta tttgtggcaa tttccttttt agaatcttta gagaaatagg    52620
ttggtccatc taaaaaata ttatattttt tattaaacta accatataat taattagtca    52680
tttataaaaa tattttttgt tattttctta aataaaagtt acaaaattac ataatgtgac    52740
taaaatatat atgacaatta ataatttga ataataaga tttaataaca gtttgtgtat    52800
catcctcttt ttaattata ttatgaaaat aaataacact atcaaataat taaaattcag    52860
ttttcccgta tataatatat atttttta aatgaatata aattaaaaat aaagttccac    52920
attgaattct ttggggtcaa tggcatatat tttaatataa caagatacat atgatcataa    52980
aatcatatga ttataaaatt tcttttaata gatgtttata ttaatatata tataatttaa    53040
attaaactat atatcatatt gaaaatatat aatcttattt taaaatcaa gaatatgtat    53100 tatatttgaa ttgataaata taactctata ctatataaaa gttgagctat aagccatcga    53160
gagcgtccac gtaggattta aaacttccaa tcgtagtatg acaaatcatt atttaaattt    53220 actatttta aatatgttaa tgttgcgata caaaatgttt atttcaaact aaaatataaa    53280
tcaatatcaa ataaggtaaa tctacaaaaa tagaaatact attttaagtt aacataatgt    53340
ttaatatttt tagaaaattt aaaaataaat aacaaaaaga acaattaatt taaaaataca    53400
tgactttcaa acaagtataa ctatataaat ataaattta attcatgatt ggggaaatta    53460
catgtttacc acttcatgg taccaatttt cattttacc accactaaga agatatttc    53520 cgttaattat ggttgtgtaa gtgacatatg ttatactgtt gaaaaagttt acacattcat    53580
gtacttcttt aattcttat agattttgaa aaatcgaaaa ttatgtttga aactattttt    53640 taatttttt tatattttta agtatttatt tatatattta ttagaatcct aaatttcgca    53700
ttccaaaaac tctatcccac ctctcaactc taaaccctaa gtctagatta attaaccgta    53760
agggtataat cgtatttag tcttcattaa aagtgagggt aaaagtgatt agtgtaaaca    53820
taagaagtgt tactatgaat atgctatttg tagcaatttc acttcatgat tttcaaagtt    53880
taggttatat actattgaaa atattcaaaa taacatatac tatatataag ttgatattat    53940
aaattattga gaatgtttac atattatttt agagcaccaa aaatatacca aatcgttttt    54000
taatttggta tttctcaaaa tgttaatatt acgaaatttc ttttttcaaa ataaattata    54060
aataaatatc aaataagtta aacttacaaa attaaaagca tcatgtacaa atcatattat    54120
```

```
ataaaataaa gtttgaaaat taacataaaa ataacaaaca aatataatag ttaatttaaa    54180
aatacaatat tgtcaaacaa ttataactat ataaatctaa aacacatgat ttacaaaatt    54240
taggttatgt actatatgta atttgatgca atagatcatt gagaatatcc atatattatt    54300
tttaagcacc aaaatatgtc aaattaccat tttatatatt attttacaaa tttcaagatt    54360
ttaaaaaaat atttatttca aataaaaaag gaaactacta ttcaattcag tgaaaaggca    54420
aaattattaa aggaatcaat ttaatataaa aaagtaaacc tttgaaagac catcataaaa    54480
ttaactaaca aaaaaaatcg ggaaattgcc acaaatagca cattcatagt acaactttc    54540 atgtttacac taactatttt taccctcatt tttattgaaa ggtttagagt tgaggggtgg    54600
agtaggattt ttggaatgtt aaatttatga ttctaattaa tatataaata aatacttaaa    54660
tntaaaaagt ttgaatttaa aagtataatt cgaaaacata aaaaaaaatt ttacttttt    54720 tttaattttt tttatttttt tttatttttt tttaattttt taatttttta tttaaataat    54780
gatttattat atataaataa caagggcata agagtcttt gccacttaat gaagaatgta    54840
tttttgaaaa tgtctcttta gtggtggtaa aaataaaaag tggtaccata aaaatggtaa    54900
acatgtaatt tccccaaaaa aatcttaaag aatacaaaaa tttcaaataa taaaaacact    54960
atgaatctaa agcacttttc attacatatg aatctaggaa aattgccaca aatagcacat    55020
tcatagtacc acttttcatg tttacactaa ccacttttac gctcacttt aatgaaggt    55080 aaaagacaat tataccctta gggttaacta atctagagtt gagggatggg atagggtttt    55140
tggaatgtga aatttaggat tcaaacatat tttttgtttt tcaaaaagga atttaccatc    55200
aattccagga cgatggtgtt ttgtggatgc atcctggaaa gaatgtgact cgatggccgg    55260
acaaggttgg tatagcaatt tagaaggttt tgacggtttg atgggtgcaa ggaatgttag    55320
ggctcctctg tctcccctc acgcggagat ggatgcacta ctttgaacta tgaaatgtat    55380
gcgaaactta cgtcaatttc aggtcacatt tgtaacggat tgtttccaat tgctgaagat    55440
ggtttcggaa ccagaggaat gaccagcttt tgaagcttac ttggaagatc tcaagatttt    55500
gaaggatagt ttttacagct cacagatcat tcatatctcg cggacgcaaa ataagaaagc    55560
ggatagtcta gcacggaata caaggaaaca gccgtctttc gttgtccata tggatgcgaa    55620 gcaaccttt tggttttcag aggctacatg agtctctttg ttgttgtgaa aaaaaaatta    55680
tgtgtttatt tttcttaaa atatctttag ataatgcttg tgattgtcac agcttcattt    55740
tcagactatt ttggatttcg atatttaact gccccataga gattacttaa ccacttgatc    55800
tagaataaaa ttttatataa aaagggatgt tggtttgaaa tcatttctg tttctaaatg    55860 agtaatctga tttctttgac ttcataagac aatactaaac ccataaccca attttggtat    55920
attgatgtac tctattccgt aagctttaaa gtttaaactt gacaaatgat tataatttta    55980
gatgtatttt agtataagta atcaaaattg ttagtattaa aaaaacatat tttacagcaa    56040
caaacgtttt gtaatatata tggcattagg agttttcatg cgccatgcgc agatataaaa    56100
tatttaaaaa tattataaat aaaaaaatta tttttatatt ttacttttat tagttttttt    56160
ttttgctaga atattaatat catataaaat gaacaaagaa tttacaaaag agttctagac    56220
aaaatgtttc cgaggcaaaa aaataaaaca agaaaaacat tacacacacc tcataagata    56280
aaactagaga gatggctgat cagcttaatc tcagccacag agatagaaga gca           56333
```

<210> SEQ ID NO 2
<211> LENGTH: 5404
<212> TYPE: DNA

<213> ORGANISM: Brassica napus
<220> FEATURE:
<221> NAME/KEY: CDS
<222> LOCATION: (52)..(5343)

<400> SEQUENCE: 2

```
gaggagtact cacacaacct agagaaaaat ctggaggatt tggaggtgga a atg gga        57
                                                        Met Gly
                                                          1 acc ctc aat gca atg ata tat gag ttg tta aaa agg gtg tcg aaa gag       105
Thr Leu Asn Ala Met Ile Tyr Glu Leu Leu Lys Arg Val Ser Lys Glu
        5                  10                  15 aag gac aga ggt ata gaa acg cta gct gaa gtg gag gaa tgg att tca       153
Lys Asp Arg Gly Ile Glu Thr Leu Ala Glu Val Glu Glu Trp Ile Ser
 20                  25                  30 atg gca gaa gaa act gaa tcg aag gcg agt agt ctc ctt gat gaa agt       201
Met Ala Glu Glu Thr Glu Ser Lys Ala Ser Ser Leu Leu Asp Glu Ser
 35                  40                  45                  50 att tca gga tgt cac gat tta tca atg tat gat gat att tcc aag ata       249
Ile Ser Gly Cys His Asp Leu Ser Met Tyr Asp Asp Ile Ser Lys Ile
                 55                  60                  65 tct caa tcg acc ctt cat tat agc gag acg gtg tgt acg acg ttg aaa       297
Ser Gln Ser Thr Leu His Tyr Ser Glu Thr Val Cys Thr Thr Leu Lys
                 70                  75                  80 gaa gtt aaa gca ctg aga tct aag gga gtt ttt aaa gta ata gtt gag       345
Glu Val Lys Ala Leu Arg Ser Lys Gly Val Phe Lys Val Ile Val Glu
         85                  90                  95 aga gct ccc ttg tct tac gtc aaa aag atg ctc cca ctt cac cca att       393
Arg Ala Pro Leu Ser Tyr Val Lys Lys Met Leu Pro Leu His Pro Ile
100                 105                 110 gat tct gga gaa atg ttg gca gaa gaa gca tgg gat ttt ttt caa gag       441
Asp Ser Gly Glu Met Leu Ala Glu Glu Ala Trp Asp Phe Phe Gln Glu
115                 120                 125                 130 att att gga gaa aca acg tta aaa agt cat cca gac ata ccc cag ctg       489
Ile Ile Gly Glu Thr Thr Leu Lys Ser His Pro Asp Ile Pro Gln Leu
                135                 140                 145 gca aga ata gtt tgt aga aaa tgt cgt ggt ttg ccc att gct ctc agt       537
Ala Arg Ile Val Cys Arg Lys Cys Arg Gly Leu Pro Ile Ala Leu Ser
                150                 155                 160 ctc atc ggc gag acc atg tca cgc aaa agg act gta caa gaa tgg cat       585
Leu Ile Gly Glu Thr Met Ser Arg Lys Arg Thr Val Gln Glu Trp His
        165                 170                 175 caa gca att agt gtt ttg gtt tcg tct acc cca gaa gtt tca ggc act       633
Gln Ala Ile Ser Val Leu Val Ser Ser Thr Pro Glu Val Ser Gly Thr
        180                 185                 190 gaa gat gag ctt ctt tac att ttg aag ttt gcg tac gat aat ctg cct       681
Glu Asp Glu Leu Leu Tyr Ile Leu Lys Phe Ala Tyr Asp Asn Leu Pro
195                 200                 205                 210 ggt gag aat atc aag tcg tgc ttc ttg tat tgt gct ctg ttt ccg aaa       729
Gly Glu Asn Ile Lys Ser Cys Phe Leu Tyr Cys Ala Leu Phe Pro Lys
                215                 220                 225 agt tgt gat ata aat aaa caa gat ctg gta gac tgt tgg ata gcc gaa       777
Ser Cys Asp Ile Asn Lys Gln Asp Leu Val Asp Cys Trp Ile Ala Glu
                230                 235                 240 gga gta att gaa gat gaa gac aga gag ata gct gag ata cag gga tat       825
Gly Val Ile Glu Asp Glu Asp Arg Glu Ile Ala Glu Ile Gln Gly Tyr
        245                 250                 255 gaa atg atg gct gat ttg gtt atg atg aga ttg ttg att gat gat gaa       873
Glu Met Met Ala Asp Leu Val Met Met Arg Leu Leu Ile Asp Asp Glu
        260                 265                 270
```

| | | | | | | | | | | | | | | | | |
|---|---|---|---|---|---|---|---|---|---|---|---|---|---|---|---|---|
| tct | gaa | cat | gag | gta | aag | atg | cat | gac | atg | gtt | cgt | gga | atg | gcc | ttg | 921 |
| Ser | Glu | His | Glu | Val | Lys | Met | His | Asp | Met | Val | Arg | Gly | Met | Ala | Leu | |
| 275 | | | | 280 | | | | 285 | | | | 290 | | | | |
| tgg | ata | gcc | act | gac | tgc | ggg | agg | cag | aaa | gaa | aac | ttt | gtc | gtg | gta | 969 |
| Trp | Ile | Ala | Thr | Asp | Cys | Gly | Arg | Gln | Lys | Glu | Asn | Phe | Val | Val | Val | |
| | | | | 295 | | | | 300 | | | | 305 | | | | |
| agc | ggt | gag | gat | aga | cat | cag | atg | cca | gag | gtg | aat | gat | tgg | agt | aac | 1017 |
| Ser | Gly | Glu | Asp | Arg | His | Gln | Met | Pro | Glu | Val | Asn | Asp | Trp | Ser | Asn | |
| | | 310 | | | | 315 | | | | 320 | | | | | | |
| gtt | aga | agg | atg | tca | gta | aca | tct | act | cag | gtt | gac | aag | ata | tcc | gac | 1065 |
| Val | Arg | Arg | Met | Ser | Val | Thr | Ser | Thr | Gln | Val | Asp | Lys | Ile | Ser | Asp | |
| | | 325 | | | | 330 | | | | 335 | | | | | | |
| tct | cat | gat | tgt | ccc | aag | ctt | acg | act | cta | ttt | ctc | caa | gaa | aac | aac | 1113 |
| Ser | His | Asp | Cys | Pro | Lys | Leu | Thr | Thr | Leu | Phe | Leu | Gln | Glu | Asn | Asn | |
| | 340 | | | | 345 | | | | 350 | | | | | | | |
| tta | aaa | tgg | gtc | tcg | ggt | gat | ttc | ttt | cgg | tgg | atg | acc | agt | ctt | gtg | 1161 |
| Leu | Lys | Trp | Val | Ser | Gly | Asp | Phe | Phe | Arg | Trp | Met | Thr | Ser | Leu | Val | |
| 355 | | | | 360 | | | | 365 | | | | 370 | | | | |
| gtc | ttg | aat | cta | tcg | cgt | aac | tta | gaa | ctt | tct | gag | ttg | ccg | gaa | gaa | 1209 |
| Val | Leu | Asn | Leu | Ser | Arg | Asn | Leu | Glu | Leu | Ser | Glu | Leu | Pro | Glu | Glu | |
| | | | | 375 | | | | 380 | | | | 385 | | | | |
| gtt | tca | agc | ctg | gtg | tcc | ctg | cgg | ctt | ctc | aac | tta | tca | tgg | acg | tgg | 1257 |
| Val | Ser | Ser | Leu | Val | Ser | Leu | Arg | Leu | Leu | Asn | Leu | Ser | Trp | Thr | Trp | |
| | | 390 | | | | 395 | | | | 400 | | | | | | |
| ata | aaa | cgt | ttg | ccg | ctt | ggt | ctg | aca | gag | ctg | aaa | agg | ttg | atg | cac | 1305 |
| Ile | Lys | Arg | Leu | Pro | Leu | Gly | Leu | Thr | Glu | Leu | Lys | Arg | Leu | Met | His | |
| | | 405 | | | | 410 | | | | 415 | | | | | | |
| ttg | gat | ttg | gat | gac | acc | cct | cgt | ctt | cta | gaa | gtt | gac | gtg | ata | ggt | 1353 |
| Leu | Asp | Leu | Asp | Asp | Thr | Pro | Arg | Leu | Leu | Glu | Val | Asp | Val | Ile | Gly | |
| | 420 | | | | 425 | | | | 430 | | | | | | | |
| tat | tta | ctg | aat | ttg | caa | gtg | ctg | aga | tta | ttc | cgg | tca | gtt | ccg | atg | 1401 |
| Tyr | Leu | Leu | Asn | Leu | Gln | Val | Leu | Arg | Leu | Phe | Arg | Ser | Val | Pro | Met | |
| 435 | | | | 440 | | | | 445 | | | | 450 | | | | |
| gat | cgc | agc | tta | ttg | gag | aat | ata | caa | ctt | ttg | gaa | aat | ctg | aaa | gag | 1449 |
| Asp | Arg | Ser | Leu | Leu | Glu | Asn | Ile | Gln | Leu | Leu | Glu | Asn | Leu | Lys | Glu | |
| | | | | 455 | | | | 460 | | | | 465 | | | | |
| ctg | aat | cta | acc | gtg | aga | gaa | gtt | gat | gtt | ttg | gag | cgg | cta | caa | agt | 1497 |
| Leu | Asn | Leu | Thr | Val | Arg | Glu | Val | Asp | Val | Leu | Glu | Arg | Leu | Gln | Ser | |
| | | | 470 | | | | 475 | | | | 480 | | | | | |
| atc | cac | aag | ttg | gca | agt | tgt | atc | cga | cat | tta | cat | ctc | aaa | ggg | att | 1545 |
| Ile | His | Lys | Leu | Ala | Ser | Cys | Ile | Arg | His | Leu | His | Leu | Lys | Gly | Ile | |
| | | 485 | | | | 490 | | | | 495 | | | | | | |
| aca | ata | aaa | gat | gga | gga | aca | cta | ctg | ctg | aac | tct | atg | ttg | agt | ctt | 1593 |
| Thr | Ile | Lys | Asp | Gly | Gly | Thr | Leu | Leu | Leu | Asn | Ser | Met | Leu | Ser | Leu | |
| | | 500 | | | | 505 | | | | 510 | | | | | | |
| cgc | gaa | ctt | aat | att | ggg | atg | tgt | gat | atc | ccg | gag | ata | acc | gtt | gat | 1641 |
| Arg | Glu | Leu | Asn | Ile | Gly | Met | Cys | Asp | Ile | Pro | Glu | Ile | Thr | Val | Asp | |
| 515 | | | | 520 | | | | 525 | | | | 530 | | | | |
| tgg | aga | agc | acc | atc | caa | aga | gag | acg | ata | cat | ttt | ggt | aac | att | cag | 1689 |
| Trp | Arg | Ser | Thr | Ile | Gln | Arg | Glu | Thr | Ile | His | Phe | Gly | Asn | Ile | Gln | |
| | | | 535 | | | | 540 | | | | 545 | | | | | |
| aaa | att | ccg | tat | tta | cag | aac | ata | cgc | aca | gtg | gct | ctt | tct | tgg | tgc | 1737 |
| Lys | Ile | Pro | Tyr | Leu | Gln | Asn | Ile | Arg | Thr | Val | Ala | Leu | Ser | Trp | Cys | |
| | | | 550 | | | | 555 | | | | 560 | | | | | |
| aaa | ggt | ctc | aag | gac | ttg | aca | tgg | ttg | cta | tta | gcc | ccg | aat | ctc | ggc | 1785 |
| Lys | Gly | Leu | Lys | Asp | Leu | Thr | Trp | Leu | Leu | Leu | Ala | Pro | Asn | Leu | Gly | |
| | | 565 | | | | 570 | | | | 575 | | | | | | |
| gat | cta | agg | tta | ctt | gaa | tgt | cag | caa | ata | gaa | cat | ata | ata | aac | aaa | 1833 |
| Asp | Leu | Arg | Leu | Leu | Glu | Cys | Gln | Gln | Ile | Glu | His | Ile | Ile | Asn | Lys | |
| | 580 | | | | 585 | | | | 590 | | | | | | | |

| | | | | | | | | | | | | | | | | |
|---|---|---|---|---|---|---|---|---|---|---|---|---|---|---|---|---|
| gag | aaa | ccc | aca | ggt | gat | atg | agt | gag | gag | cct | ttt | caa | aat | cta | act | 1881 |
| Glu | Lys | Pro | Thr | Gly | Asp | Met | Ser | Glu | Glu | Pro | Phe | Gln | Asn | Leu | Thr | |
| 595 | | | | 600 | | | | 605 | | | | 610 | | | | |
| agg | ctc | agc | cta | gaa | agt | ttg | cct | caa | cta | gag | agc | atc | tac | tgg | act | 1929 |
| Arg | Leu | Ser | Leu | Glu | Ser | Leu | Pro | Gln | Leu | Glu | Ser | Ile | Tyr | Trp | Thr | |
| | | | | 615 | | | | 620 | | | | | 625 | | | |
| cct | cta | ccc | ttt | cca | gtt | ctg | aaa | gat | ctt | tgc | ata | aga | ggt | tgt | cca | 1977 |
| Pro | Leu | Pro | Phe | Pro | Val | Leu | Lys | Asp | Leu | Cys | Ile | Arg | Gly | Cys | Pro | |
| | | | 630 | | | | | 635 | | | | | 640 | | | |
| aag | ctg | aga | aga | cgt | ccg | ttt | agc | aat | aaa | gga | aat | caa | gtg | cga | tca | 2025 |
| Lys | Leu | Arg | Arg | Arg | Pro | Phe | Ser | Asn | Lys | Gly | Asn | Gln | Val | Arg | Ser | |
| 645 | | | | | 650 | | | | | 655 | | | | | | |
| gat | gtt | ggc | caa | aaa | gga | gtt | gaa | agg | gag | gat | gaa | gct | atg | aag | caa | 2073 |
| Asp | Val | Gly | Gln | Lys | Gly | Val | Glu | Arg | Glu | Asp | Glu | Ala | Met | Lys | Gln | |
| | 660 | | | | | 665 | | | | | 670 | | | | | |
| cat | ctc | tcc | aat | ttt | gat | gac | agg | gat | ttt | ctg | aag | atg | gat | gaa | gac | 2121 |
| His | Leu | Ser | Asn | Phe | Asp | Asp | Arg | Asp | Phe | Leu | Lys | Met | Asp | Glu | Asp | |
| 675 | | | | | 680 | | | | | 685 | | | | | 690 | |
| cag | aac | atg | gag | ggt | ttg | gca | tct | gag | tcg | cat | ccc | aat | aag | aac | ata | 2169 |
| Gln | Asn | Met | Glu | Gly | Leu | Ala | Ser | Glu | Ser | His | Pro | Asn | Lys | Asn | Ile | |
| | | | | 695 | | | | | 700 | | | | | 705 | | |
| gcc | ctg | gtc | gac | act | tca | gag | aga | gga | aaa | ttt | agt | acc | aat | gca | aac | 2217 |
| Ala | Leu | Val | Asp | Thr | Ser | Glu | Arg | Gly | Lys | Phe | Ser | Thr | Asn | Ala | Asn | |
| | | | 710 | | | | | 715 | | | | | 720 | | | |
| agc | atg | acc | gat | ttt | gat | gac | agg | agc | gga | tac | gtg | gaa | gcg | gaa | acg | 2265 |
| Ser | Met | Thr | Asp | Phe | Asp | Asp | Arg | Ser | Gly | Tyr | Val | Glu | Ala | Glu | Thr | |
| | | 725 | | | | | 730 | | | | | 735 | | | | |
| tat | gca | agc | gca | gaa | gcg | aga | tta | tta | aga | aaa | tta | gga | agc | ggg | gat | 2313 |
| Tyr | Ala | Ser | Ala | Glu | Ala | Arg | Leu | Leu | Arg | Lys | Leu | Gly | Ser | Gly | Asp | |
| | 740 | | | | | 745 | | | | | 750 | | | | | |
| atc | cca | aca | gtg | gct | gaa | gac | cag | aag | atg | ggt | ggt | ttg | gta | tct | gag | 2361 |
| Ile | Pro | Thr | Val | Ala | Glu | Asp | Gln | Lys | Met | Gly | Gly | Leu | Val | Ser | Glu | |
| 755 | | | | 760 | | | | | 765 | | | | | 770 | | |
| tta | cac | ccc | aat | gaa | aac | gta | gcc | ctg | gtc | gag | act | tca | gag | aga | gga | 2409 |
| Leu | His | Pro | Asn | Glu | Asn | Val | Ala | Leu | Val | Glu | Thr | Ser | Glu | Arg | Gly | |
| | | | 775 | | | | | 780 | | | | | 785 | | | |
| aaa | agt | acc | atc | gca | aac | agc | atc | acc | aat | ttt | gat | gac | agg | gat | ttt | 2457 |
| Lys | Ser | Thr | Ile | Ala | Asn | Ser | Ile | Thr | Asn | Phe | Asp | Asp | Arg | Asp | Phe | |
| | | | 790 | | | | | 795 | | | | | 800 | | | |
| ccg | aca | ttg | gct | gaa | gac | cag | aag | atg | gat | ggt | ttg | gca | tct | gag | tca | 2505 |
| Pro | Thr | Leu | Ala | Glu | Asp | Gln | Lys | Met | Asp | Gly | Leu | Ala | Ser | Glu | Ser | |
| | | 805 | | | | | 810 | | | | | 815 | | | | |
| cac | cca | gtc | gaa | gac | ata | gtc | ctg | gta | gag | act | tta | gaa | agt | gaa | aaa | 2553 |
| His | Pro | Val | Glu | Asp | Ile | Val | Leu | Val | Glu | Thr | Leu | Glu | Ser | Glu | Lys | |
| | 820 | | | | | 825 | | | | | 830 | | | | | |
| ggt | acc | atc | cca | aac | agc | atc | acc | gaa | gag | aat | gtg | ttt | caa | tcg | gga | 2601 |
| Gly | Thr | Ile | Pro | Asn | Ser | Ile | Thr | Glu | Glu | Asn | Val | Phe | Gln | Ser | Gly | |
| 835 | | | | 840 | | | | | 845 | | | | | 850 | | |
| aaa | cac | gca | act | ctg | gaa | cac | aca | caa | tca | tac | cca | gtt | ttg | gcg | cca | 2649 |
| Lys | His | Ala | Thr | Leu | Glu | His | Thr | Gln | Ser | Tyr | Pro | Val | Leu | Ala | Pro | |
| | | | | 855 | | | | | 860 | | | | | 865 | | |
| gat | ggc | atg | atc | cac | aat | atg | act | gac | act | cct | gca | gga | gga | acc | att | 2697 |
| Asp | Gly | Met | Ile | His | Asn | Met | Thr | Asp | Thr | Pro | Ala | Gly | Gly | Thr | Ile | |
| | | | 870 | | | | | 875 | | | | | 880 | | | |
| atg | gct | ggg | gaa | ctt | gtg | tct | ttt | gga | ata | caa | aag | ctt | tgg | gag | ttg | 2745 |
| Met | Ala | Gly | Glu | Leu | Val | Ser | Phe | Gly | Ile | Gln | Lys | Leu | Trp | Glu | Leu | |
| | | 885 | | | | | 890 | | | | | 895 | | | | |
| ctt | cgc | caa | gaa | agc | gag | cgt | ttt | cag | gga | gct | tcg | gat | gaa | ata | gat | 2793 |
| Leu | Arg | Gln | Glu | Ser | Glu | Arg | Phe | Gln | Gly | Ala | Ser | Asp | Glu | Ile | Asp | |

|  |  |
|---|---:|
| atg gta aaa agt gat tta ctc tat tta agg gga ttt tta gca gat gca<br>Met Val Lys Ser Asp Leu Leu Tyr Leu Arg Gly Phe Leu Ala Asp Ala<br>915                    920                  925              930 | 2841 |
| aat gcc aaa aaa cat aca agg gag gtg aaa agt tgt att gaa gag atc<br>Asn Ala Lys Lys His Thr Arg Glu Val Lys Ser Cys Ile Glu Glu Ile<br>                  935                  940                  945 | 2889 |
| aaa gaa att ttt ttt gac gcg gaa gat att att gag aca tat ctt ctt<br>Lys Glu Ile Phe Phe Asp Ala Glu Asp Ile Ile Glu Thr Tyr Leu Leu<br>                950                  955                  960 | 2937 |
| gaa gaa aac ccc cca aaa act ggt gtc ttc aag agg ctt ttc aga ggg<br>Glu Glu Asn Pro Pro Lys Thr Gly Val Phe Lys Arg Leu Phe Arg Gly<br>           965                  970                  975 | 2985 |
| cgt gct ggc agg aaa ttt gct ttg gat atg aat agc tta agc aag agg<br>Arg Ala Gly Arg Lys Phe Ala Leu Asp Met Asn Ser Leu Ser Lys Arg<br>           980                  985                  990 | 3033 |
| att tct aag ata atc agc gtt atg caa gct ttt gga gta cac cag<br>Ile Ser Lys Ile Ile Ser Val Met Gln Ala Phe Gly Val His Gln<br>995                  1000                 1005 | 3078 |
| gtt att act gaa ggc aag gat tca caa cct ctt cta caa aga caa<br>Val Ile Thr Glu Gly Lys Asp Ser Gln Pro Leu Leu Gln Arg Gln<br>1010                1015                1020 | 3123 |
| aaa agg atg cga caa aaa ttt gct gga gag tac aaa ccc aat ttt<br>Lys Arg Met Arg Gln Lys Phe Ala Gly Glu Tyr Lys Pro Asn Phe<br>1025                1030                1035 | 3168 |
| gtg ggg ctg gaa gaa aat gtt gag aaa ttg gtt agt ctt ttg gtc<br>Val Gly Leu Glu Glu Asn Val Glu Lys Leu Val Ser Leu Leu Val<br>1040                1045                1050 | 3213 |
| gag gaa gac aat att caa gtg gtt tcc ata acc ggg atg ggt ggt<br>Glu Glu Asp Asn Ile Gln Val Val Ser Ile Thr Gly Met Gly Gly<br>1055                1060                1065 | 3258 |
| ctt ggt aaa act acc ctc gct aga caa act ttt aat cac gat atg<br>Leu Gly Lys Thr Thr Leu Ala Arg Gln Thr Phe Asn His Asp Met<br>1070                1075                1080 | 3303 |
| gta aaa cac aag ttt gat agg ttc gca tgg gtg ggt att tca caa<br>Val Lys His Lys Phe Asp Arg Phe Ala Trp Val Gly Ile Ser Gln<br>1085                1090                1095 | 3348 |
| gct tgt aac cga aag att gtg tgg caa atg atc ttg cgg agt ctc<br>Ala Cys Asn Arg Lys Ile Val Trp Gln Met Ile Leu Arg Ser Leu<br>1100                1105                1110 | 3393 |
| ttg gcc aaa aaa gat gaa gat agt att ttg cat atg act gaa tct<br>Leu Ala Lys Lys Asp Glu Asp Ser Ile Leu His Met Thr Glu Ser<br>1115                1120                1125 | 3438 |
| gaa ctc caa gag caa atc ttt cta ttg ctg gaa gca tcc aaa tca<br>Glu Leu Gln Glu Gln Ile Phe Leu Leu Leu Glu Ala Ser Lys Ser<br>1130                1135                1140 | 3483 |
| ttg att gtc ata gat gac ata tgg aaa gaa gaa gac tgg aag cga<br>Leu Ile Val Ile Asp Asp Ile Trp Lys Glu Glu Asp Trp Lys Arg<br>1145                1150                1155 | 3528 |
| atc agt caa ata ctt cca aac aca aaa ggt tgg aag gtg cta ctt<br>Ile Ser Gln Ile Leu Pro Asn Thr Lys Gly Trp Lys Val Leu Leu<br>1160                1165                1170 | 3573 |
| act tct cga aat gag aat gtc gct gga gac aca aga cac atc aac<br>Thr Ser Arg Asn Glu Asn Val Ala Gly Asp Thr Arg His Ile Asn<br>1175                1180                1185 | 3618 |
| ttc aat cta gaa tta tta aca act gat gac agt tgg aca ctt ttg<br>Phe Asn Leu Glu Leu Leu Thr Thr Asp Asp Ser Trp Thr Leu Leu<br>1190                1195                1200 | 3663 |
| caa acg ata gca ttt cct aga aag gat gca ttc ggg gaa gca tat | 3708 |

-continued

| | | | | | | | | | | | | |
|---|---|---|---|---|---|---|---|---|---|---|---|---|
| Gln<br>1205 | Thr | Ile | Ala | Phe<br>1210 | Pro | Arg | Lys | Asp | Ala | Phe<br>1215 | Gly | Glu | Ala | Tyr |

| | | | | | | | | | | | | |
|---|---|---|---|---|---|---|---|---|---|---|---|---|
| gag | gaa | atg | gaa | aag | atg | ggt | aag | cat | atg | atc | aaa tat tgt ggg | 3753 |
| Glu<br>1220 | Glu | Met | Glu | Lys<br>1225 | Met | Gly | Lys | His | Met<br>1230 | Ile | Lys Tyr Cys Gly | |
| gga | ctg | cca | ttg | gct | gtg | aga | ata | tta | gga | ggt | tta tta gcg aag | 3798 |
| Gly<br>1235 | Leu | Pro | Leu | Ala<br>1240 | Val | Arg | Ile | Leu | Gly<br>1245 | Gly | Leu Leu Ala Lys | |
| aaa | tac | aaa | ctg | cat | gag | tgg | gaa | atg | ata | tgt | gag aat gtt gaa | 3843 |
| Lys<br>1250 | Tyr | Lys | Leu | His<br>1255 | Glu | Trp | Glu | Met | Ile<br>1260 | Cys | Glu Asn Val Glu | |
| cgc | cat | ctc | atg | gga | aga | act | gat | ttc | aat | gat | gac aac aat att | 3888 |
| Arg<br>1265 | His | Leu | Met | Gly<br>1270 | Arg | Thr | Asp | Phe | Asn<br>1275 | Asp | Asp Asn Asn Ile | |
| ttg | cgc | ttc | cat | gta | atg | tct | ctg | agc | ttt | gaa | gag ttg tct agt | 3933 |
| Leu<br>1280 | Arg | Phe | His | Val<br>1285 | Met | Ser | Leu | Ser | Phe<br>1290 | Glu | Glu Leu Ser Ser | |
| tat | ttg | aag | caa | tgc | ttc | ctt | tat | ttg | gca | att | ttt cca gaa gat | 3978 |
| Tyr<br>1295 | Leu | Lys | Gln | Cys<br>1300 | Phe | Leu | Tyr | Leu | Ala<br>1305 | Ile | Phe Pro Glu Asp | |
| cat | cga | ata | agt | gtg | ggg | aaa | ctg | tct | tat | tac | tgg gca gca gaa | 4023 |
| His<br>1310 | Arg | Ile | Ser | Val<br>1315 | Gly | Lys | Leu | Ser | Tyr<br>1320 | Tyr | Trp Ala Ala Glu | |
| gga | ttc | acc | ggt | acg | tat | tac | gat | gaa | gag | acc | att cga gat gtt | 4068 |
| Gly<br>1325 | Phe | Thr | Gly | Thr<br>1330 | Tyr | Tyr | Asp | Glu | Glu<br>1335 | Thr | Ile Arg Asp Val | |
| gga | gat | agc | tat | ata | gag | gag | ctc | gcg | agg | aga | aat atg gtt act | 4113 |
| Gly<br>1340 | Asp | Ser | Tyr | Ile<br>1345 | Glu | Glu | Leu | Ala | Arg<br>1350 | Arg | Asn Met Val Thr | |
| ttc | gaa | aga | gac | agc | acg | ggc | ttg | agg | ttt | gaa | acc tgt agt atg | 4158 |
| Phe<br>1355 | Glu | Arg | Asp | Ser<br>1360 | Thr | Gly | Leu | Arg | Phe<br>1365 | Glu | Thr Cys Ser Met | |
| cat | gac | att | atg | agg | gaa | atg | tgt | ttg | act | aaa | gca aaa gaa gag | 4203 |
| His<br>1370 | Asp | Ile | Met | Arg<br>1375 | Glu | Met | Cys | Leu | Thr<br>1380 | Lys | Ala Lys Glu Glu | |
| aac | ttc | cta | caa | act | gat | gtt | act | cgc | aga | ttt | gtc tgc caa aat | 4248 |
| Asn<br>1385 | Phe | Leu | Gln | Thr<br>1390 | Asp | Val | Thr | Arg | Arg<br>1395 | Phe | Val Cys Gln Asn | |
| act | acc | aca | tta | gat | gtt | gag | aga | gat | ata | aat | aat cca aaa ctt | 4293 |
| Thr<br>1400 | Thr | Thr | Leu | Asp<br>1405 | Val | Glu | Arg | Asp | Ile<br>1410 | Asn | Asn Pro Lys Leu | |
| cgg | tct | ctc | tta | gtt | atc | ctt | aat | tcg | gag | ggg | gat ttt tgt agg | 4338 |
| Arg<br>1415 | Ser | Leu | Leu | Val<br>1420 | Ile | Leu | Asn | Ser | Glu<br>1425 | Gly | Asp Phe Cys Arg | |
| cta | tct | ggt | tta | agg | ttc | aca | agg | cta | caa | ctt | ctg agg gtg tta | 4383 |
| Leu<br>1430 | Ser | Gly | Leu | Arg<br>1435 | Phe | Thr | Arg | Leu | Gln<br>1440 | Leu | Leu Arg Val Leu | |
| gat | ctc | gat | aaa | gcc | aag | ttt | gaa | gga | ggg | aag | tta cct tct gac | 4428 |
| Asp<br>1445 | Leu | Asp | Lys | Ala<br>1450 | Lys | Phe | Glu | Gly | Gly<br>1455 | Lys | Leu Pro Ser Asp | |
| ata | gga | aag | ctc | atc | cac | tta | aga | tac | ttg | agc | tta gaa tct gct | 4473 |
| Ile<br>1460 | Gly | Lys | Leu | Ile<br>1465 | His | Leu | Arg | Tyr | Leu<br>1470 | Ser | Leu Glu Ser Ala | |
| gag | gta | tct | cat | cta | cct | tct | tcc | cta | cga | aac | ctg atg ttg ctg | 4518 |
| Glu<br>1475 | Val | Ser | His | Leu<br>1480 | Pro | Ser | Ser | Leu | Arg<br>1485 | Asn | Leu Met Leu Leu | |
| atc | tat | ttg | aac | ata | gat | gta | gct | gat | att | gat | ata cat gtg ccc | 4563 |
| Ile<br>1490 | Tyr | Leu | Asn | Ile<br>1495 | Asp | Val | Ala | Asp | Ile<br>1500 | Asp | Ile His Val Pro | |

| | | |
|---|---|---|
| aac gtt ctg atg gag atg cga gaa ttg aga tac ctt gca tta cca<br>Asn Val Leu Met Glu Met Arg Glu Leu Arg Tyr Leu Ala Leu Pro<br>1505      1510      1515 | | 4608 |
| aag ttt atg cat gag aag acc aag ttg gaa ttg ggt aat cta gta<br>Lys Phe Met His Glu Lys Thr Lys Leu Glu Leu Gly Asn Leu Val<br>1520      1525      1530 | | 4653 |
| aac ttg gag acc ttg gag aat ttc tca aca aag aat agc aga tta<br>Asn Leu Glu Thr Leu Glu Asn Phe Ser Thr Lys Asn Ser Arg Leu<br>1535      1540      1545 | | 4698 |
| gag gat ctc cgt tgt atg atc aga ttg agg act ctt tca atc aaa<br>Glu Asp Leu Arg Cys Met Ile Arg Leu Arg Thr Leu Ser Ile Lys<br>1550      1555      1560 | | 4743 |
| gta act ggt gag acc tct tca gaa act ctc tct tta tca ata agt<br>Val Thr Gly Glu Thr Ser Ser Glu Thr Leu Ser Leu Ser Ile Ser<br>1565      1570      1575 | | 4788 |
| ggc ctg aga cac ctg gaa aat ctc gtc ata cat gat cgc ctg agc<br>Gly Leu Arg His Leu Glu Asn Leu Val Ile His Asp Arg Leu Ser<br>1580      1585      1590 | | 4833 |
| tgg atc aaa gag gga att gtt tta cat tgc gat gat ctc ata aag<br>Trp Ile Lys Glu Gly Ile Val Leu His Cys Asp Asp Leu Ile Lys<br>1595      1600      1605 | | 4878 |
| ctg gag ctg ttt atg tat agg cca gtg agg cta gaa aaa caa cgc<br>Leu Glu Leu Phe Met Tyr Arg Pro Val Arg Leu Glu Lys Gln Arg<br>1610      1615      1620 | | 4923 |
| ttc cct tct cac att aca tac ata tct cta act gag tgt cgt ttc<br>Phe Pro Ser His Ile Thr Tyr Ile Ser Leu Thr Glu Cys Arg Phe<br>1625      1630      1635 | | 4968 |
| gag cat gat ccg atg cca cta tta gag acg ttg cag cac ttg aga<br>Glu His Asp Pro Met Pro Leu Leu Glu Thr Leu Gln His Leu Arg<br>1640      1645      1650 | | 5013 |
| aag gtt aag tta ttg gat cgg tct cat tgt gcg aga aga atg gtt<br>Lys Val Lys Leu Leu Asp Arg Ser His Cys Ala Arg Arg Met Val<br>1655      1660      1665 | | 5058 |
| tgc tcg ggt agt ggg ttt ccg cag ttg cgt gag ctt gag tta gtc<br>Cys Ser Gly Ser Gly Phe Pro Gln Leu Arg Glu Leu Glu Leu Val<br>1670      1675      1680 | | 5103 |
| tta cta gag cag ttg gaa gag tgg ata ata gag gaa ggc tcc atg<br>Leu Leu Glu Gln Leu Glu Glu Trp Ile Ile Glu Glu Gly Ser Met<br>1685      1690      1695 | | 5148 |
| cct ctt ctt cat agt ttg gac att act gac tgt aac aag tta aag<br>Pro Leu Leu His Ser Leu Asp Ile Thr Asp Cys Asn Lys Leu Lys<br>1700      1705      1710 | | 5193 |
| gaa att cca gag ggg ctg cga att atc cct tcc tta aag aat ctg<br>Glu Ile Pro Glu Gly Leu Arg Ile Ile Pro Ser Leu Lys Asn Leu<br>1715      1720      1725 | | 5238 |
| act tgt tat agt atg ggt aag gaa tgg gag gga aga ttg tcg gaa<br>Thr Cys Tyr Ser Met Gly Lys Glu Trp Glu Gly Arg Leu Ser Glu<br>1730      1735      1740 | | 5283 |
| gga gga gaa gaa tat tac aaa gtc cag cac att ccc tct gtt aag<br>Gly Gly Glu Glu Tyr Tyr Lys Val Gln His Ile Pro Ser Val Lys<br>1745      1750      1755 | | 5328 |
| ttc tat ggt gca tga ggtcctcagc aattacaggt aaaatgtttt cttccctaat<br>Phe Tyr Gly Ala<br>1760 | | 5383 |
| taaaataaca tccataagaa a | | 5404 |

<210> SEQ ID NO 3
<211> LENGTH: 1763
<212> TYPE: PRT
<213> ORGANISM: Brassica napus

```
<400> SEQUENCE: 3

Met Gly Thr Leu Asn Ala Met Ile Tyr Glu Leu Leu Lys Arg Val Ser
1               5                   10                  15

Lys Glu Lys Asp Arg Gly Ile Glu Thr Leu Ala Glu Val Glu Glu Trp
            20                  25                  30

Ile Ser Met Ala Glu Glu Thr Glu Ser Lys Ala Ser Ser Leu Leu Asp
        35                  40                  45

Glu Ser Ile Ser Gly Cys His Asp Leu Ser Met Tyr Asp Asp Ile Ser
    50                  55                  60

Lys Ile Ser Gln Ser Thr Leu His Tyr Ser Glu Thr Val Cys Thr Thr
65                  70                  75                  80

Leu Lys Glu Val Lys Ala Leu Arg Ser Lys Gly Val Phe Lys Val Ile
                85                  90                  95

Val Glu Arg Ala Pro Leu Ser Tyr Val Lys Lys Met Leu Pro Leu His
            100                 105                 110

Pro Ile Asp Ser Gly Glu Met Leu Ala Glu Ala Trp Asp Phe Phe
        115                 120                 125

Gln Glu Ile Ile Gly Glu Thr Thr Leu Lys Ser His Pro Asp Ile Pro
130                 135                 140

Gln Leu Ala Arg Ile Val Cys Arg Lys Cys Arg Gly Leu Pro Ile Ala
145                 150                 155                 160

Leu Ser Leu Ile Gly Glu Thr Met Ser Arg Lys Arg Thr Val Gln Glu
                165                 170                 175

Trp His Gln Ala Ile Ser Val Leu Val Ser Ser Thr Pro Glu Val Ser
            180                 185                 190

Gly Thr Glu Asp Glu Leu Leu Tyr Ile Leu Lys Phe Ala Tyr Asp Asn
        195                 200                 205

Leu Pro Gly Glu Asn Ile Lys Ser Cys Phe Leu Tyr Cys Ala Leu Phe
    210                 215                 220

Pro Lys Ser Cys Asp Ile Asn Lys Gln Asp Leu Val Asp Cys Trp Ile
225                 230                 235                 240

Ala Glu Gly Val Ile Glu Asp Glu Arg Glu Ile Ala Glu Ile Gln
                245                 250                 255

Gly Tyr Glu Met Met Ala Asp Leu Val Met Met Arg Leu Leu Ile Asp
            260                 265                 270

Asp Glu Ser Glu His Glu Val Lys Met His Asp Met Val Arg Gly Met
        275                 280                 285

Ala Leu Trp Ile Ala Thr Asp Cys Gly Arg Gln Lys Glu Asn Phe Val
    290                 295                 300

Val Val Ser Gly Glu Asp Arg His Gln Met Pro Glu Val Asn Asp Trp
305                 310                 315                 320

Ser Asn Val Arg Arg Met Ser Val Thr Ser Thr Gln Val Asp Lys Ile
                325                 330                 335

Ser Asp Ser His Asp Cys Pro Lys Leu Thr Thr Leu Phe Leu Gln Glu
            340                 345                 350

Asn Asn Leu Lys Trp Val Ser Gly Asp Phe Phe Arg Trp Met Thr Ser
        355                 360                 365

Leu Val Val Leu Asn Leu Ser Arg Asn Leu Glu Ser Glu Leu Pro
    370                 375                 380

Glu Glu Val Ser Ser Leu Val Ser Leu Arg Leu Leu Asn Leu Ser Trp
385                 390                 395                 400

Thr Trp Ile Lys Arg Leu Pro Leu Gly Leu Thr Glu Leu Lys Arg Leu
```

```
            405                 410                 415
Met His Leu Asp Leu Asp Asp Thr Pro Arg Leu Leu Glu Val Asp Val
            420                 425                 430

Ile Gly Tyr Leu Leu Asn Leu Gln Val Leu Arg Leu Phe Arg Ser Val
            435                 440                 445

Pro Met Asp Arg Ser Leu Leu Glu Asn Ile Gln Leu Leu Glu Asn Leu
            450                 455                 460

Lys Glu Leu Asn Leu Thr Val Arg Glu Val Asp Val Leu Glu Arg Leu
465                 470                 475                 480

Gln Ser Ile His Lys Leu Ala Ser Cys Ile Arg His Leu His Leu Lys
                    485                 490                 495

Gly Ile Thr Ile Lys Asp Gly Thr Leu Leu Leu Asn Ser Met Leu
                    500                 505                 510

Ser Leu Arg Glu Leu Asn Ile Gly Met Cys Asp Ile Pro Glu Ile Thr
                    515                 520                 525

Val Asp Trp Arg Ser Thr Ile Gln Arg Glu Thr Ile His Phe Gly Asn
                    530                 535                 540

Ile Gln Lys Ile Pro Tyr Leu Gln Asn Ile Arg Thr Val Ala Leu Ser
545                 550                 555                 560

Trp Cys Lys Gly Leu Lys Asp Leu Thr Trp Leu Leu Ala Pro Asn
                    565                 570                 575

Leu Gly Asp Leu Arg Leu Leu Glu Cys Gln Gln Ile Glu His Ile Ile
                    580                 585                 590

Asn Lys Glu Lys Pro Thr Gly Asp Met Ser Glu Glu Pro Phe Gln Asn
                    595                 600                 605

Leu Thr Arg Leu Ser Leu Glu Ser Leu Pro Gln Leu Glu Ser Ile Tyr
                    610                 615                 620

Trp Thr Pro Leu Pro Phe Pro Val Leu Lys Asp Leu Cys Ile Arg Gly
625                 630                 635                 640

Cys Pro Lys Leu Arg Arg Arg Pro Phe Ser Asn Lys Gly Asn Gln Val
                    645                 650                 655

Arg Ser Asp Val Gly Gln Lys Gly Val Glu Arg Glu Asp Glu Ala Met
                    660                 665                 670

Lys Gln His Leu Ser Asn Phe Asp Asp Arg Asp Phe Leu Lys Met Asp
                    675                 680                 685

Glu Asp Gln Asn Met Glu Gly Leu Ala Ser Glu Ser His Pro Asn Lys
                    690                 695                 700

Asn Ile Ala Leu Val Asp Thr Ser Glu Arg Gly Lys Phe Ser Thr Asn
705                 710                 715                 720

Ala Asn Ser Met Thr Asp Phe Asp Asp Arg Ser Gly Tyr Val Glu Ala
                    725                 730                 735

Glu Thr Tyr Ala Ser Ala Glu Ala Leu Leu Arg Lys Leu Gly Ser
                    740                 745                 750

Gly Asp Ile Pro Thr Val Ala Glu Asp Gln Lys Met Gly Gly Leu Val
                    755                 760                 765

Ser Glu Leu His Pro Asn Glu Asn Val Ala Leu Val Glu Thr Ser Glu
                    770                 775                 780

Arg Gly Lys Ser Thr Ile Ala Asn Ser Ile Thr Asn Phe Asp Asp Arg
785                 790                 795                 800

Asp Phe Pro Thr Leu Ala Glu Asp Gln Lys Met Asp Gly Leu Ala Ser
                    805                 810                 815

Glu Ser His Pro Val Glu Asp Ile Val Leu Val Glu Thr Leu Glu Ser
                    820                 825                 830
```

-continued

Glu Lys Gly Thr Ile Pro Asn Ser Ile Thr Glu Glu Asn Val Phe Gln
        835                 840                 845

Ser Gly Lys His Ala Thr Leu Glu His Thr Gln Ser Tyr Pro Val Leu
850                 855                 860

Ala Pro Asp Gly Met Ile His Asn Met Thr Asp Thr Pro Ala Gly Gly
865                 870                 875                 880

Thr Ile Met Ala Gly Glu Leu Val Ser Phe Gly Ile Gln Lys Leu Trp
                885                 890                 895

Glu Leu Leu Arg Gln Glu Ser Glu Arg Phe Gln Gly Ala Ser Asp Glu
                900                 905                 910

Ile Asp Met Val Lys Ser Asp Leu Leu Tyr Leu Arg Gly Phe Leu Ala
            915                 920                 925

Asp Ala Asn Ala Lys Lys His Thr Arg Glu Val Lys Ser Cys Ile Glu
930                 935                 940

Glu Ile Lys Glu Ile Phe Phe Asp Ala Glu Asp Ile Ile Glu Thr Tyr
945                 950                 955                 960

Leu Leu Glu Glu Asn Pro Pro Lys Thr Gly Val Phe Lys Arg Leu Phe
                965                 970                 975

Arg Gly Arg Ala Gly Arg Lys Phe Ala Leu Asp Met Asn Ser Leu Ser
            980                 985                 990

Lys Arg Ile Ser Lys Ile Ile Ser Val Met Gln Ala Phe Gly Val His
            995                 1000                1005

Gln Val Ile Thr Glu Gly Lys Asp Ser Gln Pro Leu Leu Gln Arg
    1010                1015                1020

Gln Lys Arg Met Arg Gln Lys Phe Ala Gly Glu Tyr Lys Pro Asn
    1025                1030                1035

Phe Val Gly Leu Glu Glu Asn Val Glu Lys Leu Val Ser Leu Leu
    1040                1045                1050

Val Glu Glu Asp Asn Ile Gln Val Val Ser Ile Thr Gly Met Gly
    1055                1060                1065

Gly Leu Gly Lys Thr Thr Leu Ala Arg Gln Thr Phe Asn His Asp
    1070                1075                1080

Met Val Lys His Lys Phe Asp Arg Phe Ala Trp Val Gly Ile Ser
    1085                1090                1095

Gln Ala Cys Asn Arg Lys Ile Val Trp Gln Met Ile Leu Arg Ser
    1100                1105                1110

Leu Leu Ala Lys Lys Asp Glu Asp Ser Ile Leu His Met Thr Glu
    1115                1120                1125

Ser Glu Leu Gln Glu Gln Ile Phe Leu Leu Leu Glu Ala Ser Lys
    1130                1135                1140

Ser Leu Ile Val Ile Asp Asp Ile Trp Lys Glu Glu Asp Trp Lys
    1145                1150                1155

Arg Ile Ser Gln Ile Leu Pro Asn Thr Lys Gly Trp Lys Val Leu
    1160                1165                1170

Leu Thr Ser Arg Asn Glu Asn Val Ala Gly Asp Thr Arg His Ile
    1175                1180                1185

Asn Phe Asn Leu Glu Leu Leu Thr Thr Asp Asp Ser Trp Thr Leu
    1190                1195                1200

Leu Gln Thr Ile Ala Phe Pro Arg Lys Asp Ala Phe Gly Glu Ala
    1205                1210                1215

Tyr Glu Glu Met Glu Lys Met Gly Lys His Met Ile Lys Tyr Cys
    1220                1225                1230

-continued

```
Gly Gly Leu Pro Leu Ala Val Arg Ile Leu Gly Gly Leu Leu Ala
    1235                1240                1245
Lys Lys Tyr Lys Leu His Glu Trp Glu Met Ile Cys Glu Asn Val
    1250                1255                1260
Glu Arg His Leu Met Gly Arg Thr Asp Phe Asn Asp Asp Asn Asn
    1265                1270                1275
Ile Leu Arg Phe His Val Met Ser Leu Ser Phe Glu Glu Leu Ser
    1280                1285                1290
Ser Tyr Leu Lys Gln Cys Phe Leu Tyr Leu Ala Ile Phe Pro Glu
    1295                1300                1305
Asp His Arg Ile Ser Val Gly Lys Leu Ser Tyr Tyr Trp Ala Ala
    1310                1315                1320
Glu Gly Phe Thr Gly Thr Tyr Tyr Asp Glu Glu Thr Ile Arg Asp
    1325                1330                1335
Val Gly Asp Ser Tyr Ile Glu Glu Leu Ala Arg Arg Asn Met Val
    1340                1345                1350
Thr Phe Glu Arg Asp Ser Thr Gly Leu Arg Phe Glu Thr Cys Ser
    1355                1360                1365
Met His Asp Ile Met Arg Glu Met Cys Leu Thr Lys Ala Lys Glu
    1370                1375                1380
Glu Asn Phe Leu Gln Thr Asp Val Thr Arg Arg Phe Val Cys Gln
    1385                1390                1395
Asn Thr Thr Thr Leu Asp Val Glu Arg Asp Ile Asn Asn Pro Lys
    1400                1405                1410
Leu Arg Ser Leu Leu Val Ile Leu Asn Ser Glu Gly Asp Phe Cys
    1415                1420                1425
Arg Leu Ser Gly Leu Arg Phe Thr Arg Leu Gln Leu Leu Arg Val
    1430                1435                1440
Leu Asp Leu Asp Lys Ala Lys Phe Glu Gly Gly Lys Leu Pro Ser
    1445                1450                1455
Asp Ile Gly Lys Leu Ile His Leu Arg Tyr Leu Ser Leu Glu Ser
    1460                1465                1470
Ala Glu Val Ser His Leu Pro Ser Ser Leu Arg Asn Leu Met Leu
    1475                1480                1485
Leu Ile Tyr Leu Asn Ile Asp Val Ala Asp Ile Asp Ile His Val
    1490                1495                1500
Pro Asn Val Leu Met Glu Met Arg Glu Leu Arg Tyr Leu Ala Leu
    1505                1510                1515
Pro Lys Phe Met His Glu Lys Thr Lys Leu Glu Leu Gly Asn Leu
    1520                1525                1530
Val Asn Leu Glu Thr Leu Glu Asn Phe Ser Thr Lys Asn Ser Arg
    1535                1540                1545
Leu Glu Asp Leu Arg Cys Met Ile Arg Leu Arg Thr Leu Ser Ile
    1550                1555                1560
Lys Val Thr Gly Glu Thr Ser Ser Glu Thr Leu Ser Leu Ser Ile
    1565                1570                1575
Ser Gly Leu Arg His Leu Glu Asn Leu Val Ile His Asp Arg Leu
    1580                1585                1590
Ser Trp Ile Lys Glu Gly Ile Val Leu His Cys Asp Asp Leu Ile
    1595                1600                1605
Lys Leu Glu Leu Phe Met Tyr Arg Pro Val Arg Leu Glu Lys Gln
    1610                1615                1620
Arg Phe Pro Ser His Ile Thr Tyr Ile Ser Leu Thr Glu Cys Arg
```

-continued

```
              1625                1630                1635
Phe Glu His Asp Pro Met Pro Leu Leu Glu Thr Leu Gln His Leu
            1640                1645                1650

Arg Lys Val Lys Leu Leu Asp Arg Ser His Cys Ala Arg Arg Met
            1655                1660                1665

Val Cys Ser Gly Ser Gly Phe Pro Gln Leu Arg Glu Leu Glu Leu
            1670                1675                1680

Val Leu Leu Glu Gln Leu Glu Glu Trp Ile Ile Glu Glu Gly Ser
            1685                1690                1695

Met Pro Leu Leu His Ser Leu Asp Ile Thr Asp Cys Asn Lys Leu
            1700                1705                1710

Lys Glu Ile Pro Glu Gly Leu Arg Ile Ile Pro Ser Leu Lys Asn
            1715                1720                1725

Leu Thr Cys Tyr Ser Met Gly Lys Glu Trp Glu Gly Arg Leu Ser
            1730                1735                1740

Glu Gly Gly Glu Glu Tyr Tyr Lys Val Gln His Ile Pro Ser Val
            1745                1750                1755

Lys Phe Tyr Gly Ala
            1760

<210> SEQ ID NO 4
<211> LENGTH: 5401
<212> TYPE: DNA
<213> ORGANISM: Brassica napus
<220> FEATURE:
<221> NAME/KEY: CDS
<222> LOCATION: (52)..(5340)

<400> SEQUENCE: 4
gaggagtact cacacaacct agagaaaaat ctggaggatt tggaggtgga a atg gga      57
                                                        Met Gly
                                                          1 acc ctc aat gca atg ata tat gag ttg tta aaa agg gtg tcg aaa gag     105
Thr Leu Asn Ala Met Ile Tyr Glu Leu Leu Lys Arg Val Ser Lys Glu
        5                   10                  15 aag gac aga ggt ata gaa acg cta gct gaa gtg gag gaa tgg att tca     153
Lys Asp Arg Gly Ile Glu Thr Leu Ala Glu Val Glu Glu Trp Ile Ser
    20                  25                  30 atg gca gaa gaa act gaa tcg aag gcg agt agt ctc ctt gat gaa agt     201
Met Ala Glu Glu Thr Glu Ser Lys Ala Ser Ser Leu Leu Asp Glu Ser
35                  40                  45                  50 att tca gga tgt cac gat tta tca atg tat gat gat att tcc aag ata     249
Ile Ser Gly Cys His Asp Leu Ser Met Tyr Asp Asp Ile Ser Lys Ile
                55                  60                  65 tct caa tcg acc ctt cat tat agc gag acg gtg tgt acg acg ttg aaa     297
Ser Gln Ser Thr Leu His Tyr Ser Glu Thr Val Cys Thr Thr Leu Lys
            70                  75                  80 gaa gtt aaa gca ctg aga tct aag gga gtt ttt aaa gta ata gtt gag     345
Glu Val Lys Ala Leu Arg Ser Lys Gly Val Phe Lys Val Ile Val Glu
        85                  90                  95 aga gct ccc ttg tct tac gtc aaa aag atg ctc cca ctt cac cca att     393
Arg Ala Pro Leu Ser Tyr Val Lys Lys Met Leu Pro Leu His Pro Ile
    100                 105                 110 gat tct gga gaa atg ttg gca gaa gaa gca tgg gat ttt ttt caa gag     441
Asp Ser Gly Glu Met Leu Ala Glu Glu Ala Trp Asp Phe Phe Gln Glu
115                 120                 125                 130 att att gga gaa aca acg tta aaa agt cat cca gac ata ccc cag ctg     489
Ile Ile Gly Glu Thr Thr Leu Lys Ser His Pro Asp Ile Pro Gln Leu
                135                 140                 145
```

```
gca aga ata gtt tgt aga aaa tgt cgt ggt ttg ccc att gct ctc agt    537
Ala Arg Ile Val Cys Arg Lys Cys Arg Gly Leu Pro Ile Ala Leu Ser
            150                 155                 160 ctc atc ggc gag acc atg tca cgc aaa agg act gta caa gaa tgg cat    585
Leu Ile Gly Glu Thr Met Ser Arg Lys Arg Thr Val Gln Glu Trp His
        165                 170                 175 caa gca att agt gtt ttg gtt tcg tct acc cca gaa gtt tca ggc act    633
Gln Ala Ile Ser Val Leu Val Ser Ser Thr Pro Glu Val Ser Gly Thr
    180                 185                 190 gaa gat gag ctt ctt tac att ttg aag ttt gcg tac gat aat ctg cct    681
Glu Asp Glu Leu Leu Tyr Ile Leu Lys Phe Ala Tyr Asp Asn Leu Pro
195                 200                 205                 210 ggt gag aat atc aag tcg tgc ttc ttg tat tgt gct ctg ttt ccg aaa    729
Gly Glu Asn Ile Lys Ser Cys Phe Leu Tyr Cys Ala Leu Phe Pro Lys
            215                 220                 225 agt tgt gat ata aat aaa caa gat ctg gta gac tgt tgg ata gcc gaa    777
Ser Cys Asp Ile Asn Lys Gln Asp Leu Val Asp Cys Trp Ile Ala Glu
        230                 235                 240 gga gta att gaa gat gaa gac aga gag ata gct gag ata cag gga tat    825
Gly Val Ile Glu Asp Glu Asp Arg Glu Ile Ala Glu Ile Gln Gly Tyr
    245                 250                 255 gaa atg atg gct gat ttg gtt atg atg aga ttg ttg att gat gat gaa    873
Glu Met Met Ala Asp Leu Val Met Met Arg Leu Leu Ile Asp Asp Glu
260                 265                 270 tct gaa cat gag gta aag atg cat gac atg gtt cgt gga atg gcc ttg    921
Ser Glu His Glu Val Lys Met His Asp Met Val Arg Gly Met Ala Leu
275                 280                 285                 290 tgg ata gcc act gac tgc ggg agg cag aaa gaa aac ttt gtc gtg gta    969
Trp Ile Ala Thr Asp Cys Gly Arg Gln Lys Glu Asn Phe Val Val Val
            295                 300                 305 agc ggt gag gat aga cat cag atg cca gag gtg aat gat tgg agt aac   1017
Ser Gly Glu Asp Arg His Gln Met Pro Glu Val Asn Asp Trp Ser Asn
        310                 315                 320 gtt aga agg atg tca gta aca tct act cag gtt gac aag ata tcc gac   1065
Val Arg Arg Met Ser Val Thr Ser Thr Gln Val Asp Lys Ile Ser Asp
    325                 330                 335 tct cat gat tgt ccc aag ctt acg act cta ttt ctc caa gaa aac aac   1113
Ser His Asp Cys Pro Lys Leu Thr Thr Leu Phe Leu Gln Glu Asn Asn
340                 345                 350 tta aaa tgg gtc tcg ggt gat ttc ttt cgg tgg atg acc agt ctt gtg   1161
Leu Lys Trp Val Ser Gly Asp Phe Phe Arg Trp Met Thr Ser Leu Val
355                 360                 365                 370 gtc ttg aat cta tcg cgt aac tta gaa ctt tct gag ttg ccg gaa gaa   1209
Val Leu Asn Leu Ser Arg Asn Leu Glu Leu Ser Glu Leu Pro Glu Glu
            375                 380                 385 gtt tca agc ctg gtg tcc ctg cgg ctt ctc aac tta tca tgg acg tgg   1257
Val Ser Ser Leu Val Ser Leu Arg Leu Leu Asn Leu Ser Trp Thr Trp
        390                 395                 400 ata aaa cgt ttg ccg ctt ggt ctg aca gag ctg aaa agg ttg atg cac   1305
Ile Lys Arg Leu Pro Leu Gly Leu Thr Glu Leu Lys Arg Leu Met His
    405                 410                 415 ttg gat ttg gat gac acc cct cgt ctt cta gaa gtt gac gtg ata ggt   1353
Leu Asp Leu Asp Asp Thr Pro Arg Leu Leu Glu Val Asp Val Ile Gly
420                 425                 430 tat tta ctg aat ttg caa gtg ctg aga tta ttc cgg tca gtt ccg atg   1401
Tyr Leu Leu Asn Leu Gln Val Leu Arg Leu Phe Arg Ser Val Pro Met
435                 440                 445                 450 gat cgc agc tta ttg gag aat ata caa ctt ttg gaa aat ctg aaa gag   1449
Asp Arg Ser Leu Leu Glu Asn Ile Gln Leu Leu Glu Asn Leu Lys Glu
```

-continued

|  |  |  |  |  |  |  |  |  |  |  |  |  |  |
|---|---|---|---|---|---|---|---|---|---|---|---|---|---|
| | | 455 | | | | 460 | | | | | 465 | | |

| ctg | aat | cta | acc | gtg | aga | gaa | gtt | gat | gtt | ttg | gag | cgg | cta | caa | agt | 1497 |
|-----|-----|-----|-----|-----|-----|-----|-----|-----|-----|-----|-----|-----|-----|-----|-----|------|
| Leu | Asn | Leu | Thr | Val | Arg | Glu | Val | Asp | Val | Leu | Glu | Arg | Leu | Gln | Ser | |
| | | 470 | | | | 475 | | | | 480 | | | | | | |

| atc | cac | aag | ttg | gca | agt | tgt | atc | cga | cat | tta | cat | ctc | aaa | ggg | att | 1545 |
| Ile | His | Lys | Leu | Ala | Ser | Cys | Ile | Arg | His | Leu | His | Leu | Lys | Gly | Ile | |
| | 485 | | | | | 490 | | | | 495 | | | | | | |

| aca | ata | aaa | gat | gga | gga | aca | cta | ctg | ctg | aac | tct | atg | ttg | agt | ctt | 1593 |
| Thr | Ile | Lys | Asp | Gly | Gly | Thr | Leu | Leu | Leu | Asn | Ser | Met | Leu | Ser | Leu | |
| 500 | | | | | 505 | | | | | 510 | | | | | | |

| cgc | gaa | ctt | aat | att | ggg | atg | tgt | gat | atc | ccg | gag | ata | acc | gtt | gat | 1641 |
| Arg | Glu | Leu | Asn | Ile | Gly | Met | Cys | Asp | Ile | Pro | Glu | Ile | Thr | Val | Asp | |
| 515 | | | | | 520 | | | | | 525 | | | | | 530 | |

| tgg | aga | agc | acc | atc | caa | aga | gag | acg | ata | cat | ttt | ggt | aac | att | cag | 1689 |
| Trp | Arg | Ser | Thr | Ile | Gln | Arg | Glu | Thr | Ile | His | Phe | Gly | Asn | Ile | Gln | |
| | | | 535 | | | | | 540 | | | | | 545 | | | |

| aaa | att | ccg | tat | tta | cag | aac | ata | cgc | aca | gtg | gct | ctt | tct | tgg | tgc | 1737 |
| Lys | Ile | Pro | Tyr | Leu | Gln | Asn | Ile | Arg | Thr | Val | Ala | Leu | Ser | Trp | Cys | |
| | | | 550 | | | | | 555 | | | | | 560 | | | |

| aaa | ggt | ctc | aag | gac | ttg | aca | tgg | ttg | cta | tta | gcc | ccg | aat | ctc | ggc | 1785 |
| Lys | Gly | Leu | Lys | Asp | Leu | Thr | Trp | Leu | Leu | Leu | Ala | Pro | Asn | Leu | Gly | |
| | | | 565 | | | | | 570 | | | | | 575 | | | |

| gat | cta | agg | tta | ctt | gaa | tgt | cag | caa | ata | gaa | cat | ata | ata | aac | aaa | 1833 |
| Asp | Leu | Arg | Leu | Leu | Glu | Cys | Gln | Gln | Ile | Glu | His | Ile | Ile | Asn | Lys | |
| | 580 | | | | | 585 | | | | | 590 | | | | | |

| gag | aaa | ccc | aca | ggt | gat | atg | agt | gag | gag | cct | ttt | caa | aat | cta | act | 1881 |
| Glu | Lys | Pro | Thr | Gly | Asp | Met | Ser | Glu | Glu | Pro | Phe | Gln | Asn | Leu | Thr | |
| 595 | | | | | 600 | | | | | 605 | | | | | 610 | |

| agg | ctc | agc | cta | gaa | agt | ttg | cct | caa | cta | gag | agc | atc | tac | tgg | act | 1929 |
| Arg | Leu | Ser | Leu | Glu | Ser | Leu | Pro | Gln | Leu | Glu | Ser | Ile | Tyr | Trp | Thr | |
| | | | 615 | | | | | 620 | | | | | 625 | | | |

| cct | cta | ccc | ttt | cca | gtt | ctg | aaa | gat | ctt | tgc | ata | aga | ggt | tgt | cca | 1977 |
| Pro | Leu | Pro | Phe | Pro | Val | Leu | Lys | Asp | Leu | Cys | Ile | Arg | Gly | Cys | Pro | |
| | | | 630 | | | | | 635 | | | | | 640 | | | |

| aag | ctg | aga | aga | cgt | ccg | ttt | agc | aat | aaa | gga | aat | caa | gtg | cga | tca | 2025 |
| Lys | Leu | Arg | Arg | Arg | Pro | Phe | Ser | Asn | Lys | Gly | Asn | Gln | Val | Arg | Ser | |
| | | | | 645 | | | | | 650 | | | | | 655 | | |

| gat | gtt | ggc | caa | aaa | gga | gtt | gaa | agg | gag | gat | gaa | gct | atg | aag | caa | 2073 |
| Asp | Val | Gly | Gln | Lys | Gly | Val | Glu | Arg | Glu | Asp | Glu | Ala | Met | Lys | Gln | |
| | | 660 | | | | | 665 | | | | | 670 | | | | |

| cat | ctc | tcc | aat | ttt | gat | gac | agg | gat | ttt | ctg | aag | atg | gat | gaa | gac | 2121 |
| His | Leu | Ser | Asn | Phe | Asp | Asp | Arg | Asp | Phe | Leu | Lys | Met | Asp | Glu | Asp | |
| 675 | | | | | 680 | | | | | 685 | | | | | 690 | |

| cag | aac | atg | gag | ggt | ttg | gca | tct | gag | tcg | cat | ccc | aat | aag | aac | ata | 2169 |
| Gln | Asn | Met | Glu | Gly | Leu | Ala | Ser | Glu | Ser | His | Pro | Asn | Lys | Asn | Ile | |
| | | | | 695 | | | | | 700 | | | | | 705 | | |

| gcc | ctg | gtc | gac | act | tca | gag | aga | gga | aaa | ttt | agt | acc | aat | gca | aac | 2217 |
| Ala | Leu | Val | Asp | Thr | Ser | Glu | Arg | Gly | Lys | Phe | Ser | Thr | Asn | Ala | Asn | |
| | | | 710 | | | | | 715 | | | | | 720 | | | |

| agc | atg | acc | gat | ttt | gat | gac | agg | agc | gga | tac | gtg | gaa | gcg | gaa | acg | 2265 |
| Ser | Met | Thr | Asp | Phe | Asp | Asp | Arg | Ser | Gly | Tyr | Val | Glu | Ala | Glu | Thr | |
| | | | 725 | | | | | 730 | | | | | 735 | | | |

| tat | gca | agc | gca | gaa | gcg | aga | tta | tta | aga | aaa | tta | gga | agc | ggg | gat | 2313 |
| Tyr | Ala | Ser | Ala | Glu | Ala | Arg | Leu | Leu | Arg | Lys | Leu | Gly | Ser | Gly | Asp | |
| | | 740 | | | | | 745 | | | | | 750 | | | | |

| atc | cca | aca | gtg | gct | gaa | gac | cag | aag | atg | ggt | ggt | ttg | gta | tct | gag | 2361 |
| Ile | Pro | Thr | Val | Ala | Glu | Asp | Gln | Lys | Met | Gly | Gly | Leu | Val | Ser | Glu | |
| 755 | | | | | 760 | | | | | 765 | | | | | 770 | |

| tta | cac | ccc | aat | gaa | aac | gta | gcc | ctg | gtc | gag | act | tca | gag | aga | gga | 2409 |

```
                Leu His Pro Asn Glu Asn Val Ala Leu Val Glu Thr Ser Glu Arg Gly
                            775                 780                 785 aaa agt acc atc gca aac agc atc acc aat ttt gat gac agg gat ttt            2457
Lys Ser Thr Ile Ala Asn Ser Ile Thr Asn Phe Asp Asp Arg Asp Phe
            790                 795                 800 ccg aca ttg gct gaa gac cag aag atg gat ggt ttg gca tct gag tca            2505
Pro Thr Leu Ala Glu Asp Gln Lys Met Asp Gly Leu Ala Ser Glu Ser
            805                 810                 815 cac cca gtc gaa gac ata gtc ctg gta gag act tta gaa agt gaa aaa            2553
His Pro Val Glu Asp Ile Val Leu Val Glu Thr Leu Glu Ser Glu Lys
            820                 825                 830 ggt acc atc cca aac agc atc acc gaa gag aat gtg ttt caa tcg gga            2601
Gly Thr Ile Pro Asn Ser Ile Thr Glu Glu Asn Val Phe Gln Ser Gly
835                 840                 845                 850 aaa cac gca act ctg gaa cac aca caa tca tac cca gtt ttg gcg cca            2649
Lys His Ala Thr Leu Glu His Thr Gln Ser Tyr Pro Val Leu Ala Pro
            855                 860                 865 gat ggc atg atc cac aat atg act gac act cct gga gga acc att atg            2697
Asp Gly Met Ile His Asn Met Thr Asp Thr Pro Gly Gly Thr Ile Met
            870                 875                 880 gct ggg gaa ctt gtg tct ttt gga ata caa aag ctt tgg gag ttg ctt            2745
Ala Gly Glu Leu Val Ser Phe Gly Ile Gln Lys Leu Trp Glu Leu Leu
            885                 890                 895 cgc caa gaa agc gag cgt ttt cag gga gct tcg gat gaa ata gat atg            2793
Arg Gln Glu Ser Glu Arg Phe Gln Gly Ala Ser Asp Glu Ile Asp Met
900                 905                 910 gta aaa agt gat tta ctc tat tta agg gga ttt tta gca gat gca aat            2841
Val Lys Ser Asp Leu Leu Tyr Leu Arg Gly Phe Leu Ala Asp Ala Asn
915                 920                 925                 930 gcc aaa aaa cat aca agg gag gtg aaa agt tgt att gaa gag atc aaa            2889
Ala Lys Lys His Thr Arg Glu Val Lys Ser Cys Ile Glu Glu Ile Lys
            935                 940                 945 gaa att ttt ttt gac gcg gaa gat att att gag aca tat ctt ctt gaa            2937
Glu Ile Phe Phe Asp Ala Glu Asp Ile Ile Glu Thr Tyr Leu Leu Glu
            950                 955                 960 gaa aac ccc cca aaa act ggt gtc ttc aag agg ctt ttc aga ggg cgt            2985
Glu Asn Pro Pro Lys Thr Gly Val Phe Lys Arg Leu Phe Arg Gly Arg
            965                 970                 975 gct ggc agg aaa ttt gct ttg gat atg aat agc tta agc aag agg att            3033
Ala Gly Arg Lys Phe Ala Leu Asp Met Asn Ser Leu Ser Lys Arg Ile
            980                 985                 990 tct aag ata atc agc gtt  atg caa gct ttt gga  gta cac cag gtt              3078
Ser Lys Ile Ile Ser Val Met Gln Ala Phe Gly  Val His Gln Val
995                 1000                1005 att act gaa ggc aag gat  tca caa cct ctt cta  caa aga caa aaa              3123
Ile Thr Glu Gly Lys Asp Ser Gln Pro Leu Leu  Gln Arg Gln Lys
1010                1015                1020 agg atg cga caa aaa ttt  gct gga gag tac aaa  ccc aat ttt gtg              3168
Arg Met Arg Gln Lys Phe Ala Gly Glu Tyr Lys  Pro Asn Phe Val
1025                1030                1035 ggg ctg gaa gaa aat gtt  gag aaa ttg gtt agt  ctt ttg gtc gag              3213
Gly Leu Glu Glu Asn Val Glu Lys Leu Val Ser  Leu Leu Val Glu
1040                1045                1050 gaa gac aat att caa gtg  gtt tcc ata acc ggg  atg ggt ggt ctt              3258
Glu Asp Asn Ile Gln Val Val Ser Ile Thr Gly  Met Gly Gly Leu
1055                1060                1065 ggt aaa act acc ctc gct  aga caa act ttt aat  cac gat atg gta              3303
Gly Lys Thr Thr Leu Ala Arg Gln Thr Phe Asn  His Asp Met Val
1070                1075                1080
```

| | | | | | | | | | | | | | | |
|---|---|---|---|---|---|---|---|---|---|---|---|---|---|---|
| aaa | cac | aag | ttt | gat | agg | ttc | gca | tgg | gtg | ggt | att | tca | caa | gct | 3348 |
| Lys | His | Lys | Phe | Asp | Arg | Phe | Ala | Trp | Val | Gly | Ile | Ser | Gln | Ala | |
| 1085 | | | | 1090 | | | | | 1095 | | | | | | |
| tgt | aac | cga | aag | att | gtg | tgg | caa | atg | atc | ttg | cgg | agt | ctc | ttg | 3393 |
| Cys | Asn | Arg | Lys | Ile | Val | Trp | Gln | Met | Ile | Leu | Arg | Ser | Leu | Leu | |
| 1100 | | | | | 1105 | | | | | 1110 | | | | | |
| gcc | aaa | aaa | gat | gaa | gat | agt | att | ttg | cat | atg | act | gaa | tct | gaa | 3438 |
| Ala | Lys | Lys | Asp | Glu | Asp | Ser | Ile | Leu | His | Met | Thr | Glu | Ser | Glu | |
| 1115 | | | | | 1120 | | | | | 1125 | | | | | |
| ctc | caa | gag | caa | atc | ttt | cta | ttg | ctg | gaa | gca | tcc | aaa | tca | ttg | 3483 |
| Leu | Gln | Glu | Gln | Ile | Phe | Leu | Leu | Leu | Glu | Ala | Ser | Lys | Ser | Leu | |
| 1130 | | | | | 1135 | | | | | 1140 | | | | | |
| att | gtc | ata | gat | gac | ata | tgg | aaa | gaa | gaa | gac | tgg | aag | cga | atc | 3528 |
| Ile | Val | Ile | Asp | Asp | Ile | Trp | Lys | Glu | Glu | Asp | Trp | Lys | Arg | Ile | |
| 1145 | | | | | 1150 | | | | | 1155 | | | | | |
| agt | caa | ata | ctt | cca | aac | aca | aaa | ggt | tgg | aag | gtg | cta | ctt | act | 3573 |
| Ser | Gln | Ile | Leu | Pro | Asn | Thr | Lys | Gly | Trp | Lys | Val | Leu | Leu | Thr | |
| 1160 | | | | | 1165 | | | | | 1170 | | | | | |
| tct | cga | aat | gag | aat | gtc | gct | gga | gac | aca | aga | cac | atc | aac | ttc | 3618 |
| Ser | Arg | Asn | Glu | Asn | Val | Ala | Gly | Asp | Thr | Arg | His | Ile | Asn | Phe | |
| 1175 | | | | | 1180 | | | | | 1185 | | | | | |
| aat | cta | gaa | tta | tta | aca | act | gat | gac | agt | tgg | aca | ctt | ttg | caa | 3663 |
| Asn | Leu | Glu | Leu | Leu | Thr | Thr | Asp | Asp | Ser | Trp | Thr | Leu | Leu | Gln | |
| 1190 | | | | | 1195 | | | | | 1200 | | | | | |
| acg | ata | gca | ttt | cct | aga | aag | gat | gca | ttc | ggg | gaa | gca | tat | gag | 3708 |
| Thr | Ile | Ala | Phe | Pro | Arg | Lys | Asp | Ala | Phe | Gly | Glu | Ala | Tyr | Glu | |
| 1205 | | | | | 1210 | | | | | 1215 | | | | | |
| gaa | atg | gaa | aag | atg | ggt | aag | cat | atg | atc | aaa | tat | tgt | ggg | gga | 3753 |
| Glu | Met | Glu | Lys | Met | Gly | Lys | His | Met | Ile | Lys | Tyr | Cys | Gly | Gly | |
| 1220 | | | | | 1225 | | | | | 1230 | | | | | |
| ctg | cca | ttg | gct | gtg | aga | ata | tta | gga | ggt | tta | tta | gcg | aag | aaa | 3798 |
| Leu | Pro | Leu | Ala | Val | Arg | Ile | Leu | Gly | Gly | Leu | Leu | Ala | Lys | Lys | |
| 1235 | | | | | 1240 | | | | | 1245 | | | | | |
| tac | aaa | ctg | cat | gag | tgg | gaa | atg | ata | tgt | gag | aat | gtt | gaa | cgc | 3843 |
| Tyr | Lys | Leu | His | Glu | Trp | Glu | Met | Ile | Cys | Glu | Asn | Val | Glu | Arg | |
| 1250 | | | | | 1255 | | | | | 1260 | | | | | |
| cat | ctc | atg | gga | aga | act | gat | ttc | aat | gat | gac | aac | aat | att | ttg | 3888 |
| His | Leu | Met | Gly | Arg | Thr | Asp | Phe | Asn | Asp | Asp | Asn | Asn | Ile | Leu | |
| 1265 | | | | | 1270 | | | | | 1275 | | | | | |
| cgc | ttc | cat | gta | atg | tct | ctg | agc | ttt | gaa | gag | ttg | tct | agt | tat | 3933 |
| Arg | Phe | His | Val | Met | Ser | Leu | Ser | Phe | Glu | Glu | Leu | Ser | Ser | Tyr | |
| 1280 | | | | | 1285 | | | | | 1290 | | | | | |
| ttg | aag | caa | tgc | ttc | ctt | tat | ttg | gca | att | ttt | cca | gaa | gat | cat | 3978 |
| Leu | Lys | Gln | Cys | Phe | Leu | Tyr | Leu | Ala | Ile | Phe | Pro | Glu | Asp | His | |
| 1295 | | | | | 1300 | | | | | 1305 | | | | | |
| cga | ata | agt | gtg | ggg | aaa | ctg | tct | tat | tac | tgg | gca | gca | gaa | gga | 4023 |
| Arg | Ile | Ser | Val | Gly | Lys | Leu | Ser | Tyr | Tyr | Trp | Ala | Ala | Glu | Gly | |
| 1310 | | | | | 1315 | | | | | 1320 | | | | | |
| ttc | acc | ggt | acg | tat | tac | gat | gaa | gag | acc | att | cga | gat | gtt | gga | 4068 |
| Phe | Thr | Gly | Thr | Tyr | Tyr | Asp | Glu | Glu | Thr | Ile | Arg | Asp | Val | Gly | |
| 1325 | | | | | 1330 | | | | | 1335 | | | | | |
| gat | agc | tat | ata | gag | gag | ctc | gcg | agg | aga | aat | atg | gtt | act | ttc | 4113 |
| Asp | Ser | Tyr | Ile | Glu | Glu | Leu | Ala | Arg | Arg | Asn | Met | Val | Thr | Phe | |
| 1340 | | | | | 1345 | | | | | 1350 | | | | | |
| gaa | aga | gac | agc | acg | ggc | ttg | agg | ttt | gaa | acc | tgt | agt | atg | cat | 4158 |
| Glu | Arg | Asp | Ser | Thr | Gly | Leu | Arg | Phe | Glu | Thr | Cys | Ser | Met | His | |
| 1355 | | | | | 1360 | | | | | 1365 | | | | | |
| gac | att | atg | agg | gaa | atg | tgt | ttg | act | aaa | gca | aaa | gaa | gag | aac | 4203 |
| Asp | Ile | Met | Arg | Glu | Met | Cys | Leu | Thr | Lys | Ala | Lys | Glu | Glu | Asn | |
| 1370 | | | | | 1375 | | | | | 1380 | | | | | |

```
ttc cta caa act gat gtt act cgc aga ttt gtc tgc caa aat act    4248
Phe Leu Gln Thr Asp Val Thr Arg Arg Phe Val Cys Gln Asn Thr
1385                1390                1395 acc aca tta gat gtt gag aga gat ata aat aat cca aaa ctt cgg    4293
Thr Thr Leu Asp Val Glu Arg Asp Ile Asn Asn Pro Lys Leu Arg
1400                1405                1410 tct ctc tta gtt atc ctt aat tcg gag ggg gat ttt tgt agg cta    4338
Ser Leu Leu Val Ile Leu Asn Ser Glu Gly Asp Phe Cys Arg Leu
1415                1420                1425 tct ggt tta agg ttc aca agg cta caa ctt ctg agg gtg tta gat    4383
Ser Gly Leu Arg Phe Thr Arg Leu Gln Leu Leu Arg Val Leu Asp
1430                1435                1440 ctc gat aaa gcc aag ttt gaa gga ggg aag tta cct tct gac ata    4428
Leu Asp Lys Ala Lys Phe Glu Gly Gly Lys Leu Pro Ser Asp Ile
1445                1450                1455 gga aag ctc atc cac tta aga tac ttg agc tta gaa tct gct gag    4473
Gly Lys Leu Ile His Leu Arg Tyr Leu Ser Leu Glu Ser Ala Glu
1460                1465                1470 gta tct cat cta cct tct tcc cta cga aac ctg atg ttg ctg atc    4518
Val Ser His Leu Pro Ser Ser Leu Arg Asn Leu Met Leu Leu Ile
1475                1480                1485 tat ttg aac ata gat gta gct gat att gat ata cat gtg ccc aac    4563
Tyr Leu Asn Ile Asp Val Ala Asp Ile Asp Ile His Val Pro Asn
1490                1495                1500 gtt ctg atg gag atg cga gaa ttg aga tac ctt gca tta cca aag    4608
Val Leu Met Glu Met Arg Glu Leu Arg Tyr Leu Ala Leu Pro Lys
1505                1510                1515 ttt atg cat gag aag acc aag ttg gaa ttg ggt aat cta gta aac    4653
Phe Met His Glu Lys Thr Lys Leu Glu Leu Gly Asn Leu Val Asn
1520                1525                1530 ttg gag acc ttg gag aat ttc tca aca aag aat agc aga tta gag    4698
Leu Glu Thr Leu Glu Asn Phe Ser Thr Lys Asn Ser Arg Leu Glu
1535                1540                1545 gat ctc cgt tgt atg atc aga ttg agg act ctt tca atc aaa gta    4743
Asp Leu Arg Cys Met Ile Arg Leu Arg Thr Leu Ser Ile Lys Val
1550                1555                1560 act ggt gag acc tct tca gaa act ctc tct tta tca ata agt ggc    4788
Thr Gly Glu Thr Ser Ser Glu Thr Leu Ser Leu Ser Ile Ser Gly
1565                1570                1575 ctg aga cac ctg gaa aat ctc gtc ata cat gat cgc ctg agc tgg    4833
Leu Arg His Leu Glu Asn Leu Val Ile His Asp Arg Leu Ser Trp
1580                1585                1590 atc aaa gag gga att gtt tta cat tgc gat gat ctc ata aag ctg    4878
Ile Lys Glu Gly Ile Val Leu His Cys Asp Asp Leu Ile Lys Leu
1595                1600                1605 gag ctg ttt atg tat agg cca gtg agg cta gaa aaa caa cgc ttc    4923
Glu Leu Phe Met Tyr Arg Pro Val Arg Leu Glu Lys Gln Arg Phe
1610                1615                1620 cct tct cac att aca tac ata tct cta act gag tgt cgt ttc gag    4968
Pro Ser His Ile Thr Tyr Ile Ser Leu Thr Glu Cys Arg Phe Glu
1625                1630                1635 cat gat ccg atg cca cta tta gag acg ttg cag cac ttg aga aag    5013
His Asp Pro Met Pro Leu Leu Glu Thr Leu Gln His Leu Arg Lys
1640                1645                1650 gtt aag tta ttg gat cgg tct cat tgt gcg aga aga atg gtt tgc    5058
Val Lys Leu Leu Asp Arg Ser His Cys Ala Arg Arg Met Val Cys
1655                1660                1665 tcg ggt agt ggg ttt ccg cag ttg cgt gag ctt gag tta gtc tta    5103
Ser Gly Ser Gly Phe Pro Gln Leu Arg Glu Leu Glu Leu Val Leu
```

-continued

```
cta gag cag ttg gaa gag tgg ata ata gag gaa ggc tcc atg cct      5148
Leu Glu Gln Leu Glu Glu Trp Ile Ile Glu Glu Gly Ser Met Pro
1685                1690                1695 ctt ctt cat agt ttg gac att act gac tgt aac aag tta aag gaa      5193
Leu Leu His Ser Leu Asp Ile Thr Asp Cys Asn Lys Leu Lys Glu
1700                1705                1710 att cca gag ggg ctg cga att atc cct tcc tta aag aat ctg act      5238
Ile Pro Glu Gly Leu Arg Ile Ile Pro Ser Leu Lys Asn Leu Thr
1715                1720                1725 tgt tat agt atg ggt aag gaa tgg gag gga aga ttg tcg gaa gga      5283
Cys Tyr Ser Met Gly Lys Glu Trp Glu Gly Arg Leu Ser Glu Gly
1730                1735                1740 gga gaa gaa tat tac aaa gtc cag cac att ccc tct gtt aag ttc      5328
Gly Glu Glu Tyr Tyr Lys Val Gln His Ile Pro Ser Val Lys Phe
1745                1750                1755 tat ggt gca tga ggtcctcagc aattacaggt aaaatgtttt cttccctaat      5380
Tyr Gly Ala
1760 taaaataaca tccataagaa a                                           5401

<210> SEQ ID NO 5
<211> LENGTH: 1762
<212> TYPE: PRT
<213> ORGANISM: Brassica napus

<400> SEQUENCE: 5

Met Gly Thr Leu Asn Ala Met Ile Tyr Glu Leu Leu Lys Arg Val Ser
1               5                   10                  15

Lys Glu Lys Asp Arg Gly Ile Glu Thr Leu Ala Glu Val Glu Glu Trp
            20                  25                  30

Ile Ser Met Ala Glu Glu Thr Glu Ser Lys Ala Ser Ser Leu Leu Asp
        35                  40                  45

Glu Ser Ile Ser Gly Cys His Asp Leu Ser Met Tyr Asp Asp Ile Ser
    50                  55                  60

Lys Ile Ser Gln Ser Thr Leu His Tyr Ser Glu Thr Val Cys Thr Thr
65                  70                  75                  80

Leu Lys Glu Val Lys Ala Leu Arg Ser Lys Gly Val Phe Lys Val Ile
                85                  90                  95

Val Glu Arg Ala Pro Leu Ser Tyr Val Lys Lys Met Leu Pro Leu His
            100                 105                 110

Pro Ile Asp Ser Gly Glu Met Leu Ala Glu Ala Trp Asp Phe Phe
        115                 120                 125

Gln Glu Ile Ile Gly Glu Thr Thr Leu Lys Ser His Pro Asp Ile Pro
    130                 135                 140

Gln Leu Ala Arg Ile Val Cys Arg Lys Cys Arg Gly Leu Pro Ile Ala
145                 150                 155                 160

Leu Ser Leu Ile Gly Glu Thr Met Ser Arg Lys Arg Thr Val Gln Glu
                165                 170                 175

Trp His Gln Ala Ile Ser Val Leu Val Ser Ser Thr Pro Glu Val Ser
            180                 185                 190

Gly Thr Glu Asp Glu Leu Leu Tyr Ile Leu Lys Phe Ala Tyr Asp Asn
        195                 200                 205

Leu Pro Gly Glu Asn Ile Lys Ser Cys Phe Leu Tyr Cys Ala Leu Phe
    210                 215                 220

Pro Lys Ser Cys Asp Ile Asn Lys Gln Asp Leu Val Asp Cys Trp Ile
```

```
                225                 230                 235                 240
Ala Glu Gly Val Ile Glu Asp Glu Asp Arg Glu Ile Ala Glu Ile Gln
                    245                 250                 255
Gly Tyr Glu Met Met Ala Asp Leu Val Met Met Arg Leu Leu Ile Asp
                    260                 265                 270
Asp Glu Ser Glu His Glu Val Lys Met His Asp Met Val Arg Gly Met
                    275                 280                 285
Ala Leu Trp Ile Ala Thr Asp Cys Gly Arg Gln Lys Glu Asn Phe Val
                290                 295                 300
Val Val Ser Gly Glu Asp Arg His Gln Met Pro Glu Val Asn Asp Trp
305                 310                 315                 320
Ser Asn Val Arg Arg Met Ser Val Thr Ser Thr Gln Val Asp Lys Ile
                    325                 330                 335
Ser Asp Ser His Asp Cys Pro Lys Leu Thr Thr Leu Phe Leu Gln Glu
                    340                 345                 350
Asn Asn Leu Lys Trp Val Ser Gly Asp Phe Phe Arg Trp Met Thr Ser
                    355                 360                 365
Leu Val Val Leu Asn Leu Ser Arg Asn Leu Glu Leu Ser Glu Leu Pro
                370                 375                 380
Glu Glu Val Ser Ser Leu Val Ser Leu Arg Leu Leu Asn Leu Ser Trp
385                 390                 395                 400
Thr Trp Ile Lys Arg Leu Pro Leu Gly Leu Thr Glu Leu Lys Arg Leu
                    405                 410                 415
Met His Leu Asp Leu Asp Asp Thr Pro Arg Leu Leu Glu Val Asp Val
                    420                 425                 430
Ile Gly Tyr Leu Leu Asn Leu Gln Val Leu Arg Leu Phe Arg Ser Val
                435                 440                 445
Pro Met Asp Arg Ser Leu Leu Glu Asn Ile Gln Leu Glu Asn Leu
                    450                 455                 460
Lys Glu Leu Asn Leu Thr Val Arg Glu Val Asp Val Leu Glu Arg Leu
465                 470                 475                 480
Gln Ser Ile His Lys Leu Ala Ser Cys Ile Arg His Leu His Leu Lys
                    485                 490                 495
Gly Ile Thr Ile Lys Asp Gly Gly Thr Leu Leu Leu Asn Ser Met Leu
                    500                 505                 510
Ser Leu Arg Glu Leu Asn Ile Gly Met Cys Asp Ile Pro Glu Ile Thr
                    515                 520                 525
Val Asp Trp Arg Ser Thr Ile Gln Arg Glu Thr Ile His Phe Gly Asn
                530                 535                 540
Ile Gln Lys Ile Pro Tyr Leu Gln Asn Ile Arg Thr Val Ala Leu Ser
545                 550                 555                 560
Trp Cys Lys Gly Leu Lys Asp Leu Thr Trp Leu Leu Leu Ala Pro Asn
                    565                 570                 575
Leu Gly Asp Leu Arg Leu Leu Glu Cys Gln Gln Ile Glu His Ile Ile
                    580                 585                 590
Asn Lys Glu Lys Pro Thr Gly Asp Met Ser Glu Glu Pro Phe Gln Asn
                    595                 600                 605
Leu Thr Arg Leu Ser Leu Glu Ser Leu Pro Gln Leu Glu Ser Ile Tyr
                610                 615                 620
Trp Thr Pro Leu Pro Phe Pro Val Leu Lys Asp Leu Cys Ile Arg Gly
625                 630                 635                 640
Cys Pro Lys Leu Arg Arg Arg Pro Phe Ser Asn Lys Gly Asn Gln Val
                    645                 650                 655
```

Arg Ser Asp Val Gly Gln Lys Gly Val Glu Arg Glu Asp Glu Ala Met
                660                 665                 670

Lys Gln His Leu Ser Asn Phe Asp Asp Arg Asp Phe Leu Lys Met Asp
            675                 680                 685

Glu Asp Gln Asn Met Glu Gly Leu Ala Ser Ser His Pro Asn Lys
    690                 695                 700

Asn Ile Ala Leu Val Asp Thr Ser Glu Arg Gly Lys Phe Ser Thr Asn
705                 710                 715                 720

Ala Asn Ser Met Thr Asp Phe Asp Asp Arg Ser Gly Tyr Val Glu Ala
            725                 730                 735

Glu Thr Tyr Ala Ser Ala Glu Ala Arg Leu Leu Arg Lys Leu Gly Ser
            740                 745                 750

Gly Asp Ile Pro Thr Val Ala Glu Asp Gln Lys Met Gly Gly Leu Val
            755                 760                 765

Ser Glu Leu His Pro Asn Glu Asn Val Ala Leu Val Glu Thr Ser Glu
            770                 775                 780

Arg Gly Lys Ser Thr Ile Ala Asn Ser Ile Thr Asn Phe Asp Asp Arg
785                 790                 795                 800

Asp Phe Pro Thr Leu Ala Glu Asp Gln Lys Met Asp Gly Leu Ala Ser
            805                 810                 815

Glu Ser His Pro Val Glu Asp Ile Val Leu Val Glu Thr Leu Glu Ser
            820                 825                 830

Glu Lys Gly Thr Ile Pro Asn Ser Ile Thr Glu Glu Asn Val Phe Gln
            835                 840                 845

Ser Gly Lys His Ala Thr Leu Glu His Thr Gln Ser Tyr Pro Val Leu
            850                 855                 860

Ala Pro Asp Gly Met Ile His Asn Met Thr Asp Thr Pro Gly Gly Thr
865                 870                 875                 880

Ile Met Ala Gly Glu Leu Val Ser Phe Gly Ile Gln Lys Leu Trp Glu
            885                 890                 895

Leu Leu Arg Gln Glu Ser Glu Arg Phe Gln Gly Ala Ser Asp Glu Ile
            900                 905                 910

Asp Met Val Lys Ser Asp Leu Leu Tyr Leu Arg Gly Phe Leu Ala Asp
            915                 920                 925

Ala Asn Ala Lys Lys His Thr Arg Glu Val Lys Ser Cys Ile Glu Glu
            930                 935                 940

Ile Lys Glu Ile Phe Phe Asp Ala Glu Asp Ile Ile Glu Thr Tyr Leu
945                 950                 955                 960

Leu Glu Glu Asn Pro Pro Lys Thr Gly Val Phe Lys Arg Leu Phe Arg
            965                 970                 975

Gly Arg Ala Gly Arg Lys Phe Ala Leu Asp Met Asn Ser Leu Ser Lys
            980                 985                 990

Arg Ile Ser Lys Ile Ile Ser Val Met Gln Ala Phe Gly Val His Gln
            995                 1000                1005

Val Ile Thr Glu Gly Lys Asp Ser Gln Pro Leu Leu Gln Arg Gln
    1010                1015                1020

Lys Arg Met Arg Gln Lys Phe Ala Gly Glu Tyr Lys Pro Asn Phe
    1025                1030                1035

Val Gly Leu Glu Glu Asn Val Glu Lys Leu Val Ser Leu Leu Val
    1040                1045                1050

Glu Glu Asp Asn Ile Gln Val Val Ser Ile Thr Gly Met Gly Gly
    1055                1060                1065

```
Leu Gly Lys Thr Thr Leu Ala Arg Gln Thr Phe Asn His Asp Met
    1070                1075                1080

Val Lys His Lys Phe Asp Arg Phe Ala Trp Val Gly Ile Ser Gln
    1085                1090                1095

Ala Cys Asn Arg Lys Ile Val Trp Gln Met Ile Leu Arg Ser Leu
    1100                1105                1110

Leu Ala Lys Lys Asp Glu Asp Ser Ile Leu His Met Thr Glu Ser
    1115                1120                1125

Glu Leu Gln Glu Gln Ile Phe Leu Leu Leu Glu Ala Ser Lys Ser
    1130                1135                1140

Leu Ile Val Ile Asp Asp Ile Trp Lys Glu Glu Asp Trp Lys Arg
    1145                1150                1155

Ile Ser Gln Ile Leu Pro Asn Thr Lys Gly Trp Lys Val Leu Leu
    1160                1165                1170

Thr Ser Arg Asn Glu Asn Val Ala Gly Asp Thr Arg His Ile Asn
    1175                1180                1185

Phe Asn Leu Glu Leu Leu Thr Thr Asp Asp Ser Trp Thr Leu Leu
    1190                1195                1200

Gln Thr Ile Ala Phe Pro Arg Lys Asp Ala Phe Gly Glu Ala Tyr
    1205                1210                1215

Glu Glu Met Glu Lys Met Gly Lys His Met Ile Lys Tyr Cys Gly
    1220                1225                1230

Gly Leu Pro Leu Ala Val Arg Ile Leu Gly Gly Leu Leu Ala Lys
    1235                1240                1245

Lys Tyr Lys Leu His Glu Trp Glu Met Ile Cys Glu Asn Val Glu
    1250                1255                1260

Arg His Leu Met Gly Arg Thr Asp Phe Asn Asp Asn Asn Ile
    1265                1270                1275

Leu Arg Phe His Val Met Ser Leu Ser Phe Glu Glu Leu Ser Ser
    1280                1285                1290

Tyr Leu Lys Gln Cys Phe Leu Tyr Leu Ala Ile Phe Pro Glu Asp
    1295                1300                1305

His Arg Ile Ser Val Gly Lys Leu Ser Tyr Tyr Trp Ala Ala Glu
    1310                1315                1320

Gly Phe Thr Gly Thr Tyr Tyr Asp Glu Glu Thr Ile Arg Asp Val
    1325                1330                1335

Gly Asp Ser Tyr Ile Glu Glu Leu Ala Arg Arg Asn Met Val Thr
    1340                1345                1350

Phe Glu Arg Asp Ser Thr Gly Leu Arg Phe Glu Thr Cys Ser Met
    1355                1360                1365

His Asp Ile Met Arg Glu Met Cys Leu Thr Lys Ala Lys Glu Glu
    1370                1375                1380

Asn Phe Leu Gln Thr Asp Val Thr Arg Arg Phe Val Cys Gln Asn
    1385                1390                1395

Thr Thr Thr Leu Asp Val Glu Arg Asp Ile Asn Asn Pro Lys Leu
    1400                1405                1410

Arg Ser Leu Leu Val Ile Leu Asn Ser Glu Gly Asp Phe Cys Arg
    1415                1420                1425

Leu Ser Gly Leu Arg Phe Thr Arg Leu Gln Leu Leu Arg Val Leu
    1430                1435                1440

Asp Leu Asp Lys Ala Lys Phe Glu Gly Gly Lys Leu Pro Ser Asp
    1445                1450                1455

Ile Gly Lys Leu Ile His Leu Arg Tyr Leu Ser Leu Glu Ser Ala
```

```
          1460                1465                1470
Glu Val Ser His Leu Pro Ser  Ser Leu Arg Asn Leu  Met Leu Leu
    1475                1480                1485

Ile Tyr Leu Asn Ile Asp Val  Ala Asp Ile Asp Ile  His Val Pro
    1490                1495                1500

Asn Val Leu Met Glu Met Arg  Glu Leu Arg Tyr Leu  Ala Leu Pro
    1505                1510                1515

Lys Phe Met His Glu Lys Thr  Lys Leu Glu Leu Gly  Asn Leu Val
    1520                1525                1530

Asn Leu Glu Thr Leu Glu Asn  Phe Ser Thr Lys Asn  Ser Arg Leu
    1535                1540                1545

Glu Asp Leu Arg Cys Met Ile  Arg Leu Arg Thr Leu  Ser Ile Lys
    1550                1555                1560

Val Thr Gly Glu Thr Ser Ser  Glu Thr Leu Ser Leu  Ser Ile Ser
    1565                1570                1575

Gly Leu Arg His Leu Glu Asn  Leu Val Ile His Asp  Arg Leu Ser
    1580                1585                1590

Trp Ile Lys Glu Gly Ile Val  Leu His Cys Asp Asp  Leu Ile Lys
    1595                1600                1605

Leu Glu Leu Phe Met Tyr Arg  Pro Val Arg Leu Glu  Lys Gln Arg
    1610                1615                1620

Phe Pro Ser His Ile Thr Tyr  Ile Ser Leu Thr Glu  Cys Arg Phe
    1625                1630                1635

Glu His Asp Pro Met Pro Leu  Leu Glu Thr Leu Gln  His Leu Arg
    1640                1645                1650

Lys Val Lys Leu Leu Asp Arg  Ser His Cys Ala Arg  Arg Met Val
    1655                1660                1665

Cys Ser Gly Ser Gly Phe Pro  Gln Leu Arg Glu Leu  Glu Leu Val
    1670                1675                1680

Leu Leu Glu Gln Leu Glu Glu  Trp Ile Ile Glu Glu  Gly Ser Met
    1685                1690                1695

Pro Leu Leu His Ser Leu Asp  Ile Thr Asp Cys Asn  Lys Leu Lys
    1700                1705                1710

Glu Ile Pro Glu Gly Leu Arg  Ile Ile Pro Ser Leu  Lys Asn Leu
    1715                1720                1725

Thr Cys Tyr Ser Met Gly Lys  Glu Trp Glu Gly Arg  Leu Ser Glu
    1730                1735                1740

Gly Gly Glu Glu Tyr Tyr Lys  Val Gln His Ile Pro  Ser Val Lys
    1745                1750                1755

Phe Tyr Gly Ala
    1760

<210> SEQ ID NO 6
<211> LENGTH: 5422
<212> TYPE: DNA
<213> ORGANISM: Brassica napus
<220> FEATURE:
<221> NAME/KEY: CDS
<222> LOCATION: (52)..(5361)

<400> SEQUENCE: 6
gaggagtact cacacaacct agagaaaaat ctggaggatt tggaggtgga a atg gga        57
                                                        Met Gly
                                                          1 acc ctc aat gca atg ata tat gag ttg tta aaa agg gtg tcg aaa gag       105
Thr Leu Asn Ala Met Ile Tyr Glu Leu Leu Lys Arg Val Ser Lys Glu
```

-continued

```
          5                   10                  15
aag gac aga ggt ata gaa acg cta gct gaa gtg gag gaa tgg att tca      153
Lys Asp Arg Gly Ile Glu Thr Leu Ala Glu Val Glu Glu Trp Ile Ser
         20                  25                  30 atg gca gaa gaa act gaa tcg aag gcg agt agt ctc ctt gat gaa agt      201
Met Ala Glu Glu Thr Glu Ser Lys Ala Ser Ser Leu Leu Asp Glu Ser
 35                  40                  45                  50 att tca gga tgt cac gat tta tca atg tat gat gat att tcc aag ata      249
Ile Ser Gly Cys His Asp Leu Ser Met Tyr Asp Asp Ile Ser Lys Ile
                     55                  60                  65 tct caa tcg acc ctt cat tat agc gag acg gtg tgt acg acg ttg aaa      297
Ser Gln Ser Thr Leu His Tyr Ser Glu Thr Val Cys Thr Thr Leu Lys
             70                  75                  80 gaa gtt aaa gca ctg aga tct aag gga gtt ttt aaa gta ata gtt gag      345
Glu Val Lys Ala Leu Arg Ser Lys Gly Val Phe Lys Val Ile Val Glu
         85                  90                  95 aga gct ccc ttg tct tac gtc aaa aag atg ctc cca ctt cac cca att      393
Arg Ala Pro Leu Ser Tyr Val Lys Lys Met Leu Pro Leu His Pro Ile
100                 105                 110 gat tct gga gaa atg ttg gca gaa gaa gca tgg gat ttt ttt caa gag      441
Asp Ser Gly Glu Met Leu Ala Glu Glu Ala Trp Asp Phe Phe Gln Glu
115                 120                 125                 130 att att gga gaa aca acg tta aaa agt cat cca gac ata ccc cag ctg      489
Ile Ile Gly Glu Thr Thr Leu Lys Ser His Pro Asp Ile Pro Gln Leu
                135                 140                 145 gca aga ata gtt tgt aga aaa tgt cgt ggt ttg ccc att gct ctc agt      537
Ala Arg Ile Val Cys Arg Lys Cys Arg Gly Leu Pro Ile Ala Leu Ser
            150                 155                 160 ctc atc ggc gag acc atg tca cgc aaa agg act gta caa gaa tgg cat      585
Leu Ile Gly Glu Thr Met Ser Arg Lys Arg Thr Val Gln Glu Trp His
        165                 170                 175 caa gca att agt gtt ttg gtt tcg tct acc cca gaa gtt tca ggc act      633
Gln Ala Ile Ser Val Leu Val Ser Ser Thr Pro Glu Val Ser Gly Thr
180                 185                 190 gaa gat gag ctt ctt tac att ttg aag ttt gcg tac gat aat ctg cct      681
Glu Asp Glu Leu Leu Tyr Ile Leu Lys Phe Ala Tyr Asp Asn Leu Pro
195                 200                 205                 210 ggt gag aat atc aag tcg tgc ttc ttg tat tgt gct ctg ttt ccg aaa      729
Gly Glu Asn Ile Lys Ser Cys Phe Leu Tyr Cys Ala Leu Phe Pro Lys
                215                 220                 225 agt tgt gat ata aat aaa caa gat ctg gta gac tgt tgg ata gcc gaa      777
Ser Cys Asp Ile Asn Lys Gln Asp Leu Val Asp Cys Trp Ile Ala Glu
            230                 235                 240 gga gta att gaa gat gaa gac aga gag ata gct gag ata cag gga tat      825
Gly Val Ile Glu Asp Glu Asp Arg Glu Ile Ala Glu Ile Gln Gly Tyr
        245                 250                 255 gaa atg atg gct gat ttg gtt atg atg aga ttg ttg att gat gat gaa      873
Glu Met Met Ala Asp Leu Val Met Met Arg Leu Leu Ile Asp Asp Glu
260                 265                 270 tct gaa cat gag gta aag atg cat gac atg gtt cgt gga atg gcc ttg      921
Ser Glu His Glu Val Lys Met His Asp Met Val Arg Gly Met Ala Leu
275                 280                 285                 290 tgg ata gcc act gac tgc ggg agg cag aaa gaa aac ttt gtc gtg gta      969
Trp Ile Ala Thr Asp Cys Gly Arg Gln Lys Glu Asn Phe Val Val Val
                295                 300                 305 agc ggt gag gat aga cat cag atg cca gag gtg aat gat tgg agt aac     1017
Ser Gly Glu Asp Arg His Gln Met Pro Glu Val Asn Asp Trp Ser Asn
            310                 315                 320 gtt aga agg atg tca gta aca tct act cag gtt gac aag ata tcc gac     1065
```

```
                Val Arg Arg Met Ser Val Thr Ser Thr Gln Val Asp Lys Ile Ser Asp
                    325                 330                 335 tct cat gat tgt ccc aag ctt acg act cta ttt ctc caa gaa aac aac            1113
Ser His Asp Cys Pro Lys Leu Thr Thr Leu Phe Leu Gln Glu Asn Asn
    340                 345                 350 tta aaa tgg gtc tcg ggt gat ttc ttt cgg tgg atg acc agt ctt gtg            1161
Leu Lys Trp Val Ser Gly Asp Phe Phe Arg Trp Met Thr Ser Leu Val
355                 360                 365                 370 gtc ttg aat cta tcg cgt aac tta gaa ctt tct gag ttg ccg gaa gaa            1209
Val Leu Asn Leu Ser Arg Asn Leu Glu Leu Ser Glu Leu Pro Glu Glu
                375                 380                 385 gtt tca agc ctg gtg tcc ctg cgg ctt ctc aac tta tca tgg acg tgg            1257
Val Ser Ser Leu Val Ser Leu Arg Leu Leu Asn Leu Ser Trp Thr Trp
            390                 395                 400 ata aaa cgt ttg ccg ctt ggt ctg aca gag ctg aaa agg ttg atg cac            1305
Ile Lys Arg Leu Pro Leu Gly Leu Thr Glu Leu Lys Arg Leu Met His
        405                 410                 415 ttg gat ttg gat gac acc cct cgt ctt cta gaa gtt gac gtg ata ggt            1353
Leu Asp Leu Asp Asp Thr Pro Arg Leu Leu Glu Val Asp Val Ile Gly
    420                 425                 430 tat tta ctg aat ttg caa gtg ctg aga tta ttc cgg tca gtt ccg atg            1401
Tyr Leu Leu Asn Leu Gln Val Leu Arg Leu Phe Arg Ser Val Pro Met
435                 440                 445                 450 gat cgc agc tta ttg gag aat ata caa ctt ttg gaa aat ctg aaa gag            1449
Asp Arg Ser Leu Leu Glu Asn Ile Gln Leu Leu Glu Asn Leu Lys Glu
                455                 460                 465 ctg aat cta acc gtg aga gaa gtt gat gtt ttg gag cgg cta caa agt            1497
Leu Asn Leu Thr Val Arg Glu Val Asp Val Leu Glu Arg Leu Gln Ser
            470                 475                 480 atc cac aag ttg gca agt tgt atc cga cat tta cat ctc aaa ggg att            1545
Ile His Lys Leu Ala Ser Cys Ile Arg His Leu His Leu Lys Gly Ile
        485                 490                 495 aca ata aaa gat gga gga aca cta ctg ctg aac tct atg ttg agt ctt            1593
Thr Ile Lys Asp Gly Gly Thr Leu Leu Leu Asn Ser Met Leu Ser Leu
    500                 505                 510 cgc gaa ctt aat att ggg atg tgt gat atc ccg gag ata acc gtt gat            1641
Arg Glu Leu Asn Ile Gly Met Cys Asp Ile Pro Glu Ile Thr Val Asp
515                 520                 525                 530 tgg aga agc acc atc caa aga gag acg ata cat ttt ggt aac att cag            1689
Trp Arg Ser Thr Ile Gln Arg Glu Thr Ile His Phe Gly Asn Ile Gln
                535                 540                 545 aaa att ccg tat tta cag aac ata cgc aca gtg gct ctt tct tgg tgc            1737
Lys Ile Pro Tyr Leu Gln Asn Ile Arg Thr Val Ala Leu Ser Trp Cys
            550                 555                 560 aaa ggt ctc aag gac ttg aca tgg ttg cta tta gcc ccg aat ctc ggc            1785
Lys Gly Leu Lys Asp Leu Thr Trp Leu Leu Leu Ala Pro Asn Leu Gly
        565                 570                 575 gat cta agg tta ctt gaa tgt cag caa ata gaa cat ata ata aac aaa            1833
Asp Leu Arg Leu Leu Glu Cys Gln Gln Ile Glu His Ile Ile Asn Lys
    580                 585                 590 gag aaa ccc aca ggt gat atg agt gag gag cct ttt caa aat cta act            1881
Glu Lys Pro Thr Gly Asp Met Ser Glu Glu Pro Phe Gln Asn Leu Thr
595                 600                 605                 610 agg ctc agc cta gaa agt ttg cct caa cta gag agc atc tac tgg act            1929
Arg Leu Ser Leu Glu Ser Leu Pro Gln Leu Glu Ser Ile Tyr Trp Thr
                615                 620                 625 cct cta ccc ttt cca gtt ctg aaa gat ctt tgc ata aga ggt tgt cca            1977
Pro Leu Pro Phe Pro Val Leu Lys Asp Leu Cys Ile Arg Gly Cys Pro
            630                 635                 640
```

```
aag ctg aga aga cgt ccg ttt agc aat aaa gga aat caa gtg cga tca    2025
Lys Leu Arg Arg Arg Pro Phe Ser Asn Lys Gly Asn Gln Val Arg Ser
        645                 650                 655 gat gtt ggc caa aaa gga gtt gaa agg gag gat gaa gct atg aag caa    2073
Asp Val Gly Gln Lys Gly Val Glu Arg Glu Asp Glu Ala Met Lys Gln
660                 665                 670 cat ctc tcc aat ttt gat gac agg gat ttt ctg aag atg gat gaa gac    2121
His Leu Ser Asn Phe Asp Asp Arg Asp Phe Leu Lys Met Asp Glu Asp
675                 680                 685                 690 cag aac atg gag ggt ttg gca tct gag tcg cat ccc aat aag aac ata    2169
Gln Asn Met Glu Gly Leu Ala Ser Glu Ser His Pro Asn Lys Asn Ile
            695                 700                 705 gcc ctg gtc gac act tca gag aga gga aaa ttt agt acc aat gca aac    2217
Ala Leu Val Asp Thr Ser Glu Arg Gly Lys Phe Ser Thr Asn Ala Asn
            710                 715                 720 agc atg acc gat ttt gat gac agt cct atg tta cat gga aac agg agc    2265
Ser Met Thr Asp Phe Asp Asp Ser Pro Met Leu His Gly Asn Arg Ser
            725                 730                 735 gga tac gtg gaa gcg gaa acg tat gca agc gca gaa gcg aga tta tta    2313
Gly Tyr Val Glu Ala Glu Thr Tyr Ala Ser Ala Glu Ala Arg Leu Leu
740                 745                 750 aga aaa tta gga agc ggg gat atc cca aca gtg gct gaa gac cag aag    2361
Arg Lys Leu Gly Ser Gly Asp Ile Pro Thr Val Ala Glu Asp Gln Lys
755                 760                 765                 770 atg ggt ggt ttg gta tct gag tta cac ccc aat gaa aac gta gcc ctg    2409
Met Gly Gly Leu Val Ser Glu Leu His Pro Asn Glu Asn Val Ala Leu
                775                 780                 785 gtc gag act tca gag aga gga aaa agt acc atc gca aac agc atc acc    2457
Val Glu Thr Ser Glu Arg Gly Lys Ser Thr Ile Ala Asn Ser Ile Thr
            790                 795                 800 aat ttt gat gac agg gat ttt ccg aca ttg gct gaa gac cag aag atg    2505
Asn Phe Asp Asp Arg Asp Phe Pro Thr Leu Ala Glu Asp Gln Lys Met
            805                 810                 815 gat ggt ttg gca tct gag tca cac cca gtc gaa gac ata gtc ctg gta    2553
Asp Gly Leu Ala Ser Glu Ser His Pro Val Glu Asp Ile Val Leu Val
        820                 825                 830 gag act tta gaa agt gaa aaa ggt acc atc cca aac agc atc acc gaa    2601
Glu Thr Leu Glu Ser Glu Lys Gly Thr Ile Pro Asn Ser Ile Thr Glu
835                 840                 845                 850 gag aat gtg ttt caa tcg gga aaa cac gca act ctg gaa cac aca caa    2649
Glu Asn Val Phe Gln Ser Gly Lys His Ala Thr Leu Glu His Thr Gln
                855                 860                 865 tca tac cca gtt ttg gcg cca gat ggc atg atc cac aat atg act gac    2697
Ser Tyr Pro Val Leu Ala Pro Asp Gly Met Ile His Asn Met Thr Asp
            870                 875                 880 act cct gga gga acc att atg gct ggg gaa ctt gtg tct ttt gga ata    2745
Thr Pro Gly Gly Thr Ile Met Ala Gly Glu Leu Val Ser Phe Gly Ile
            885                 890                 895 caa aag ctt tgg gag ttg ctt cgc caa gaa agc gag cgt ttt cag gga    2793
Gln Lys Leu Trp Glu Leu Leu Arg Gln Glu Ser Glu Arg Phe Gln Gly
        900                 905                 910 gct tcg gat gaa ata gat atg gta aaa agt gat tta ctc tat tta agg    2841
Ala Ser Asp Glu Ile Asp Met Val Lys Ser Asp Leu Leu Tyr Leu Arg
915                 920                 925                 930 gga ttt tta gca gat gca aat gcc aaa aaa cat aca agg gag gtg aaa    2889
Gly Phe Leu Ala Asp Ala Asn Ala Lys Lys His Thr Arg Glu Val Lys
                935                 940                 945 agt tgt att gaa gag atc aaa gaa att ttt ttt gac gcg gaa gat att    2937
Ser Cys Ile Glu Glu Ile Lys Glu Ile Phe Phe Asp Ala Glu Asp Ile
            950                 955                 960
```

| | | |
|---|---|---|
| att gag aca tat ctt ctt gaa gaa aac ccc cca aaa act ggt gtc ttc<br>Ile Glu Thr Tyr Leu Leu Glu Glu Asn Pro Pro Lys Thr Gly Val Phe<br>965                       970                      975 | | 2985 |
| aag agg ctt ttc aga ggg cgt gct ggc agg aaa ttt gct ttg gat atg<br>Lys Arg Leu Phe Arg Gly Arg Ala Gly Arg Lys Phe Ala Leu Asp Met<br>    980                   985                     990 | | 3033 |
| aat agc tta agc aag agg att tct aag ata atc agc gtt atg caa<br>Asn Ser Leu Ser Lys Arg Ile Ser Lys Ile Ile Ser Val Met Gln<br>995              1000                 1005 | | 3078 |
| gct ttt gga gta cac cag gtt att act gaa ggc aag gat tca caa<br>Ala Phe Gly Val His Gln Val Ile Thr Glu Gly Lys Asp Ser Gln<br>1010              1015                1020 | | 3123 |
| cct ctt cta caa aga caa aaa agg atg cga caa aaa ttt gct gga<br>Pro Leu Leu Gln Arg Gln Lys Arg Met Arg Gln Lys Phe Ala Gly<br>1025            1030                1035 | | 3168 |
| gag tac aaa ccc aat ttt gtg ggg ctg gaa gaa aat gtt gag aaa<br>Glu Tyr Lys Pro Asn Phe Val Gly Leu Glu Glu Asn Val Glu Lys<br>1040            1045                1050 | | 3213 |
| ttg gtt agt ctt ttg gtc gag gaa gac aat att caa gtg gtt tcc<br>Leu Val Ser Leu Leu Val Glu Glu Asp Asn Ile Gln Val Val Ser<br>1055            1060                1065 | | 3258 |
| ata acc ggg atg ggt ggt ctt ggt aaa act acc ctc gct aga caa<br>Ile Thr Gly Met Gly Gly Leu Gly Lys Thr Thr Leu Ala Arg Gln<br>1070            1075                1080 | | 3303 |
| act ttt aat cac gat atg gta aaa cac aag ttt gat agg ttc gca<br>Thr Phe Asn His Asp Met Val Lys His Lys Phe Asp Arg Phe Ala<br>1085            1090                1095 | | 3348 |
| tgg gtg ggt att tca caa gct tgt aac cga aag att gtg tgg caa<br>Trp Val Gly Ile Ser Gln Ala Cys Asn Arg Lys Ile Val Trp Gln<br>1100            1105                1110 | | 3393 |
| atg atc ttg cgg agt ctc ttg gcc aaa aaa gat gaa gat agt att<br>Met Ile Leu Arg Ser Leu Leu Ala Lys Lys Asp Glu Asp Ser Ile<br>1115            1120                1125 | | 3438 |
| ttg cat atg act gaa tct gaa ctc caa gag caa atc ttt cta ttg<br>Leu His Met Thr Glu Ser Glu Leu Gln Glu Gln Ile Phe Leu Leu<br>1130            1135                1140 | | 3483 |
| ctg gaa gca tcc aaa tca ttg att gtc ata gat gac ata tgg aaa<br>Leu Glu Ala Ser Lys Ser Leu Ile Val Ile Asp Asp Ile Trp Lys<br>1145            1150                1155 | | 3528 |
| gaa gaa gac tgg aag cga atc agt caa ata ctt cca aac aca aaa<br>Glu Glu Asp Trp Lys Arg Ile Ser Gln Ile Leu Pro Asn Thr Lys<br>1160            1165                1170 | | 3573 |
| ggt tgg aag gtg cta ctt act tct cga aat gag aat gtc gct gga<br>Gly Trp Lys Val Leu Leu Thr Ser Arg Asn Glu Asn Val Ala Gly<br>1175            1180                1185 | | 3618 |
| gac aca aga cac atc aac ttc aat cta gaa tta tta aca act gat<br>Asp Thr Arg His Ile Asn Phe Asn Leu Glu Leu Leu Thr Thr Asp<br>1190            1195                1200 | | 3663 |
| gac agt tgg aca ctt ttg caa acg ata gca ttt cct aga aag gat<br>Asp Ser Trp Thr Leu Leu Gln Thr Ile Ala Phe Pro Arg Lys Asp<br>1205            1210                1215 | | 3708 |
| gca ttc ggg gaa gca tat gag gaa atg gaa aag atg ggt aag cat<br>Ala Phe Gly Glu Ala Tyr Glu Glu Met Glu Lys Met Gly Lys His<br>1220            1225                1230 | | 3753 |
| atg atc aaa tat tgt ggg gga ctg cca ttg gct gtg aga ata tta<br>Met Ile Lys Tyr Cys Gly Gly Leu Pro Leu Ala Val Arg Ile Leu<br>1235            1240                1245 | | 3798 |
| gga ggt tta tta gcg aag aaa tac aaa ctg cat gag tgg gaa atg<br>Gly Gly Leu Leu Ala Lys Lys Tyr Lys Leu His Glu Trp Glu Met | | 3843 |

```
                1250                1255                1260
ata tgt gag aat gtt gaa cgc cat ctc atg gga aga act gat ttc     3888
Ile Cys Glu Asn Val Glu Arg His Leu Met Gly Arg Thr Asp Phe
1265                1270                1275 aat gat gac aac aat att ttg cgc ttc cat gta atg tct ctg agc     3933
Asn Asp Asp Asn Asn Ile Leu Arg Phe His Val Met Ser Leu Ser
1280                1285                1290 ttt gaa gag ttg tct agt tat ttg aag caa tgc ttc ctt tat ttg     3978
Phe Glu Glu Leu Ser Ser Tyr Leu Lys Gln Cys Phe Leu Tyr Leu
1295                1300                1305 gca att ttt cca gaa gat cat cga ata agt gtg ggg aaa ctg tct     4023
Ala Ile Phe Pro Glu Asp His Arg Ile Ser Val Gly Lys Leu Ser
1310                1315                1320 tat tac tgg gca gca gaa gga ttc acc ggt acg tat tac gat gaa     4068
Tyr Tyr Trp Ala Ala Glu Gly Phe Thr Gly Thr Tyr Tyr Asp Glu
1325                1330                1335 gag acc att cga gat gtt gga gat agc tat ata gag gag ctc gcg     4113
Glu Thr Ile Arg Asp Val Gly Asp Ser Tyr Ile Glu Glu Leu Ala
1340                1345                1350 agg aga aat atg gtt act ttc gaa aga gac agc acg ggc ttg agg     4158
Arg Arg Asn Met Val Thr Phe Glu Arg Asp Ser Thr Gly Leu Arg
1355                1360                1365 ttt gaa acc tgt agt atg cat gac att atg agg gaa atg tgt ttg     4203
Phe Glu Thr Cys Ser Met His Asp Ile Met Arg Glu Met Cys Leu
1370                1375                1380 act aaa gca aaa gaa gag aac ttc cta caa act gat gtt act cgc     4248
Thr Lys Ala Lys Glu Glu Asn Phe Leu Gln Thr Asp Val Thr Arg
1385                1390                1395 aga ttt gtc tgc caa aat act acc aca tta gat gtt gag aga gat     4293
Arg Phe Val Cys Gln Asn Thr Thr Thr Leu Asp Val Glu Arg Asp
1400                1405                1410 ata aat aat cca aaa ctt cgg tct ctc tta gtt atc ctt aat tcg     4338
Ile Asn Asn Pro Lys Leu Arg Ser Leu Leu Val Ile Leu Asn Ser
1415                1420                1425 gag ggg gat ttt tgt agg cta tct ggt tta agg ttc aca agg cta     4383
Glu Gly Asp Phe Cys Arg Leu Ser Gly Leu Arg Phe Thr Arg Leu
1430                1435                1440 caa ctt ctg agg gtg tta gat ctc gat aaa gcc aag ttt gaa gga     4428
Gln Leu Leu Arg Val Leu Asp Leu Asp Lys Ala Lys Phe Glu Gly
1445                1450                1455 ggg aag tta cct tct gac ata gga aag ctc atc cac tta aga tac     4473
Gly Lys Leu Pro Ser Asp Ile Gly Lys Leu Ile His Leu Arg Tyr
1460                1465                1470 ttg agc tta gaa tct gct gag gta tct cat cta cct tct tcc cta     4518
Leu Ser Leu Glu Ser Ala Glu Val Ser His Leu Pro Ser Ser Leu
1475                1480                1485 cga aac ctg atg ttg ctg atc tat ttg aac ata gat gta gct gat     4563
Arg Asn Leu Met Leu Leu Ile Tyr Leu Asn Ile Asp Val Ala Asp
1490                1495                1500 att gat ata cat gtg ccc aac gtt ctg atg gag atg cga gaa ttg     4608
Ile Asp Ile His Val Pro Asn Val Leu Met Glu Met Arg Glu Leu
1505                1510                1515 aga tac ctt gca tta cca aag ttt atg cat gag aag acc aag ttg     4653
Arg Tyr Leu Ala Leu Pro Lys Phe Met His Glu Lys Thr Lys Leu
1520                1525                1530 gaa ttg ggt aat cta gta aac ttg gag acc ttg gag aat ttc tca     4698
Glu Leu Gly Asn Leu Val Asn Leu Glu Thr Leu Glu Asn Phe Ser
1535                1540                1545 aca aag aat agc aga tta gag gat ctc cgt tgt atg atc aga ttg     4743
```

-continued

```
Thr Lys Asn Ser Arg Leu Glu Asp Leu Arg Cys Met Ile Arg Leu
1550                1555                1560 agg act ctt tca atc aaa gta act ggt gag acc tct tca gaa act    4788
Arg Thr Leu Ser Ile Lys Val Thr Gly Glu Thr Ser Ser Glu Thr
1565                1570                1575 ctc tct tta tca ata agt ggc ctg aga cac ctg gaa aat ctc gtc    4833
Leu Ser Leu Ser Ile Ser Gly Leu Arg His Leu Glu Asn Leu Val
1580                1585                1590 ata cat gat cgc ctg agc tgg atc aaa gag gga att gtt tta cat    4878
Ile His Asp Arg Leu Ser Trp Ile Lys Glu Gly Ile Val Leu His
1595                1600                1605 tgc gat gat ctc ata aag ctg gag ctg ttt atg tat agg cca gtg    4923
Cys Asp Asp Leu Ile Lys Leu Glu Leu Phe Met Tyr Arg Pro Val
1610                1615                1620 agg cta gaa aaa caa cgc ttc cct tct cac att aca tac ata tct    4968
Arg Leu Glu Lys Gln Arg Phe Pro Ser His Ile Thr Tyr Ile Ser
1625                1630                1635 cta act gag tgt cgt ttc gag cat gat ccg atg cca cta tta gag    5013
Leu Thr Glu Cys Arg Phe Glu His Asp Pro Met Pro Leu Leu Glu
1640                1645                1650 acg ttg cag cac ttg aga aag gtt aag tta ttg gat cgg tct cat    5058
Thr Leu Gln His Leu Arg Lys Val Lys Leu Leu Asp Arg Ser His
1655                1660                1665 tgt gcg aga aga atg gtt tgc tcg ggt agt ggg ttt ccg cag ttg    5103
Cys Ala Arg Arg Met Val Cys Ser Gly Ser Gly Phe Pro Gln Leu
1670                1675                1680 cgt gag ctt gag tta gtc tta cta gag cag ttg gaa gag tgg ata    5148
Arg Glu Leu Glu Leu Val Leu Leu Glu Gln Leu Glu Glu Trp Ile
1685                1690                1695 ata gag gaa ggc tcc atg cct ctt ctt cat agt ttg gac att act    5193
Ile Glu Glu Gly Ser Met Pro Leu Leu His Ser Leu Asp Ile Thr
1700                1705                1710 gac tgt aac aag tta aag gaa att cca gag ggg ctg cga att atc    5238
Asp Cys Asn Lys Leu Lys Glu Ile Pro Glu Gly Leu Arg Ile Ile
1715                1720                1725 cct tcc tta aag aat ctg act tgt tat agt atg ggt aag gaa tgg    5283
Pro Ser Leu Lys Asn Leu Thr Cys Tyr Ser Met Gly Lys Glu Trp
1730                1735                1740 gag gga aga ttg tcg gaa gga gga gaa gaa tat tac aaa gtc cag    5328
Glu Gly Arg Leu Ser Glu Gly Gly Glu Glu Tyr Tyr Lys Val Gln
1745                1750                1755 cac att ccc tct gtt aag ttc tat ggt gca tga ggtcctcagc         5371
His Ile Pro Ser Val Lys Phe Tyr Gly Ala
1760                1765 aattacaggt aaaatgtttt cttccctaat taaaataaca tccataagaa a       5422

<210> SEQ ID NO 7
<211> LENGTH: 1769
<212> TYPE: PRT
<213> ORGANISM: Brassica napus

<400> SEQUENCE: 7

Met Gly Thr Leu Asn Ala Met Ile Tyr Glu Leu Leu Lys Arg Val Ser
1               5                   10                  15

Lys Glu Lys Asp Arg Gly Ile Glu Thr Leu Ala Glu Val Glu Glu Trp
            20                  25                  30

Ile Ser Met Ala Glu Glu Thr Glu Ser Lys Ala Ser Ser Leu Leu Asp
        35                  40                  45

Glu Ser Ile Ser Gly Cys His Asp Leu Ser Met Tyr Asp Asp Ile Ser
```

```
            50                  55                  60
Lys Ile Ser Gln Ser Thr Leu His Tyr Ser Glu Thr Val Cys Thr Thr
 65                  70                  75                  80
Leu Lys Glu Val Lys Ala Leu Arg Ser Lys Gly Val Phe Lys Val Ile
                 85                  90                  95
Val Glu Arg Ala Pro Leu Ser Tyr Val Lys Lys Met Leu Pro Leu His
                100                 105                 110
Pro Ile Asp Ser Gly Glu Met Leu Ala Glu Ala Trp Asp Phe Phe
                115                 120                 125
Gln Glu Ile Ile Gly Glu Thr Thr Leu Lys Ser His Pro Asp Ile Pro
                130                 135                 140
Gln Leu Ala Arg Ile Val Cys Arg Lys Cys Arg Gly Leu Pro Ile Ala
145                 150                 155                 160
Leu Ser Leu Ile Gly Glu Thr Met Ser Arg Lys Arg Thr Val Gln Glu
                165                 170                 175
Trp His Gln Ala Ile Ser Val Leu Val Ser Ser Thr Pro Glu Val Ser
                180                 185                 190
Gly Thr Glu Asp Glu Leu Leu Tyr Ile Leu Lys Phe Ala Tyr Asp Asn
                195                 200                 205
Leu Pro Gly Glu Asn Ile Lys Ser Cys Phe Leu Tyr Cys Ala Leu Phe
                210                 215                 220
Pro Lys Ser Cys Asp Ile Asn Lys Gln Asp Leu Val Asp Cys Trp Ile
225                 230                 235                 240
Ala Glu Gly Val Ile Glu Asp Glu Arg Glu Ile Ala Glu Ile Gln
                    245                 250                 255
Gly Tyr Glu Met Met Ala Asp Leu Val Met Met Arg Leu Leu Ile Asp
                260                 265                 270
Asp Glu Ser Glu His Glu Val Lys Met His Asp Met Val Arg Gly Met
                275                 280                 285
Ala Leu Trp Ile Ala Thr Asp Cys Gly Arg Gln Lys Glu Asn Phe Val
                290                 295                 300
Val Val Ser Gly Glu Asp Arg His Gln Met Pro Glu Val Asn Asp Trp
305                 310                 315                 320
Ser Asn Val Arg Arg Met Ser Val Thr Ser Thr Gln Val Asp Lys Ile
                325                 330                 335
Ser Asp Ser His Asp Cys Pro Lys Leu Thr Thr Leu Phe Leu Gln Glu
                340                 345                 350
Asn Asn Leu Lys Trp Val Ser Gly Asp Phe Phe Arg Trp Met Thr Ser
                355                 360                 365
Leu Val Val Leu Asn Leu Ser Arg Asn Leu Glu Leu Ser Glu Leu Pro
                370                 375                 380
Glu Glu Val Ser Ser Leu Val Ser Leu Arg Leu Leu Asn Leu Ser Trp
385                 390                 395                 400
Thr Trp Ile Lys Arg Leu Pro Leu Gly Leu Thr Glu Leu Lys Arg Leu
                405                 410                 415
Met His Leu Asp Leu Asp Asp Thr Pro Arg Leu Leu Glu Val Asp Val
                420                 425                 430
Ile Gly Tyr Leu Leu Asn Leu Gln Val Leu Arg Leu Phe Arg Ser Val
                435                 440                 445
Pro Met Asp Arg Ser Leu Leu Glu Asn Ile Gln Leu Leu Glu Asn Leu
                450                 455                 460
Lys Glu Leu Asn Leu Thr Val Arg Glu Val Asp Val Leu Glu Arg Leu
465                 470                 475                 480
```

```
Gln Ser Ile His Lys Leu Ala Ser Cys Ile Arg His Leu His Leu Lys
            485                 490                 495
Gly Ile Thr Ile Lys Asp Gly Gly Thr Leu Leu Leu Asn Ser Met Leu
        500                 505                 510
Ser Leu Arg Glu Leu Asn Ile Gly Met Cys Asp Ile Pro Glu Ile Thr
            515                 520                 525
Val Asp Trp Arg Ser Thr Ile Gln Arg Glu Thr Ile His Phe Gly Asn
    530                 535                 540
Ile Gln Lys Ile Pro Tyr Leu Gln Asn Ile Arg Thr Val Ala Leu Ser
545                 550                 555                 560
Trp Cys Lys Gly Leu Lys Asp Leu Thr Trp Leu Leu Ala Pro Asn
                565                 570                 575
Leu Gly Asp Leu Arg Leu Leu Glu Cys Gln Gln Ile Glu His Ile Ile
            580                 585                 590
Asn Lys Glu Lys Pro Thr Gly Asp Met Ser Glu Glu Pro Phe Gln Asn
            595                 600                 605
Leu Thr Arg Leu Ser Leu Glu Ser Leu Pro Gln Leu Glu Ser Ile Tyr
        610                 615                 620
Trp Thr Pro Leu Pro Phe Pro Val Leu Lys Asp Leu Cys Ile Arg Gly
625                 630                 635                 640
Cys Pro Lys Leu Arg Arg Arg Pro Phe Ser Asn Lys Gly Asn Gln Val
                645                 650                 655
Arg Ser Asp Val Gly Gln Lys Gly Val Glu Arg Glu Asp Glu Ala Met
                660                 665                 670
Lys Gln His Leu Ser Asn Phe Asp Asp Arg Asp Phe Leu Lys Met Asp
            675                 680                 685
Glu Asp Gln Asn Met Glu Gly Leu Ala Ser Glu Ser His Pro Asn Lys
        690                 695                 700
Asn Ile Ala Leu Val Asp Thr Ser Glu Arg Gly Lys Phe Ser Thr Asn
705                 710                 715                 720
Ala Asn Ser Met Thr Asp Phe Asp Asp Ser Pro Met Leu His Gly Asn
                725                 730                 735
Arg Ser Gly Tyr Val Glu Ala Glu Thr Tyr Ala Ser Ala Glu Ala Arg
            740                 745                 750
Leu Leu Arg Lys Leu Gly Ser Gly Asp Ile Pro Thr Val Ala Glu Asp
        755                 760                 765
Gln Lys Met Gly Gly Leu Val Ser Glu Leu His Pro Asn Glu Asn Val
    770                 775                 780
Ala Leu Val Glu Thr Ser Glu Arg Gly Lys Ser Thr Ile Ala Asn Ser
785                 790                 795                 800
Ile Thr Asn Phe Asp Asp Arg Asp Phe Pro Thr Leu Ala Glu Asp Gln
                805                 810                 815
Lys Met Asp Gly Leu Ala Ser Glu Ser His Pro Val Glu Asp Ile Val
            820                 825                 830
Leu Val Glu Thr Leu Glu Ser Glu Lys Gly Thr Ile Pro Asn Ser Ile
        835                 840                 845
Thr Glu Glu Asn Val Phe Gln Ser Gly Lys His Ala Thr Leu Glu His
    850                 855                 860
Thr Gln Ser Tyr Pro Val Leu Ala Pro Asp Gly Met Ile His Asn Met
865                 870                 875                 880
Thr Asp Thr Pro Gly Gly Thr Ile Met Ala Gly Glu Leu Val Ser Phe
                885                 890                 895
```

```
Gly Ile Gln Lys Leu Trp Glu Leu Leu Arg Gln Ser Glu Arg Phe
             900                 905                 910

Gln Gly Ala Ser Asp Glu Ile Asp Met Val Lys Ser Asp Leu Leu Tyr
         915                 920                 925

Leu Arg Gly Phe Leu Ala Asp Ala Asn Ala Lys Lys His Thr Arg Glu
     930                 935                 940

Val Lys Ser Cys Ile Glu Glu Ile Lys Glu Ile Phe Phe Asp Ala Glu
945                 950                 955                 960

Asp Ile Ile Glu Thr Tyr Leu Leu Glu Glu Asn Pro Pro Lys Thr Gly
                 965                 970                 975

Val Phe Lys Arg Leu Phe Arg Gly Arg Ala Gly Arg Lys Phe Ala Leu
             980                 985                 990

Asp Met Asn Ser Leu Ser Lys Arg Ile Ser Lys Ile Ile Ser Val Met
         995                 1000                1005

Gln Ala Phe Gly Val His Gln Val Ile Thr Glu Gly Lys Asp Ser
     1010                1015                1020

Gln Pro Leu Leu Gln Arg Gln Lys Arg Met Arg Gln Lys Phe Ala
     1025                1030                1035

Gly Glu Tyr Lys Pro Asn Phe Val Gly Leu Glu Glu Asn Val Glu
     1040                1045                1050

Lys Leu Val Ser Leu Leu Val Glu Glu Asp Asn Ile Gln Val Val
     1055                1060                1065

Ser Ile Thr Gly Met Gly Gly Leu Gly Lys Thr Thr Leu Ala Arg
     1070                1075                1080

Gln Thr Phe Asn His Asp Met Val Lys His Lys Phe Asp Arg Phe
     1085                1090                1095

Ala Trp Val Gly Ile Ser Gln Ala Cys Asn Arg Lys Ile Val Trp
     1100                1105                1110

Gln Met Ile Leu Arg Ser Leu Leu Ala Lys Lys Asp Glu Asp Ser
     1115                1120                1125

Ile Leu His Met Thr Glu Ser Glu Leu Gln Glu Gln Ile Phe Leu
     1130                1135                1140

Leu Leu Glu Ala Ser Lys Ser Leu Ile Val Ile Asp Asp Ile Trp
     1145                1150                1155

Lys Glu Glu Asp Trp Lys Arg Ile Ser Gln Ile Leu Pro Asn Thr
     1160                1165                1170

Lys Gly Trp Lys Val Leu Leu Thr Ser Arg Asn Glu Asn Val Ala
     1175                1180                1185

Gly Asp Thr Arg His Ile Asn Phe Asn Leu Glu Leu Leu Thr Thr
     1190                1195                1200

Asp Asp Ser Trp Thr Leu Leu Gln Thr Ile Ala Phe Pro Arg Lys
     1205                1210                1215

Asp Ala Phe Gly Glu Ala Tyr Glu Glu Met Glu Lys Met Gly Lys
     1220                1225                1230

His Met Ile Lys Tyr Cys Gly Gly Leu Pro Leu Ala Val Arg Ile
     1235                1240                1245

Leu Gly Gly Leu Leu Ala Lys Lys Tyr Lys Leu His Glu Trp Glu
     1250                1255                1260

Met Ile Cys Glu Asn Val Glu Arg His Leu Met Gly Arg Thr Asp
     1265                1270                1275

Phe Asn Asp Asp Asn Asn Ile Leu Arg Phe His Val Met Ser Leu
     1280                1285                1290

Ser Phe Glu Glu Leu Ser Ser Tyr Leu Lys Gln Cys Phe Leu Tyr
```

```
            1295                1300                1305
Leu Ala Ile Phe Pro Glu Asp His Arg Ile Ser Val Gly Lys Leu
        1310                1315                1320
Ser Tyr Tyr Trp Ala Ala Glu Gly Phe Thr Gly Thr Tyr Tyr Asp
        1325                1330                1335
Glu Glu Thr Ile Arg Asp Val Gly Asp Ser Tyr Ile Glu Glu Leu
        1340                1345                1350
Ala Arg Arg Asn Met Val Thr Phe Glu Arg Asp Ser Thr Gly Leu
        1355                1360                1365
Arg Phe Glu Thr Cys Ser Met His Asp Ile Met Arg Glu Met Cys
        1370                1375                1380
Leu Thr Lys Ala Lys Glu Glu Asn Phe Leu Gln Thr Asp Val Thr
        1385                1390                1395
Arg Arg Phe Val Cys Gln Asn Thr Thr Thr Leu Asp Val Glu Arg
        1400                1405                1410
Asp Ile Asn Asn Pro Lys Leu Arg Ser Leu Leu Val Ile Leu Asn
        1415                1420                1425
Ser Glu Gly Asp Phe Cys Arg Leu Ser Gly Leu Arg Phe Thr Arg
        1430                1435                1440
Leu Gln Leu Leu Arg Val Leu Asp Leu Asp Lys Ala Lys Phe Glu
        1445                1450                1455
Gly Gly Lys Leu Pro Ser Asp Ile Gly Lys Leu Ile His Leu Arg
        1460                1465                1470
Tyr Leu Ser Leu Glu Ser Ala Glu Val Ser His Leu Pro Ser Ser
        1475                1480                1485
Leu Arg Asn Leu Met Leu Leu Ile Tyr Leu Asn Ile Asp Val Ala
        1490                1495                1500
Asp Ile Asp Ile His Val Pro Asn Val Leu Met Glu Met Arg Glu
        1505                1510                1515
Leu Arg Tyr Leu Ala Leu Pro Lys Phe Met His Glu Lys Thr Lys
        1520                1525                1530
Leu Glu Leu Gly Asn Leu Val Asn Leu Glu Thr Leu Glu Asn Phe
        1535                1540                1545
Ser Thr Lys Asn Ser Arg Leu Glu Asp Leu Arg Cys Met Ile Arg
        1550                1555                1560
Leu Arg Thr Leu Ser Ile Lys Val Thr Gly Glu Thr Ser Ser Glu
        1565                1570                1575
Thr Leu Ser Leu Ser Ile Ser Gly Leu Arg His Leu Glu Asn Leu
        1580                1585                1590
Val Ile His Asp Arg Leu Ser Trp Ile Lys Glu Gly Ile Val Leu
        1595                1600                1605
His Cys Asp Asp Leu Ile Lys Leu Glu Leu Phe Met Tyr Arg Pro
        1610                1615                1620
Val Arg Leu Glu Lys Gln Arg Phe Pro Ser His Ile Thr Tyr Ile
        1625                1630                1635
Ser Leu Thr Glu Cys Arg Phe Glu His Asp Pro Met Pro Leu Leu
        1640                1645                1650
Glu Thr Leu Gln His Leu Arg Lys Val Lys Leu Leu Asp Arg Ser
        1655                1660                1665
His Cys Ala Arg Arg Met Val Cys Ser Gly Ser Gly Phe Pro Gln
        1670                1675                1680
Leu Arg Glu Leu Glu Leu Val Leu Leu Glu Gln Leu Glu Glu Trp
        1685                1690                1695
```

```
Ile Ile Glu Glu Gly Ser Met Pro Leu Leu His Ser Leu Asp Ile
    1700                1705                1710

Thr Asp Cys Asn Lys Leu Lys Glu Ile Pro Glu Gly Leu Arg Ile
    1715                1720                1725

Ile Pro Ser Leu Lys Asn Leu Thr Cys Tyr Ser Met Gly Lys Glu
    1730                1735                1740

Trp Glu Gly Arg Leu Ser Glu Gly Gly Glu Tyr Tyr Lys Val
    1745                1750                1755

Gln His Ile Pro Ser Val Lys Phe Tyr Gly Ala
    1760                1765

<210> SEQ ID NO 8
<211> LENGTH: 3268
<212> TYPE: DNA
<213> ORGANISM: Brassica napus
<220> FEATURE:
<221> NAME/KEY: CDS
<222> LOCATION: (220)..(2898)

<400> SEQUENCE: 8
aaggacacca tttattttag atactgctcc aatctttttt tttaaaaaaa gcttctcttt      60
tggaaatgat tgccaagctc taccttattc caaagtctca acacaaaatg attatgcaga    120
atggtctgct tccctctggc tgctccctag tccttacgta cttttagtct ttcttttcaa    180
ataatctgca cttcccattt ttcttgaatc ctaagcaca atg gct gaa ttt gtg      234
                                              Met Ala Glu Phe Val
                                                1               5 tcg gct att tgt tca gtg gtt caa tgt tta aca cca tgt ttt aat tcc      282
Ser Ala Ile Cys Ser Val Val Gln Cys Leu Thr Pro Cys Phe Asn Ser
            10                  15                  20 tgg gct gca cat gca agg tac gtt tct aag ttt gat ggt tat ctt aac      330
Trp Ala Ala His Ala Arg Tyr Val Ser Lys Phe Asp Gly Tyr Leu Asn
                25                  30                  35 gag ttg agg aat gct tta agg gat ctt gaa gca aaa aga aat gat gtg      378
Glu Leu Arg Asn Ala Leu Arg Asp Leu Glu Ala Lys Arg Asn Asp Val
        40                  45                  50 aaa cac aag gtt gat gat gaa gaa ctc act ggt aag gtt ccg cta gac      426
Lys His Lys Val Asp Asp Glu Glu Leu Thr Gly Lys Val Pro Leu Asp
55                  60                  65 gaa gtg aaa agg tgg ctt tca aaa ttc aac acc att aaa aca gaa acc      474
Glu Val Lys Arg Trp Leu Ser Lys Phe Asn Thr Ile Lys Thr Glu Thr
 70                  75                  80                  85 gat agg ctg gtt gct gat gct tcc gct gag caa caa agg cgg aca aca      522
Asp Arg Leu Val Ala Asp Ala Ser Ala Glu Gln Gln Arg Arg Thr Thr
                90                  95                 100 tct ggg tgt tgt tgc aac aac atc act tca acc tac cgt tgt ggc aaa      570
Ser Gly Cys Cys Cys Asn Asn Ile Thr Ser Thr Tyr Arg Cys Gly Lys
            105                 110                 115 aag tta tcc aag atg ttg agg gaa gtt cag caa ctc tat tct gaa caa      618
Lys Leu Ser Lys Met Leu Arg Glu Val Gln Gln Leu Tyr Ser Glu Gln
        120                 125                 130 ttt tcg caa ggg tta act agg cga ggg acg att cct gtg gta gta gaa      666
Phe Ser Gln Gly Leu Thr Arg Arg Gly Thr Ile Pro Val Val Val Glu
    135                 140                 145 gaa cct gtc cgg caa act gtt ggt ctt gac aca aaa ctt gct agc aca      714
Glu Pro Val Arg Gln Thr Val Gly Leu Asp Thr Lys Leu Ala Ser Thr
150                 155                 160                 165 tgg agc ctt ctt atg gac gaa ggt acc aga atg ttg ggt cta tac ggt      762
Trp Ser Leu Leu Met Asp Glu Gly Thr Arg Met Leu Gly Leu Tyr Gly
```

-continued

|  |  |  |  |
|---|---|---|---|
| | 170 | 175 | 180 |
| ttt ggg gga gta ggt aaa act acc ctc ctc act ctt ata tct aac aag<br>Phe Gly Gly Val Gly Lys Thr Thr Leu Leu Thr Leu Ile Ser Asn Lys<br>185 190 195 | | | 810 |
| ttc gtt gaa gtc gag gat aag ttt gat gtt gtc att tgg gtt gac gtg<br>Phe Val Glu Val Glu Asp Lys Phe Asp Val Val Ile Trp Val Asp Val<br>200 205 210 | | | 858 |
| tct aaa gat gta gat atc ttg aag att caa gat gat atc ggc aaa agg<br>Ser Lys Asp Val Asp Ile Leu Lys Ile Gln Asp Asp Ile Gly Lys Arg<br>215 220 225 | | | 906 |
| tta ggc ctc gat gat gag aaa tgg tgc aag gaa acg caa agg ggg aaa<br>Leu Gly Leu Asp Asp Glu Lys Trp Cys Lys Glu Thr Gln Arg Gly Lys<br>230 235 240 245 | | | 954 |
| agc ctt aat ata aga agg gtt cta aaa gaa aag aaa ccc cga ttt gtg<br>Ser Leu Asn Ile Arg Arg Val Leu Lys Glu Lys Lys Pro Arg Phe Val<br>250 255 260 | | | 1002 |
| ctg tta ttt gat ggc ttg tgg aag gga gtg agt tta tca gcc att gga<br>Leu Leu Phe Asp Gly Leu Trp Lys Gly Val Ser Leu Ser Ala Ile Gly<br>265 270 275 | | | 1050 |
| att cca ttg agg ggg aaa gaa tac aaa atc gtt ttt acg act cgt cag<br>Ile Pro Leu Arg Gly Lys Glu Tyr Lys Ile Val Phe Thr Thr Arg Gln<br>280 285 290 | | | 1098 |
| aag gat gta tgc caa aag atg ggg gga att tac aga aaa gtt gaa tgt<br>Lys Asp Val Cys Gln Lys Met Gly Gly Ile Tyr Arg Lys Val Glu Cys<br>295 300 305 | | | 1146 |
| ttg gcg gag aag gac gca ttg gat ttg tta aca caa ata tca gga aga<br>Leu Ala Glu Lys Asp Ala Leu Asp Leu Leu Thr Gln Ile Ser Gly Arg<br>310 315 320 325 | | | 1194 |
| gac tcc tta act agc gag atg ctt agt ctc gca gaa aag att gca aaa<br>Asp Ser Leu Thr Ser Glu Met Leu Ser Leu Ala Glu Lys Ile Ala Lys<br>330 335 340 | | | 1242 |
| aag tgt tat ggc tta ccc ctt gca ctt caa gtc att gga aag tgt ctg<br>Lys Cys Tyr Gly Leu Pro Leu Ala Leu Gln Val Ile Gly Lys Cys Leu<br>345 350 355 | | | 1290 |
| tca tct aaa acg act gaa gat gaa tgg cgt ggt gta cac gag tat ttg<br>Ser Ser Lys Thr Thr Glu Asp Glu Trp Arg Gly Val His Glu Tyr Leu<br>360 365 370 | | | 1338 |
| gtt cgt ttt cca gat caa ttg gaa ggt atg gtg gat atg ttt ggt gtt<br>Val Arg Phe Pro Asp Gln Leu Glu Gly Met Val Asp Met Phe Gly Val<br>375 380 385 | | | 1386 |
| tta aaa cta agc tat gat aat tta gaa gag ggg gat gca cag tcg tgt<br>Leu Lys Leu Ser Tyr Asp Asn Leu Glu Glu Gly Asp Ala Gln Ser Cys<br>390 395 400 405 | | | 1434 |
| ttc ctg tac tgt gct tta ttt ccc atg gca tac agt atc cac caa gat<br>Phe Leu Tyr Cys Ala Leu Phe Pro Met Ala Tyr Ser Ile His Gln Asp<br>410 415 420 | | | 1482 |
| gag ctg gtc gag tac tgg ata ggt gag ggt atc ata gag gta gga cgc<br>Glu Leu Val Glu Tyr Trp Ile Gly Glu Gly Ile Ile Glu Val Gly Arg<br>425 430 435 | | | 1530 |
| aga aga gac aga gca aag aat cga ggt gct cag ata atc gat aca ctt<br>Arg Arg Asp Arg Ala Lys Asn Arg Gly Ala Gln Ile Ile Asp Thr Leu<br>440 445 450 | | | 1578 |
| gtt agg gca ggt ttg ctg ttg aag gat gac gag tct aat ccg aaa gtg<br>Val Arg Ala Gly Leu Leu Leu Lys Asp Asp Glu Ser Asn Pro Lys Val<br>455 460 465 | | | 1626 |
| tat atg cac aat ata atc cga gag atg gcg ttg tgg ata gta tct gaa<br>Tyr Met His Asn Ile Ile Arg Glu Met Ala Leu Trp Ile Val Ser Glu<br>470 475 480 485 | | | 1674 |
| att aag gat gga caa atg tat ctt gtt gaa aca gat gct ggg tta agg | | | 1722 |

```
                Ile Lys Asp Gly Gln Met Tyr Leu Val Glu Thr Asp Ala Gly Leu Arg
                                    490                 495                 500 aca ctg cca cct aac acg gac tgg aca atc gtg tcg agg atg tct ctg              1770
Thr Leu Pro Pro Asn Thr Asp Trp Thr Ile Val Ser Arg Met Ser Leu
            505                 510                 515 atg aac aat gat att cag gac ata cca gat gat cct gaa ttt cct gac              1818
Met Asn Asn Asp Ile Gln Asp Ile Pro Asp Asp Pro Glu Phe Pro Asp
            520                 525                 530 caa gct ctt ctt atg act ctg ttc ctt caa aac aac aag ctg gtc gag              1866
Gln Ala Leu Leu Met Thr Leu Phe Leu Gln Asn Asn Lys Leu Val Glu
535                 540                 545 att ggt tgc aga ttc ttt gtg gtc atg tcg gct ctg gtc gtt ttg gat              1914
Ile Gly Cys Arg Phe Phe Val Val Met Ser Ala Leu Val Val Leu Asp
550                 555                 560                 565 tta tct ttg aac ccc gat atc acc aag ttg ccg gat cag att tca gaa              1962
Leu Ser Leu Asn Pro Asp Ile Thr Lys Leu Pro Asp Gln Ile Ser Glu
                570                 575                 580 ttg gtt tct ttg cgg tat ctc aaa tta ttc ggg acg agg ata aag ttt              2010
Leu Val Ser Leu Arg Tyr Leu Lys Leu Phe Gly Thr Arg Ile Lys Phe
            585                 590                 595 tta ccg gag ggt ttc agc aaa ttg ctc aaa ctg atc cac ttg gat ttg              2058
Leu Pro Glu Gly Phe Ser Lys Leu Leu Lys Leu Ile His Leu Asp Leu
        600                 605                 610 gag ctt aca tcc aat ctt cgt agt atc aga cag att tca gga cta cta              2106
Glu Leu Thr Ser Asn Leu Arg Ser Ile Arg Gln Ile Ser Gly Leu Leu
    615                 620                 625 aag ttg cag gtt tta aga ttt tat ggt tcc gct gct gca tta gat ggc              2154
Lys Leu Gln Val Leu Arg Phe Tyr Gly Ser Ala Ala Ala Leu Asp Gly
630                 635                 640                 645 tcc cta ctg aag aac ttg gag cgt ttg aag tct tta caa ttt ttg acc              2202
Ser Leu Leu Lys Asn Leu Glu Arg Leu Lys Ser Leu Gln Phe Leu Thr
                650                 655                 660 att act gtg aga gaa gtt gat gtt ttg aat gct ttc cta gga agc aaa              2250
Ile Thr Val Arg Glu Val Asp Val Leu Asn Ala Phe Leu Gly Ser Lys
            665                 670                 675 gaa ttg cca agg tgt aca caa ggt ctt gat ctt ggg ggt ctt gaa ata              2298
Glu Leu Pro Arg Cys Thr Gln Gly Leu Asp Leu Gly Gly Leu Glu Ile
        680                 685                 690 tca gga gta tca gga aaa tca ttt gca gcc acc ttt ggt gag ttg gtt              2346
Ser Gly Val Ser Gly Lys Ser Phe Ala Ala Thr Phe Gly Glu Leu Val
    695                 700                 705 act ctt tct aaa ctt cga atg aca gat tgc gat atc aaa gag tca gat              2394
Thr Leu Ser Lys Leu Arg Met Thr Asp Cys Asp Ile Lys Glu Ser Asp
710                 715                 720                 725 ata gaa tgg gaa gaa aac ata aag gtc caa tgt tca tct cca gtt cca              2442
Ile Glu Trp Glu Glu Asn Ile Lys Val Gln Cys Ser Ser Pro Val Pro
                730                 735                 740 tcc aat caa atc att cca agg act ata tgg ttc aag aac ctc tca gct              2490
Ser Asn Gln Ile Ile Pro Arg Thr Ile Trp Phe Lys Asn Leu Ser Ala
            745                 750                 755 gtg gta cta cac tca tgc tta ggt cta aag gat ttg aca tgg ctg atg              2538
Val Val Leu His Ser Cys Leu Gly Leu Lys Asp Leu Thr Trp Leu Met
        760                 765                 770 tat gct gca aat ctc gag tct cta gag gtc aaa act tca cct aag atg              2586
Tyr Ala Ala Asn Leu Glu Ser Leu Glu Val Lys Thr Ser Pro Lys Met
    775                 780                 785 aaa gaa gta ata agc caa cag aaa gct ggg gat ctc ggg gtt gag cct              2634
Lys Glu Val Ile Ser Gln Gln Lys Ala Gly Asp Leu Gly Val Glu Pro
790                 795                 800                 805
```

| | | |
|---|---|---|
| ttt caa aac cta caa gtt ctt gag ttg ggt ttt ttg aac gaa ctg gag<br>Phe Gln Asn Leu Gln Val Leu Glu Leu Gly Phe Leu Asn Glu Leu Glu<br>810                        815                    820 | | 2682 |
| agc atc tat tgg acc tca ctc ctt ttt cca aga ctg cag aat gtc act<br>Ser Ile Tyr Trp Thr Ser Leu Leu Phe Pro Arg Leu Gln Asn Val Thr<br>          825                        830                    835 | | 2730 |
| ata aca gag tgc ccg aag ctg cgt aag ctt cca tta aat tcc acg agt<br>Ile Thr Glu Cys Pro Lys Leu Arg Lys Leu Pro Leu Asn Ser Thr Ser<br>840                        845                    850 | | 2778 |
| gta gag aga gtt gat gct ctt cgc ata gaa gtg gat gac gga tgg tta<br>Val Glu Arg Val Asp Ala Leu Arg Ile Glu Val Asp Asp Gly Trp Leu<br>     855                        860                    865 | | 2826 |
| gtc gga gtt gaa tgg gag aat gga gct gaa gag cgg ttt cgt ctt gcc<br>Val Gly Val Glu Trp Glu Asn Gly Ala Glu Glu Arg Phe Arg Leu Ala<br>870                        875                    880                885 | | 2874 |
| atc cac aca gct tct att tct taa cttcatccgg tactatatat gtatttcata<br>Ile His Thr Ala Ser Ile Ser<br>                    890 | | 2928 |
| tgttccatta tagaatctct ggttttacca tattttatat tatatcttca cttcgtttac | | 2988 |
| ttttttttct tcctatcatc tttttaggtg cacgagacat gcaagcctgc acaaaagacc | | 3048 |
| ttgtgtgaca agcagacatc aatgcatgca attcaatgtc ctctctttgt tttgttcttt | | 3108 |
| tacggtaaaa cctgactcga agtcatttgt tcattatcaa tgggtgtgtc aagaaacgtt | | 3168 |
| tgtgtataat ggtttctctt atctcattca tactagcata aaacctgcac cttgtgcaag | | 3228 |
| ataaatttgt atgaaaatta tttaaaaaat atcatacgga | | 3268 |

<210> SEQ ID NO 9
<211> LENGTH: 892
<212> TYPE: PRT
<213> ORGANISM: Brassica napus

<400> SEQUENCE: 9

Met Ala Glu Phe Val Ser Ala Ile Cys Ser Val Val Gln Cys Leu Thr
1                 5                    10                   15

Pro Cys Phe Asn Ser Trp Ala Ala His Ala Arg Tyr Val Ser Lys Phe
                 20                    25                    30

Asp Gly Tyr Leu Asn Glu Leu Arg Asn Ala Leu Arg Asp Leu Glu Ala
           35                    40                    45

Lys Arg Asn Asp Val Lys His Lys Val Asp Glu Glu Leu Thr Gly
50                        55                    60

Lys Val Pro Leu Asp Glu Val Lys Arg Trp Leu Ser Lys Phe Asn Thr
65                  70                    75                    80

Ile Lys Thr Glu Thr Asp Arg Leu Val Ala Asp Ala Ser Ala Glu Gln
                 85                    90                    95

Gln Arg Arg Thr Thr Ser Gly Cys Cys Cys Asn Asn Ile Thr Ser Thr
                100                  105                  110

Tyr Arg Cys Gly Lys Lys Leu Ser Lys Met Leu Arg Glu Val Gln Gln
          115                    120                  125

Leu Tyr Ser Glu Gln Phe Ser Gln Gly Leu Thr Arg Arg Gly Thr Ile
      130                    135                  140

Pro Val Val Glu Glu Pro Val Arg Gln Thr Val Gly Leu Asp Thr
145                     150                    155                  160

Lys Leu Ala Ser Thr Trp Ser Leu Leu Met Asp Glu Gly Thr Arg Met
                165                  170                  175

Leu Gly Leu Tyr Gly Phe Gly Gly Val Gly Lys Thr Thr Leu Leu Thr
          180                    185                  190

```
Leu Ile Ser Asn Lys Phe Val Glu Val Glu Asp Lys Phe Asp Val Val
            195                 200                 205

Ile Trp Val Asp Val Ser Lys Asp Val Asp Ile Leu Lys Ile Gln Asp
210                 215                 220

Asp Ile Gly Lys Arg Leu Gly Leu Asp Asp Glu Lys Trp Cys Lys Glu
225                 230                 235                 240

Thr Gln Arg Gly Lys Ser Leu Asn Ile Arg Arg Val Leu Lys Glu Lys
                245                 250                 255

Lys Pro Arg Phe Val Leu Leu Phe Asp Gly Leu Trp Lys Gly Val Ser
            260                 265                 270

Leu Ser Ala Ile Gly Ile Pro Leu Arg Gly Lys Glu Tyr Lys Ile Val
            275                 280                 285

Phe Thr Thr Arg Gln Lys Asp Val Cys Gln Lys Met Gly Gly Ile Tyr
            290                 295                 300

Arg Lys Val Glu Cys Leu Ala Glu Lys Asp Ala Leu Asp Leu Leu Thr
305                 310                 315                 320

Gln Ile Ser Gly Arg Asp Ser Leu Thr Ser Glu Met Leu Ser Leu Ala
                325                 330                 335

Glu Lys Ile Ala Lys Lys Cys Tyr Gly Leu Pro Leu Ala Leu Gln Val
            340                 345                 350

Ile Gly Lys Cys Leu Ser Ser Lys Thr Thr Glu Asp Glu Trp Arg Gly
            355                 360                 365

Val His Glu Tyr Leu Val Arg Phe Pro Asp Gln Leu Glu Gly Met Val
            370                 375                 380

Asp Met Phe Gly Val Leu Lys Leu Ser Tyr Asp Asn Leu Glu Glu Gly
385                 390                 395                 400

Asp Ala Gln Ser Cys Phe Leu Tyr Cys Ala Leu Phe Pro Met Ala Tyr
                405                 410                 415

Ser Ile His Gln Asp Glu Leu Val Glu Tyr Trp Ile Gly Glu Gly Ile
            420                 425                 430

Ile Glu Val Gly Arg Arg Asp Arg Ala Lys Asn Arg Gly Ala Gln
            435                 440                 445

Ile Ile Asp Thr Leu Val Arg Ala Gly Leu Leu Leu Lys Asp Asp Glu
            450                 455                 460

Ser Asn Pro Lys Val Tyr Met His Asn Ile Ile Arg Glu Met Ala Leu
465                 470                 475                 480

Trp Ile Val Ser Glu Ile Lys Asp Gly Gln Met Tyr Leu Val Glu Thr
                485                 490                 495

Asp Ala Gly Leu Arg Thr Leu Pro Pro Asn Thr Asp Trp Thr Ile Val
            500                 505                 510

Ser Arg Met Ser Leu Met Asn Asn Asp Ile Gln Asp Ile Pro Asp Asp
            515                 520                 525

Pro Glu Phe Pro Asp Gln Ala Leu Leu Met Thr Leu Phe Leu Gln Asn
            530                 535                 540

Asn Lys Leu Val Glu Ile Gly Cys Arg Phe Val Val Met Ser Ala
545                 550                 555                 560

Leu Val Val Leu Asp Leu Ser Leu Asn Pro Asp Ile Thr Lys Leu Pro
                565                 570                 575

Asp Gln Ile Ser Glu Leu Val Ser Leu Arg Tyr Leu Lys Leu Phe Gly
            580                 585                 590

Thr Arg Ile Lys Phe Leu Pro Glu Gly Phe Ser Lys Leu Leu Lys Leu
            595                 600                 605
```

```
Ile His Leu Asp Leu Glu Leu Thr Ser Asn Leu Arg Ser Ile Arg Gln
            610                 615                 620

Ile Ser Gly Leu Leu Lys Leu Gln Val Leu Arg Phe Tyr Gly Ser Ala
625                 630                 635                 640

Ala Ala Leu Asp Gly Ser Leu Leu Lys Asn Leu Glu Arg Leu Lys Ser
                645                 650                 655

Leu Gln Phe Leu Thr Ile Thr Val Arg Glu Val Asp Val Leu Asn Ala
            660                 665                 670

Phe Leu Gly Ser Lys Glu Leu Pro Arg Cys Thr Gln Gly Leu Asp Leu
            675                 680                 685

Gly Gly Leu Glu Ile Ser Gly Val Ser Gly Lys Ser Phe Ala Ala Thr
690                 695                 700

Phe Gly Glu Leu Val Thr Leu Ser Lys Leu Arg Met Thr Asp Cys Asp
705                 710                 715                 720

Ile Lys Glu Ser Asp Ile Glu Trp Glu Glu Asn Ile Lys Val Gln Cys
                725                 730                 735

Ser Ser Pro Val Pro Ser Asn Gln Ile Ile Pro Arg Thr Ile Trp Phe
            740                 745                 750

Lys Asn Leu Ser Ala Val Val Leu His Ser Cys Leu Gly Leu Lys Asp
            755                 760                 765

Leu Thr Trp Leu Met Tyr Ala Ala Asn Leu Glu Ser Leu Glu Val Lys
770                 775                 780

Thr Ser Pro Lys Met Lys Glu Val Ile Ser Gln Gln Lys Ala Gly Asp
785                 790                 795                 800

Leu Gly Val Glu Pro Phe Gln Asn Leu Gln Val Leu Glu Leu Gly Phe
                805                 810                 815

Leu Asn Glu Leu Glu Ser Ile Tyr Trp Thr Ser Leu Leu Phe Pro Arg
            820                 825                 830

Leu Gln Asn Val Thr Ile Thr Glu Cys Pro Lys Leu Arg Lys Leu Pro
            835                 840                 845

Leu Asn Ser Thr Ser Val Glu Arg Val Asp Ala Leu Arg Ile Glu Val
850                 855                 860

Asp Asp Gly Trp Leu Val Gly Val Glu Trp Glu Asn Gly Ala Glu Glu
865                 870                 875                 880

Arg Phe Arg Leu Ala Ile His Thr Ala Ser Ile Ser
            885                 890

<210> SEQ ID NO 10
<211> LENGTH: 5259
<212> TYPE: DNA
<213> ORGANISM: Brassica napus
<220> FEATURE:
<221> NAME/KEY: CDS
<222> LOCATION: (1)..(5259)

<400> SEQUENCE: 10 atg gca gaa gaa act gaa tcg aag gcg agt agt ctc ctt gat gaa agt        48
Met Ala Glu Glu Thr Glu Ser Lys Ala Ser Ser Leu Leu Asp Glu Ser
1               5                   10                  15 att tca gga tgt cac gat tta tca atg tat gat gat att tcc aag ata        96
Ile Ser Gly Cys His Asp Leu Ser Met Tyr Asp Asp Ile Ser Lys Ile
                20                  25                  30 tct caa tcg acc ctt cat tat agc gag acg gtg tgt acg acg ttg aaa      144
Ser Gln Ser Thr Leu His Tyr Ser Glu Thr Val Cys Thr Thr Leu Lys
            35                  40                  45 gaa gtt aaa gca ctg aga tct aag gga gtt ttt aaa gta ata gtt gag      192
Glu Val Lys Ala Leu Arg Ser Lys Gly Val Phe Lys Val Ile Val Glu
        50                  55                  60
```

-continued

```
         50                  55                  60
aga gct ccc ttg tct tac gtc aaa aag atg ctc cca ctt cac cca att        240
Arg Ala Pro Leu Ser Tyr Val Lys Lys Met Leu Pro Leu His Pro Ile
 65                  70                  75                  80 gat tct gga gaa atg ttg gca gaa gaa gca tgg gat ttt ttt caa gag        288
Asp Ser Gly Glu Met Leu Ala Glu Glu Ala Trp Asp Phe Phe Gln Glu
                     85                  90                  95 att att gga gaa aca acg tta aaa agt cat cca gac ata ccc cag ctg        336
Ile Ile Gly Glu Thr Thr Leu Lys Ser His Pro Asp Ile Pro Gln Leu
            100                 105                 110 gca aga ata gtt tgt aga aaa tgt cgt ggt ttg ccc att gct ctc agt        384
Ala Arg Ile Val Cys Arg Lys Cys Arg Gly Leu Pro Ile Ala Leu Ser
        115                 120                 125 ctc atc ggc gag acc atg tca cgc aaa agg act gta caa gaa tgg cat        432
Leu Ile Gly Glu Thr Met Ser Arg Lys Arg Thr Val Gln Glu Trp His
    130                 135                 140 caa gca att agt gtt ttg gtt tcg tct acc cca gaa gtt tca ggc act        480
Gln Ala Ile Ser Val Leu Val Ser Ser Thr Pro Glu Val Ser Gly Thr
145                 150                 155                 160 gaa gat gag ctt ctt tac att ttg aag ttt gcg tac gat aat ctg cct        528
Glu Asp Glu Leu Leu Tyr Ile Leu Lys Phe Ala Tyr Asp Asn Leu Pro
                165                 170                 175 ggt gag aat atc aag tcg tgc ttc ttg tat tgt gct ctg ttt ccg aaa        576
Gly Glu Asn Ile Lys Ser Cys Phe Leu Tyr Cys Ala Leu Phe Pro Lys
            180                 185                 190 agt tgt gat ata aat aaa caa gat ctg gta gac tgt tgg ata gcc gaa        624
Ser Cys Asp Ile Asn Lys Gln Asp Leu Val Asp Cys Trp Ile Ala Glu
        195                 200                 205 gga gta att gaa gat gaa gac aga gag ata gct gag ata cag gga tat        672
Gly Val Ile Glu Asp Glu Asp Arg Glu Ile Ala Glu Ile Gln Gly Tyr
    210                 215                 220 gaa atg atg gct gat ttg gtt atg atg aga ttg ttg att gat gat gaa        720
Glu Met Met Ala Asp Leu Val Met Met Arg Leu Leu Ile Asp Asp Glu
225                 230                 235                 240 tct gaa cat gag gta aag atg cat gac atg gtt cgt gga atg gcc ttg        768
Ser Glu His Glu Val Lys Met His Asp Met Val Arg Gly Met Ala Leu
                245                 250                 255 tgg ata gcc act gac tgc ggg agg cag aaa gaa aac ttt gtc gtg gta        816
Trp Ile Ala Thr Asp Cys Gly Arg Gln Lys Glu Asn Phe Val Val Val
            260                 265                 270 agc ggt gag gat aga cat cag atg cca gag gtg aat gat tgg agt aac        864
Ser Gly Glu Asp Arg His Gln Met Pro Glu Val Asn Asp Trp Ser Asn
        275                 280                 285 gtt aga agg atg tca gta aca tct act cag gtt gac aag ata tcc gac        912
Val Arg Arg Met Ser Val Thr Ser Thr Gln Val Asp Lys Ile Ser Asp
    290                 295                 300 tct cat gat tgt ccc aag ctt acg act cta ttt ctc caa gaa aac aac        960
Ser His Asp Cys Pro Lys Leu Thr Thr Leu Phe Leu Gln Glu Asn Asn
305                 310                 315                 320 tta aaa tgg gtc tcg ggt gat ttc ttt cgg tgg atg acc agt ctt gtg       1008
Leu Lys Trp Val Ser Gly Asp Phe Phe Arg Trp Met Thr Ser Leu Val
                325                 330                 335 gtc ttg aat cta tcg cgt aac tta gaa ctt tct gag ttg ccg gaa gaa       1056
Val Leu Asn Leu Ser Arg Asn Leu Glu Leu Ser Glu Leu Pro Glu Glu
            340                 345                 350 gtt tca agc ctg gtg tcc ctg cgg ctt ctc aac tta tca tgg acg tgg       1104
Val Ser Ser Leu Val Ser Leu Arg Leu Leu Asn Leu Ser Trp Thr Trp
        355                 360                 365 ata aaa cgt ttg ccg ctt ggt ctg aca gag ctg aaa agg ttg atg cac       1152
```

```
              Ile Lys Arg Leu Pro Leu Gly Leu Thr Glu Leu Lys Arg Leu Met His
                  370                 375                 380 ttg gat ttg gat gac acc cct cgt ctt cta gaa gtt gac gta ata ggt        1200
Leu Asp Leu Asp Asp Thr Pro Arg Leu Leu Glu Val Asp Val Ile Gly
385                 390                 395                 400 tat tta ctg aat ttg caa gtg ctg aga tta ttc cgg tca gtt ccg atg        1248
Tyr Leu Leu Asn Leu Gln Val Leu Arg Leu Phe Arg Ser Val Pro Met
                405                 410                 415 gat cgc agc tta ttg gag aat ata caa ctt ttg gaa aat ctg aaa gag        1296
Asp Arg Ser Leu Leu Glu Asn Ile Gln Leu Leu Glu Asn Leu Lys Glu
            420                 425                 430 ctg aat cta acc gtg aga gaa gtt gat gtt ttg gag cgg cta caa agt        1344
Leu Asn Leu Thr Val Arg Glu Val Asp Val Leu Glu Arg Leu Gln Ser
        435                 440                 445 atc cac aag ttg gca agt tgt atc cga cat tta cat ctc aaa ggg att        1392
Ile His Lys Leu Ala Ser Cys Ile Arg His Leu His Leu Lys Gly Ile
    450                 455                 460 aca ata aaa gat gga gga aca cta ctg ctg aac tct atg ttg agt ctt        1440
Thr Ile Lys Asp Gly Gly Thr Leu Leu Leu Asn Ser Met Leu Ser Leu
465                 470                 475                 480 cgc gaa ctt aat att ggg atg tgt gat atc ccg gag ata acc gtt gat        1488
Arg Glu Leu Asn Ile Gly Met Cys Asp Ile Pro Glu Ile Thr Val Asp
                485                 490                 495 tgg aga agc acc atc caa aga gag acg ata cat ttt ggt aac att cag        1536
Trp Arg Ser Thr Ile Gln Arg Glu Thr Ile His Phe Gly Asn Ile Gln
            500                 505                 510 aaa att ccg tat tta cag aac ata cgc aca gtg gct ctt tct tgg tgc        1584
Lys Ile Pro Tyr Leu Gln Asn Ile Arg Thr Val Ala Leu Ser Trp Cys
        515                 520                 525 aaa ggt ctc aag gac ttg aca tgg ttg cta tta gcc ccg aat ctc ggc        1632
Lys Gly Leu Lys Asp Leu Thr Trp Leu Leu Leu Ala Pro Asn Leu Gly
    530                 535                 540 gat cta agg tta ctt gaa tgt cag caa ata gaa cat ata ata aac aaa        1680
Asp Leu Arg Leu Leu Glu Cys Gln Gln Ile Glu His Ile Ile Asn Lys
545                 550                 555                 560 gag aaa ccc aca ggt gat atg agt gag gag cct ttt caa aat cta act        1728
Glu Lys Pro Thr Gly Asp Met Ser Glu Glu Pro Phe Gln Asn Leu Thr
                565                 570                 575 agg ctc agc cta gaa agt ttg cct caa cta gag agc atc tac tgg act        1776
Arg Leu Ser Leu Glu Ser Leu Pro Gln Leu Glu Ser Ile Tyr Trp Thr
            580                 585                 590 cct cta ccc ttt cca gtt ctg aaa gat ctt tgc ata aga ggt tgt cca        1824
Pro Leu Pro Phe Pro Val Leu Lys Asp Leu Cys Ile Arg Gly Cys Pro
        595                 600                 605 aag ctg aga aga cgt ccg ttt agc aat aaa gga aat caa gtg cga tca        1872
Lys Leu Arg Arg Arg Pro Phe Ser Asn Lys Gly Asn Gln Val Arg Ser
    610                 615                 620 gat gtt ggc caa aaa gga gtt gaa agg gag gat gaa gct atg aag caa        1920
Asp Val Gly Gln Lys Gly Val Glu Arg Glu Asp Glu Ala Met Lys Gln
625                 630                 635                 640 cat ctc tcc aat ttt gat gac agg gat ttt ctg aag atg gat gaa gac        1968
His Leu Ser Asn Phe Asp Asp Arg Asp Phe Leu Lys Met Asp Glu Asp
                645                 650                 655 cag aac atg gag ggt ttg gca tct gag tcg cat ccc aat aag aac ata        2016
Gln Asn Met Glu Gly Leu Ala Ser Glu Ser His Pro Asn Lys Asn Ile
            660                 665                 670 gcc ctg gtc gac act tca gag aga gga aaa ttt agt acc aat gca aac        2064
Ala Leu Val Asp Thr Ser Glu Arg Gly Lys Phe Ser Thr Asn Ala Asn
        675                 680                 685
```

|  |  |
|---|---|
| agc atg acc gat ttt gat gac agg agc gga tac gtg gaa gcg gaa acg<br>Ser Met Thr Asp Phe Asp Asp Arg Ser Gly Tyr Val Glu Ala Glu Thr<br>690                           695                     700 | 2112 |
| tat gca agc gca gaa gcg aga tta tta aga aaa tta gga agc ggg gat<br>Tyr Ala Ser Ala Glu Ala Arg Leu Leu Arg Lys Leu Gly Ser Gly Asp<br>705                     710                     715                   720 | 2160 |
| atc cca aca gtg gct gaa gac cag aag atg ggt ggt ttg gta tct gag<br>Ile Pro Thr Val Ala Glu Asp Gln Lys Met Gly Gly Leu Val Ser Glu<br>                   725                     730                    735 | 2208 |
| tta cac ccc aat gaa aac gta gcc ctg gtc gag act tca gag aga gga<br>Leu His Pro Asn Glu Asn Val Ala Leu Val Glu Thr Ser Glu Arg Gly<br>740                         745                     750 | 2256 |
| aaa agt acc atc gca aac agc atc acc aat ttt gat gac agg gat ttt<br>Lys Ser Thr Ile Ala Asn Ser Ile Thr Asn Phe Asp Asp Arg Asp Phe<br>        755                     760                    765 | 2304 |
| ccg aca ttg gct gaa gac cag aag atg gat ggt ttg gca tct gag tca<br>Pro Thr Leu Ala Glu Asp Gln Lys Met Asp Gly Leu Ala Ser Glu Ser<br>770                         775                     780 | 2352 |
| cac cca gtc gaa gac ata gtc ctg gta gag act tta gaa agt gaa aaa<br>His Pro Val Glu Asp Ile Val Leu Val Glu Thr Leu Glu Ser Glu Lys<br>785                         790                     795                   800 | 2400 |
| ggt acc atc cca aac agc atc acc gaa gag aat gtg ttt caa tcg gga<br>Gly Thr Ile Pro Asn Ser Ile Thr Glu Glu Asn Val Phe Gln Ser Gly<br>                   805                     810                    815 | 2448 |
| aaa cac gca act ctg gaa cac aca caa tca tac cca gtt ttg gcg cca<br>Lys His Ala Thr Leu Glu His Thr Gln Ser Tyr Pro Val Leu Ala Pro<br>        820                     825                    830 | 2496 |
| gat ggc atg atc cac aat atg act gac act cct gga gga acc att atg<br>Asp Gly Met Ile His Asn Met Thr Asp Thr Pro Gly Gly Thr Ile Met<br>835                         840                     845 | 2544 |
| gct ggg gaa ctt gtg tct ttt gga ata caa aag ctt tgg gag ttg ctt<br>Ala Gly Glu Leu Val Ser Phe Gly Ile Gln Lys Leu Trp Glu Leu Leu<br>850                         855                     860 | 2592 |
| cgc caa gaa agc gag cgt ttt cag gga gct tcg gat gaa ata gat atg<br>Arg Gln Glu Ser Glu Arg Phe Gln Gly Ala Ser Asp Glu Ile Asp Met<br>865                         870                     875                   880 | 2640 |
| gta aaa aat gca aat gcc aaa aaa cat aca agg gag gtg aaa agt tgt<br>Val Lys Asn Ala Asn Ala Lys Lys His Thr Arg Glu Val Lys Ser Cys<br>                   885                     890                    895 | 2688 |
| att gaa gag atc aaa gaa att ttt ttt gac gcg gaa gat att att gag<br>Ile Glu Glu Ile Lys Glu Ile Phe Phe Asp Ala Glu Asp Ile Ile Glu<br>                   900                     905                    910 | 2736 |
| aca tat ctt ctt gaa gaa aac ccc cca aaa act ggt gtc ttc aag agg<br>Thr Tyr Leu Leu Glu Glu Asn Pro Pro Lys Thr Gly Val Phe Lys Arg<br>        915                     920                    925 | 2784 |
| ctt ttc aga ggg cgt gct ggc agg aaa ttt gct ttg gat atg aat agc<br>Leu Phe Arg Gly Arg Ala Gly Arg Lys Phe Ala Leu Asp Met Asn Ser<br>930                         935                     940 | 2832 |
| tta agc aag agg att tct aag ata atc agc gtt atg caa gct ttt gga<br>Leu Ser Lys Arg Ile Ser Lys Ile Ile Ser Val Met Gln Ala Phe Gly<br>945                         950                     955                   960 | 2880 |
| gta cac cag gtt att act gaa ggc aag gat tca caa cct ctt cta caa<br>Val His Gln Val Ile Thr Glu Gly Lys Asp Ser Gln Pro Leu Leu Gln<br>                   965                     970                    975 | 2928 |
| aga caa aaa agg atg cga caa aaa ttt gct gga gag tac aaa ccc aat<br>Arg Gln Lys Arg Met Arg Gln Lys Phe Ala Gly Glu Tyr Lys Pro Asn<br>        980                     985                    990 | 2976 |
| ttt gtg ggg ctg gaa gaa aat gtt gag aaa ttg gtt agt ctt ttg gtc<br>Phe Val Gly Leu Glu Glu Asn Val Glu Lys Leu Val Ser Leu Leu Val<br>995                         1000                   1005 | 3024 |

```
gag gaa gac aat att caa gtg gtt tcc ata acc ggg atg ggt ggt        3069
Glu Glu Asp Asn Ile Gln Val Val Ser Ile Thr Gly Met Gly Gly
    1010                1015                1020 ctt ggt aaa act acc ctc gct aga caa act ttt aat cac gat atg        3114
Leu Gly Lys Thr Thr Leu Ala Arg Gln Thr Phe Asn His Asp Met
1025                1030                1035 gta aaa cac aag ttt gat agg ttc gca tgg gtg ggt att tca caa        3159
Val Lys His Lys Phe Asp Arg Phe Ala Trp Val Gly Ile Ser Gln
    1040                1045                1050 gct tgt aac cga aag att gtg tgg caa atg atc ttg cgg agt ctc        3204
Ala Cys Asn Arg Lys Ile Val Trp Gln Met Ile Leu Arg Ser Leu
1055                1060                1065 ttg gcc aaa aaa gat gaa gat agt att ttg cat atg act gaa tct        3249
Leu Ala Lys Lys Asp Glu Asp Ser Ile Leu His Met Thr Glu Ser
    1070                1075                1080 gaa ctc caa gag caa atc ttt cta ttg ctg gaa gca tcc aaa tca        3294
Glu Leu Gln Glu Gln Ile Phe Leu Leu Leu Glu Ala Ser Lys Ser
1085                1090                1095 ttg att gtc ata gat gac ata tgg aaa gaa gaa gac tgg aag cga        3339
Leu Ile Val Ile Asp Asp Ile Trp Lys Glu Glu Asp Trp Lys Arg
    1100                1105                1110 atc agt caa ata ctt cca aac aca aaa ggt tgg aag gtg cta ctt        3384
Ile Ser Gln Ile Leu Pro Asn Thr Lys Gly Trp Lys Val Leu Leu
1115                1120                1125 act tct cga aat gag aat gtc gct gga gac aca aga cac atc aac        3429
Thr Ser Arg Asn Glu Asn Val Ala Gly Asp Thr Arg His Ile Asn
    1130                1135                1140 ttc aat cta gaa tta tta aca act gat gac agt tgg aca ctt ttg        3474
Phe Asn Leu Glu Leu Leu Thr Thr Asp Asp Ser Trp Thr Leu Leu
1145                1150                1155 caa acg ata gca ttt cct aga aag gat gca ttc ggg gaa gca tat        3519
Gln Thr Ile Ala Phe Pro Arg Lys Asp Ala Phe Gly Glu Ala Tyr
    1160                1165                1170 gag gaa atg gaa aag atg ggt aag cat atg atc aaa tat tgt ggg        3564
Glu Glu Met Glu Lys Met Gly Lys His Met Ile Lys Tyr Cys Gly
1175                1180                1185 gga ctg cca ttg gct gtg aga ata tta gga ggt tta tta gcg aag        3609
Gly Leu Pro Leu Ala Val Arg Ile Leu Gly Gly Leu Leu Ala Lys
    1190                1195                1200 aaa tac aaa ctg cat gag tgg gaa atg ata tgt gag aat gtt gaa        3654
Lys Tyr Lys Leu His Glu Trp Glu Met Ile Cys Glu Asn Val Glu
1205                1210                1215 cgc cat ctc atg gga aga act gat ttc aat gat gac aac aat att        3699
Arg His Leu Met Gly Arg Thr Asp Phe Asn Asp Asp Asn Asn Ile
    1220                1225                1230 ttg cgc ttc cat gta atg tct ctg agc ttt gaa gag ttg tct agt        3744
Leu Arg Phe His Val Met Ser Leu Ser Phe Glu Glu Leu Ser Ser
1235                1240                1245 tat ttg aag caa tgc ttc ctt tat ttg gca att ttt cca gaa gat        3789
Tyr Leu Lys Gln Cys Phe Leu Tyr Leu Ala Ile Phe Pro Glu Asp
    1250                1255                1260 cat cga ata agt gtg ggg aaa ctg tct tat tac tgg gca gca gaa        3834
His Arg Ile Ser Val Gly Lys Leu Ser Tyr Tyr Trp Ala Ala Glu
1265                1270                1275 gga ttc acc ggt acg tat tac gat gaa gag acc att cga gat gtt        3879
Gly Phe Thr Gly Thr Tyr Tyr Asp Glu Glu Thr Ile Arg Asp Val
    1280                1285                1290 gga gat agc tat ata gag gag ctc gcg agg aga aat atg gtt act        3924
Gly Asp Ser Tyr Ile Glu Glu Leu Ala Arg Arg Asn Met Val Thr
1295                1300                1305
```

-continued

```
         1295                1300                1305
ttc gaa aga gac agc acg ggc ttg agg ttt gaa acc tgt agt atg    3969
Phe Glu Arg Asp Ser Thr Gly Leu Arg Phe Glu Thr Cys Ser Met
1310                1315                1320 cat gac att atg agg gaa atg tgt ttg act aaa gca aaa gaa gag    4014
His Asp Ile Met Arg Glu Met Cys Leu Thr Lys Ala Lys Glu Glu
1325                1330                1335 aac ttc cta caa act gat gtt act cgc aga ttt gtc tgc caa aat    4059
Asn Phe Leu Gln Thr Asp Val Thr Arg Arg Phe Val Cys Gln Asn
1340                1345                1350 act acc aca tta gat gtt gag aga gat ata aat aat cca aaa ctt    4104
Thr Thr Thr Leu Asp Val Glu Arg Asp Ile Asn Asn Pro Lys Leu
1355                1360                1365 cgg tct ctc tta gtt atc ctt aat tcg gag ggg gat ttt tgt agg    4149
Arg Ser Leu Leu Val Ile Leu Asn Ser Glu Gly Asp Phe Cys Arg
1370                1375                1380 cta tct ggt tta agg ttc aca agg cta caa ctt ctg agg gtg tta    4194
Leu Ser Gly Leu Arg Phe Thr Arg Leu Gln Leu Leu Arg Val Leu
1385                1390                1395 gat ctc gat aaa gcc aag ttt gaa gga ggg aag tta cct tct gac    4239
Asp Leu Asp Lys Ala Lys Phe Glu Gly Gly Lys Leu Pro Ser Asp
1400                1405                1410 ata gga aag ctc atc cac tta aga tac ttg agc tta gaa tct gct    4284
Ile Gly Lys Leu Ile His Leu Arg Tyr Leu Ser Leu Glu Ser Ala
1415                1420                1425 gag gta tct cat cta cct tct tcc cta cga aac ctg atg ttg ctg    4329
Glu Val Ser His Leu Pro Ser Ser Leu Arg Asn Leu Met Leu Leu
1430                1435                1440 atc tat ttg aac ata gat gta gct gat att gat ata cat gtg ccc    4374
Ile Tyr Leu Asn Ile Asp Val Ala Asp Ile Asp Ile His Val Pro
1445                1450                1455 aac gtt ctg atg gag atg cga gaa ttg aga tac ctt gca tta cca    4419
Asn Val Leu Met Glu Met Arg Glu Leu Arg Tyr Leu Ala Leu Pro
1460                1465                1470 aag ttt atg cat gag aag acc aag ttg gaa ttg ggt aat cta gta    4464
Lys Phe Met His Glu Lys Thr Lys Leu Glu Leu Gly Asn Leu Val
1475                1480                1485 aac ttg gag acc ttg gag aat ttc tca aca aag aat agc aga tta    4509
Asn Leu Glu Thr Leu Glu Asn Phe Ser Thr Lys Asn Ser Arg Leu
1490                1495                1500 gag gat ctc cgt tgt atg atc aga ttg agg act ctt tca atc aaa    4554
Glu Asp Leu Arg Cys Met Ile Arg Leu Arg Thr Leu Ser Ile Lys
1505                1510                1515 gta act ggt gag acc tct tca gaa act ctc tct tta tca ata agt    4599
Val Thr Gly Glu Thr Ser Ser Glu Thr Leu Ser Leu Ser Ile Ser
1520                1525                1530 ggc ctg aga cac ctg gaa aat ctc gtc ata cat gat cgc ctg agc    4644
Gly Leu Arg His Leu Glu Asn Leu Val Ile His Asp Arg Leu Ser
1535                1540                1545 tgg atc aaa gag gga att gtt tta cat tgc gat gat ctc ata aag    4689
Trp Ile Lys Glu Gly Ile Val Leu His Cys Asp Asp Leu Ile Lys
1550                1555                1560 ctg gag ctg ttt atg tat agg cca gtg agg cta gaa aaa caa cgc    4734
Leu Glu Leu Phe Met Tyr Arg Pro Val Arg Leu Glu Lys Gln Arg
1565                1570                1575 ttc cct tct cac att aca tac ata tct cta act gag tgt cgt ttc    4779
Phe Pro Ser His Ile Thr Tyr Ile Ser Leu Thr Glu Cys Arg Phe
1580                1585                1590 gag cat gat ccg atg cca cta tta gag acg ttg cag cac ttg aga    4824
```

```
Glu His Asp Pro Met Pro Leu Leu Glu Thr Leu Gln His Leu Arg
    1595            1600                1605 aag gtt aag tta ttg gat cgg tct cat tgt gcg aga aga atg gtt       4869
Lys Val Lys Leu Leu Asp Arg Ser His Cys Ala Arg Arg Met Val
1610            1615                1620 tgc tcg ggt agt ggg ttt ccg cag ttg cgt gag ctt gag tta gtc       4914
Cys Ser Gly Ser Gly Phe Pro Gln Leu Arg Glu Leu Glu Leu Val
    1625            1630                1635 tta cta gag cag ttg gaa gag tgg ata ata gag gaa ggc tcc atg       4959
Leu Leu Glu Gln Leu Glu Glu Trp Ile Ile Glu Glu Gly Ser Met
1640            1645                1650 cct ctt ctt cat agt ttg gac att act gac tgt aac aag tta aag       5004
Pro Leu Leu His Ser Leu Asp Ile Thr Asp Cys Asn Lys Leu Lys
    1655            1660                1665 gaa att cca gag ggg ctg cga att atc cct tcc tta aag aat ctg       5049
Glu Ile Pro Glu Gly Leu Arg Ile Ile Pro Ser Leu Lys Asn Leu
1670            1675                1680 act tgt tat agt atg ggt aag gaa tgg gag gga aga ttg tcg gaa       5094
Thr Cys Tyr Ser Met Gly Lys Glu Trp Glu Gly Arg Leu Ser Glu
    1685            1690                1695 gga gga gaa gaa tat tac aaa gtc cag cac att ccc tct gtt aag       5139
Gly Gly Glu Glu Tyr Tyr Lys Val Gln His Ile Pro Ser Val Lys
1700            1705                1710 ttc tat gac gaa tct gat ctg aaa ctt gcc gtt ttc tgt tgg agt       5184
Phe Tyr Asp Glu Ser Asp Leu Lys Leu Ala Val Phe Cys Trp Ser
    1715            1720                1725 atc atg aag aag aac aaa aat ttc ttt gtt gtt gga atc aaa gtt       5229
Ile Met Lys Lys Asn Lys Asn Phe Phe Val Val Gly Ile Lys Val
1730            1735                1740 gat ttt ata tat ttt tgc ttg ttt gac tga                           5259
Asp Phe Ile Tyr Phe Cys Leu Phe Asp
    1745            1750

<210> SEQ ID NO 11
<211> LENGTH: 1752
<212> TYPE: PRT
<213> ORGANISM: Brassica napus

<400> SEQUENCE: 11

Met Ala Glu Glu Thr Glu Ser Lys Ala Ser Ser Leu Leu Asp Glu Ser
1               5                   10                  15

Ile Ser Gly Cys His Asp Leu Ser Met Tyr Asp Asp Ile Ser Lys Ile
            20                  25                  30

Ser Gln Ser Thr Leu His Tyr Ser Glu Thr Val Cys Thr Thr Leu Lys
        35                  40                  45

Glu Val Lys Ala Leu Arg Ser Lys Gly Val Phe Lys Val Ile Val Glu
    50                  55                  60

Arg Ala Pro Leu Ser Tyr Val Lys Lys Met Leu Pro Leu His Pro Ile
65                  70                  75                  80

Asp Ser Gly Glu Met Leu Ala Glu Ala Trp Asp Phe Phe Gln Glu
                85                  90                  95

Ile Ile Gly Glu Thr Thr Leu Lys Ser His Pro Asp Ile Pro Gln Leu
            100                 105                 110

Ala Arg Ile Val Cys Arg Lys Cys Arg Gly Leu Pro Ile Ala Leu Ser
        115                 120                 125

Leu Ile Gly Glu Thr Met Ser Arg Lys Arg Thr Val Gln Glu Trp His
    130                 135                 140

Gln Ala Ile Ser Val Leu Val Ser Ser Thr Pro Glu Val Ser Gly Thr
```

-continued

```
            145                 150                 155                 160
        Glu Asp Glu Leu Leu Tyr Ile Leu Lys Phe Ala Tyr Asp Asn Leu Pro
                            165                 170                 175
        Gly Glu Asn Ile Lys Ser Cys Phe Leu Tyr Cys Ala Leu Phe Pro Lys
                        180                 185                 190
        Ser Cys Asp Ile Asn Lys Gln Asp Leu Val Asp Cys Trp Ile Ala Glu
                    195                 200                 205
        Gly Val Ile Glu Asp Glu Asp Arg Glu Ile Ala Glu Ile Gln Gly Tyr
                210                 215                 220
        Glu Met Met Ala Asp Leu Val Met Met Arg Leu Leu Ile Asp Asp Glu
        225                 230                 235                 240
        Ser Glu His Glu Val Lys Met His Asp Met Val Arg Gly Met Ala Leu
                            245                 250                 255
        Trp Ile Ala Thr Asp Cys Gly Arg Gln Lys Glu Asn Phe Val Val Val
                        260                 265                 270
        Ser Gly Glu Asp Arg His Gln Met Pro Glu Val Asn Asp Trp Ser Asn
                    275                 280                 285
        Val Arg Arg Met Ser Val Thr Ser Thr Gln Val Asp Lys Ile Ser Asp
                290                 295                 300
        Ser His Asp Cys Pro Lys Leu Thr Thr Leu Phe Leu Gln Glu Asn Asn
        305                 310                 315                 320
        Leu Lys Trp Val Ser Gly Asp Phe Phe Arg Trp Met Thr Ser Leu Val
                            325                 330                 335
        Val Leu Asn Leu Ser Arg Asn Leu Glu Leu Ser Glu Leu Pro Glu Glu
                        340                 345                 350
        Val Ser Ser Leu Val Ser Leu Arg Leu Leu Asn Leu Ser Trp Thr Trp
                    355                 360                 365
        Ile Lys Arg Leu Pro Leu Gly Leu Thr Glu Leu Lys Arg Leu Met His
                370                 375                 380
        Leu Asp Leu Asp Asp Thr Pro Arg Leu Leu Glu Val Asp Val Ile Gly
        385                 390                 395                 400
        Tyr Leu Leu Asn Leu Gln Val Leu Arg Leu Phe Arg Ser Val Pro Met
                            405                 410                 415
        Asp Arg Ser Leu Leu Glu Asn Ile Gln Leu Leu Glu Asn Leu Lys Glu
                        420                 425                 430
        Leu Asn Leu Thr Val Arg Glu Val Asp Val Leu Glu Arg Leu Gln Ser
                    435                 440                 445
        Ile His Lys Leu Ala Ser Cys Ile Arg His Leu His Leu Lys Gly Ile
                450                 455                 460
        Thr Ile Lys Asp Gly Gly Thr Leu Leu Leu Asn Ser Met Leu Ser Leu
        465                 470                 475                 480
        Arg Glu Leu Asn Ile Gly Met Cys Asp Ile Pro Glu Ile Thr Val Asp
                            485                 490                 495
        Trp Arg Ser Thr Ile Gln Arg Glu Thr Ile His Phe Gly Asn Ile Gln
                        500                 505                 510
        Lys Ile Pro Tyr Leu Gln Asn Ile Arg Thr Val Ala Leu Ser Trp Cys
                    515                 520                 525
        Lys Gly Leu Lys Asp Leu Thr Trp Leu Leu Ala Pro Asn Leu Gly
                530                 535                 540
        Asp Leu Arg Leu Leu Glu Cys Gln Gln Ile Glu His Ile Ile Asn Lys
        545                 550                 555                 560
        Glu Lys Pro Thr Gly Asp Met Ser Glu Glu Pro Phe Gln Asn Leu Thr
                            565                 570                 575
```

-continued

Arg Leu Ser Leu Glu Ser Leu Pro Gln Leu Glu Ser Ile Tyr Trp Thr
                580                 585                 590

Pro Leu Pro Phe Pro Val Leu Lys Asp Leu Cys Ile Arg Gly Cys Pro
            595                 600                 605

Lys Leu Arg Arg Arg Pro Phe Ser Asn Lys Gly Asn Gln Val Arg Ser
        610                 615                 620

Asp Val Gly Gln Lys Gly Val Glu Arg Glu Asp Glu Ala Met Lys Gln
625                 630                 635                 640

His Leu Ser Asn Phe Asp Asp Arg Asp Phe Leu Lys Met Asp Glu Asp
                645                 650                 655

Gln Asn Met Glu Gly Leu Ala Ser Glu Ser His Pro Asn Lys Asn Ile
            660                 665                 670

Ala Leu Val Asp Thr Ser Glu Arg Gly Lys Phe Ser Thr Asn Ala Asn
        675                 680                 685

Ser Met Thr Asp Phe Asp Asp Arg Ser Gly Tyr Val Glu Ala Glu Thr
690                 695                 700

Tyr Ala Ser Ala Glu Ala Arg Leu Leu Arg Lys Leu Gly Ser Gly Asp
705                 710                 715                 720

Ile Pro Thr Val Ala Glu Asp Gln Lys Met Gly Gly Leu Val Ser Glu
                725                 730                 735

Leu His Pro Asn Glu Asn Val Ala Leu Val Glu Thr Ser Glu Arg Gly
            740                 745                 750

Lys Ser Thr Ile Ala Asn Ser Ile Thr Asn Phe Asp Asp Arg Asp Phe
        755                 760                 765

Pro Thr Leu Ala Glu Asp Gln Lys Met Asp Gly Leu Ala Ser Glu Ser
            770                 775                 780

His Pro Val Glu Asp Ile Val Leu Val Glu Thr Leu Glu Ser Glu Lys
785                 790                 795                 800

Gly Thr Ile Pro Asn Ser Ile Thr Glu Glu Asn Val Phe Gln Ser Gly
                805                 810                 815

Lys His Ala Thr Leu Glu His Thr Gln Ser Tyr Pro Val Leu Ala Pro
            820                 825                 830

Asp Gly Met Ile His Asn Met Thr Asp Thr Pro Gly Gly Thr Ile Met
        835                 840                 845

Ala Gly Glu Leu Val Ser Phe Gly Ile Gln Lys Leu Trp Glu Leu Leu
850                 855                 860

Arg Gln Glu Ser Glu Arg Phe Gln Gly Ala Ser Asp Glu Ile Asp Met
865                 870                 875                 880

Val Lys Asn Ala Asn Ala Lys Lys His Thr Arg Glu Val Lys Ser Cys
                885                 890                 895

Ile Glu Glu Ile Lys Glu Ile Phe Phe Asp Ala Glu Asp Ile Ile Glu
            900                 905                 910

Thr Tyr Leu Leu Glu Glu Asn Pro Pro Lys Thr Gly Val Phe Lys Arg
        915                 920                 925

Leu Phe Arg Gly Arg Ala Gly Arg Lys Phe Ala Leu Asp Met Asn Ser
            930                 935                 940

Leu Ser Lys Arg Ile Ser Lys Ile Ile Ser Val Met Gln Ala Phe Gly
945                 950                 955                 960

Val His Gln Val Ile Thr Glu Gly Lys Asp Ser Gln Pro Leu Leu Gln
                965                 970                 975

Arg Gln Lys Arg Met Arg Gln Lys Phe Ala Gly Glu Tyr Lys Pro Asn
            980                 985                 990

-continued

```
Phe Val Gly Leu Glu Glu Asn Val Glu Lys Leu Val Ser Leu Leu Val
            995                 1000                1005

Glu Glu Asp Asn Ile Gln Val Val Ser Ile Thr Gly Met Gly Gly
1010                1015                1020

Leu Gly Lys Thr Thr Leu Ala Arg Gln Thr Phe Asn His Asp Met
1025                1030                1035

Val Lys His Lys Phe Asp Arg Phe Ala Trp Val Gly Ile Ser Gln
1040                1045                1050

Ala Cys Asn Arg Lys Ile Val Trp Gln Met Ile Leu Arg Ser Leu
1055                1060                1065

Leu Ala Lys Lys Asp Glu Asp Ser Ile Leu His Met Thr Glu Ser
1070                1075                1080

Glu Leu Gln Glu Gln Ile Phe Leu Leu Leu Glu Ala Ser Lys Ser
1085                1090                1095

Leu Ile Val Ile Asp Asp Ile Trp Lys Glu Asp Trp Lys Arg
1100                1105                1110

Ile Ser Gln Ile Leu Pro Asn Thr Lys Gly Trp Lys Val Leu Leu
1115                1120                1125

Thr Ser Arg Asn Glu Asn Val Ala Gly Asp Thr Arg His Ile Asn
1130                1135                1140

Phe Asn Leu Glu Leu Leu Thr Thr Asp Asp Ser Trp Thr Leu Leu
1145                1150                1155

Gln Thr Ile Ala Phe Pro Arg Lys Asp Ala Phe Gly Glu Ala Tyr
1160                1165                1170

Glu Glu Met Glu Lys Met Gly Lys His Met Ile Lys Tyr Cys Gly
1175                1180                1185

Gly Leu Pro Leu Ala Val Arg Ile Leu Gly Gly Leu Leu Ala Lys
1190                1195                1200

Lys Tyr Lys Leu His Glu Trp Glu Met Ile Cys Glu Asn Val Glu
1205                1210                1215

Arg His Leu Met Gly Arg Thr Asp Phe Asn Asp Asn Asn Ile
1220                1225                1230

Leu Arg Phe His Val Met Ser Leu Ser Phe Glu Glu Leu Ser Ser
1235                1240                1245

Tyr Leu Lys Gln Cys Phe Leu Tyr Leu Ala Ile Phe Pro Glu Asp
1250                1255                1260

His Arg Ile Ser Val Gly Lys Leu Ser Tyr Tyr Trp Ala Ala Glu
1265                1270                1275

Gly Phe Thr Gly Thr Tyr Tyr Asp Glu Glu Thr Ile Arg Asp Val
1280                1285                1290

Gly Asp Ser Tyr Ile Glu Glu Leu Ala Arg Arg Asn Met Val Thr
1295                1300                1305

Phe Glu Arg Asp Ser Thr Gly Leu Arg Phe Glu Thr Cys Ser Met
1310                1315                1320

His Asp Ile Met Arg Glu Met Cys Leu Thr Lys Ala Lys Glu Glu
1325                1330                1335

Asn Phe Leu Gln Thr Asp Val Thr Arg Arg Phe Val Cys Gln Asn
1340                1345                1350

Thr Thr Thr Leu Asp Val Glu Arg Asp Ile Asn Asn Pro Lys Leu
1355                1360                1365

Arg Ser Leu Leu Val Ile Leu Asn Ser Glu Gly Asp Phe Cys Arg
1370                1375                1380

Leu Ser Gly Leu Arg Phe Thr Arg Leu Gln Leu Leu Arg Val Leu
```

1385                1390                1395

Asp Leu Asp Lys Ala Lys Phe Glu Gly Gly Lys Leu Pro Ser Asp
        1400                1405                1410

Ile Gly Lys Leu Ile His Leu Arg Tyr Leu Ser Leu Glu Ser Ala
        1415                1420                1425

Glu Val Ser His Leu Pro Ser Ser Leu Arg Asn Leu Met Leu Leu
        1430                1435                1440

Ile Tyr Leu Asn Ile Asp Val Ala Asp Ile Asp Ile His Val Pro
        1445                1450                1455

Asn Val Leu Met Glu Met Arg Glu Leu Arg Tyr Leu Ala Leu Pro
        1460                1465                1470

Lys Phe Met His Glu Lys Thr Lys Leu Glu Leu Gly Asn Leu Val
        1475                1480                1485

Asn Leu Glu Thr Leu Glu Asn Phe Ser Thr Lys Asn Ser Arg Leu
        1490                1495                1500

Glu Asp Leu Arg Cys Met Ile Arg Leu Arg Thr Leu Ser Ile Lys
        1505                1510                1515

Val Thr Gly Glu Thr Ser Ser Glu Thr Leu Ser Leu Ser Ile Ser
        1520                1525                1530

Gly Leu Arg His Leu Glu Asn Leu Val Ile His Asp Arg Leu Ser
        1535                1540                1545

Trp Ile Lys Glu Gly Ile Val Leu His Cys Asp Leu Ile Lys
        1550                1555                1560

Leu Glu Leu Phe Met Tyr Arg Pro Val Arg Leu Glu Lys Gln Arg
        1565                1570                1575

Phe Pro Ser His Ile Thr Tyr Ile Ser Leu Thr Glu Cys Arg Phe
        1580                1585                1590

Glu His Asp Pro Met Pro Leu Leu Glu Thr Leu Gln His Leu Arg
        1595                1600                1605

Lys Val Lys Leu Leu Asp Arg Ser His Cys Ala Arg Arg Met Val
        1610                1615                1620

Cys Ser Gly Ser Gly Phe Pro Gln Leu Arg Glu Leu Glu Leu Val
        1625                1630                1635

Leu Leu Glu Gln Leu Glu Glu Trp Ile Ile Glu Glu Gly Ser Met
        1640                1645                1650

Pro Leu Leu His Ser Leu Asp Ile Thr Asp Cys Asn Lys Leu Lys
        1655                1660                1665

Glu Ile Pro Glu Gly Leu Arg Ile Ile Pro Ser Leu Lys Asn Leu
        1670                1675                1680

Thr Cys Tyr Ser Met Gly Lys Glu Trp Glu Gly Arg Leu Ser Glu
        1685                1690                1695

Gly Gly Glu Glu Tyr Tyr Lys Val Gln His Ile Pro Ser Val Lys
        1700                1705                1710

Phe Tyr Asp Glu Ser Asp Leu Lys Leu Ala Val Phe Cys Trp Ser
        1715                1720                1725

Ile Met Lys Lys Asn Lys Asn Phe Phe Val Val Gly Ile Lys Val
        1730                1735                1740

Asp Phe Ile Tyr Phe Cys Leu Phe Asp
        1745                1750

<210> SEQ ID NO 12
<211> LENGTH: 42
<212> TYPE: DNA
<213> ORGANISM: Artificial Sequence -continued

```
<220> FEATURE:
<223> OTHER INFORMATION: Primer

<400> SEQUENCE: 12
gaaggtcgga gtcaacggat tcygtatcct ctggcgacat gc                          42

<210> SEQ ID NO 13
<211> LENGTH: 43
<212> TYPE: DNA
<213> ORGANISM: Artificial Sequence
<220> FEATURE:
<223> OTHER INFORMATION: Primer

<400> SEQUENCE: 13
gaaggtgacc aagttcatgc tacygtatcc tctggcgaca tgt                         43

<210> SEQ ID NO 14
<211> LENGTH: 29
<212> TYPE: DNA
<213> ORGANISM: Artificial Sequence
<220> FEATURE:
<223> OTHER INFORMATION: Primer

<400> SEQUENCE: 14
cgaggagaac caagttttkgt aatcatcat                                        29

<210> SEQ ID NO 15
<211> LENGTH: 45
<212> TYPE: DNA
<213> ORGANISM: Artificial Sequence
<220> FEATURE:
<223> OTHER INFORMATION: Primer

<400> SEQUENCE: 15
gaaggtcgga gtcaacggat taatggatca ggacgttacc caaac                       45

<210> SEQ ID NO 16
<211> LENGTH: 48
<212> TYPE: DNA
<213> ORGANISM: Artificial Sequence
<220> FEATURE:
<223> OTHER INFORMATION: Primer

<400> SEQUENCE: 16
gaaggtgacc aagttcatgc tattaatgga tcaggacgtt acccaaat                    48

<210> SEQ ID NO 17
<211> LENGTH: 30
<212> TYPE: DNA
<213> ORGANISM: Artificial Sequence
<220> FEATURE:
<223> OTHER INFORMATION: Primer

<400> SEQUENCE: 17
tctattgaag gaagagaata catggtgaaa                                        30

<210> SEQ ID NO 18
<211> LENGTH: 43
<212> TYPE: DNA
<213> ORGANISM: Artificial Sequence
<220> FEATURE:
<223> OTHER INFORMATION: Primer

<400> SEQUENCE: 18
gaaggtcgga gtcaacggat tatttgccag cgagaagaaa gcc                         43
```

<210> SEQ ID NO 19
<211> LENGTH: 43
<212> TYPE: DNA
<213> ORGANISM: Artificial Sequence
<220> FEATURE:
<223> OTHER INFORMATION: Primer

<400> SEQUENCE: 19
gaaggtgacc aagttcatgc tatttgccag cgagaagaaa gcg                43

<210> SEQ ID NO 20
<211> LENGTH: 27
<212> TYPE: DNA
<213> ORGANISM: Artificial Sequence
<220> FEATURE:
<223> OTHER INFORMATION: Primer

<400> SEQUENCE: 20
gtgatgggag acgactattt ackgttt                                   27

<210> SEQ ID NO 21
<211> LENGTH: 42
<212> TYPE: DNA
<213> ORGANISM: Artificial Sequence
<220> FEATURE:
<223> OTHER INFORMATION: Primer

<400> SEQUENCE: 21
gaaggtgacc aagttcatgc tgcagtcagg csgatgcgtt gt                  42

<210> SEQ ID NO 22
<211> LENGTH: 41
<212> TYPE: DNA
<213> ORGANISM: Artificial Sequence
<220> FEATURE:
<223> OTHER INFORMATION: Primer

<400> SEQUENCE: 22
gaaggtcgga gtcaacggat tcagtcaggc sgatgcgttg g                   41

<210> SEQ ID NO 23
<211> LENGTH: 27
<212> TYPE: DNA
<213> ORGANISM: Artificial Sequence
<220> FEATURE:
<223> OTHER INFORMATION: Primer

<400> SEQUENCE: 23
cagtctcctc gaagttcama tttccaa                                   27

<210> SEQ ID NO 24
<211> LENGTH: 51
<212> TYPE: DNA
<213> ORGANISM: Artificial Sequence
<220> FEATURE:
<223> OTHER INFORMATION: Primer

<400> SEQUENCE: 24
gaaggtgacc aagttcatgc taagcttatt ggcttttttct cttttgtcta t       51

<210> SEQ ID NO 25
<211> LENGTH: 49
<212> TYPE: DNA
<213> ORGANISM: Artificial Sequence
<220> FEATURE:
<223> OTHER INFORMATION: Primer

<400> SEQUENCE: 25
gaaggtcgga gtcaacggat tgcttattgg cttttctct tttgtctac        49

<210> SEQ ID NO 26
<211> LENGTH: 26
<212> TYPE: DNA
<213> ORGANISM: Artificial Sequence
<220> FEATURE:
<223> OTHER INFORMATION: Primer

<400> SEQUENCE: 26
ggaatgatga ccatgtcgac cttgaa        26

<210> SEQ ID NO 27
<211> LENGTH: 50
<212> TYPE: DNA
<213> ORGANISM: Artificial Sequence
<220> FEATURE:
<223> OTHER INFORMATION: Primer

<400> SEQUENCE: 27
gaaggtgacc aagttcatgc tactgtaaga gtactgaatt tgtaagagaa        50

<210> SEQ ID NO 28
<211> LENGTH: 49
<212> TYPE: DNA
<213> ORGANISM: Artificial Sequence
<220> FEATURE:
<223> OTHER INFORMATION: Primer

<400> SEQUENCE: 28
gaaggtcgga gtcaacggat tctgtaagag tactgaattt gtaagagag        49

<210> SEQ ID NO 29
<211> LENGTH: 30
<212> TYPE: DNA
<213> ORGANISM: Artificial Sequence
<220> FEATURE:
<223> OTHER INFORMATION: Primer

<400> SEQUENCE: 29
ctcmctcaca tctcatctat attgtaagtt        30

<210> SEQ ID NO 30
<211> LENGTH: 54
<212> TYPE: DNA
<213> ORGANISM: Artificial Sequence
<220> FEATURE:
<223> OTHER INFORMATION: Primer

<400> SEQUENCE: 30
gaaggtgacc aagttcatgc tattcaaata tgattggtat gttacattta taaa        54

<210> SEQ ID NO 31
<211> LENGTH: 51
<212> TYPE: DNA
<213> ORGANISM: Artificial Sequence
<220> FEATURE:
<223> OTHER INFORMATION: Primer

<400> SEQUENCE: 31
gaaggtcgga gtcaacggat tcaaatatga ttggtatgtt acatttataa t        51

<210> SEQ ID NO 32

<211> LENGTH: 29
<212> TYPE: DNA
<213> ORGANISM: Artificial Sequence
<220> FEATURE:
<223> OTHER INFORMATION: Primer

<400> SEQUENCE: 32
tacatgcctg tttgagtcac cttactaaa                               29

<210> SEQ ID NO 33
<211> LENGTH: 45
<212> TYPE: DNA
<213> ORGANISM: Artificial Sequence
<220> FEATURE:
<223> OTHER INFORMATION: Primer

<400> SEQUENCE: 33
gaaggtcgga gtcaacggat tatcgwaggt acttcaagag gatcg             45

<210> SEQ ID NO 34
<211> LENGTH: 46
<212> TYPE: DNA
<213> ORGANISM: Artificial Sequence
<220> FEATURE:
<223> OTHER INFORMATION: Primer

<400> SEQUENCE: 34
gaaggtgacc aagttcatgc tgatcgwagg tacttcaaga ggatca            46

<210> SEQ ID NO 35
<211> LENGTH: 30
<212> TYPE: DNA
<213> ORGANISM: Artificial Sequence
<220> FEATURE:
<223> OTHER INFORMATION: Primer

<400> SEQUENCE: 35
caaacktaac cttccctgtt atctctttat                              30

<210> SEQ ID NO 36
<211> LENGTH: 47
<212> TYPE: DNA
<213> ORGANISM: Artificial Sequence
<220> FEATURE:
<223> OTHER INFORMATION: Primer

<400> SEQUENCE: 36
gaaggtgacc aagttcatgc ttcaaagacr ctacgatcaa taatttt           47

<210> SEQ ID NO 37
<211> LENGTH: 49
<212> TYPE: DNA
<213> ORGANISM: Artificial Sequence
<220> FEATURE:
<223> OTHER INFORMATION: Primer

<400> SEQUENCE: 37
gaaggtcgga gtcaacggat tcttcaaaga crctacgatc aataatttc         49

<210> SEQ ID NO 38
<211> LENGTH: 24
<212> TYPE: DNA
<213> ORGANISM: Artificial Sequence
<220> FEATURE:
<223> OTHER INFORMATION: Primer

<400> SEQUENCE: 38

-continued gcaacggaac ctccatccma caat    24

<210> SEQ ID NO 39
<211> LENGTH: 51
<212> TYPE: DNA
<213> ORGANISM: Artificial Sequence
<220> FEATURE:
<223> OTHER INFORMATION: Primer

<400> SEQUENCE: 39
gaaggtgacc aagttcatgc tcggayaccc aactttcttt acaaaaaaaa t    51

<210> SEQ ID NO 40
<211> LENGTH: 51
<212> TYPE: DNA
<213> ORGANISM: Artificial Sequence
<220> FEATURE:
<223> OTHER INFORMATION: Primer

<400> SEQUENCE: 40
gaaggtcgga gtcaacggat tcggayaccc aactttcttt acaaaaaaaa a    51

<210> SEQ ID NO 41
<211> LENGTH: 30
<212> TYPE: DNA
<213> ORGANISM: Artificial Sequence
<220> FEATURE:
<223> OTHER INFORMATION: Primer

<400> SEQUENCE: 41
gttmtagaca tggatttgaa tgcatacgat    30

<210> SEQ ID NO 42
<211> LENGTH: 50
<212> TYPE: DNA
<213> ORGANISM: Artificial Sequence
<220> FEATURE:
<223> OTHER INFORMATION: Primer

<400> SEQUENCE: 42
gaaggtgacc aagttcatgc tagaacatca gaggaggtta aatttagttt    50

<210> SEQ ID NO 43
<211> LENGTH: 49
<212> TYPE: DNA
<213> ORGANISM: Artificial Sequence
<220> FEATURE:
<223> OTHER INFORMATION: Primer

<400> SEQUENCE: 43
gaaggtcgga gtcaacggat tgaacatcag aggaggttaa atttagttg    49

<210> SEQ ID NO 44
<211> LENGTH: 29
<212> TYPE: DNA
<213> ORGANISM: Artificial Sequence
<220> FEATURE:
<223> OTHER INFORMATION: Primer

<400> SEQUENCE: 44
ctagaggacc agtctacact ttattctta    29

<210> SEQ ID NO 45
<211> LENGTH: 46
<212> TYPE: DNA

```
<213> ORGANISM: Artificial Sequence
<220> FEATURE:
<223> OTHER INFORMATION: Primer

<400> SEQUENCE: 45
gaaggtgacc aagttcatgc tacgccttcc agtaaagatc caaaca          46

<210> SEQ ID NO 46
<211> LENGTH: 44
<212> TYPE: DNA
<213> ORGANISM: Artificial Sequence
<220> FEATURE:
<223> OTHER INFORMATION: Primer

<400> SEQUENCE: 46
gaaggtcgga gtcaacggat tgccttccag taaagatcca aacc            44

<210> SEQ ID NO 47
<211> LENGTH: 30
<212> TYPE: DNA
<213> ORGANISM: Artificial Sequence
<220> FEATURE:
<223> OTHER INFORMATION: Primer

<400> SEQUENCE: 47
ccatggtact ttaacrttta aggtcatgtt                            30

<210> SEQ ID NO 48
<211> LENGTH: 45
<212> TYPE: DNA
<213> ORGANISM: Artificial Sequence
<220> FEATURE:
<223> OTHER INFORMATION: Primer

<400> SEQUENCE: 48
gaaggtgacc aagttcatgc ttgggcattc agatcttagg gtcaa           45

<210> SEQ ID NO 49
<211> LENGTH: 44
<212> TYPE: DNA
<213> ORGANISM: Artificial Sequence
<220> FEATURE:
<223> OTHER INFORMATION: Primer

<400> SEQUENCE: 49
gaaggtcgga gtcaacggat tgggcattca gatcttaggg tcag            44

<210> SEQ ID NO 50
<211> LENGTH: 22
<212> TYPE: DNA
<213> ORGANISM: Artificial Sequence
<220> FEATURE:
<223> OTHER INFORMATION: Primer

<400> SEQUENCE: 50
ttgagaggag caccggcctg aa                                    22

<210> SEQ ID NO 51
<211> LENGTH: 53
<212> TYPE: DNA
<213> ORGANISM: Artificial Sequence
<220> FEATURE:
<223> OTHER INFORMATION: Primer

<400> SEQUENCE: 51
gaaggtgacc aagttcatgc tgttgttttt ccatactctg tttttgtaaa gaa  53
```

<210> SEQ ID NO 52
<211> LENGTH: 53
<212> TYPE: DNA
<213> ORGANISM: Artificial Sequence
<220> FEATURE:
<223> OTHER INFORMATION: Primer

<400> SEQUENCE: 52
gaaggtcgga gtcaacggat tgttgttttt ccatactctg tttttgtaaa gat    53

<210> SEQ ID NO 53
<211> LENGTH: 30
<212> TYPE: DNA
<213> ORGANISM: Artificial Sequence
<220> FEATURE:
<223> OTHER INFORMATION: Primer

<400> SEQUENCE: 53
aaaaaacatg ggaacttaca gacactgttt    30

<210> SEQ ID NO 54
<211> LENGTH: 47
<212> TYPE: DNA
<213> ORGANISM: Artificial Sequence
<220> FEATURE:
<223> OTHER INFORMATION: Primer

<400> SEQUENCE: 54
gaaggtcgga gtcaacggat tcttcatatc cccaataatg tgtgacg    47

<210> SEQ ID NO 55
<211> LENGTH: 48
<212> TYPE: DNA
<213> ORGANISM: Artificial Sequence
<220> FEATURE:
<223> OTHER INFORMATION: Primer

<400> SEQUENCE: 55
gaaggtgacc aagttcatgc tacttcatat ccccaataat gtgtgaca    48

<210> SEQ ID NO 56
<211> LENGTH: 30
<212> TYPE: DNA
<213> ORGANISM: Artificial Sequence
<220> FEATURE:
<223> OTHER INFORMATION: Primer

<400> SEQUENCE: 56
tgctaatcac attaacgcat catcaataaa    30

<210> SEQ ID NO 57
<211> LENGTH: 53
<212> TYPE: DNA
<213> ORGANISM: Artificial Sequence
<220> FEATURE:
<223> OTHER INFORMATION: Primer

<400> SEQUENCE: 57
gaaggtcgga gtcaacggat tgaaacrgaa aagattataa gctcaagaaa tta    53

<210> SEQ ID NO 58
<211> LENGTH: 52
<212> TYPE: DNA
<213> ORGANISM: Artificial Sequence
<220> FEATURE:

<223> OTHER INFORMATION: Primer

<400> SEQUENCE: 58
gaaggtgacc aagttcatgc taaacrgaaa agattataag ctcaagaaat tg    52

<210> SEQ ID NO 59
<211> LENGTH: 29
<212> TYPE: DNA
<213> ORGANISM: Artificial Sequence
<220> FEATURE:
<223> OTHER INFORMATION: Primer

<400> SEQUENCE: 59
ccaaaactcc atcamctaca taaacctat    29

<210> SEQ ID NO 60
<211> LENGTH: 48
<212> TYPE: DNA
<213> ORGANISM: Artificial Sequence
<220> FEATURE:
<223> OTHER INFORMATION: Primer

<400> SEQUENCE: 60
gaaggtcgga gtcaacggat tgctgcttga gattctgaat ctgattat    48

<210> SEQ ID NO 61
<211> LENGTH: 45
<212> TYPE: DNA
<213> ORGANISM: Artificial Sequence
<220> FEATURE:
<223> OTHER INFORMATION: Primer

<400> SEQUENCE: 61
gaaggtgacc aagttcatgc tgcttgagat tctgaatctg attac    45

<210> SEQ ID NO 62
<211> LENGTH: 30
<212> TYPE: DNA
<213> ORGANISM: Artificial Sequence
<220> FEATURE:
<223> OTHER INFORMATION: Primer

<400> SEQUENCE: 62
cactttaaga cacaatctcr cttcttcttt    30

<210> SEQ ID NO 63
<211> LENGTH: 51
<212> TYPE: DNA
<213> ORGANISM: Artificial Sequence
<220> FEATURE:
<223> OTHER INFORMATION: Primer

<400> SEQUENCE: 63
gaaggtcgga gtcaacggat tagtatagaa tctatagata gatagatcca c    51

<210> SEQ ID NO 64
<211> LENGTH: 52
<212> TYPE: DNA
<213> ORGANISM: Artificial Sequence
<220> FEATURE:
<223> OTHER INFORMATION: Primer

<400> SEQUENCE: 64
gaaggtgacc aagttcatgc ttagtataga atctatagat agatagatcc at    52

```
<210> SEQ ID NO 65
<211> LENGTH: 27
<212> TYPE: DNA
<213> ORGANISM: Artificial Sequence
<220> FEATURE:
<223> OTHER INFORMATION: Primer

<400> SEQUENCE: 65
ctcctacmtc gtttctgtat cacgaat                                         27

<210> SEQ ID NO 66
<211> LENGTH: 53
<212> TYPE: DNA
<213> ORGANISM: Artificial Sequence
<220> FEATURE:
<223> OTHER INFORMATION: Primer

<400> SEQUENCE: 66
gaaggtcgga gtcaacggat tatataagct gttttctttt ttaagtctt ttg            53

<210> SEQ ID NO 67
<211> LENGTH: 53
<212> TYPE: DNA
<213> ORGANISM: Artificial Sequence
<220> FEATURE:
<223> OTHER INFORMATION: Primer

<400> SEQUENCE: 67
gaaggtgacc aagttcatgc tatataagct gttttctttt ttaagtctt tta            53

<210> SEQ ID NO 68
<211> LENGTH: 27
<212> TYPE: DNA
<213> ORGANISM: Artificial Sequence
<220> FEATURE:
<223> OTHER INFORMATION: Primer

<400> SEQUENCE: 68
atcgttttcg caarcacctg agttcta                                         27

<210> SEQ ID NO 69
<211> LENGTH: 52
<212> TYPE: DNA
<213> ORGANISM: Artificial Sequence
<220> FEATURE:
<223> OTHER INFORMATION: Primer

<400> SEQUENCE: 69
gaaggtgacc aagttcatgc tgccaaaatg tagaacctaa amtatatact aa             52

<210> SEQ ID NO 70
<211> LENGTH: 52
<212> TYPE: DNA
<213> ORGANISM: Artificial Sequence
<220> FEATURE:
<223> OTHER INFORMATION: Primer

<400> SEQUENCE: 70
gaaggtcgga gtcaacggat tgccaaaatg tagaacctaa amtatatact at             52

<210> SEQ ID NO 71
<211> LENGTH: 30
<212> TYPE: DNA
<213> ORGANISM: Artificial Sequence
<220> FEATURE:
<223> OTHER INFORMATION: Primer
```

```
<400> SEQUENCE: 71
ctgaagatat cgttgcacac kttatttctt                                30

<210> SEQ ID NO 72
<211> LENGTH: 49
<212> TYPE: DNA
<213> ORGANISM: Artificial Sequence
<220> FEATURE:
<223> OTHER INFORMATION: Primer

<400> SEQUENCE: 72
gaaggtgacc aagttcatgc ttagatttag agakttacaa ctggttgaa           49

<210> SEQ ID NO 73
<211> LENGTH: 48
<212> TYPE: DNA
<213> ORGANISM: Artificial Sequence
<220> FEATURE:
<223> OTHER INFORMATION: Primer

<400> SEQUENCE: 73
gaaggtcgga gtcaacggat tagatttaga gakttacaac tggttgag            48

<210> SEQ ID NO 74
<211> LENGTH: 30
<212> TYPE: DNA
<213> ORGANISM: Artificial Sequence
<220> FEATURE:
<223> OTHER INFORMATION: Primer

<400> SEQUENCE: 74
accattacag actattgttt tcmtgttcat                                30

<210> SEQ ID NO 75
<211> LENGTH: 44
<212> TYPE: DNA
<213> ORGANISM: Artificial Sequence
<220> FEATURE:
<223> OTHER INFORMATION: Primer

<400> SEQUENCE: 75
gaaggtcgga gtcaacggat tgagaagtga tttggcacat gtct                44

<210> SEQ ID NO 76
<211> LENGTH: 45
<212> TYPE: DNA
<213> ORGANISM: Artificial Sequence
<220> FEATURE:
<223> OTHER INFORMATION: Primer

<400> SEQUENCE: 76
gaaggtgacc aagttcatgc ttgagaagtg atttggcaca tgtcc               45

<210> SEQ ID NO 77
<211> LENGTH: 30
<212> TYPE: DNA
<213> ORGANISM: Artificial Sequence
<220> FEATURE:
<223> OTHER INFORMATION: Primer

<400> SEQUENCE: 77
ctagcagtca tttcacattt cttttgtgaa                                30

<210> SEQ ID NO 78
<211> LENGTH: 49
```

```
<212> TYPE: DNA
<213> ORGANISM: Artificial Sequence
<220> FEATURE:
<223> OTHER INFORMATION: Primer

<400> SEQUENCE: 78
gaaggtgacc aagttcatgc ttttcaaaat catcgaacat ggatctcat         49

<210> SEQ ID NO 79
<211> LENGTH: 46
<212> TYPE: DNA
<213> ORGANISM: Artificial Sequence
<220> FEATURE:
<223> OTHER INFORMATION: Primer

<400> SEQUENCE: 79
gaaggtcgga gtcaacggat tcaaaatcat cgaacatgga tctcac            46

<210> SEQ ID NO 80
<211> LENGTH: 27
<212> TYPE: DNA
<213> ORGANISM: Artificial Sequence
<220> FEATURE:
<223> OTHER INFORMATION: Primer

<400> SEQUENCE: 80
tctmccacca tatgataatg cacgtct                                 27

<210> SEQ ID NO 81
<211> LENGTH: 43
<212> TYPE: DNA
<213> ORGANISM: Artificial Sequence
<220> FEATURE:
<223> OTHER INFORMATION: Primer

<400> SEQUENCE: 81
gaaggtgacc aagttcatgc ttgccacttt gccgaccgyt tta               43

<210> SEQ ID NO 82
<211> LENGTH: 42
<212> TYPE: DNA
<213> ORGANISM: Artificial Sequence
<220> FEATURE:
<223> OTHER INFORMATION: Primer

<400> SEQUENCE: 82
gaaggtcgga gtcaacggat tgccactttg ccgaccgytt tc                42

<210> SEQ ID NO 83
<211> LENGTH: 30
<212> TYPE: DNA
<213> ORGANISM: Artificial Sequence
<220> FEATURE:
<223> OTHER INFORMATION: Primer

<400> SEQUENCE: 83
tgttgataat tggtgatcgt gstattgaaa                              30

<210> SEQ ID NO 84
<211> LENGTH: 50
<212> TYPE: DNA
<213> ORGANISM: Artificial Sequence
<220> FEATURE:
<223> OTHER INFORMATION: Primer

<400> SEQUENCE: 84
```
gaaggtcgga gtcaacggat tgaaactcaa tcgaaaggat gaaggattat        50

<210> SEQ ID NO 85
<211> LENGTH: 48
<212> TYPE: DNA
<213> ORGANISM: Artificial Sequence
<220> FEATURE:
<223> OTHER INFORMATION: Primer

<400> SEQUENCE: 85
gaaggtgacc aagttcatgc taactcaatc gaaaggatga aggattac          48

<210> SEQ ID NO 86
<211> LENGTH: 27
<212> TYPE: DNA
<213> ORGANISM: Artificial Sequence
<220> FEATURE:
<223> OTHER INFORMATION: Primer

<400> SEQUENCE: 86
tctctcagct tgagtgtcta gcaaraa                                 27

<210> SEQ ID NO 87
<211> LENGTH: 49
<212> TYPE: DNA
<213> ORGANISM: Artificial Sequence
<220> FEATURE:
<223> OTHER INFORMATION: Primer

<400> SEQUENCE: 87
gaaggtgacc aagttcatgc tcatagacaa gaagataaaa gagaccgaa         49

<210> SEQ ID NO 88
<211> LENGTH: 48
<212> TYPE: DNA
<213> ORGANISM: Artificial Sequence
<220> FEATURE:
<223> OTHER INFORMATION: Primer

<400> SEQUENCE: 88
gaaggtcgga gtcaacggat tatagacaag aagataaaag agaccgag          48

<210> SEQ ID NO 89
<211> LENGTH: 30
<212> TYPE: DNA
<213> ORGANISM: Artificial Sequence
<220> FEATURE:
<223> OTHER INFORMATION: Primer

<400> SEQUENCE: 89
ctctagcaaa tacatctctc ttcattcttt                              30

<210> SEQ ID NO 90
<211> LENGTH: 54
<212> TYPE: DNA
<213> ORGANISM: Artificial Sequence
<220> FEATURE:
<223> OTHER INFORMATION: Primer

<400> SEQUENCE: 90
gaaggtgacc aagttcatgc tgaattagtg aagagtttga gtagtttttt tttt   54

<210> SEQ ID NO 91
<211> LENGTH: 54
<212> TYPE: DNA
<213> ORGANISM: Artificial Sequence

```
<220> FEATURE:
<223> OTHER INFORMATION: Primer

<400> SEQUENCE: 91
gaaggtcgga gtcaacggat tgaattagtg aagagtttga gtagtttttt ttta        54

<210> SEQ ID NO 92
<211> LENGTH: 27
<212> TYPE: DNA
<213> ORGANISM: Artificial Sequence
<220> FEATURE:
<223> OTHER INFORMATION: Primer

<400> SEQUENCE: 92
ccatgcctat ccataagaca kaccttt                                      27

<210> SEQ ID NO 93
<211> LENGTH: 53
<212> TYPE: DNA
<213> ORGANISM: Artificial Sequence
<220> FEATURE:
<223> OTHER INFORMATION: Primer

<400> SEQUENCE: 93
gaaggtgacc aagttcatgc taacttcttt cttttttka ctaaatacag gtg          53

<210> SEQ ID NO 94
<211> LENGTH: 53
<212> TYPE: DNA
<213> ORGANISM: Artificial Sequence
<220> FEATURE:
<223> OTHER INFORMATION: Primer

<400> SEQUENCE: 94
gaaggtcgga gtcaacggat taacttcttt cttttttka ctaaatacag gtc          53

<210> SEQ ID NO 95
<211> LENGTH: 29
<212> TYPE: DNA
<213> ORGANISM: Artificial Sequence
<220> FEATURE:
<223> OTHER INFORMATION: Primer

<400> SEQUENCE: 95
ccagygttgg gtcttacaaa atacttttt                                    29

<210> SEQ ID NO 96
<211> LENGTH: 54
<212> TYPE: DNA
<213> ORGANISM: Artificial Sequence
<220> FEATURE:
<223> OTHER INFORMATION: Primer

<400> SEQUENCE: 96
gaaggtcgga gtcaacggat taaaaactaa gaaaacaatt atggactcta tcat        54

<210> SEQ ID NO 97
<211> LENGTH: 54
<212> TYPE: DNA
<213> ORGANISM: Artificial Sequence
<220> FEATURE:
<223> OTHER INFORMATION: Primer

<400> SEQUENCE: 97
gaaggtgacc aagttcatgc taaaaactaa gaaaacaatt atggactcta tcaa        54
```

```
<210> SEQ ID NO 98
<211> LENGTH: 27
<212> TYPE: DNA
<213> ORGANISM: Artificial Sequence
<220> FEATURE:
<223> OTHER INFORMATION: Primer

<400> SEQUENCE: 98
ggtatagkcg aatagaaaac cctcgat                                        27

<210> SEQ ID NO 99
<211> LENGTH: 54
<212> TYPE: DNA
<213> ORGANISM: Artificial Sequence
<220> FEATURE:
<223> OTHER INFORMATION: Primer

<400> SEQUENCE: 99
gaaggtcgga gtcaacggat tcactataat ttattttgaa ttgtttaaaa tcat          54

<210> SEQ ID NO 100
<211> LENGTH: 54
<212> TYPE: DNA
<213> ORGANISM: Artificial Sequence
<220> FEATURE:
<223> OTHER INFORMATION: Primer

<400> SEQUENCE: 100
gaaggtgacc aagttcatgc tcactataat ttattttgaa ttgtttaaaa tcaa          54

<210> SEQ ID NO 101
<211> LENGTH: 30
<212> TYPE: DNA
<213> ORGANISM: Artificial Sequence
<220> FEATURE:
<223> OTHER INFORMATION: Primer

<400> SEQUENCE: 101
gtaaatgmaa tcgtttgaaa taactgcaaa                                     30

<210> SEQ ID NO 102
<211> LENGTH: 47
<212> TYPE: DNA
<213> ORGANISM: Artificial Sequence
<220> FEATURE:
<223> OTHER INFORMATION: Primer

<400> SEQUENCE: 102
gaaggtcgga gtcaacggat tagaatcaag aagctcatcc tgtagat                  47

<210> SEQ ID NO 103
<211> LENGTH: 47
<212> TYPE: DNA
<213> ORGANISM: Artificial Sequence
<220> FEATURE:
<223> OTHER INFORMATION: Primer

<400> SEQUENCE: 103
gaaggtgacc aagttcatgc tagaatcaag aagctcatcc tgtagaa                  47

<210> SEQ ID NO 104
<211> LENGTH: 27
<212> TYPE: DNA
<213> ORGANISM: Artificial Sequence
<220> FEATURE:
<223> OTHER INFORMATION: Primer
```

<400> SEQUENCE: 104
caaackggag gacatggaag aacttaa                                    27

<210> SEQ ID NO 105
<211> LENGTH: 46
<212> TYPE: DNA
<213> ORGANISM: Artificial Sequence
<220> FEATURE:
<223> OTHER INFORMATION: Primer

<400> SEQUENCE: 105
gaaggtgacc aagttcatgc ttaagaccaa gcaagaaatg gtccat               46

<210> SEQ ID NO 106
<211> LENGTH: 45
<212> TYPE: DNA
<213> ORGANISM: Artificial Sequence
<220> FEATURE:
<223> OTHER INFORMATION: Primer

<400> SEQUENCE: 106
gaaggtcgga gtcaacggat taagaccaag caagaaatgg tccag                45

<210> SEQ ID NO 107
<211> LENGTH: 30
<212> TYPE: DNA
<213> ORGANISM: Artificial Sequence
<220> FEATURE:
<223> OTHER INFORMATION: Primer

<400> SEQUENCE: 107
cggttttggt aaaataagct ctattyttta                                 30

<210> SEQ ID NO 108
<211> LENGTH: 46
<212> TYPE: DNA
<213> ORGANISM: Artificial Sequence
<220> FEATURE:
<223> OTHER INFORMATION: Primer

<400> SEQUENCE: 108
gaaggtgacc aagttcatgc taacacaagt cgttactctt cctggt               46

<210> SEQ ID NO 109
<211> LENGTH: 44
<212> TYPE: DNA
<213> ORGANISM: Artificial Sequence
<220> FEATURE:
<223> OTHER INFORMATION: Primer

<400> SEQUENCE: 109
gaaggtcgga gtcaacggat tcacaagtcg ttactcttcc tggc                 44

<210> SEQ ID NO 110
<211> LENGTH: 27
<212> TYPE: DNA
<213> ORGANISM: Artificial Sequence
<220> FEATURE:
<223> OTHER INFORMATION: Primer

<400> SEQUENCE: 110
acacaaagag tagagagtag tgcrctt                                    27

<210> SEQ ID NO 111

```
<211> LENGTH: 54
<212> TYPE: DNA
<213> ORGANISM: Artificial Sequence
<220> FEATURE:
<223> OTHER INFORMATION: Primer

<400> SEQUENCE: 111
gaaggtgacc aagttcatgc taaactattt acacaaatgc cattaactttt tttt        54

<210> SEQ ID NO 112
<211> LENGTH: 54
<212> TYPE: DNA
<213> ORGANISM: Artificial Sequence
<220> FEATURE:
<223> OTHER INFORMATION: Primer

<400> SEQUENCE: 112
gaaggtcgga gtcaacggat taaactattt acacaaatgc cattaactttt ttta        54

<210> SEQ ID NO 113
<211> LENGTH: 30
<212> TYPE: DNA
<213> ORGANISM: Artificial Sequence
<220> FEATURE:
<223> OTHER INFORMATION: Primer

<400> SEQUENCE: 113
caagtatcgc agattttaa tagcagactt                                     30

<210> SEQ ID NO 114
<211> LENGTH: 54
<212> TYPE: DNA
<213> ORGANISM: Artificial Sequence
<220> FEATURE:
<223> OTHER INFORMATION: Primer

<400> SEQUENCE: 114
gaaggtgacc aagttcatgc tcccttattt cttttggtaa caaaaaaact attt         54

<210> SEQ ID NO 115
<211> LENGTH: 54
<212> TYPE: DNA
<213> ORGANISM: Artificial Sequence
<220> FEATURE:
<223> OTHER INFORMATION: Primer

<400> SEQUENCE: 115
gaaggtcgga gtcaacggat tcccttattt cttttggtaa caaaaaaact atta         54

<210> SEQ ID NO 116
<211> LENGTH: 30
<212> TYPE: DNA
<213> ORGANISM: Artificial Sequence
<220> FEATURE:
<223> OTHER INFORMATION: Primer

<400> SEQUENCE: 116
cargtatcgc agattttaa tagcagactt                                     30

<210> SEQ ID NO 117
<211> LENGTH: 47
<212> TYPE: DNA
<213> ORGANISM: Artificial Sequence
<220> FEATURE:
<223> OTHER INFORMATION: Primer

<400> SEQUENCE: 117
```
gaaggtgacc aagttcatgc tgccaaactg tgggaatcga aattcaa                    47

<210> SEQ ID NO 118
<211> LENGTH: 46
<212> TYPE: DNA
<213> ORGANISM: Artificial Sequence
<220> FEATURE:
<223> OTHER INFORMATION: Primer

<400> SEQUENCE: 118
gaaggtcgga gtcaacggat tccaaactgt gggaatcgaa attcac                     46

<210> SEQ ID NO 119
<211> LENGTH: 27
<212> TYPE: DNA
<213> ORGANISM: Artificial Sequence
<220> FEATURE:
<223> OTHER INFORMATION: Primer

<400> SEQUENCE: 119
tgctttcttc ctctaatmaa tttgact                                          27

<210> SEQ ID NO 120
<211> LENGTH: 46
<212> TYPE: DNA
<213> ORGANISM: Artificial Sequence
<220> FEATURE:
<223> OTHER INFORMATION: Primer

<400> SEQUENCE: 120
gaaggtgacc aagttcatgc tgatattata cgattgtcga acctcc                     46

<210> SEQ ID NO 121
<211> LENGTH: 46
<212> TYPE: DNA
<213> ORGANISM: Artificial Sequence
<220> FEATURE:
<223> OTHER INFORMATION: Primer

<400> SEQUENCE: 121
gaaggtcgga gtcaacggat tgatattata cgattgtcga acctcg                     46

<210> SEQ ID NO 122
<211> LENGTH: 29
<212> TYPE: DNA
<213> ORGANISM: Artificial Sequence
<220> FEATURE:
<223> OTHER INFORMATION: Primer

<400> SEQUENCE: 122
ggaagaacat tgtgttggga atgttctaa                                        29

<210> SEQ ID NO 123
<211> LENGTH: 51
<212> TYPE: DNA
<213> ORGANISM: Artificial Sequence
<220> FEATURE:
<223> OTHER INFORMATION: Primer

<400> SEQUENCE: 123
gaaggtgacc aagttcatgc taaaagtgat tctcaaaaga aaagaacggt t               51

<210> SEQ ID NO 124
<211> LENGTH: 48
<212> TYPE: DNA

```
<213> ORGANISM: Artificial Sequence
<220> FEATURE:
<223> OTHER INFORMATION: Primer

<400> SEQUENCE: 124
gaaggtcgga gtcaacggat tagtgattct caaaagaaaa gaacggtc                48

<210> SEQ ID NO 125
<211> LENGTH: 25
<212> TYPE: DNA
<213> ORGANISM: Artificial Sequence
<220> FEATURE:
<223> OTHER INFORMATION: Primer

<400> SEQUENCE: 125
ggaggaacct ctccatatac gagat                                         25

<210> SEQ ID NO 126
<211> LENGTH: 46
<212> TYPE: DNA
<213> ORGANISM: Artificial Sequence
<220> FEATURE:
<223> OTHER INFORMATION: Primer

<400> SEQUENCE: 126
gaaggtcgga gtcaacggat tgtggtcttg aatctatcgc gtaact                  46

<210> SEQ ID NO 127
<211> LENGTH: 46
<212> TYPE: DNA
<213> ORGANISM: Artificial Sequence
<220> FEATURE:
<223> OTHER INFORMATION: Primer

<400> SEQUENCE: 127
gaaggtgacc aagttcatgc tgtggtcttg aatctatcgc gtaaca                  46

<210> SEQ ID NO 128
<211> LENGTH: 21
<212> TYPE: DNA
<213> ORGANISM: Artificial Sequence
<220> FEATURE:
<223> OTHER INFORMATION: Primer

<400> SEQUENCE: 128
cgcagggaca ccaggcktga a                                             21

<210> SEQ ID NO 129
<211> LENGTH: 54
<212> TYPE: DNA
<213> ORGANISM: Artificial Sequence
<220> FEATURE:
<223> OTHER INFORMATION: Primer

<400> SEQUENCE: 129
gaaggtgacc aagttcatgc tgacaaattt taggacataa atattaaaat accc         54

<210> SEQ ID NO 130
<211> LENGTH: 54
<212> TYPE: DNA
<213> ORGANISM: Artificial Sequence
<220> FEATURE:
<223> OTHER INFORMATION: Primer

<400> SEQUENCE: 130
gaaggtcgga gtcaacggat tgacaaattt taggacataa atattaaaat acct         54
```

<210> SEQ ID NO 131
<211> LENGTH: 30
<212> TYPE: DNA
<213> ORGANISM: Artificial Sequence
<220> FEATURE:
<223> OTHER INFORMATION: Primer

<400> SEQUENCE: 131
ctagatattt gactcttaat agttgcgata                              30

<210> SEQ ID NO 132
<211> LENGTH: 50
<212> TYPE: DNA
<213> ORGANISM: Artificial Sequence
<220> FEATURE:
<223> OTHER INFORMATION: Primer

<400> SEQUENCE: 132
gaaggtgacc aagttcatgc tcgaatttat gacgtgtaat tctatgcgta        50

<210> SEQ ID NO 133
<211> LENGTH: 49
<212> TYPE: DNA
<213> ORGANISM: Artificial Sequence
<220> FEATURE:
<223> OTHER INFORMATION: Primer

<400> SEQUENCE: 133
gaaggtcgga gtcaacggat tgaatttatg acgtgtaatt ctatgcgtc         49

<210> SEQ ID NO 134
<211> LENGTH: 30
<212> TYPE: DNA
<213> ORGANISM: Artificial Sequence
<220> FEATURE:
<223> OTHER INFORMATION: Primer

<400> SEQUENCE: 134
gtctgagaat caaattagty gtccaagtta                              30

<210> SEQ ID NO 135
<211> LENGTH: 50
<212> TYPE: DNA
<213> ORGANISM: Artificial Sequence
<220> FEATURE:
<223> OTHER INFORMATION: Primer

<400> SEQUENCE: 135
gaaggtgacc aagttcatgc tatatttaga gaagagatat tgtaggatgc        50

<210> SEQ ID NO 136
<211> LENGTH: 52
<212> TYPE: DNA
<213> ORGANISM: Artificial Sequence
<220> FEATURE:
<223> OTHER INFORMATION: Primer

<400> SEQUENCE: 136
gaaggtcgga gtcaacggat tgtatattta gagaagagat attgtaggat gt     52

<210> SEQ ID NO 137
<211> LENGTH: 30
<212> TYPE: DNA
<213> ORGANISM: Artificial Sequence
<220> FEATURE:

```
<223> OTHER INFORMATION: Primer

<400> SEQUENCE: 137
gtacatatct ttttgttgtt atctctagaa                              30

<210> SEQ ID NO 138
<211> LENGTH: 47
<212> TYPE: DNA
<213> ORGANISM: Artificial Sequence
<220> FEATURE:
<223> OTHER INFORMATION: Primer

<400> SEQUENCE: 138
gaaggtgacc aagttcatgc tcgttgaact ctcctaattc ctatacc           47

<210> SEQ ID NO 139
<211> LENGTH: 47
<212> TYPE: DNA
<213> ORGANISM: Artificial Sequence
<220> FEATURE:
<223> OTHER INFORMATION: Primer

<400> SEQUENCE: 139
gaaggtcgga gtcaacggat tcgttgaact ctcctaattc ctatact           47

<210> SEQ ID NO 140
<211> LENGTH: 25
<212> TYPE: DNA
<213> ORGANISM: Artificial Sequence
<220> FEATURE:
<223> OTHER INFORMATION: Primer

<400> SEQUENCE: 140
gggcttcaaa ctagtcsgcc taatt                                   25

<210> SEQ ID NO 141
<211> LENGTH: 49
<212> TYPE: DNA
<213> ORGANISM: Artificial Sequence
<220> FEATURE:
<223> OTHER INFORMATION: Primer

<400> SEQUENCE: 141
gaaggtcgga gtcaacggat ttagctatgt gctgtaaaga aaagatatc         49

<210> SEQ ID NO 142
<211> LENGTH: 54
<212> TYPE: DNA
<213> ORGANISM: Artificial Sequence
<220> FEATURE:
<223> OTHER INFORMATION: Primer

<400> SEQUENCE: 142
gaaggtgacc aagttcatgc tatttttagc tatgtgctgt aagaaaaga tata    54

<210> SEQ ID NO 143
<211> LENGTH: 29
<212> TYPE: DNA
<213> ORGANISM: Artificial Sequence
<220> FEATURE:
<223> OTHER INFORMATION: Primer

<400> SEQUENCE: 143
tcaataagga aggaaggaaa cagaggaaa                               29
```

```
<210> SEQ ID NO 144
<211> LENGTH: 46
<212> TYPE: DNA
<213> ORGANISM: Artificial Sequence
<220> FEATURE:
<223> OTHER INFORMATION: Primer

<400> SEQUENCE: 144
gaaggtcgga gtcaacggat tgtgttaact ccggtttkag aggaag                    46

<210> SEQ ID NO 145
<211> LENGTH: 46
<212> TYPE: DNA
<213> ORGANISM: Artificial Sequence
<220> FEATURE:
<223> OTHER INFORMATION: Primer

<400> SEQUENCE: 145
gaaggtgacc aagttcatgc tgtgttaact ccggtttkag aggaaa                    46

<210> SEQ ID NO 146
<211> LENGTH: 30
<212> TYPE: DNA
<213> ORGANISM: Artificial Sequence
<220> FEATURE:
<223> OTHER INFORMATION: Primer

<400> SEQUENCE: 146
aaaagggctm tttcccttct tacatttctt                                      30

<210> SEQ ID NO 147
<211> LENGTH: 43
<212> TYPE: DNA
<213> ORGANISM: Artificial Sequence
<220> FEATURE:
<223> OTHER INFORMATION: Primer

<400> SEQUENCE: 147
gaaggtgacc aagttcatgc tactgggtac gtgctcaacc gtt                       43

<210> SEQ ID NO 148
<211> LENGTH: 42
<212> TYPE: DNA
<213> ORGANISM: Artificial Sequence
<220> FEATURE:
<223> OTHER INFORMATION: Primer

<400> SEQUENCE: 148
gaaggtcgga gtcaacggat tctgggtacg tgctcaaccg tc                        42

<210> SEQ ID NO 149
<211> LENGTH: 27
<212> TYPE: DNA
<213> ORGANISM: Artificial Sequence
<220> FEATURE:
<223> OTHER INFORMATION: Primer

<400> SEQUENCE: 149
gccttaaagg gctgttaatc ctcakta                                         27

<210> SEQ ID NO 150
<211> LENGTH: 46
<212> TYPE: DNA
<213> ORGANISM: Artificial Sequence
<220> FEATURE:
<223> OTHER INFORMATION: Primer
```

```
<400> SEQUENCE: 150
gaaggtcgga gtcaacggat tcatgcagga ttgaatgccc aaattc                    46

<210> SEQ ID NO 151
<211> LENGTH: 47
<212> TYPE: DNA
<213> ORGANISM: Artificial Sequence
<220> FEATURE:
<223> OTHER INFORMATION: Primer

<400> SEQUENCE: 151
gaaggtgacc aagttcatgc tccatgcagg attgaatgcc caaatta                   47

<210> SEQ ID NO 152
<211> LENGTH: 27
<212> TYPE: DNA
<213> ORGANISM: Artificial Sequence
<220> FEATURE:
<223> OTHER INFORMATION: Primer

<400> SEQUENCE: 152
cagaagtctc tgctakaaag gcttcta                                         27

<210> SEQ ID NO 153
<211> LENGTH: 51
<212> TYPE: DNA
<213> ORGANISM: Artificial Sequence
<220> FEATURE:
<223> OTHER INFORMATION: Primer

<400> SEQUENCE: 153
gaaggtcgga gtcaacggat tactatctcc ttcgatwtat ataacattac g              51

<210> SEQ ID NO 154
<211> LENGTH: 51
<212> TYPE: DNA
<213> ORGANISM: Artificial Sequence
<220> FEATURE:
<223> OTHER INFORMATION: Primer

<400> SEQUENCE: 154
gaaggtgacc aagttcatgc tactatctcc ttcgatwtat ataacattac c              51

<210> SEQ ID NO 155
<211> LENGTH: 30
<212> TYPE: DNA
<213> ORGANISM: Artificial Sequence
<220> FEATURE:
<223> OTHER INFORMATION: Primer

<400> SEQUENCE: 155
gcattacaaa tmagaaaaag cagggaacaa                                      30

<210> SEQ ID NO 156
<211> LENGTH: 44
<212> TYPE: DNA
<213> ORGANISM: Artificial Sequence
<220> FEATURE:
<223> OTHER INFORMATION: Primer

<400> SEQUENCE: 156
gaaggtgacc aagttcatgc ttcttagaca tcgaaggctg taac                      44

<210> SEQ ID NO 157
<211> LENGTH: 46
```

```
<212> TYPE: DNA
<213> ORGANISM: Artificial Sequence
<220> FEATURE:
<223> OTHER INFORMATION: Primer

<400> SEQUENCE: 157
gaaggtcgga gtcaacggat tcttcttaga catcgaaggc tgtaag                    46

<210> SEQ ID NO 158
<211> LENGTH: 30
<212> TYPE: DNA
<213> ORGANISM: Artificial Sequence
<220> FEATURE:
<223> OTHER INFORMATION: Primer

<400> SEQUENCE: 158
atwggtttct ttcttgctgt aatgtgtaaa                                      30

<210> SEQ ID NO 159
<211> LENGTH: 51
<212> TYPE: DNA
<213> ORGANISM: Artificial Sequence
<220> FEATURE:
<223> OTHER INFORMATION: Primer

<400> SEQUENCE: 159
gaaggtgacc aagttcatgc tagcttttat tagcaagtct tgtttgtttg t              51

<210> SEQ ID NO 160
<211> LENGTH: 50
<212> TYPE: DNA
<213> ORGANISM: Artificial Sequence
<220> FEATURE:
<223> OTHER INFORMATION: Primer

<400> SEQUENCE: 160
gaaggtcgga gtcaacggat tgcttttatt agcaagtctt gtttgtttgg                50

<210> SEQ ID NO 161
<211> LENGTH: 23
<212> TYPE: DNA
<213> ORGANISM: Artificial Sequence
<220> FEATURE:
<223> OTHER INFORMATION: Primer

<400> SEQUENCE: 161
caagaacccg gagagaggag gat                                             23

<210> SEQ ID NO 162
<211> LENGTH: 43
<212> TYPE: DNA
<213> ORGANISM: Artificial Sequence
<220> FEATURE:
<223> OTHER INFORMATION: Primer

<400> SEQUENCE: 162
gaaggtcgga gtcaacggat tgtttctctc ccacagatca ctg                       43

<210> SEQ ID NO 163
<211> LENGTH: 43
<212> TYPE: DNA
<213> ORGANISM: Artificial Sequence
<220> FEATURE:
<223> OTHER INFORMATION: Primer

<400> SEQUENCE: 163
```

```
gaaggtgacc aagttcatgc tgtttctctc ccacagatca ctc          43

<210> SEQ ID NO 164
<211> LENGTH: 29
<212> TYPE: DNA
<213> ORGANISM: Artificial Sequence
<220> FEATURE:
<223> OTHER INFORMATION: Primer

<400> SEQUENCE: 164
tatggcggga aaatgtaaga gatgtgttt                          29

<210> SEQ ID NO 165
<211> LENGTH: 42
<212> TYPE: DNA
<213> ORGANISM: Artificial Sequence
<220> FEATURE:
<223> OTHER INFORMATION: Primer

<400> SEQUENCE: 165
gaaggtgacc aagttcatgc ttctgaagaa gctccattay gg           42

<210> SEQ ID NO 166
<211> LENGTH: 47
<212> TYPE: DNA
<213> ORGANISM: Artificial Sequence
<220> FEATURE:
<223> OTHER INFORMATION: Primer

<400> SEQUENCE: 166
gaaggtcgga gtcaacggat tatgcttctg aagaagctcc attayga      47

<210> SEQ ID NO 167
<211> LENGTH: 29
<212> TYPE: DNA
<213> ORGANISM: Artificial Sequence
<220> FEATURE:
<223> OTHER INFORMATION: Primer

<400> SEQUENCE: 167
gctcctsatt tctctaattt agtgacgta                          29

<210> SEQ ID NO 168
<211> LENGTH: 43
<212> TYPE: DNA
<213> ORGANISM: Artificial Sequence
<220> FEATURE:
<223> OTHER INFORMATION: Primer

<400> SEQUENCE: 168
gaaggtcgga gtcaacggat tgtcgstgtg tagagttggt agc          43

<210> SEQ ID NO 169
<211> LENGTH: 43
<212> TYPE: DNA
<213> ORGANISM: Artificial Sequence
<220> FEATURE:
<223> OTHER INFORMATION: Primer

<400> SEQUENCE: 169
gaaggtgacc aagttcatgc tgtcgstgtg tagagttggt aga          43

<210> SEQ ID NO 170
<211> LENGTH: 22
<212> TYPE: DNA
<213> ORGANISM: Artificial Sequence
```

```
<220> FEATURE:
<223> OTHER INFORMATION: Primer

<400> SEQUENCE: 170
gcactggata ggcctcgcca tt                                              22

<210> SEQ ID NO 171
<211> LENGTH: 51
<212> TYPE: DNA
<213> ORGANISM: Artificial Sequence
<220> FEATURE:
<223> OTHER INFORMATION: Primer

<400> SEQUENCE: 171
gaaggtgacc aagttcatgc taacaaaaag cactggtaca atcttcaaat a              51

<210> SEQ ID NO 172
<211> LENGTH: 49
<212> TYPE: DNA
<213> ORGANISM: Artificial Sequence
<220> FEATURE:
<223> OTHER INFORMATION: Primer

<400> SEQUENCE: 172
gaaggtcgga gtcaacggat tcaaaaagca ctggtacaat cttcaaatc                 49

<210> SEQ ID NO 173
<211> LENGTH: 30
<212> TYPE: DNA
<213> ORGANISM: Artificial Sequence
<220> FEATURE:
<223> OTHER INFORMATION: Primer

<400> SEQUENCE: 173
tagmatgaga atccaaagaa agcatgtcaa                                      30

<210> SEQ ID NO 174
<211> LENGTH: 51
<212> TYPE: DNA
<213> ORGANISM: Artificial Sequence
<220> FEATURE:
<223> OTHER INFORMATION: Primer

<400> SEQUENCE: 174
gaaggtgacc aagttcatgc tactgaaaat aaagcatttt gaaactgatt c              51

<210> SEQ ID NO 175
<211> LENGTH: 53
<212> TYPE: DNA
<213> ORGANISM: Artificial Sequence
<220> FEATURE:
<223> OTHER INFORMATION: Primer

<400> SEQUENCE: 175
gaaggtcgga gtcaacggat tctactgaaa ataaagcatt ttgaaactga ttt            53

<210> SEQ ID NO 176
<211> LENGTH: 30
<212> TYPE: DNA
<213> ORGANISM: Artificial Sequence
<220> FEATURE:
<223> OTHER INFORMATION: Primer

<400> SEQUENCE: 176
cactacaaaa tcactttaaa atacatcctt                                      30
```